United States Patent
Arasappan et al.

(10) Patent No.: US 10,072,003 B2
(45) Date of Patent: Sep. 11, 2018

(54) TETRAHYDRONAPHTHYRIDINE DERIVATIVES AS MGLUR2-NEGATIVE ALLOSTERIC MODULATORS, COMPOSITIONS, AND THEIR USE

(71) Applicants: Merck Sharp & Dohme Corp., Rahway, NJ (US); Merck Canada Inc., Kirkland (CA)

(72) Inventors: Ashok Arasappan, Bridgewater, NJ (US); Christopher James Bungard, Lansdale, PA (US); Jessica L. Frie, Harleysville, PA (US); Yongxin Han, Needham, MA (US); Scott B. Hoyt, Hoboken, NJ (US); Peter J. Manley, Harleysville, PA (US); Robert S. Meissner, Newton, MA (US); James J. Perkins, Churchville, PA (US); Iyassu K. Sebhat, Jersey City, NJ (US); Robert R. Wilkening, Maplewood, NJ (US); Kenneth J. Leavitt, Mount Laurel, NJ (US)

(73) Assignees: Merck Sharp & Dohme Corp.; Merck Canada Inc.

( * ) Notice: Subject to any disclaimer, the term of this patent is extended or adjusted under 35 U.S.C. 154(b) by 0 days.

(21) Appl. No.: 15/506,269

(22) PCT Filed: Aug. 24, 2015

(86) PCT No.: PCT/US2015/046458
§ 371 (c)(1),
(2) Date: Feb. 24, 2017

(87) PCT Pub. No.: WO2016/032921
PCT Pub. Date: Mar. 3, 2016

(65) Prior Publication Data
US 2017/0305902 A1    Oct. 26, 2017

(30) Foreign Application Priority Data
Aug. 29, 2014 (WO) ............... PCT/CN2014/085582

(51) Int. Cl.
C07D 471/04    (2006.01)
(52) U.S. Cl.
CPC ................ C07D 471/04 (2013.01)
(58) Field of Classification Search
CPC .................................. C07D 471/04
See application file for complete search history.

(56) References Cited

U.S. PATENT DOCUMENTS 8,080,657 B2    12/2011    Chung
2006/0122197 A1    6/2006    Yao et al.
2010/0273772 A1    10/2010    O'Neil et al.
2011/0081365 A1    4/2011    Cortez et al.
2012/0178776 A1    7/2012    Conn et al.
2014/0142108 A1    5/2014    Blackburn et al.
2014/0309227 A1*    10/2014    Bungard ............... C07D 401/14
                                                      514/236.5

FOREIGN PATENT DOCUMENTS

| EP | 2650284 A1 | 10/2013 |
| WO | 2006079467 A1 | 8/2006 |
| WO | 2012092530 | 7/2012 |
| WO | 2012097182 | 9/2012 |
| WO | 2013066736 | 5/2013 |

OTHER PUBLICATIONS

Adam, Octavian R. "Symptomatic Treatment of Huntington Disease" Neurotherapeutics: The Journal of the American Society for Experimental NeuroTherapeutics Apr. 2008, vol. 5, 181-197.*
Hook V. Y.H. "Neuroproteases in Peptide Neurotransmission and Neurodegenerative Diseases Applications to Drug Discovery Research" Biodrugs 2006, 20, 105-119.*
Chiba "Emerging Therapeutic Strategies in Alzheimer's Disease" Intech 2013, 181-225.*
Le Bars, et. al. "Animal Models of Nociception" Pharmacological Reviews 2001, 53, 597-652.*
Petit-Demouliere et. al. "Forced swimming test in mice: a review of antidepressant activity." Psychopharmacology 2005, 177, 245-255.*
Conn, P.J. "Activation of metabotropic glutamate receptors as a novel approach for the treatment of schizophrenia." Trends in Pharmacological Sciences 2008 vol. 30 No. 1 25-31.*

(Continued)

*Primary Examiner* — David K O'Dell
(74) *Attorney, Agent, or Firm* — Keith D. MacMillan; Catherine D. Fitch

(57) ABSTRACT

The present invention provides quinoline carboxamide and quinoline carbonitrile compounds of formula (I) or a pharmaceutically acceptable salt thereof, wherein $R^1$, $R^2$, L, $X_1$, $X_2$, and $X_3$, are as defined herein. The compounds of the invention, and pharmaceutically acceptable salts thereof, and pharmaceutical compositions comprising them, are useful as non-competitive mGluR2 antagonists, or mGluR2 negative allosteric modulators (NAMs), and may be useful in methods of treating a person in need thereof for diseases or disorders in which the mGluR2-NAM receptor plays a causative role, such as Alzheimer's disease, cognitive impairment, schizophrenia and other mood disorders, pain disorders and sleep disorders.

(I)

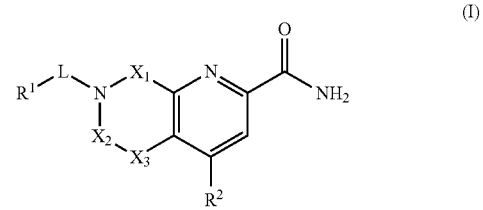

8 Claims, No Drawings

(56) References Cited

OTHER PUBLICATIONS

Eric R. Marcotte J "Animal models of schizophrenia: a critical review" Psychiatry Neurosci 2001;26(5):395-410.*
International Search Report for PCT/CN2014/085582 dated May 27, 2015, 15 pages.
International Search Report for PCT/US2015/046458 dated Nov. 27, 2015, 6 pages.
Zanger, et al, Structure-Activity Relationship and Drug Design, Remington's Pharmaceutical Sciences, 1975, 454-469, Ed. 5, Mack Publishing.

* cited by examiner

TETRAHYDRONAPHTHYRIDINE DERIVATIVES AS MGLUR2-NEGATIVE ALLOSTERIC MODULATORS, COMPOSITIONS, AND THEIR USE

FIELD OF THE INVENTION

The invention is directed to certain tetrahydronaphthyridine derivatives, salts thereof, pharmaceutical compositions comprising them and their use in therapy of the human body. The subject compounds exhibit activity as metabotropic glutamate receptor 2 negative allosteric modulators (mGluR2-NAMs), and hence are expected to be useful in the treatment of Alzheimer's Disease and other diseases mediated by the mGluR2 receptor.

BACKGROUND OF THE INVENTION

Alzheimer's Disease is a common neurodegenerative disease affecting the elderly, resulting in progressive memory impairment, loss of language and visuospatial skills, and behavior deficits. Modulation of metabotropic glutamate receptor 2, which is prevalent in the cortex and hippocampus and regulates the release of the brain's major excitatory neurotransmitter glutamate at key neural synapses has been demonstrated to have a major role in cognitive processing. Further, modulation of mGluR2 improves cognitive performance in preclinical species (Higgins, G. A. et al. (2004) Pharmacological manipulation of mGlu2 receptors influences cognitive performance in the rodent. Neuropharmacology 46, 907-917).

The metabotropic glutamate receptors are known to contain one or more allosteric sites, which may alter the affinity with which glutamate and other mGluR ligands bind to the primary binding or orthosteric sites. As the orthosteric binding site is highly conserved between all of the known metabotropic glutamate receptors, functional selectivity may best be achieved through allosteric interaction with the receptor.

SUMMARY OF THE INVENTION

The present invention provides certain novel substituted tetrahydronaphthyridine derivatives, which are collectively or individually referred to herein as "compound(s) of the invention," as described herein. The compounds of the invention are useful as non-competitive mGluR2 antagonists, or mGluR2 negative allosteric modulators (NAMs), and in methods of treating a patient (preferably a human) for diseases or disorders in which the mGluR2-NAM receptor is involved, such as Alzheimer's disease, cognitive impairment, schizophrenia and other mood disorders (including but not limited to depression), pain disorders and sleep disorders, by administering to the patient a therapeutically effective amount of a compound of the invention, or a pharmaceutically acceptable salt thereof. The invention also provides pharmaceutical compositions which include an effective amount of a compound of the invention, or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the compounds of the invention have the structural Formula (I):

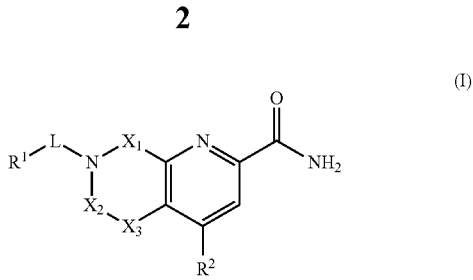

or a stereoisomer thereof, or a pharmaceutically acceptable salt of said compound or said stereoisomer, wherein:

$X_1$ is selected from the group consisting of —$C(R^{X1})_2$—,

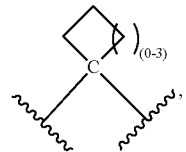

—CHcyclopropyl-, and —CHcyclobutyl-;
wherein each $R^{X1}$ is independently selected from the group consisting of H, —$(C_{1-4})$alkyl, —$(C_{2-4})$alkenyl, and —$(C_{2-4})$alkynyl;

$X_2$ is selected from the group consisting of —$C(R^{X1})_2$—,

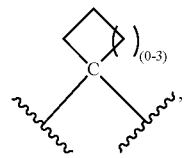

—CHcyclopropyl-, —CHcyclobutyl-;
wherein each $R^{X2}$ is independently selected from the group consisting of H, —$(C_{1-4})$alkyl, —$(C_{2-4})$alkenyl, and —$(C_{2-4})$alkynyl;

$X_3$ is selected from the group consisting of —$C(R^{X3})_2$—;
wherein each $R^{X3}$ is independently selected from the group consisting of H, —$(C_{1-4})$alkyl, and fluoro;

$R^1$ is selected from the group consisting of phenyl, heteroaryl, cycloalkyl, and heterocycloalkyl, wherein each of said phenyl, heteroaryl, cycloalkyl, and heterocycloalkyl of $R^1$ is unsubstituted or substituted with from 1 to 3 $R^{1A}$ groups;

each $R^{1A}$ (when present) is independently selected from the group consisting of halo, OH, CN, —$(C_{1-4})$alkyl, —$(C_{1-4})$haloalkyl, —$(C_{1-4})$alkoxy, —$(C_{1-4})$haloalkoxy, cyclopropyl, cyclobutyl, —$NH_2$, —$C(O)NH_2$, —$C(O)N(CH_3)_2$, —$S(O)_2(C_{1-4})$alkyl, $CH_2OH$, $CH_2CH_2OH$, $NH(CO)CH_3$, oxadiazole, triazole, and pyrazole;

or, alternatively, two $R^{1A}$ groups on the same or adjacent atoms are taken together with the ring atom of $R^1$ to which they are attached to form a a cyclopropyl, cyclobutyl, spirocyclopropyl, or spirocyclobutyl group;

-L- is a divalent moiety selected from the group consisting of —$(C(R^{L1})_2)_p$—, —$C(O)$—, —$C(O)CH_2$—, and —$CH_2C(O)$—,
wherein p is 1 to 3, and each $R^{L1}$ is independently selected from the group consisting of H, OH, —$CH_3$, —$CH_2CH_3$, —$CH_2CF_3$, —$CHF_2$, —$CF_3$, and —$CH_2OH$; and $R^2$ is selected from the group consisting of phenyl, heteroaryl, cycloalkyl, cycloalkenyl, heterocycloalkyl and heterocycloalkenyl, wherein each of said phenyl, heteroaryl, cycloalkyl, cycloalkenyl, heterocycloalkyl and heterocycloalkenyl of $R^2$ is unsubstituted or substituted with from 1 to 3 $R^{2A}$ groups;

each $R^{2A}$ (when present) is independently selected from the group consisting of halo, OH, CN, —$(C_{1-4})$alkyl, —$(C_{1-4})$haloalkyl, —$(C_{1-4})$alkoxy, —$(C_{1-4})$haloalkoxy, cyclopropyl, cyclobutyl, —$NH_2$, —$C(O)NH_2$, —$C(O)N(CH_3)_2$, —$S(O)_2(C_{1-4})$alkyl, $CH_2OH$, $CH_2CH_2OH$, $NH(CO)CH_3$, oxadiazole, triazole, and pyrazole;

or, alternatively, two $R^{2A}$ groups on the same or adjacent atoms are taken together with the ring atom of $R^2$ to which they are attached to form a cyclopropyl, cyclobutyl, spirocyclopropyl, or spirocyclobutyl group.

In another embodiment, in Formula (I), $X_1$ is —$C(R^{X1})_2$—, wherein each $R^{X1}$ is independently selected from the group consisting of H, and —$(C_{1-4})$alkyl; and $R^1$ and $R^2$ are as defined in Formula I.

In another embodiment, in Formula (I), $X_1$ is —$C(R^{X1})_2$—, wherein each $R^{X1}$ is selected from the group consisting of H, and methyl; and $R^1$ and $R^2$ are as defined in Formula I.

In another embodiment, in Formula (I), $X_1$ is —$C(R^{X1})_2$—, wherein each $R^{X1}$ is H; and $R^1$ and $R^2$ are as defined in Formula I.

In another embodiment, in Formula (I), $X_1$ is —$C(R^{X1})_2$—, wherein each $R^{X1}$ is methyl; and $R^1$ and $R^2$ are as defined in Formula I.

In one embodiment, the compounds of the invention have the structural Formula (II):

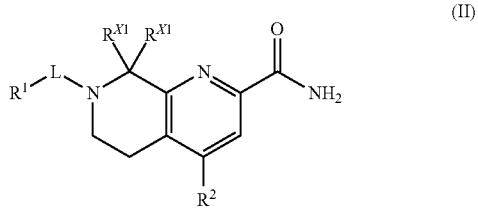

or a stereoisomer thereof, or a pharmaceutically acceptable salt of said compound or said stereoisomer, wherein:
wherein each $R^{X1}$ is independently selected from the group consisting of H, —$(C_{1-4})$alkyl, —$(C_{2-4})$alkenyl, and —$(C_{2-4})$alkynyl; and $R^1$, $R^2$, and -L- are as defined in Formula I.

In another embodiment, in Formula (II), each $R^{X1}$ is independently selected from the group consisting of H, and —$(C_{1-4})$alkyl; and $R^1$, $R^2$, and -L- are as defined in Formula I.

In another embodiment, in Formula (II), each $R^{X1}$ is independently selected from the group consisting of H, and methyl; and $R^1$, $R^2$, and -L- are as defined in Formula I.

In another embodiment, in Formula (II), each $R^{X1}$ is H; and $R^1$, $R^2$, and -L- are as defined in Formula I.

In another embodiment, in Formula (II), each $R^{X1}$ is methyl; and $R^1$, $R^2$, and -L- are as defined in Formula I.

In another embodiment, in each of Formula (I) and Formula (II):

$R^1$ is selected from the group consisting of phenyl, cyclobutyl, cyclohexyl, cyclopentyl, benzimidazolyl, imidazolyl, imidazopyridinyl, imidazopyridinyl, imidazopyrimidinyl, isoxazolyl, oxadiazolyl, oxadiazolyl, oxazolyl, oxetanyl, piperidinyl, pyrazolyl, pyridinyl, pyrimidinyl, tetrahydrofuranyl, tetrahydropyranyl, tetrazolyl, thiadiazolyl, thiazolyl, and triazolyl.

In another embodiment, in each of Formula (I) and Formula (II):

$R^1$ is selected from the group consisting of phenyl, cyclobutyl, cyclohexyl, cyclopentyl, benzimidazolyl, imidazolyl, imidazopyridinyl, imidazopyridinyl, imidazopyrimidinyl, isoxazolyl, oxadiazolyl, oxadiazolyl, oxazolyl, oxetanyl, piperidinyl, pyrazolyl, pyridinyl, pyrimidinyl, tetrahydrofuranyl, tetrahydropyranyl, tetrazolyl, thiadiazolyl, thiazolyl, and triazolyl; and $R^{1A}$ is 2, or 3 groups independently selected from the group consisting of F, OH, —$(C_{1-4})$alkyl, —$(C_{1-4})$haloalkyl, —$(C_{1-4})$alkoxy, —$(C_{1-4})$haloalkoxy, cyclopropyl, cyclobutyl, —$NH_2$, —$C(O)NH_2$, and —$S(O)_2$—$(C_{1-4})$alkyl.

In another embodiment, in each of Formula (I) and Formula (II):

$R^1$ is selected from the group consisting of phenyl, isoxazolyl, oxadiazolyl, piperidinyl, pyrazolyl, pyridinyl, pyrimidinyl, tetrahydropyranyl, tetrohydrofuranyl, thiadiazolyl, and thiazolyl.

In another embodiment, in each of Formula (I) and Formula (II):

$R^1$ is selected from the group consisting of phenyl, isoxazolyl, oxadiazolyl, piperidinyl, pyrazolyl, pyridinyl, pyrimidinyl, tetrahydropyranyl, tetrohydrofuranyl, thiadiazolyl, and thiazolyl, and $R^{1A}$ is 2, or 3 groups independently selected from the group consisting of F, OH, —$(C_{1-4})$alkyl, —$(C_{1-4})$haloalkyl, —$(C_{1-4})$alkoxy, —$(C_{1-4})$haloalkoxy, cyclopropyl, cyclobutyl, —$NH_2$, —$C(O)NH_2$, and —$S(O)_2$—$(C_{1-4})$alkyl.

In another embodiment, in each of Formula (I) and Formula (II):

$R^1$ and from 1 to 3 $R^{1A}$ groups form a moiety selected from the group consisting of:

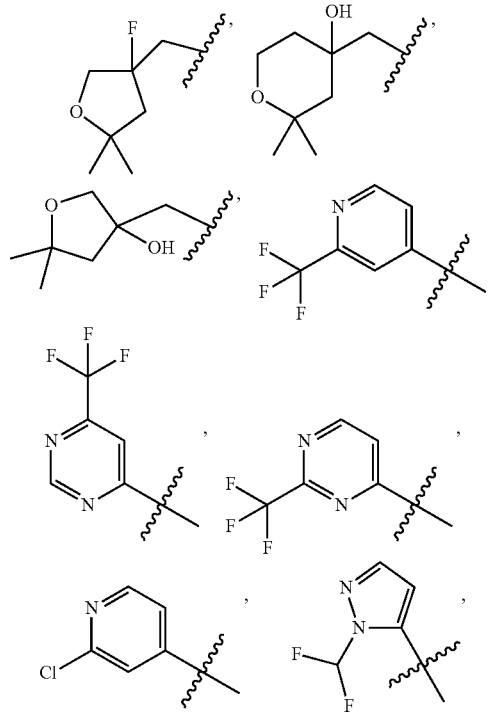

-continued
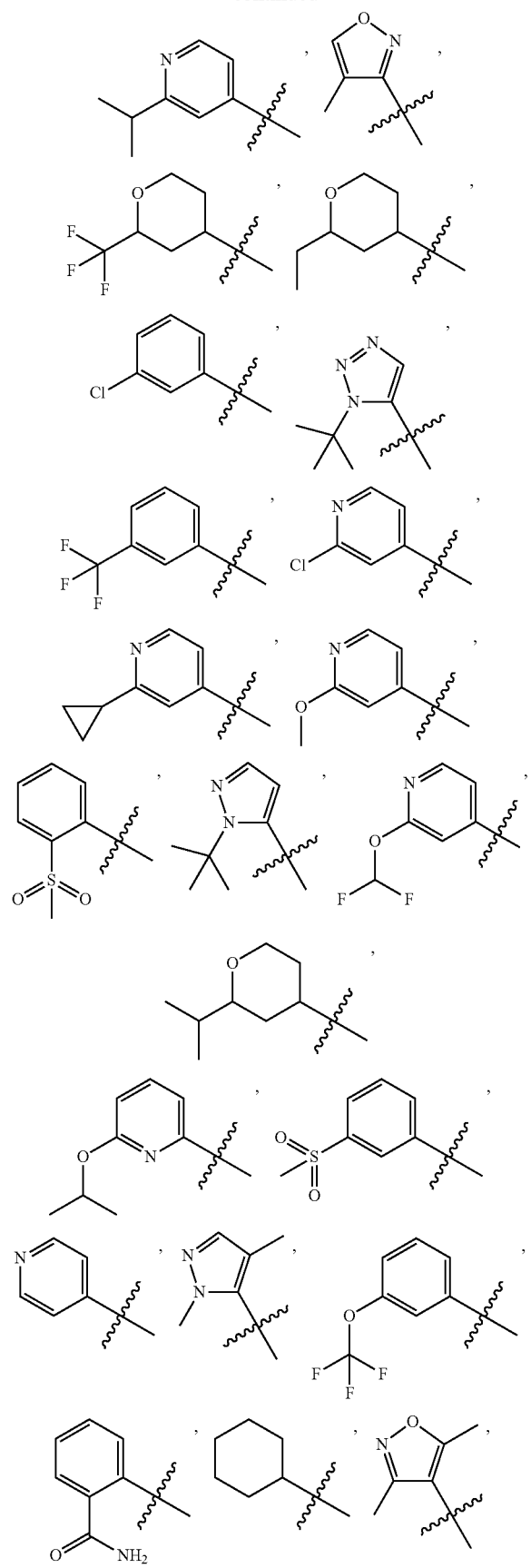
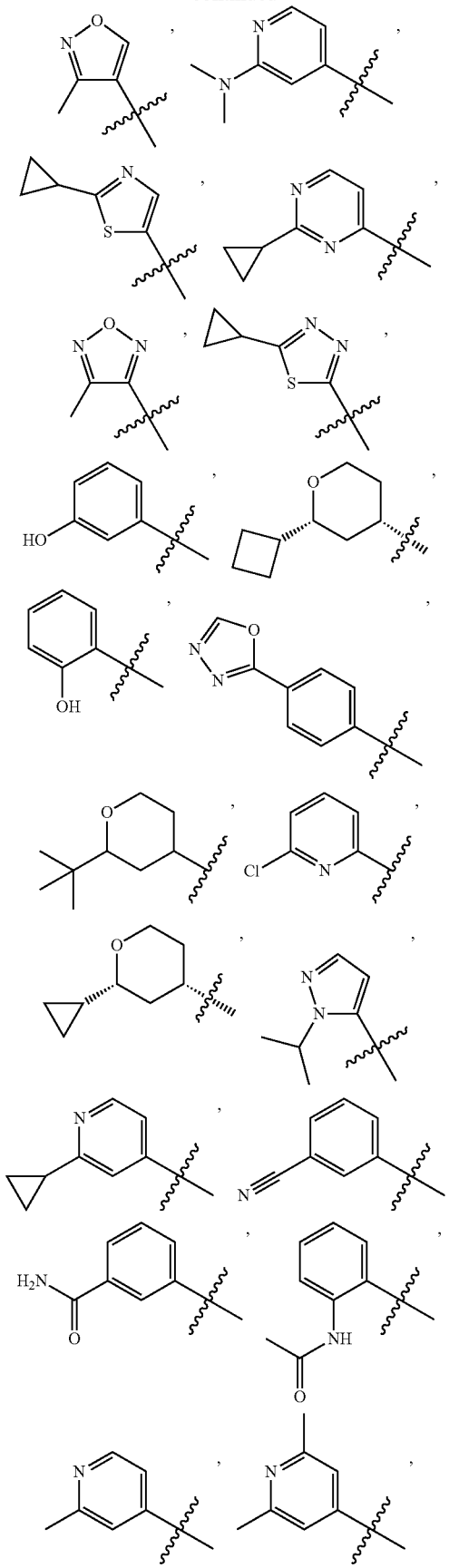

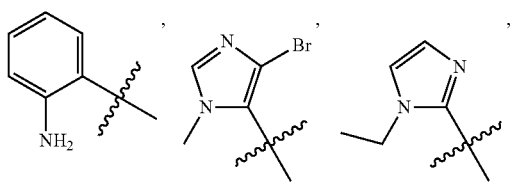
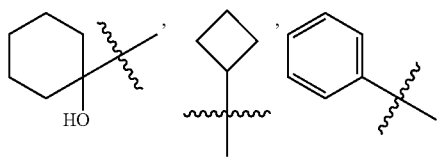
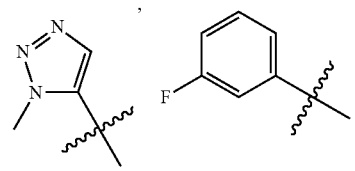
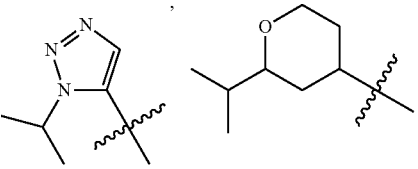
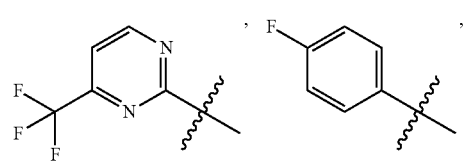
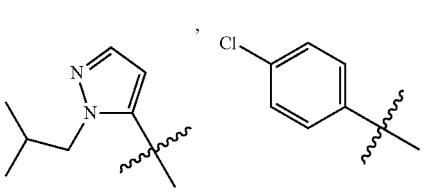
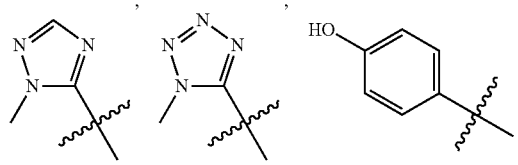
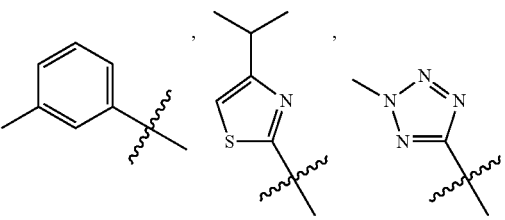
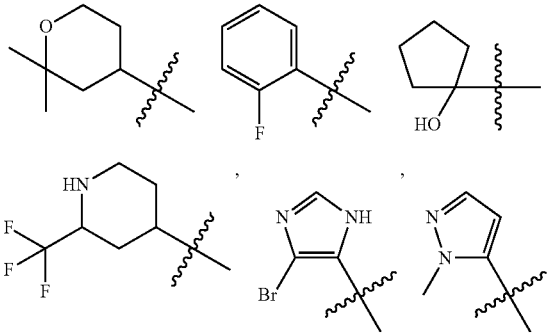
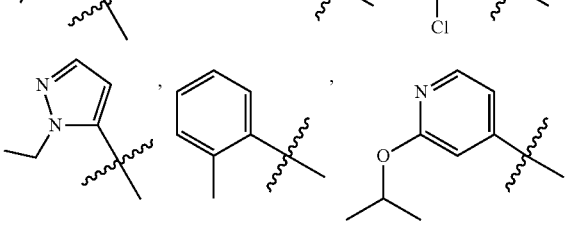
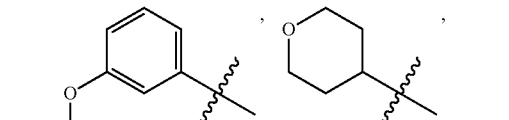
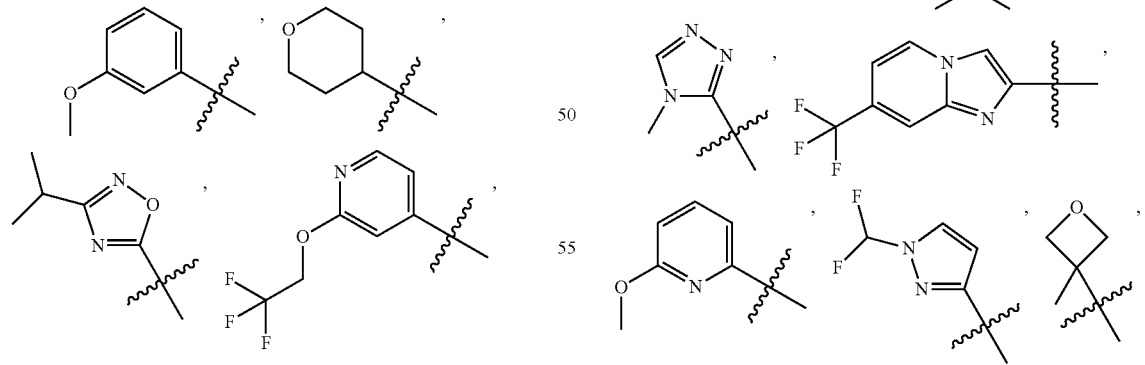
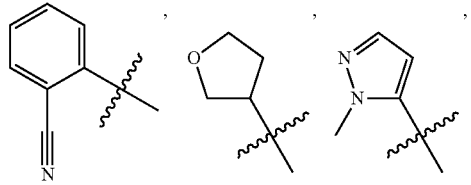
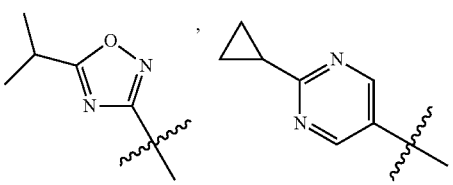

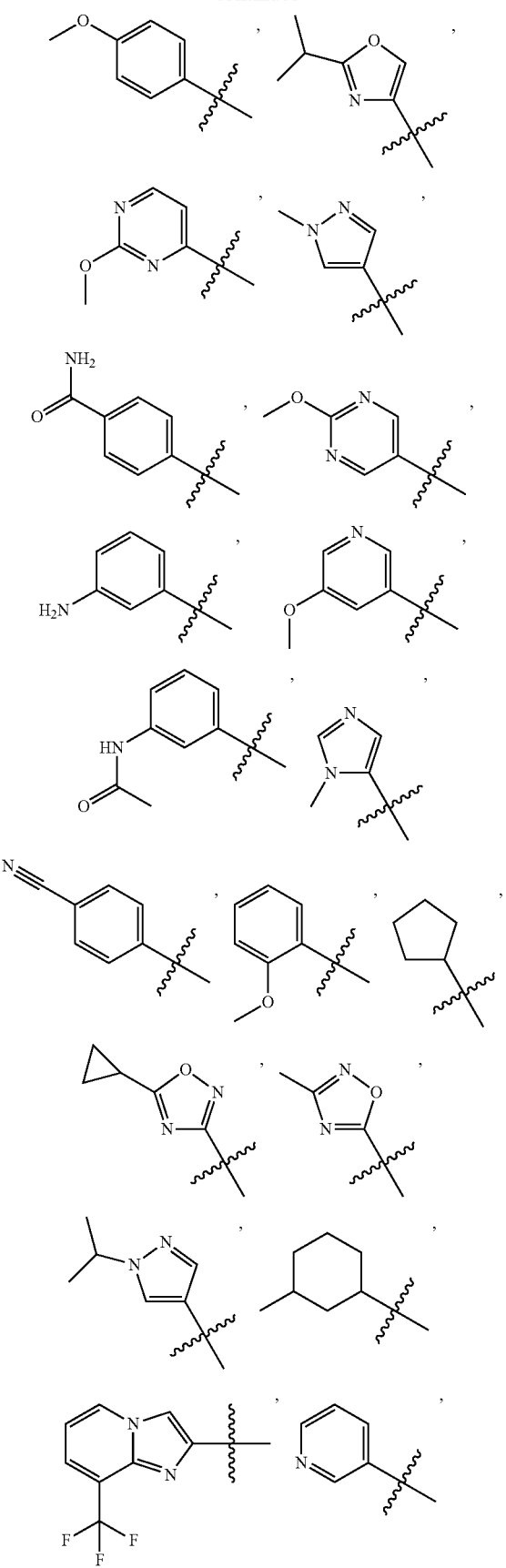

-continued
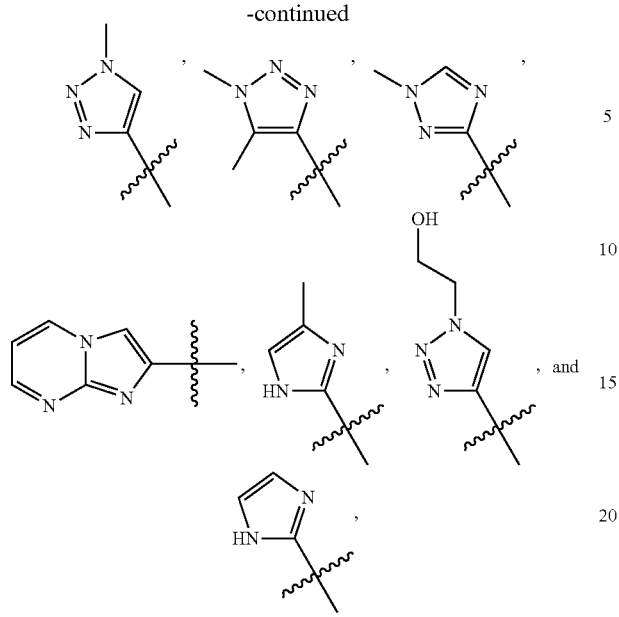
wherein the wavy line ("〰") represents the point of attachment to -L-.
In another embodiment, in each of Formula (I) and Formula (II):
$R^1$ and from 1 to 3 $R^{1.4}$ groups form a moiety selected from the group consisting of:
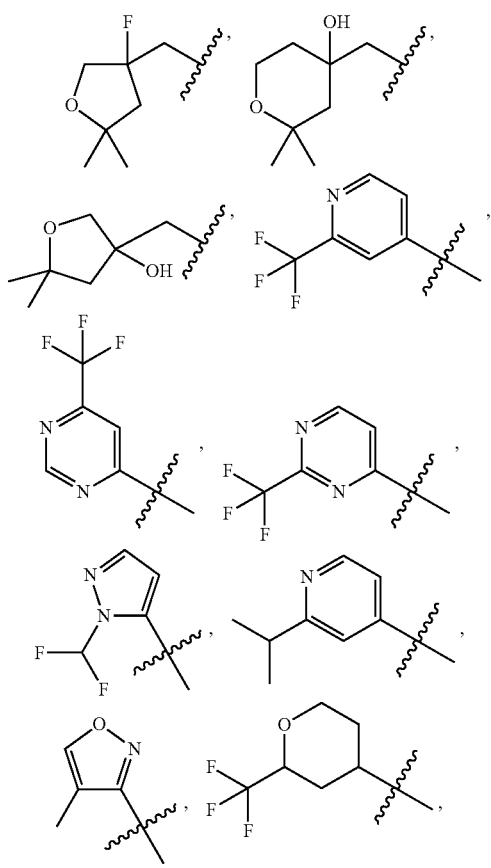
-continued
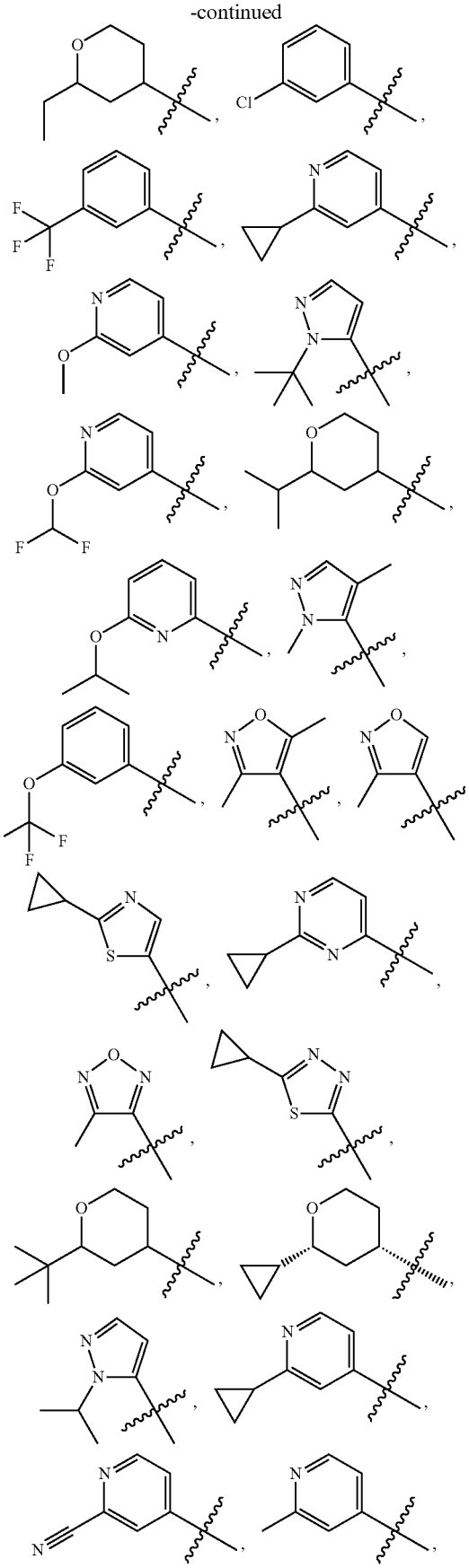

-continued
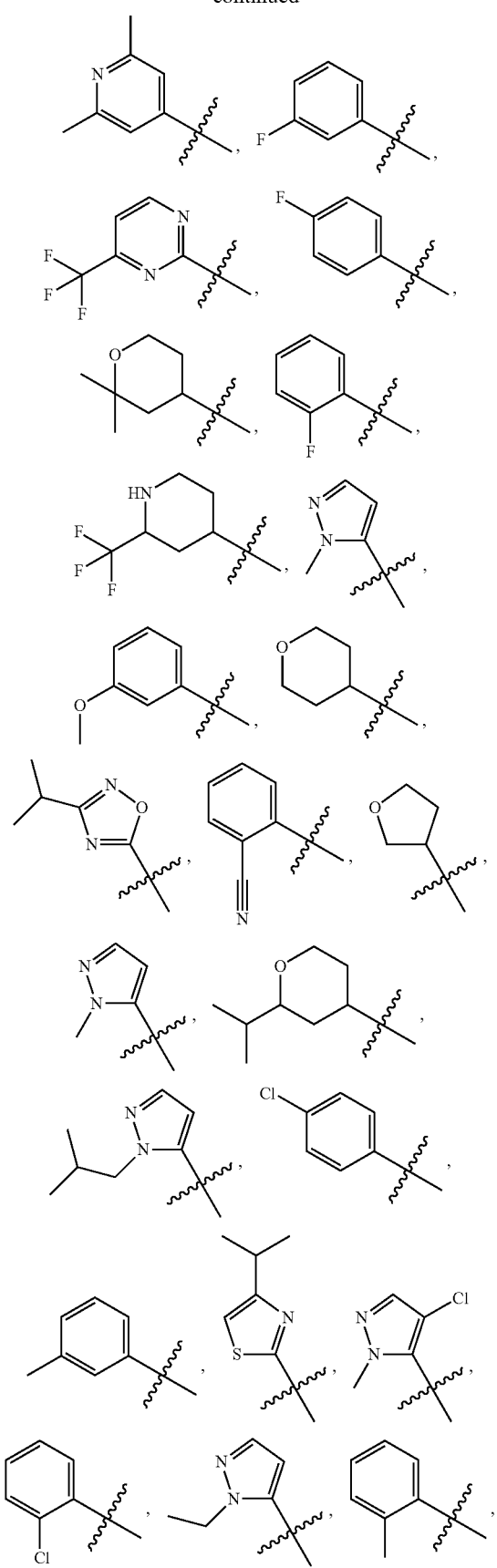
-continued
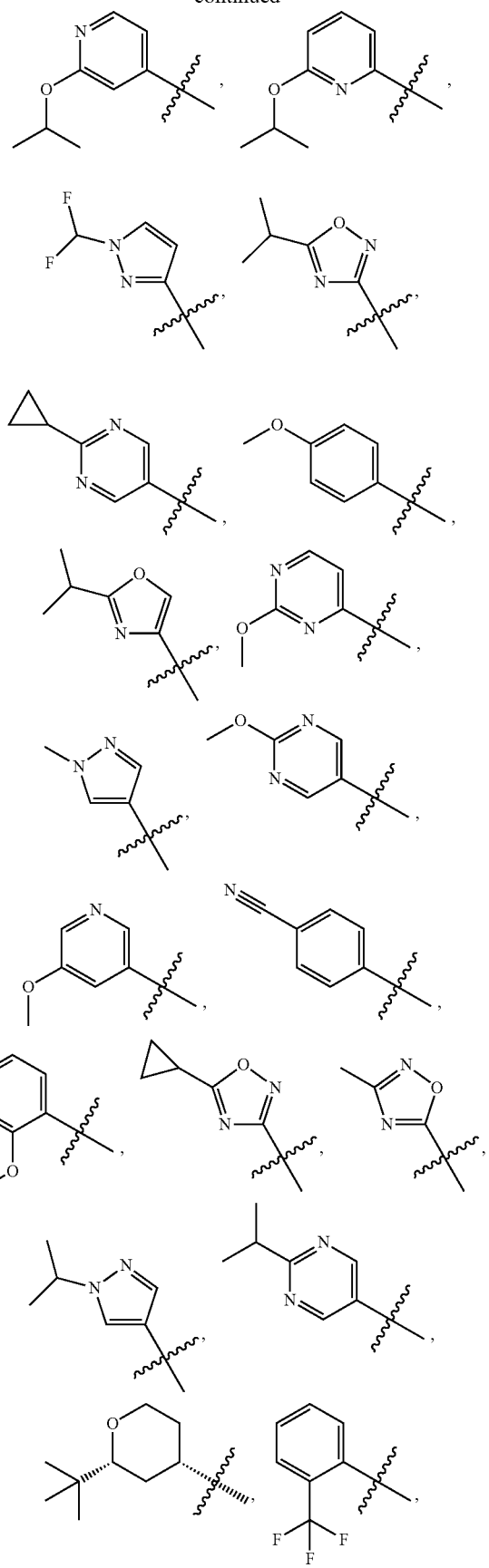

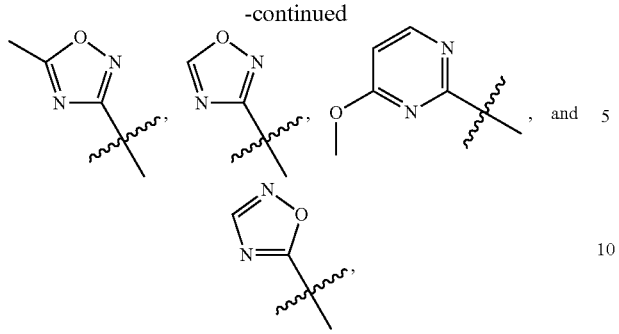

wherein the wavy line ("〰") represents the point of attachment to -L-.

In another embodiment, in each of Formula (I) and Formula (II):

$R^2$ is selected from the group consisting of phenyl, azetidinyl, cyclopropyl, cyclobutyl, cyclopentyl, cyclohexyl, imidazolyl, isothiazolyl, morpholinyl, oxazolyl, piperazinyl, piperidinyl, pyrazolyl, pyridazinyl, pyridinyl, pyrimidinyl, pyrrolidinyl, and thiazolyl.

In another embodiment, in each of Formula (I) and Formula (II):

$R^2$ is selected from the group consisting of phenyl, azetidinyl, cyclopropyl, cyclobutyl, cyclopentyl, cyclohexyl, imidazolyl, isothiazolyl, morpholinyl, oxazolyl, piperazinyl, piperidinyl, pyrazolyl, pyridazinyl, pyridinyl, pyrimidinyl, pyrrolidinyl, and thiazolyl; and $R^{2A}$ is 2, or 3 groups independently selected from the group consisting of H, halo, CN, —$(C_{1-4})$alkyl, —$(C_{1-4})$haloalkyl, —$(C_{1-4})$alkoxy, cyclopropyl, and spirocyclopropyl.

In another embodiment, in each of Formula (I) and Formula (II):

$R^2$ is selected from the group consisting of phenyl, cycloalkyl, (cyclohexyl), pyrazolyl, piperidinyl, pyridinyl, and thiazolyl.

In another embodiment, in each of Formula (I) and Formula (II):

$R^2$ is selected from the group consisting of phenyl, cycloalkyl, (cyclohexyl), pyrazolyl, piperidinyl, pyridinyl, and thiazolyl; and $R^{2A}$ is 1, 2, or 3 groups independently selected from the group consisting of H, halo, CN, —$(C_{1-4})$alkyl, —$(C_{1-4})$haloalkyl, —$(C_{1-4})$alkoxy, cyclopropyl, and spirocyclopropyl.

In another embodiment, in each of Formula (I) and Formula (II):

$R^2$ and from 1 to 3 $R^{2A}$ groups form a moiety selected from the group consisting of:

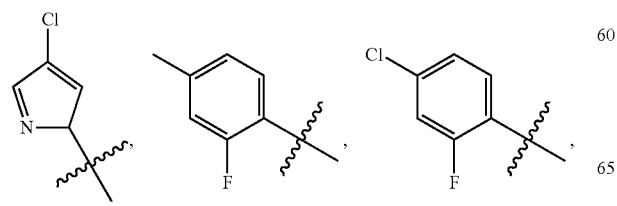

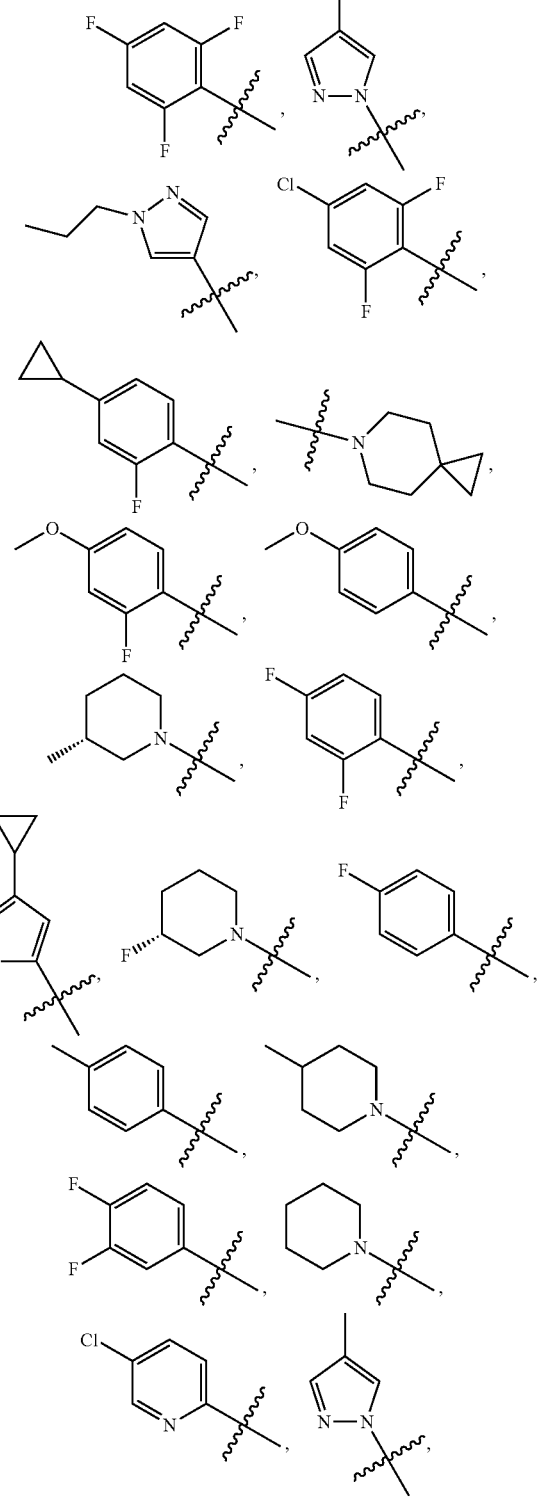

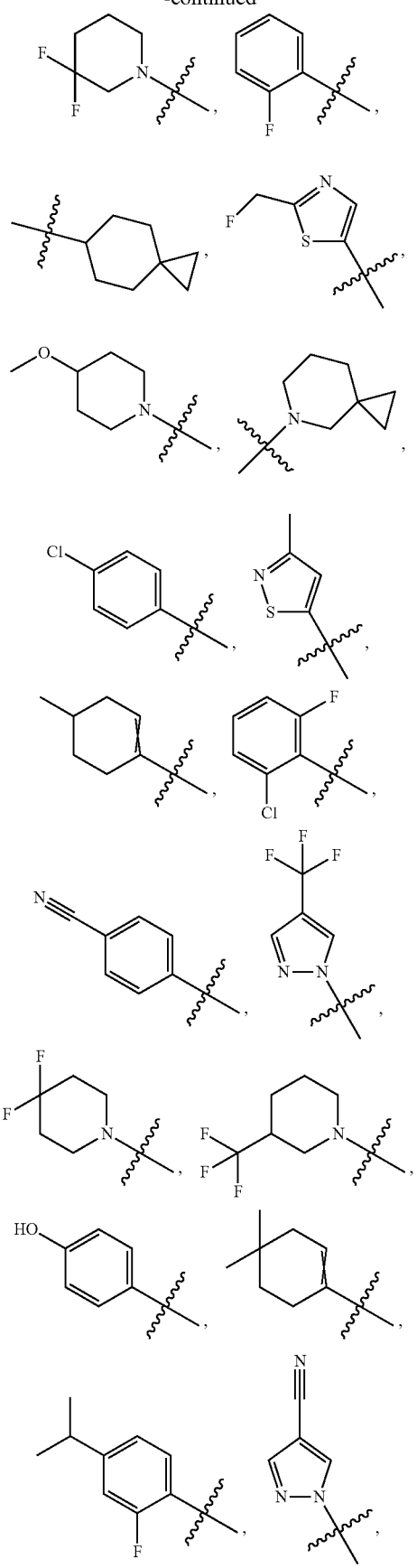
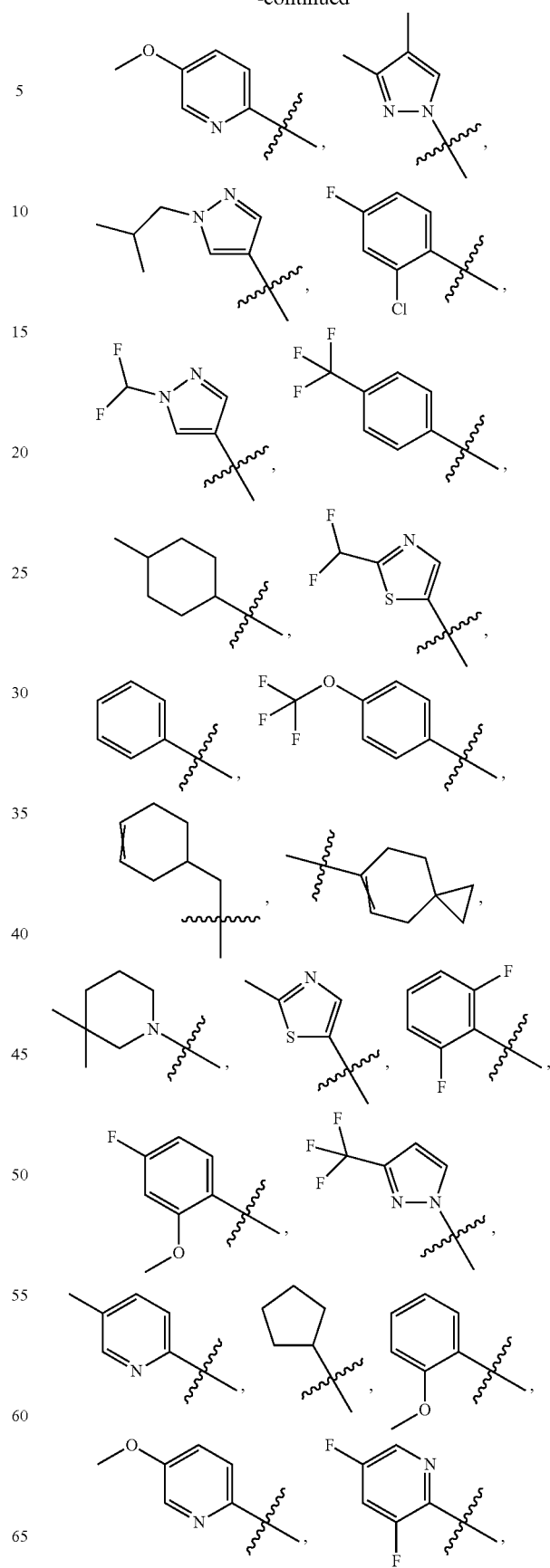

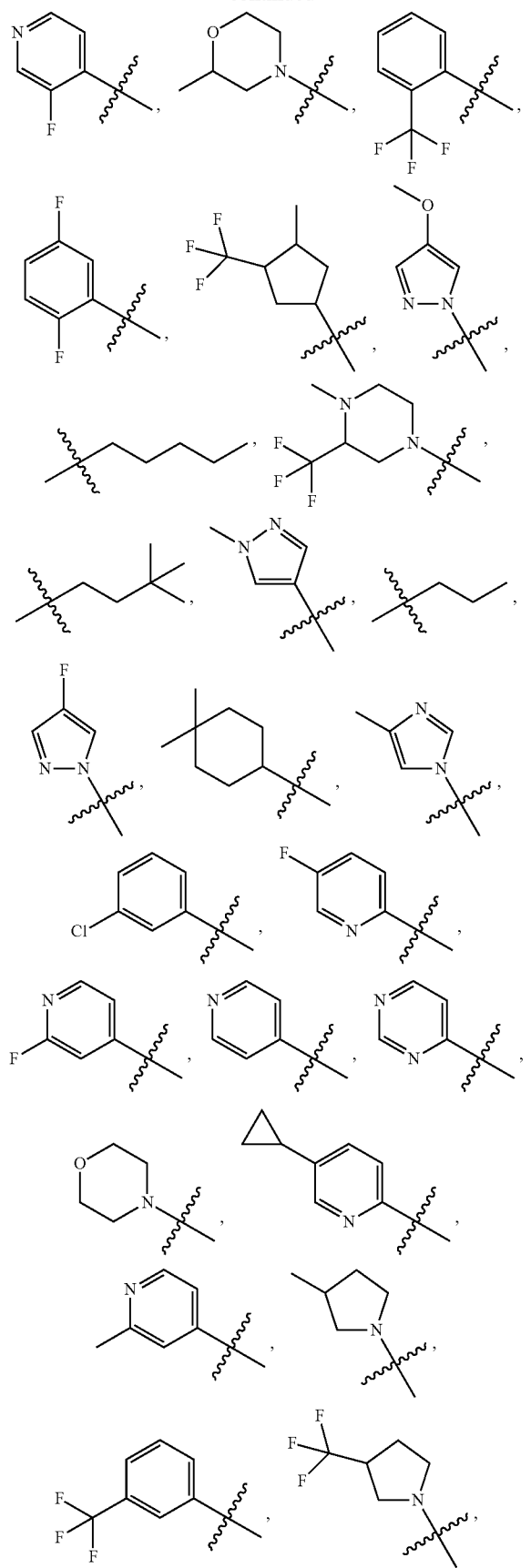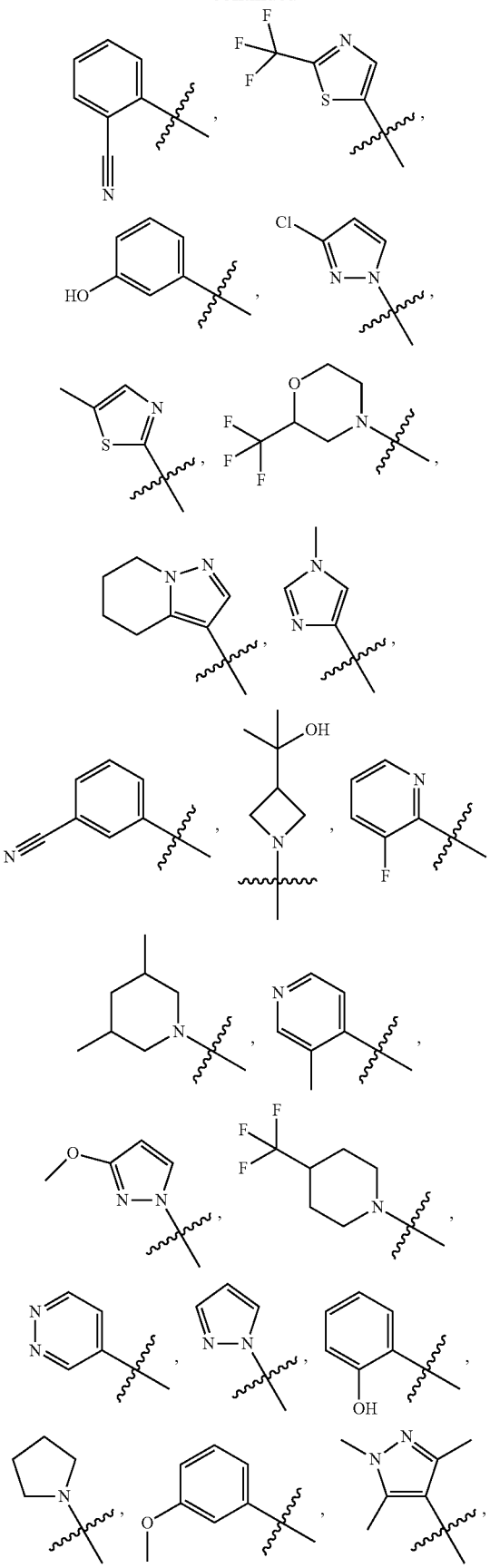

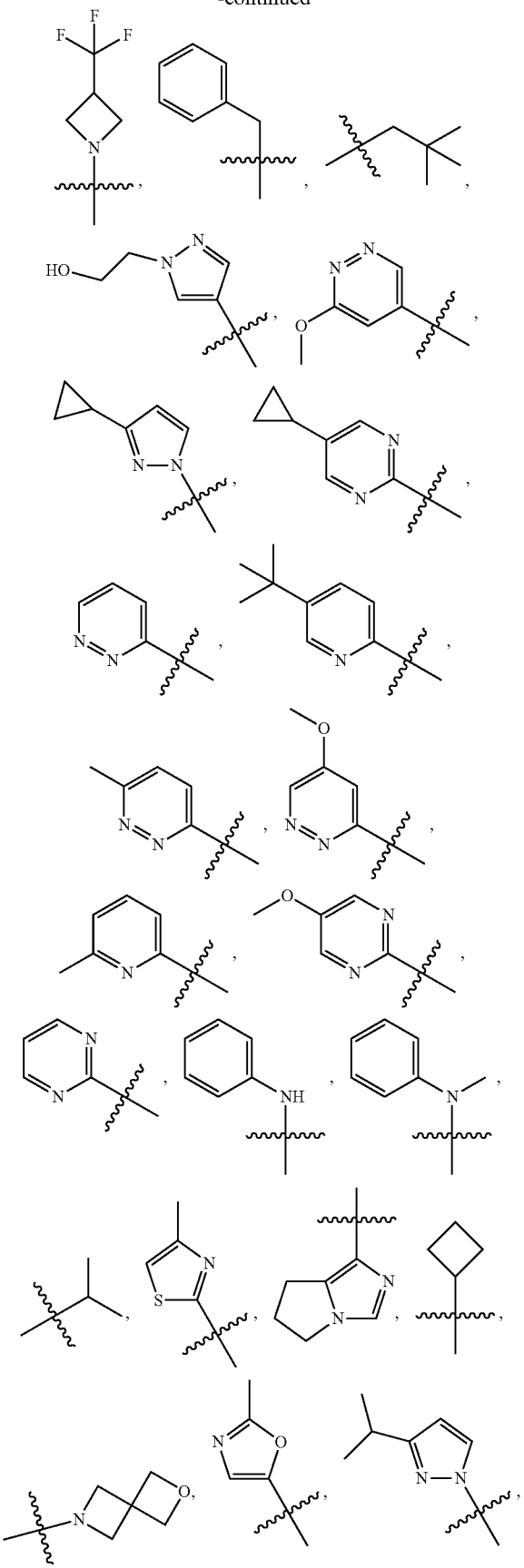
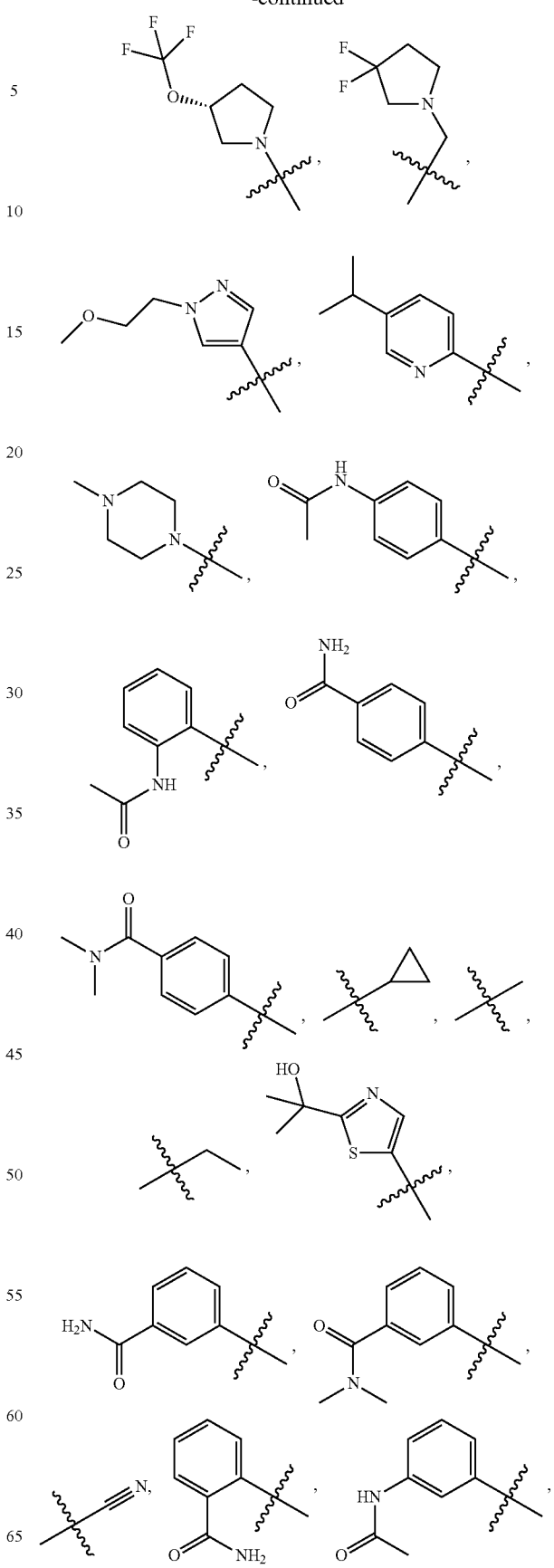

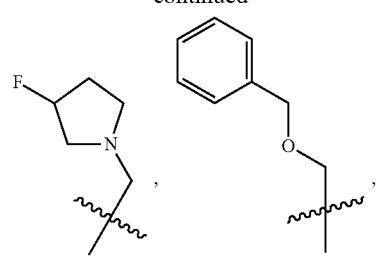
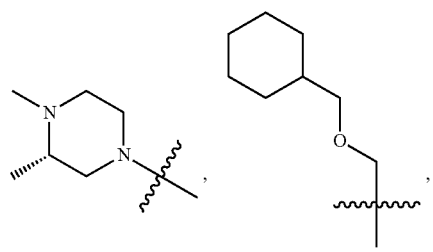
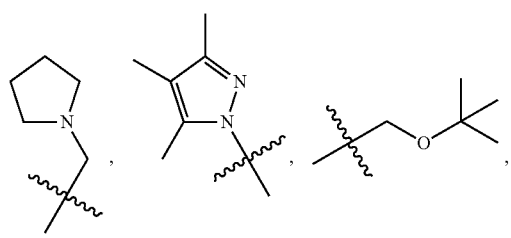
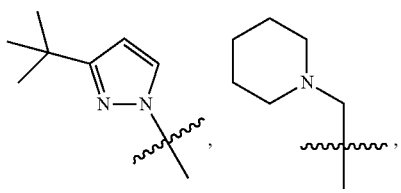
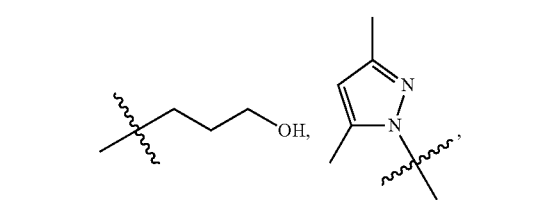
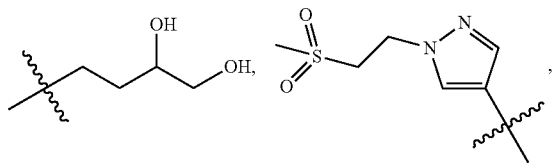
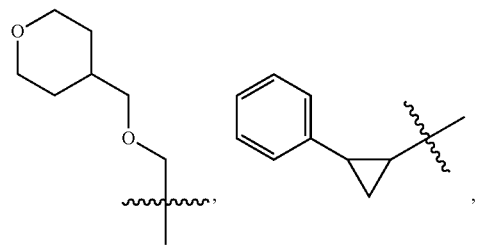
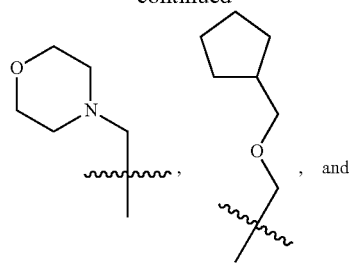
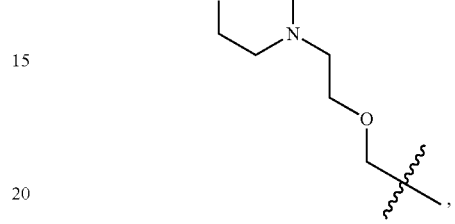
wherein the wavy line ("〰") represents the point of attachment to -L-.
In another embodiment, in each of Formula (I) and Formula (II):
$R^2$ and from 1 to 3 $R^{2A}$ groups form a moiety selected from the group consisting of:
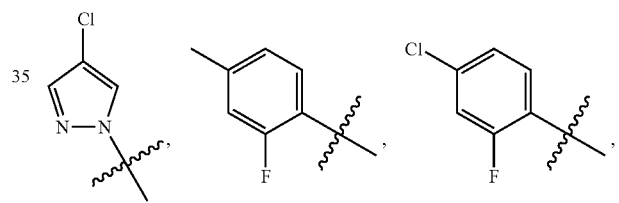
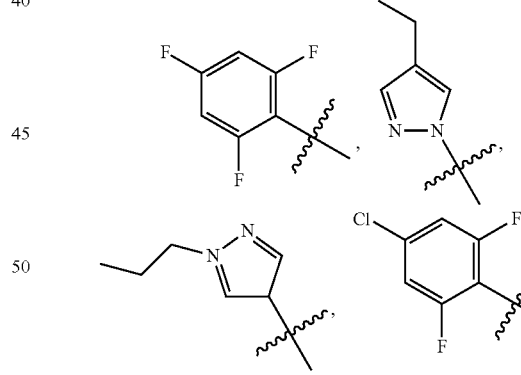
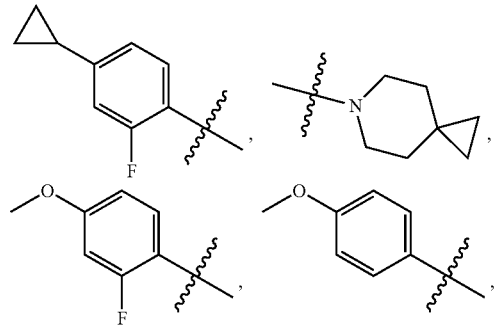

-continued

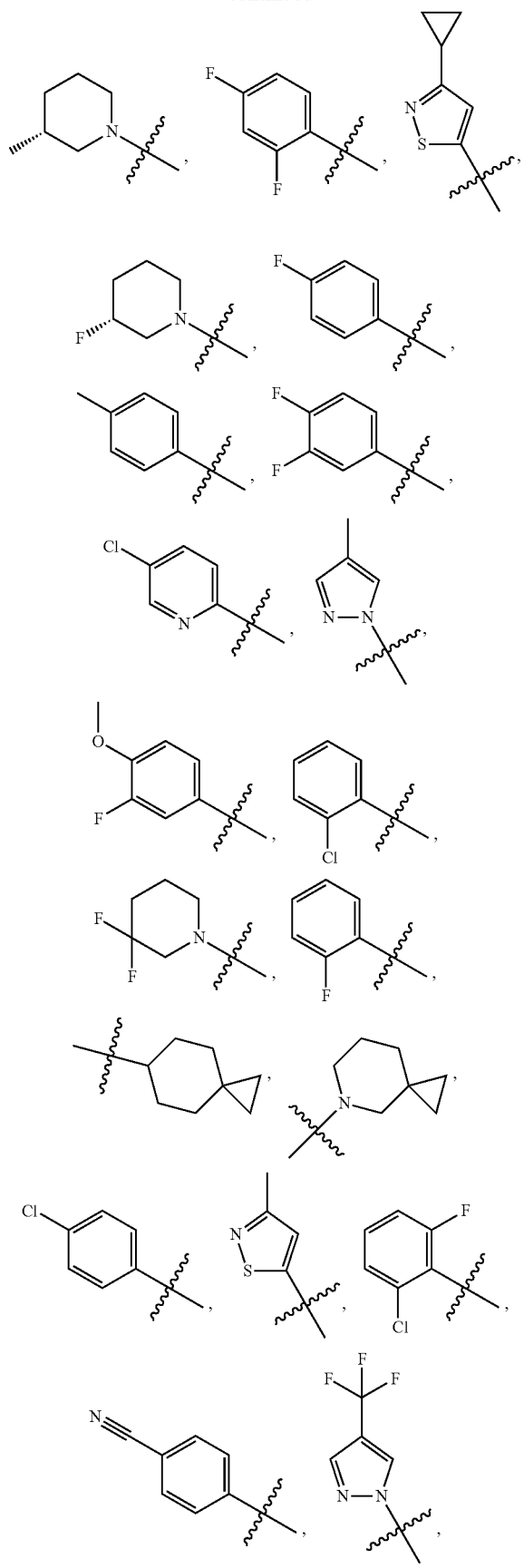

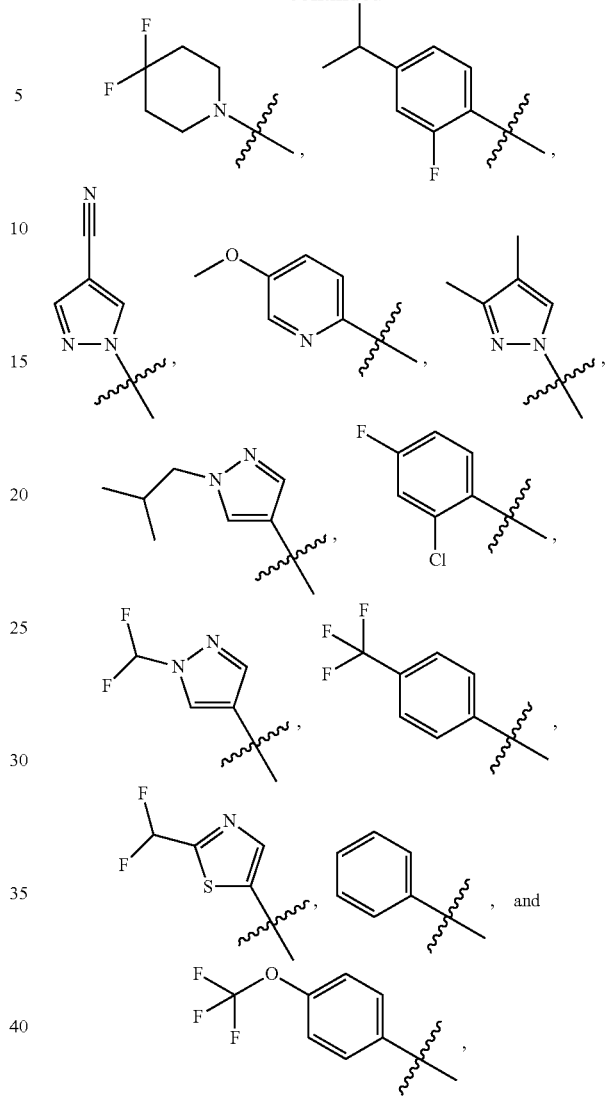

wherein the wavy line ("⁓") represents the point of attachment to -L-.

In another embodiment, in each of Formula (I) and Formula (II):

$R^{X1}$ is selected from the group consisting of H, and —($C_{1-4}$)alkyl;

$R^1$ is selected from the group consisting of phenyl, cyclobutyl, cyclohexyl, cyclopentyl, benzimidazolyl, imidazolyl, imidazopyridinyl, imidazopyridinyl, imidazopyrimidinyl, isoxazolyl, oxadiazolyl, oxadiazolyl, oxazolyl, oxetanyl, piperidinyl, pyrazolyl, pyridinyl, pyrimidinyl, tetrahydrofuranyl, tetrahydropyranyl, tetrazolyl, thiadiazolyl, thiazolyl, and triazolyl;

$R^{1A}$ is 1, 2, or 3 groups independently selected from the group consisting of F, OH, —($C_{1-4}$)alkyl, —($C_{1-4}$)haloalkyl, —($C_{1-4}$)alkoxy, —($C_{1-4}$)haloalkoxy, cyclopropyl, cyclobutyl, —$NH_2$, —C(O)$NH_2$, and —S(O)$_2$—($C_{1-4}$)alkyl;

$R^2$ is selected from the group consisting of —($C_{1-6}$)alkyl, phenyl, azetidinyl, cyclopropyl, cyclobutyl, cyclopentyl, cyclohexyl, imidazolyl, isothiazolyl, morpholinyl, oxazolyl, piperazinyl, piperidinyl, pyrazolyl, pyridazinyl, pyridinyl, pyrimidinyl, pyrrolidinyl, and thiazolyl; and $R^{2A}$ is 2, or 3 groups independently selected from the group consisting of H, halo, CN, —$(C_{1-4})$alkyl, —$(C_{1-4})$haloalkyl, —$(C_{1-4})$alkoxy, cyclopropyl, and spirocyclopropyl.

In another embodiment, in each of Formula (I) and Formula (II):

$R^{X1}$ is selected from the group consisting of H, and —$(C_{1-4})$alkyl;

$R^1$ is selected from the group consisting of phenyl, isoxazolyl, oxadiazolyl, piperidinyl, pyrazolyl, pyridinyl, pyrimidinyl, tetrahydropyranyl, tetrohydrofuranyl, thiadiazolyl, and thiazolyl, and $R^{1A}$ is 1, 2, or 3 groups independently selected from the group consisting of F, OH, —$(C_{1-4})$alkyl, —$(C_{1-4})$haloalkyl, —$(C_{1-4})$alkoxy, —$(C_{1-4})$haloalkoxy, cyclopropyl, cyclobutyl, —$NH_2$, —$C(O)NH_2$, and —$S(O)_2$—$(C_{1-4})$alkyl;

$R^2$ is selected from the group consisting of phenyl, cycloalkyl, (cyclohexyl), pyrazolyl, piperidinyl, pyridinyl, and thiazolyl; and $R^{2A}$ is 2, or 3 groups independently selected from the group consisting of H, halo, CN, —$(C_{1-4})$alkyl, —$(C_{1-4})$haloalkyl, —$(C_{1-4})$alkoxy, cyclopropyl, and spirocyclopropyl.

In an alternative to each of the preceeding embodiments, in Formula (I) or in Formula (II), -L- is —$(C(R^{L1})_2)_p$—, wherein p is 1 to 3, and each $R^{L1}$ is independently selected from the group consisting of H, OH, —$CH_3$, —$CH_2CH_3$, —$CH_2CF_3$, —$CHF_2$, —$CF_3$, and —$CH_2OH$. In one such alternative embodiment, p is 1. In another such alternative embodiment, p is 2. In another such alternative embodiment, p is 1 and each $R^{L1}$ is selected from the group consisting of H.

In another alternative to each of the preceeding embodiments, in Formula (I) or in Formula (II), -L- is —C(O)—.

In another alternative to each of the preceeding embodiments, in Formula (I) or in Formula (II), -L- is —C(O)$CH_2$—.

In another alternative to each of the preceeding embodiments, in Formula (I) or in Formula (II), -L- is —$CH_2C(O)$—.

In one embodiment, the compounds of the invention comprise, collectively and individually, each of the example compounds shown in the tables below, and pharmaceutically acceptable salts thereof. Suitable pharmaceutically acceptable salts of each of these compounds include those discussed hereinbelow.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. In the event where the chemical name and structure for a compound of the invention disagree, the structure controls. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy," etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

"Patient" includes both human and non-human animals. Non-human animals include research animals and companion animals such as mice, rats, primates, monkeys, great apes, chimpanzees, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The term "pharmaceutically acceptable" means the carrier, diluent or excipient must be compatible with the other ingredients of the formulation and not deleterious to the recipient thereof.

The terms "administration of" or "administering a" compound means providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" mean an amount of compound or a composition of the invention effective for inhibiting the herein-noted diseases and thus producing the desired therapeutic, ameliorative, inhibitory or preventative effect.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

"Halogen" (or "halo") means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, i-propyl, n-butyl,i-butyl, t-butyl, pentyl, hexyl, heptyl, octanyl, etc., each of which may be straight or branched.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, hetercycloalkyl, etc. indicates a divalent moiety, e.g., —CH$_2$CH$_2$— is ethylene, and

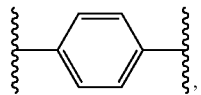

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl, cyclooctyl, and the like. Non-limiting examples of suitable multicyclic cycloalkyls include 1-decalinyl, norbornyl, adamantyl and the like. Further non-limiting examples of cycloalkyl include the following:

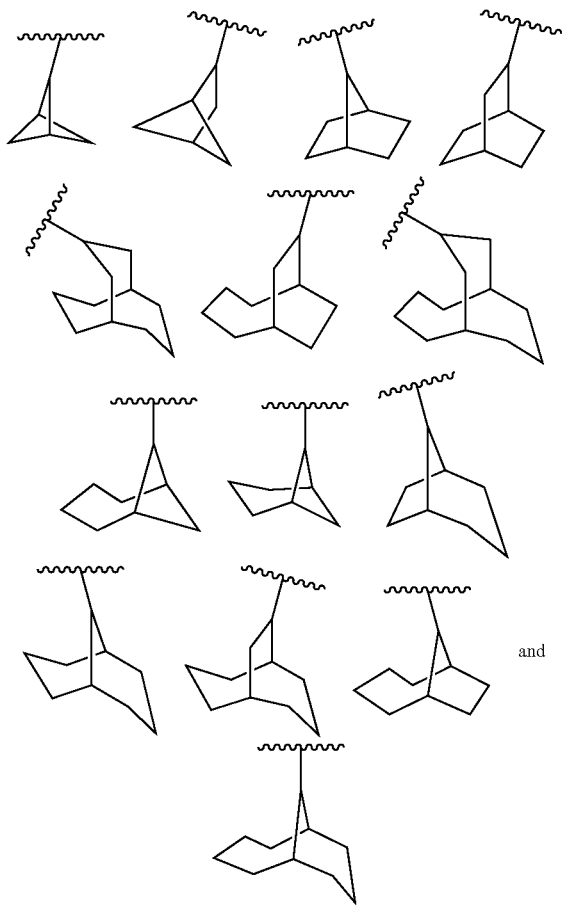

and

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

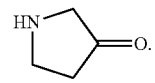

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

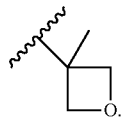

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

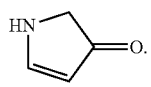

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

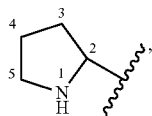

there is no —OH attached directly to carbons marked 2 and 5.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Alkoxy" means an alkyl-O-group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Spriocycloalkyl" means a cycloalkyl group attached to a parent moiety at a single carbon atom. Non-limiting examples of spirocycloalkyl wherein the parent moiety is a cycloalkyl include spiro [2.5] octane, spiro [2.4] heptane, etc. Non-limiting examples of spriocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When a variable appears more than once in a group, e.g., $R^6$ in —N($R^6$)$_2$, or a variable appears more than once in a structure presented herein, the variables can be the same or different.

The line ----, as a bond generally indicates a mixture of, or either of, the possible isomers, e.g., containing (R)- and (S)-stereochemistry. For example:

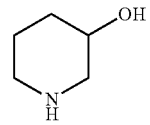

means containing both

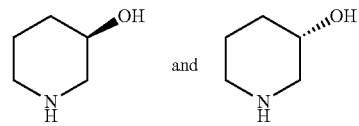

The wavy line ∿∿, as used herein, indicates a point of attachment to the rest of the compound. Lines drawn into the ring systems, such as, for example:

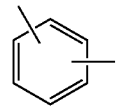

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

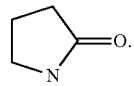

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

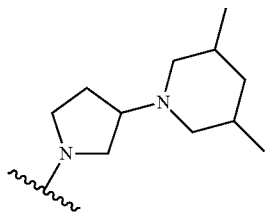 [SMILES: *N1CCC(N2CC(C)CC(C)C2)C1]

represents

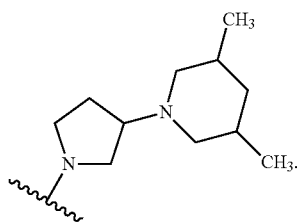 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt thereof, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$ alkyl, $(C_3-C_6)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Another embodiment provides pharmaceutically acceptable salts of the compounds of the invention. Thus, reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Another embodiment provides tautomers of the compounds of the invention, and salts, solvates, esters and prodrugs thereof. Also, for example, all keto-enol and imine-enamine forms of the compounds are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Additional examples of isotopes that can be incorporated into compounds of the invention include (when present) isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In an additional embodiment, the compounds of the invention are isotopically labeled for use as research or diagnostic agents. For example, compounds of the invention can be labeled for use in compound and/or substrate tissue distribution assays. Tritiated (i.e., $^3$H) and carbon-14 (i.e., $^{14}$C) isotopes are preferred for their ease of preparation and detectability. In another embodiment, the compounds of the invention can be labeled with heavier isotopes such as deuterium (i.e., $^2$H). Deuterium enrichment of the compounds of the invention may afford certain therapeutic advantages resulting from greater metabolic stability (e.g., increased in vivo half-life or reduced dosage requirements), or may provide a compound useful as a standard for characterization of biological samples, and hence may be preferred in some circumstances. Isotopically labelled compounds of the invention can generally be prepared without undue experimentation by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

Compositions and Administration

Another embodiment provides pharmaceutical compositions which comprise a therapeutically effective amount of a compound of the invention, or a steroisomer thereof, or a pharmaceutically acceptable salt of said compound or said stereoisomer, and a pharmaceutically acceptable carrier.

A preferred dosage is about 0.001 to 100 mg/kg of body weight/day of the compound of the invention. An especially preferred dosage is about 0.01 to 10 mg/kg of body weight/day of a compound of the invention, or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously. Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of the invention, or a stereoisomer thereof, or a pharmaceutically acceptable salt of said compound or said stereoisomer; (ii) one or more additional therapeutic agents, that are not compounds of the invention; and (iii) a pharmaceutically acceptable carrier, wherein the amounts in the composition are together effective to treat one of the disease or conditions discussed herein.

Uses of the Compounds of the Invention

Another embodiment provides a method of treating a patient (e.g., a human patient or a research animal) for diseases or disorders in which the mGluR2 receptor is involved. These methods comprise administering an effective amount of a compound of the invention, or composition comprising a compound of the invention (or a stereoisomer thereof, or a pharmaceutically acceptable salt of said compound or said stereoismer), to a patient in need thereof, to treat a disease or disorder in which the mGluR2 receptor is involved. Another embodiment provides for the use of a compound of the invention for treating a disease or disorder in which the mGluR2 receptor is involved, by administering an effective amount of a compound of the invention, or a pharmaceutically acceptable salt thereof, to a patient in need thereof.

Diseases or disorders in which the mGluR2 receptor may be involved include, but are not limited to, Alzheimer's Disease, cognitive impairment, schizophrenia, mood disorders, including depression and anxiety, gastrointestinal disorders, pain disorders and sleep disorders. Additional examples of pain disorders include acute pain, inflammatory pain and neuropathic pain. Neuropathic pain includes, but is not limited to, postherpetic neuralgia, nerve injury, the "dynias", e.g., vulvodynia, phantom limb pain, root avulsions, painful diabetic neuropathy, painful traumatic mononeuropathy, painful polyneuropathy. Additional examples of pain disorders include central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Additional examples of cognitive disorders include mild cognitive impairment. Other conditions that may be treated by the compounds and compositions of the invention include Parkinson's Disease, pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another embodiment, the present invention provides a method for treating schizophrenia or psychosis comprising administering to a patient in need thereof an effective amount of a compound (or composition providing a compound) of the invention, or a stereoisomer thereof.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom mGluR2 receptor inhibition is desired, but may also encompass other mammals such as those listed above, including dogs, cats, mice, rats, cattle, horses, sheep, rabbits, monkeys, chimpanzees or other apes or primates, for which treatment the above noted disorders, or the study of mGluR2, is desired.

Another embodiment provides a medicament or pharmaceutical composition for the inhibition of mGluR2 receptor, and/or for the treatment of any of the diseases or disorders listed above to a patient (preferably a human) in need of such treatment, which comprise a compound (or composition comprising a compound) of the invention, or a stereoisomer thereof, or a pharmaceutically acceptable salt of said compound or said stereoisomer, and a pharmaceutically acceptable carrier.

Another embodiment provides a method for the manufacture of a medicament or a pharmaceutical composition for the inhibition of an mGluR2-NAM receptor, and/or for treating one or more diseases or conditions listed above, comprising combining a compound (or composition comprising a compound) of the invention, or a stereoisomer thereof, or a pharmaceutically acceptable salt of said compound or said stereoisomer, with a pharmaceutically acceptable carrier.

Combination Therapy

The compounds and compositions of the invention may be used in combination with one or more other drugs in the treatment of diseases or conditions for which the compounds of the invention have utility, where the combination of the drugs is desired, e.g., where the combination is safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen. In one embodiment, the compounds of the invention useful in said combinations comprise a compound according to any one of Formulas (I), (I.1), (I.2), (II), (II.1), (II.2), (III), (III.1), (III.2), (IV), (IV.1), (IV.2), (V), (V.1), and/or (V.2) as described herein, or according to any of the various embodiments described herein. In another embodiment, the compounds of the invention useful in said combinations comprise the compounds of the examples, e.g., as set forth as example compounds of the invention in the Tables herein.

In another embodiment, a compound or composition of the invention may be employed in combination with acetylcholinesterase inhibitors such as donepezil and rivastigmine, NMDA antagonist such as memantine, muscarinic receptor modulators, AMPA receptor modulators, mGluR3 receptor modulators, nicotinic alpha-7 and alpha4-beta 2 receptor modulators, 5-HT6 and 5-HT4 receptor modulators, modulators of phosphodiesterases (PDEs), alpha 2c receptor anagonists, histone deacetylases, and antioxidant therapies.

In another embodiment, a compound or composition of the invention may be employed in combination with therapies that may alter or modify the course of disease progression, including beta-amyloid modulating therapies such as BACE1 inhibitors, gamma-secretase modulators, tau and/or phosphor-tau modulators, and biologic therapies which modulate placques associated with neurological disorders including antibodies, RNAi, miRNA, and cell-therapies.

In another embodiment, a compound or composition of the invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide or pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

Additional examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIP); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

In another embodiment, the compounds and compositions of the invention may be administered in combination with compounds useful for the treatment of schizophrenia or enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, or the compound of the present invention may be administered in conjunction with the use of physical methods such as with light therapy or electrical stimulation.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of the invention is administered during a time when the additional therapeutic agent(s) exert their prophylactic or therapeutic effect, or vice versa.

In another embodiment, the compound of the invention and the additional therapeutic agent(s) are administered in doses commonly employed when such agents are used as monotherapy for treating the disorder.

In another embodiment, the compound of the invention and the additional therapeutic agent(s) are administered in doses lower than the doses commonly employed when such agents are used as monotherapy for treating the disorder.

In one embodiment, the compound of the invention and the additional therapeutic agent(s) are present in the same composition, which is suitable for oral administration.

In some embodiments, the compound of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another embodiment provides a kit comprising a therapeutically effective amount of the compound (or a composition comprising a compound) of the invention, or a stereoisomer thereof, or a pharmaceutically acceptable salt of said compound or said stereoisomer, optionally together with at least one additional therapeutic agent listed above, and a pharmaceutically acceptable carrier, vehicle or diluent.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of the invention is administered during a time when the additional therapeutic agent(s) exert their prophylactic or therapeutic effect, or vice versa.

In another embodiment, the compound of the invention and the additional therapeutic agent(s) are administered in doses commonly employed when such agents are used as monotherapy for treating the disorder.

In another embodiment, the compound of the invention and the additional therapeutic agent(s) are administered in doses lower than the doses commonly employed when such agents are used as monotherapy for treating the disorder.

In one embodiment, the compound of the invention and the additional therapeutic agent(s) are present in the same composition, which is suitable for oral administration.

PREPARATIVE EXAMPLES

In general, the compounds in the invention may be produced by a variety of processes known to those skilled in the art and by know, processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented, $^1$H spectra were obtained on either a Varian 400, AVANCE III 400 or Varian AS500, and chemical shifts are reported as ppm with number of protons and multiplicities indicated parenthetically. Where LC/MS data are presented, analyses was performed using a Waters Acquity UPLC (BEH C18 column, 1.0×50 mm, 1.7 um, UV 254 nm, 2 min 10-99% MeCN/water+0.05% TFA gradient, ESI positive) or an Agilent 1200 or Shimadzu 20AB series (with a Xtimate C18 column, 2.1×30 mm, Sum, UV 220 or 254 nm, 1.5 mL/4 L TFA in water (solvent A) and 0.75 mL/4 L TFA in acetonitrile (solvent B), using the elution gradient 10%-80% (solvent B) over 0.9 minutes and holding at 80% for 0.6 minutes at a flow rate of 1.2 mL/min, ESI positive).

Preparative chiral HPLC separations were generally carried out using supercritical fluid chromatography by eluting a chiral column such as OJ-H, (4.6×250 mm, Chiral Technologies, Inc., West Chester, Pa.) with a mobile phase of supercritical CO, and isopropanol, ethanol or methanol.

The starting materials and reagents used in preparing compounds described below are either available from commercial suppliers such as Aldrich Chemical Co. (Wisconsin, USA) and Acros Organics Co. (New Jersey, USA) or were prepared by literature methods known to those skilled in the art.

Intermediate C-1

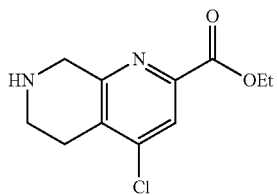

Ethyl 4-chloro-5,6,7,8-tetrahydro-1,7-naphthyridine-2-carboxylate

Step 1: Ethyl 5-chloroisoquinoline-7-carboxylate

3-Aminoisonicotinic acid (10 g, 72.4 mmol) and ethyl pyruvate (40 ml, 360 mmol) were combined neat and stirred at room temperature for 15 min. POCl₃ (200 ml, 2146 mmol) was added and the mixture was heated to 100° C. After 1 h the mixture was cooled to room temperature and concentrated in vacuo. The resulting dark oil was taken up in ice cold water. This solution was added to saturated aqueous NaHCO₃ slowly until reaching a final pH ~8. The resulting slurry was extracted with EtOAc (3×). The combined organic extracts were filtered through a pad of silica gel and concentrated. The crude product was subjected to silica gel chromatography (Silicycle-330 g, 40% EtOAc/hexanes) to give a solid.

Step 2: Ethyl 4-chloro-5,6,7,8-tetrahydro-1,7-naphthyridine-2-carboxylate

To a solution of ethyl 5-chloroisoquinoline-7-carboxylate (500 mg, 2.113 mmol) in AcOH (10 mL) was added sodium cyanoborohydride (398 mg, 6.34 mmol) in one portion at room temperature. After 2 h the mixture was concentrated in vacuo. The resdiue was taken up in saturated aqueous NaHCO₃ and extracted with DCM (3×). The combined organic layers were filtered through a pad of Celite washing with DCM then concentrated in vacuo to an oil which solidified under vacuum and was used without further purification.

Intermediate C-2

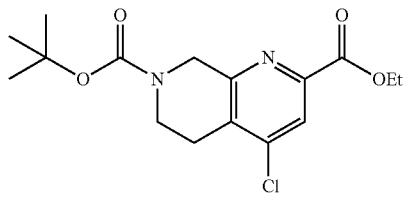 [SMILES: CCOC(=O)c1cc(Cl)c2c(n1)CN(C(=O)OC(C)(C)C)CC2]

7-tert-butyl 2-ethyl 4-chloro-5,6-dihydro-1,7-naphthyridine-2,7(8H)-dicarboxylate In the reaction vessel ethyl 4-chloro-5,6,7,8-tetrahydro-1,7-naphthyridine-2-carboxylate (5 g, 20.77 mmol) and DCM (104 ml) were combined, followed by Boc₂O (6.03 ml, 26.0 mmol). The solution was stirred at ambient temperature for 2 h. The reaction was concentrated in vacuo and the residue was purified by column chromatography on silica gel, eluting with hexanes to EtOAc over 10 column volumes to give the title compound as a solid.

Intermediate C-3A and C-3B

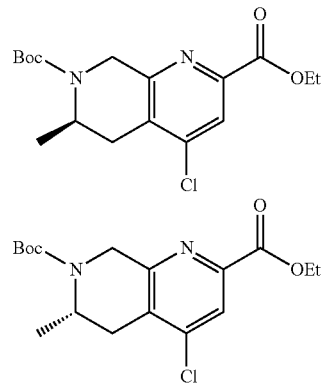

(S) and (R)-7-tert-butyl 2-ethyl 4-chloro-6-methyl-5,6-dihydro-1,7-naphthyridine-2,7(8H)-dicarboxylate Step 1: 2-chloro-5-nitroisonicotinic Acid To a solution of 2-chloro-4-methyl-5-nitropyridine (46 g, 267 mmol) in H₂SO₄ (400 ml) was added K₂Cr₂O₇ (98 g, 333 mmol) in several portions at 60° C. The resulting mixture was stirred at the same temperature for 14 h to give a dark green solution. After cooling, the mixture was poured into ice (250 g) carefully and the aqueous was extracted with EtOAc (500 ml*3). The organic phase was concentrated under reduced pressure to give the product as a solid which was used in next step without further purification. MS (ESI) calcd. for (C₆H₄ClN₂O₄) [M+H]+, 203.0, found, 203.0.

Step 2: Methyl 2-chloro-5-nitroisonicotinate

To a solution of 2-chloro-5-nitroisonicotinic acid (20.2 g, 100 mmol) in DMF (500 mL) was added dropwise iodomethane (10 mL, 160 mmol) at 0° C. After addition, the mixture was gradually warmed to 15° C. and stirred for 15 h. The reaction was quenched with saturated aqueous NH₄Cl (200 mL) and extracted with EtOAc (300 mL*3). The combined organic phase was washed with 10% aqueous LiCl (50 mL*2), dried over anhydrous Na₂SO₄, filtered and concentrated. The residue was purified by chromatography (silica gel: 200-300 mesh, petroleum ether/EtOAc=50/1 to 10/1, v/v) to give the product as a solid. ¹H NMR (400 MHz, CDCl₃) δ 9.04 (s, 1H), 7.59 (s, 1H), 3.97 (s, 3H).

Step 3: Methyl 2-methyl-5-nitroisonicotinate

A mixture of methyl 2-chloro-5-nitroisonicotinate (18 g, 83 mmol), 2,4,6-trimethyl-1,3,5,2,4,6-trioxatriborinane (37.6 g, 150 mmol, 50% wt in THF), K₂CO₃ (22.97 g, 166 mmol), Pd(OAc)₂ (0.933 g, 4.16 mmol) and PCy₃HBF₄ (3.06 g, 8.31 mmol) in 1,4-dioxane (400 mL) was degassed and backfilled with N₂ (three times). The mixture was heated to 100° C. for 13 h. After cooling, the dark mixture was filtered and the filtrate was concentrated under reduced pressure. The residue was purified by chromatography (silica gel, 200-300-mesh, petroleum ether/EtOAc=50/1 to 5/1, v/v) to give the product as a solid. MS (ESI) calcd for (C₈H₉N₂O₄) [M+H]+, 197.0, found, 197.2. ¹H NMR (400 MHz, CDCl₃) δ 9.14 (s, 1H), 7.39 (s, 1H), 3.95 (s, 3H), 2.70 (s, 3H).

Step 4: Methyl 5-amino-2-methylisonicotinate

A mixture of methyl 2-methyl-5-nitroisonicotinate (9 g, 45.9 mmol) and 10% Pd/C (1 g, 0.940 mmol) in MeOH (250 ml) was degassed and backfilled with H2 (three times). The mixture was stirred at 15° C. under 30 psi of H₂ atmosphere for 14 h. The catalyst was filtered off and the filtrate was concentrated in vacuo to give the product as a solid which was directly used in next step without further purification. MS (ESI) calcd for (C₈H₁₁N₂O₂) [M+H]+, 167.1, found, 167.1. ¹H NMR (400 MHz, DMSO-d₆) δ 8.13 (s, 1H), 7.31 (s, 1H), 6.44 (br, 2H), 3.80 (s, 3H), 2.27 (s, 3H).

Step 5: 5-amino-2-methylisonicotinic Acid

A mixture of methyl 5-amino-2-methylisonicotinate (6.2 g, 37.3 mmol) and NaOH (93 ml, 93 mmol, 1M in water) in THF (100 mL) was stirred at 15° C. for 2 h. The reaction mixture was neutralized with 1N HCl (93 mL, 93 mmol). The mixture was concentrated in vacuo to give the product as a solid which was directly used in next step without further purification.

Step 6: Ethyl 4-chloro-6-methyl-1,7-naphthyridine-2-carboxylate

To the crude 5-amino-2-methylisonicotinic acid (crude, 37.3 mmol) was added POCl₃ (70 ml, 751 mmol) at 15° C. and then treated with ethyl pyruvate (12.50 mL, 112 mmol). The resulting mixture was heated to 110° C. for 3 h and the POCl₃ was removed under reduced pressure. The residue was dissolved in H₂O (100 mL) and neutralized with saturated aqueous NaHCO₃ and the aqueous was extracted with EtOAc (300 mL*3). The organic phase was concentrated and purified by chromatography (silica gel: 200-300 mesh, petroleum ether/EtOAc=50/1 to 10/1) to give the product as a solid. MS (ESI) calcd. for (C₁₂H₁₂ClN₂O₂) [M+H]+, 251.1, found, 251.1. ¹H NMR (400 MHz, CDCl3) δ 9.67 (s, 1H), 8.43 (s, 1H), 7.89 (s, 1H), 4.58-4.64 (q, J=7.2 Hz, 2H), 2.85 (s, 3H), 1.54 (t, J=7.2 Hz, 3H).

Step 7: Ethyl 4-chloro-6-methyl-5,6,7,8-tetrahydro-1,7-naphthyridine-2-carboxylate To a mixture of ethyl 4-chloro-6-methyl-1,7-naphthyridine-2-carboxylate (4.89 g, 19.51 mmol) and AcOH (60 mL) was added Na(CN)BH₃ (3.68 g, 58.5 mmol) at 15° C. The mixture was stirred at 5° C. for 14 h and concentrated in vacuo to give the product as an oil which was used in next step without further purification. MS (ESI) calcd. for (C₁₂H₁₆ClN₂O₂) [M+H]+, 255.1, found, 255.1.

Step 7: (S) and (R)-7-tert-butyl 2-ethyl 4-chloro-6-methyl-5,6-dihydro-1,7-naphthyridine-2,7(8H)-dicarboxylate To a solution of crude ethyl 4-chloro-6-methyl-4a,5,6,7,8,8a-hexahydro-1,7-naphthyridine-2-carboxylate (19.5 mmol) in DCM (100 mL) was added DIPEA (15 mL, 86 mmol) and di-tert-butyl dicarbonate (10 g, 45.8 mmol) at 15° C. The mixture was stirred for 1 h. The mixture was concentrated under reduced pressure and the residue was purified by chromatography (silica gel: 200-300 mesh, petroleum ether/EtOAc=30/1 to 5/1, v/v) to give the product as a solid. 1H NMR (400 MHz, CDCl3) δ 8.02 (s, 1H), 5.10 (d, J=18.8 Hz, 1H), 4.86 (brs, 1H), 4.49 (q, J=7.0 Hz, 2H), 4.43 (d, J=19.2 Hz, 1H), 2.97-3.07 (m, 1H), 2.84-2.94 (m, 1H), 1.49 (s, 9H), 1.44 (t, J=7.0 Hz, 3H), 1.11 (d, J=6.6 Hz, 3H). 7-tert-butyl2-ethyl 4-chloro-6-methyl-5,6-dihydro-1,7-naphthyridine-2,7(8H)—

The enantiomers were resolved by chiral-SFC (Column, Chiralpak IC 300×50 mm I.D., 10 um; Mobile phase, supercritical CO₂/MeOH (0.1%) NH₃.H₂O=65/35 at 200 mL/min; Column Temp, 38° C.) to give enantiomer A (RT=6.9 min) and enantiomer B (RT=7.18 min).

Enantiomer A: ¹H NMR (400 MHz, CDCl₃) δ 8.03 (s, 1H), 5.10 (d, J=18.8 Hz, 1H), 4.86 (brs, 1H), 4.50 (q, J=7.0 Hz, 2H), 4.43 (d, J=19.2 Hz, 1H), 2.98-3.08 (m, 1H), 2.85-2.94 (m, 1H), 1.49 (s, 9H), 1.45 (t, J=7.0 Hz, 3H), 1.11 (d, J=6.6 Hz, 3H).

Enantiomer B: ¹H NMR (400 MHz, CDCl₃) δ 8.00 (s, 1H), 5.08 (d, J=18.8 Hz, 1H), 4.83 (brs, 1H), 4.47 (q, J=7.3 Hz, 2H), 4.40 (d, J=18.8 Hz, 1H), 2.95-3.06 (m, 1H), 2.82-2.92 (m, 1H), 1.47 (s, 9H), 1.42 (t, J=7.2 Hz, 3H), 1.08 (d, J=7.0 Hz, 3H).

Intermediate C-4

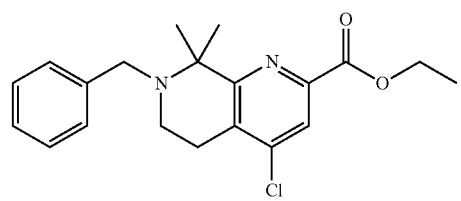 [SMILES: CCOC(=O)c1cc(Cl)c2c(n1)C(C)(C)N(Cc1ccccc1)CC2]

Ethyl 7-benzyl-4-chloro-8,8-dimethyl-5,6,7,8-tetrahydro-1,7-naphthyridine-2-carboxylate Step 1: Ethyl 2-(benzylamino)-2-methylpropanoate A solution of phenylmethanamine (60.4 g, 564 mmol), ethyl 2-bromo-2-methylpropanoate (100 g, 513 mmol), K$_2$CO$_3$ (78 g, 564 mmol) and potassium iodide (0.851 g, 5.13 mmol) in 400 mL of ethanol was stirred at 90° C. for 60 h. The resultant reaction mixture was filtered. The filtrate was evaporated under reduced pressure. The residue was purified by silica gel column chromatography using hexane-ethyl acetate (6:1) as eluent to give ethyl 2-(benzylamino)-2-methylpropanoate as a yellow oil. MS (ESI) calcd, for (C$_{13}$H$_{20}$NO$_2$) [M+H]$^+$, 222.1, found, 222.0.

Step 2: Ethyl 4-(benzyl(1-ethoxy-2-methyl-1-oxo-propan-2-yl)amino)butanoate

A mixture of ethyl 2-(benzylamino)-2-methylpropanoate (36 g, 163 mmol), ethyl 4-bromobutanoate (34.9 g, 179 mmol) and potassium iodide (0.270 g, 1.627 mmol) was stirred at 130° C. for 4 h. The mixture was purified by column chromatography on silica gel using petroleum ether-ethyl acetate (8:1) as eluent to give ethyl 4-(benzyl(1-ethoxy-2-methyl-1-oxopropan-2-yl)amino)butanoate as a yellow oil. MS (ESI) calcd. for (C$_{19}$H$_{30}$NO$_4$) [M+H]$^+$, 336.2, found, 335.9.

Step 3: Ethyl 1-benzyl-2,2-dimethyl-3-oxopiperidine-4-carboxylate

To a solution of ethyl 4-(benzyl(1-ethoxy-2-methyl-1-oxopropan-2-yl)amino)butanoate (10 g, 29.8 mmol) in 200 mL of anhydrous THF was added sodium hydride (1.312 g, 32.8 mmol, 60% in mineral oil). The mixture was heated at 90° C. for 4 h. After evaporation of the solvent, the viscous product was treated with H$_2$O (30 mL) and the resulting mixture was acidified with aqueous HCl (1M) to pH=5, maintaining the temperature under 10° C. with an ice bath. The aqueous solution was neutralized with solid K$_2$CO$_3$ and extracted with ethyl acetate (3×30 mL). The combined organic extracts were dried over Na$_2$SO$_4$ and evaporated to give ethyl 1-benzyl-2, 2-dimethyl-3-oxopiperidine-4-carboxylate as a yellow oil. MS (ESI) calcd. for (C$_{17}$H$_{24}$NO$_3$) [M+H]$^+$, 290.2, found, 290.1.

Step 4: Ethyl 5-amino-1-benzyl-6,6-dimethyl-1,2,3,6-tetrahydropyridine-4-carboxylate A solution of ethyl 1-benzyl-2, 2-dimethyl-3-oxopiperidine-4-carboxylate (7.5 g, 25.9 mmol) and ammonium acetate (5.33 g, 69.2 mmol) in MeOH (70 mL) was stirred for 7 days and concentrated under reduced pressure. To the residue was added ethyl acetate (50 mL) and the organic layer was washed with saturated aqueous sodium bicarbonate solution (50 mL). The aqueous layer was extracted with ethyl acetate (3×50 mL) and the combined organic layers were washed with saturated aqueous sodium chloride (20 mL), dried over anhydrous Na$_2$SO$_4$ and concentrated to give ethyl 5-amino-1-benzyl-6,6-dimethyl-1,2,3,6-tetrahydropyridine-4-carboxylate as a yellow solid which was used in the next step without further purification. MS (ESI) calcd. for (C$_{17}$H$_{25}$N$_2$O$_2$) [M+H]+, 289.1, found, 289.1.

Step 5: Ethyl 7-benzyl-4-chloro-8,8-dimethyl-5,6,7,8-tetrahydro-1,7-naphthyridine-2-carboxylate To a mixture of ethyl 5-amino-1-benzyl-6,6-dimethyl-1,2,3,6-tetrahydropyridine-4-carboxylate (2 g, 6.94 mmol) and ethyl pyruvate (1.611 g, 13.87 mmol) was added phosphoryl trichloride (10.28 mL, 112 mmol). The mixture was heated to 110° C. for 3 h. The reaction was quenched with water (20 mL) and the mixture was adjusted to pH=8 with saturated aqueous Na$_2$CO$_3$ and extracted with ethyl acetate (3×100 mL). The organic layers were combined, dried over Na$_2$SO$_4$, filtered, concentrated and purified by column on silica gel (DCM:MeOH=100:1~10:1) to give the title compound as a yellow oil. MS (ESI) calcd. for (C$_{20}$H$_{24}$ClN$_2$O$_2$) [M+H]+, 359.1, found, 359.2].

Intermediate R1-1

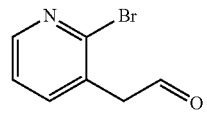

2-(2-bromopyridin-3-yl) acetaldehyde

Step 1: (E)-2-bromo-3-(2-methoxyvinyl)pyridine

LiHMDS (810 mg, 4.84 mmol) was added dropwise to a stirred, cooled −78° C. mixture of chloro(methoxymethyl)triphenylphosphorane (1.7 g, 4.84 mmol) in THF (20 mL) under N$_2$ and the mixture was stirred at −78° C. for 1 h. A solution of 2-bromonicotinaldehyde (600 mg, 3.23 mmol) in THF (2 mL) was added to the above mixture at −78° C. and stirred for 30 min. The mixture was warmed up to room temperature and stirred overnight, The mixture was diluted with ethyl acetate (60 mL), washed with aqueous ammonium chloride (saturated, 3×30 mL), dried (Na$_2$SO$_4$), filtered and the solvent was evaporated under reduced pressure. The residue was purified by column chromatography on silica gel, eluting with EtOAc/isohexane to give an oil. MS (ESI) calc'd for (C$_8$H$_8$BrNO) [M+H]$^+$, 214.0, found, 214.0;

Step 2: 2-(2-bromopyridin-3-yl) acetaldehyde

A mixture of (E)-2-bromo-3-(2-methoxyvinyl)pyridine (260 mg, 1.215 mmol) and formic acid (10 mL, 261 mmol) was stirred overnight, the mixture was cooled and concentrated in vacuo, aqueous sodium hydrogen carbonate (saturated, 60 mL) was added and the mixture was extracted with ethyl acetate (3×40 mL). The combined organic fractions were washed with brine (saturated, 1×40 mL), dried (Na$_2$SO$_4$), filtered and the solvent was evaporated under reduced pressure. The residue was purified by column chromatography on silica gel, eluting with EtOAc/isohexane to give the title compound as an oil. MS (ESI) calc'd for (C$_7$H$_6$BrNO) [M+H]$^+$, 200.0, found, 200.0;

Intermediate R1-2

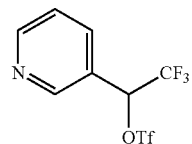 [SMILES: O=S(=O)(OC(c1cccnc1)C(F)(F)F)C(F)(F)F]

(S) and (R)-2,2,2-trifluoro-1-(pyridin-3-yl)ethyl trifluoromethanesulfonate

Step 1: 2,2,2-trifluoro-1-(pyridin-3-yl)ethanol

To a mixture of nicotinaldehyde (1 g, 9.3 mmol) and CsF (700 mg, 4.7 mmol) was added TMSCF$_3$ (2M in THF, 7 ml, 14 mmol), and stirred at room temperature overnight. The reaction was quenched with water (2 ml) and extracted with EtOAc (20 ml*3). The combined organic layers were treated with HCl (2M in H$_2$O, 10 mL) and stirred for 1 h and then adjusted to pH ~7 with aqueous saturated NaHCO$_3$. The mixture was extracted with EtOAc (10 mL*2), the combined organic layers were dried over MgSO$_4$, filtered, and the residue was purified by silica gel chromatography (petroleum ether:EtOAc=5:1). This yielded the title compound as an oil. MS (ESI): calc'd for (C$_7$H$_6$F$_3$NO) [M+H]$^+$: 178; found: 178.

Step 2: (S) and (R)-2,2,2-trifluoro-1-(pyridin-3-yl)ethyl trifluoromethanesulfonate To a solution of 2,2,2-trifluoro-1-(pyridin-3-yl)ethanol (500 mg, 2.8 mmol) in dry DCM (10 mL) at 0° C. was added 2,6-dimethylpyridine (500 mg, 4.2 mmol). The reaction was allowed to stir for 5 min. Trifluoromethanesulfonic anhydride (1.2 g, 4.2 mmol) was added dropwise. The reaction as allowed to stir for 30 min at 0° C. and then water (10 mL) was added. The mixture was extracted with DCM (30 mL*3) and brine (10 mL*2), dried over Na$_2$SO$_4$, filtered, evaporated, to afford the product which was carried into next step without purification. MS (ESI): calc'd for (C$_8$H$_5$F$_6$NO$_3$S) [M+H]$^+$: 310; found: 310.1.

Intermediate R1-3

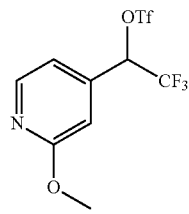 [SMILES: COc1cc(C(OS(=O)(=O)C(F)(F)F)C(F)(F)F)ccn1]

(S) and (R)-2,2,2-trifluoro-1-(2-methoxypyridin-4-yl)ethyl trifluoromethanesulfonate Step 1: 2,2,2-trifluoro-1-(2-methoxypyridin-4-yl)ethanol To a mixture of 2-methoxyisonicotinaldehyde (2 g, 14.6 mmol) and CsF (444 mg, 2.92 mmol) was added TMSCF$_3$ (2 M in THF, 9.5 mL, 19 mmol). The reaction was allowed to stir overnight at room temperature. The reaction was quenched with water (2 mL) and extracted with ethyl acetate (20 mL*3). HCl (2 M in H$_2$O, 10 mL) was added and the pH of the solution was adjusted to ~7 using saturated NaHCO$_3$ solution. The mixture was extracted with ethyl acetate (2*20 mL) and washed with brine (10 mL*2). The combined organic layers were dried over MgSO$_4$, filtered, and evaporated. The residue was purified by silica gel chromatography (petroleum ether:EtOAc=7:1) to afford the product as an oil. MS (ESI) calc'd for (C$_8$H$_8$F$_3$NO$_2$) [M+H]$^+$, 208.1; found, 208.0.

Step 2: (S) and (R)-2,2,2-trifluoro-1-(2-methoxypyridin-4-yl)ethyl trifluoromethanesulfonate To a solution of 2,2,2-trifluoro-1-(2-methoxypyridin-4-yl)ethanol (2.65 g, 12.8 mmol) in dry DCM (10 mL) at 0° C. was added 2,6-dimethylpyridine (2.19 g, 20.5 mmol). The reaction mixture was allowed to stir for for 5 min and trifluoromethanesulfonic anhydride (10.8 g, 38.4 mmol) was added dropwise. The reaction was allowed to stir for 30 min at 0° C. and then water (10 mL) was added. The mixture was extracted with DCM (30 mL*3). The combined organic layers were washed with brine (10 mL*2), dried over Na$_2$SO$_4$, filtered, evaporated to afford the title compound. MS (ESI) calc'd for (C$_9$H$_7$F$_6$NO$_4$S$_2$) [M+H]$^+$, 340.0; found, 339.9.

Intermediate R1-4

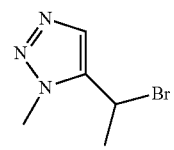

(S) and (R)-5-(1-bromoethyl)-1-methyl-1H-1,2,3-triazole

Step 1: 1-methyl-1H-1,2,3-triazole

To a solution of 1H-1,2,3-triazole (10 g, 145 mmol) in anhydrous THF (150 mL) was added powder K$_2$CO$_3$ (40.0 g, 290 mmol), then iodomethane (32.29 g, 227 mmol) was added dropwise at 30° C. After the addition was complete, the mixture was stirred at 30° C. for 16 h. The reaction mixture was filtered and the filtrate was concentrated to afford the product as an oil. $^1$H-NMR: (DMSO-d$_6$ 400 MHz) δ 8.06 (s, 1H), 7.71 (s, 1H), 4.05 (s, 3H)

Step 2: 1-(1-methyl-1H-1,2,3-triazol-5-yl)ethanone

A solution of 1-methyl-1H-1,2,3-triazole (3.0 g, 36.1 mmol) in anhydrous THF (100 mL) was cooled to −78° C., followed by the addition of butyllithium (15.89 mL, 39.7 mmol) dropwise to give a yellow suspension. The reaction mixture was stirred at −78° C. for 1 h before N-methoxy-N-methylacetamide (6.52 g, 63.2 mmol) was added. The white suspension was then allowed to warm to 10° C. and stirred for 16 h. The reaction was quenched with MeOH. This solution was purified by column chromatography on silica gel (petroleum ether/EtOAc=3:1 to 1:1) to give the product as a solid. $^1$H-NMR: (Chloroform-d 400 MHz) δ 8.16 (s, 1H), 4.31 (s, 3H), 2.58 (s, 3H).

Step 3: 1-(1-methyl-1H-1,2,3-triazol-5-yl)ethanol

To the stirred solution of 1-(1-methyl-1H-1,2,3-triazol-5-yl)ethanone (300 mg, 2.398 mmol) was added NaBH$_4$ (91 mg, 2.398 mmol) in portions at 0° C. Then the mixture was stirred at 16° C. for about 1 h. Water (10 mL) was added and the mixture was extracted with EtOAc (10 mL×3). The combined extracts were washed with brine, dried and concentrated to afford the product as a solid. MS (ESI) calcd. for (C$_5$H$_{10}$N$_3$O) [M+H]+, 128.1, found, 128.1 $^1$H-NMR: (Methanol-d$_4$ 400 MHz) δ 7.62 (s, 1H), 5.00 (q, J=6.26 Hz, 1H), 4.02-4.17 (m, 3H), 1.58 (d, J=6.65 Hz, 3H).

Step 4: (S) and (R)-5-(1-bromoethyl)-1-methyl-1H-1,2,3-triazole 1-(1-methyl-1H-1,2,3-triazol-5-yl)ethanol (60 mg, 0.472 mmol) was dissolved in DCM (6 mL), then PBr$_3$ (0.053 mL, 0.566 mmol) was added into the suspension at 15° C. under a nitrogen atmosphere. The resulting mixture was stirred for 16 h. The solvent was evaporated in vacuo to afford the title compound as a solid which was used without further purification. MS (ESI) calcd. for (C$_5$H$_9$BrN$_3$) [M+H]+, 190.1, found, 190.1.

Intermediate R1-5

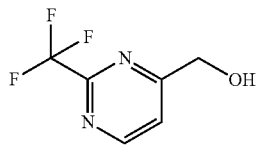 [SMILES: OCc1ccnc(C(F)(F)F)n1]

(2-(trifluoromethyl)pyrimidin-4-yl)methanol

Methyl 2-(trifluoromethyl)pyrimidine-4-carboxylate (1000 mg, 4.85 mmol) was placed under nitrogen in anhydrous DCM (20.0 ml). The reaction mixture was cooled to 0° C., then 1M DIBAL-H in DCM (11.0 ml, 11.0 mmol) was added dropwise, over 5 min. The ice bath was removed and the reaction allowed to stir at room temperature. After 1.5 h, the mixture was cooled to 0° C. Saturated aqueous ammonium chloride (20 ml) was added to the mixture. The mixture was stirred for 15 min, then saturated aqueous Rochell's salt (30 ml) was added. The mixture was stirred for 20 min at room temperature, then extracted with ethyl acetate (2×60 ml). The combined organic layers were washed with brine (40 ml), dried over sodium sulfate, and concentrated under reduced pressure. The resultant yellow oil was chromatographed using a 40 g silica gel cartridge eluted with 0-10% methanol in DCM over 20 column volumes. The product fractions were combined and concentrated under reduced pressure to provide the title compound as an oil. LC-MS: calculated for C6H5F3N2O 178.11, observed m/e: 179.18 (M+H)$^+$.

Intermediate R1-6

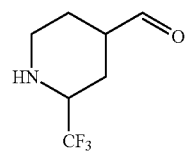

(2S,4R) and (2R,4S)-2-(trifluoromethyl)piperidine-4-carbaldehyde

Step 1: 2-(trifluoromethyl)piperidine-4-carboxylic Acid

A mixture of 2-(trifluoromethyl)isonicotinic acid (5 g, 26.2 mmol) and 10% Pd—C (0.5 g) in MeOH (100 ml) was degassed and backfilled with H$_2$ (three times). The mixture was heated to 40° C. under H$_2$ atmosphere (50 psi) for 20 h. The catalyst was filtered off and the filtrate was concentrated under reduced pressure to give the product as a solid which was used in the next step without further purification. $^1$H NMR (400 MHz, DMSO-d$_6$) δ 3.19-3.28 (m, 1H), 3.00 (d, J=11.80 Hz, 1H), 2.51-2.58 (m, 1H), 2.40 (tt, J=3.58, 12.36 Hz, 1H), 1.65-2.02 (m, 2H), 1.13-1.43 (m, 2H).

Step 2: N-methoxy-N-methyl-2-(trifluoromethyl)piperidine-4-carboxamide

A mixture of 2-(trifluoromethyl)piperidine-4-carboxylic acid (2 g, 10.14 mmol), N,O-dimethylhydroxylamine hydrochloride (2.97 g, 30.4 mmol), EDC (2.334 g, 12.17 mmol), HOBT (1.864 g, 12.17 mmol), TEA (4.24 ml, 30.4 mmol) and DMF (50 ml) was stirred at 15° C. for 15 h. The mixture was diluted with 10% LiCl (30 mL) and extracted with EtOAc (30 ml*3). The combined organics were washed with 10% aqueous LiCl (10 ml), dried over anhydrous Na$_2$SO$_4$, filtered and concentrated to give the product as an oil which was used in the next step without purification.

Step 3: (2S,4R) and (2R,4S)-2-(trifluoromethyl)piperidine-4-carbaldehyde

To a stirred solution of N-methoxy-N-methyl-2-(trifluoromethyl)piperidine-4-carboxamide (1.8 g, 7.49 mmol) in THF (20 ml) was added LiAlH$_4$ (0.313 g, 8.24 mmol) at −78° C. The mixture was gradually warmed to 0° C. for 1.5 h and TLC showed that the product was appearance. The mixture was quenched with ice-water (50 ml). The mixture was filtered and the filtrate was extracted with ethyl acetate (20 ml*3) and concentrated under reduced pressure to give the crude 2-(trifluoromethyl)piperidine-4-carbaldehyde (582 mg, 34%) as red liquid which was used in the next step directly. $^1$H NMR (400 MHz, CDCl$_3$) δ 9.67 (s, 1H), 4.08-4.10 (m, 1H), 3.28-3.47 (m, 1H), 3.15-3.17 (m, 1H), 2.37-2.71 (m, 1H), 2.00-2.13 (m, 1H), 1.95-1.98 (m, 1H), 1.21-1.45 (m, 2H).

Intermediate R1-7

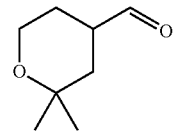

(S) and (R)-2,2-dimethyltetrahydro-2H-pyran-4-carbaldehyde

Step 1: (Z)-4-(methoxymethylene)-2,2-dimethyltetrahydro-2H-pyran

To a suspension of (methoxymethyl)triphenylphosphonium chloride (20.06 g, 58.5 mmol) in THF (1 L) was added NaHMDS (58.5 mL, 1.0 M in THF) at −40° C. and stirred for 30 min, then 2,2-dimethyldihydro-2H-pyran-4(3H)-one (5 g, 39.0 mmol) in THF (20 mL) was added to the mixture at −40° C. After addition, the mixture was warmed to 10° C. and stirred for 2 h. The mixture was quenched with saturated NH$_4$Cl (300 mL×2) and extracted with DCM (200 mL×2). The combined organic layers were washed with brine (600 mL), dried over sodium sulfate and concentrated in vacuo to give the crude product. Chromatography over silica gel column eluted with (petroleum ether:EtOAc=30:1) to give the desired product as an oil. $^1$H NMR (400 MHz, CDCl$_3$) δ 5.92 (s, 0.4H), 5.76 (s, 0.6H), 3.61-3.70 (m, 2H), 3.49-3.58 (m, 3H), 2.23 (t, J=5.5 Hz, 1.3H), 2.15 (s, 0.7H), 1.99 (t, J=5.5 Hz, 0.7H), 1.90 (s, 1.3H), 1.13-1.22 (m, 6H).

Step 2: (S) and (R)-2,2-dimethyltetrahydro-2H-pyran-4-carbaldehyde

To a solution of (Z)-4-(methoxymethylene)-2,2-dimethyltetrahydro-2H-pyran (1.0 g, 6.40 mmol) in acetonitrile (10 mL) was added 2 M aqueous HCl (10 mL) and stirred at 20° C. for 4 h. Solvent was removed under reduced pressure. The residue was dissolved in DCM (10 mL), and washed with saturated aqueous NaHCO$_3$ (20 mL). The combined organic layers were washed with brine (20 mL×2), dried over Na$_2$SO$_4$ and evaporated under reduced pressure to give the desired product as an oil. $^1$H NMR (400 MHz, CDCl$_3$) δ 9.58 (s, 1H), 3.84-3.74 (m, 1H), 3.67 (dt, J=2.2, 12.0 Hz, 1H), 2.66-2.54 (m, 1H), 1.81-1.67 (m, 2H), 1.59-1.46 (m, 1H), 1.40 (t, J=12.9 Hz, 1H), 1.22 (d, J=10.2 Hz, 6H).

Intermediate R1-8

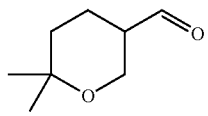

(S) and (R)-6,6-dimethyltetrahydro-2H-pyran-3-carbaldehyde

Step 1: 2-methylpent-4-en-2-ol

To a solution of propan-2-one (87 g, 1.498 mol) in THF (1 L) was added allylmagnesium bromide (1 L, 1.0 M in THF) at 0° C. under an atmosphere of N$_2$. The mixture was then stirred at 20° C. for 2 h. The mixture was quenched with saturated aqueous NH$_4$Cl (300 mL) and extracted with EtOAc (200 mL×2). The combined organic layers were dried over Na$_2$SO$_4$ and the solvent was evaporated to give the crude product as an oil which was further purified by distillation to afford the product as an oil. $^1$H NMR (400 MHz, CDCl$_3$) δ 5.92-5.75 (m, 1H), 5.12-5.03 (m, 2H), 2.19 (d, J=7.4 Hz, 2H), 1.17 (s, 6H).

Step 2: Methyl 2-(((2-methylpent-4-en-2-yl)oxy)methyl)acrylate

To a solution of 2-methylpent-4-en-2-ol (14.0 g, 140 mmol) in DMF (150 mL) was added sodium hydride (6.71 g, 168 mmol) at 0° C. After stirring for 10 min at 0° C., methyl 2-(bromomethyl)acrylate (30.0 g, 168 mmol) was dropwise added. The mixture was then stirred at the same temperature for 2 h, and warmed to 20° C. for 30 min. The reaction was quenched with saturated aqueous NH$_4$Cl (550 mL) and extracted with EtOAc (200 mL×2), and the combined organic layers were washed with brine (500 mL×2), dried over Na$_2$SO$_4$ and the solvent was evaporated in vacuo. The crude product was purified by silica gel chromatography eluted with (petroleum ether:EtOAc=100:1) to give the product as an oil. $^1$H NMR (400 MHz, CDCl$_3$) δ 6.25 (s, 1H), 5.92 (d, J=1.6 Hz, 1H), 5.89-5.76 (m, 1H), 5.08-4.99 (m, 2H), 4.12 (s, 2H), 3.75 (s, 3H), 2.28 (d, J=7.4 Hz, 2H), 1.19 (s, 6H).

Step 3: Methyl 6,6-dimethyl-5,6-dihydro-2H-pyran-3-carboxylate

To a solution of 2-(((2-methylpent-4-en-2-yl)oxy)methyl) acrylate (8.0 g, 40.4 mmol) in CH$_2$Cl$_2$ (400 mL) was added Zhan-catalyst-1B (29.6 g, 40.4 mmol) under an atmosphere of N$_2$, and the solution was stirred at 50° C. for 16 h. Solvent was removed in vacuo and the crude product was purified by the column chromatography eluted with (petroleum ether: EtOAc=30:1) to give the product as an oil. $^1$H NMR (400 MHz, CDCl$_3$) δ 6.96 (br. s., 1H), 4.31 (d, J=2.0 Hz, 2H), 3.71 (s, 3H), 2.14 (d, J=3.5 Hz, 2H), 1.20 (s, 6H).

Step 4: Methyl 6,6-dimethyltetrahydro-2H-pyran-3-carboxylate

To a solution of methyl 6,6-dimethyl-5,6-dihydro-2H-pyran-3-carboxylate (7.0 g, 41.1 mmol) in MeOH (150 mL) was added Pd—C (0.438 g, 4.11 mmol), and the slurry was stirred at 30° C. under 20 psi of H$_2$ for 15 h. The reaction mixture was filtered through a celite pad and the filtrate was evaporated under reduced pressure to give the product as a colorless oil that was used without further purification. $^1$H NMR (400 MHz, CDCl$_3$) δ 3.83 (dd, J=3.3, 11.2 Hz, 1H), 3.77-3.68 (m, 1H), 3.64 (s, 3H), 2.48 (td, J=4.8, 9.5 Hz, 1H), 1.94-1.78 (m, 2H), 1.60-1.37 (m, 2H), 1.17 (br. s., 6H).

Step 5: 6,6-dimethyltetrahydro-2H-pyran-3-carboxylic Acid

To a solution of methyl 6,6-dimethyltetrahydro-2H-pyran-3-carboxylate (1.00 g, 5.81 mmol) in MeOH (21 mL) and water (7 mL) was added lithium hydroxide hydrate (0.244 g, 5.81 mmol) at 20° C., and the reaction was stirred for 2 h. Solvent was removed in vacuo the the residue was washed with water (60 mL), extracted with EtOAc (25 mL×2). Then the aqueous was acidified with 6 N aq. HCl to pH ~3, extracted with EA (25 mL×2) and the combined organic layers were washed with brine (100 mL), dried over Na$_2$SO$_4$ and evaporated under reduced pressure to give the product as an oil. NMR (400 MHz, CDCl$_3$) δ 3.93-3.87 (m, 1H), 3.83-3.73 (m, 1H), 2.55 (tt, J=4.6, 9.5 Hz, 1H), 1.98-1.84 (m, 2H), 1.65-1.55 (m, 1H), 1.52-1.42 (m, 1H), 1.22 (d, J=2.0 Hz, 6H).

Step 6: (6,6-dimethyltetrahydro-2H-pyran-3-yl)methanol

BH$_3$/Me$_2$S (3.16 mL, 31.6 mmol) was added dropwise to a solution of 6,6-dimethyltetrahydro-2H-pyran-3-carboxylic acid (1 g, 6.32 mmol) in THF (10 mL) at 0° C. over 3 min. The mixture was stirred at 30° C. for 16 h. MeOH (10 mL) was added to the mixture to quench the reaction. The solution was refluxed for 1 h. The solvent was evaporated under reduced pressure to give the product as an oil which was used in the next step without further purification. $^1$H NMR (400 MHz, CDCl$_3$) δ 3.41-3.58 (m, 4H), 1.36-1.81 (m, 5H), 1.19 (d, J=12.13 Hz, 6H).

Step 7: (S) and (R)-6,6-dimethyltetrahydro-2H-pyran-3-carbaldehyde

To a solution of (6,6-dimethyltetrahydro-2H-pyran-3-yl)methanol (900 mg, 6.24 mmol) in CH$_2$Cl$_2$ (30 mL) was added dess-martin reagent (3176 mg, 7.49 mmol) at 0° C. After addition, the mixture was stirred at 0° C. for 2 h. The reaction was quenched with saturated aqueous NaHCO$_3$ (100 mL). Then the mixture was filtered. The filtrate was separated. The organic layers were dried over anhydrous Na$_2$SO$_4$ and evaporated under reduced pressure to give the desired product as an oil which was used in the next step without further purification. $^1$H NMR (400 MHz, CDCl$_3$) δ 9.71 (s, 1H), 3.83-4.00 (m, 2H), 2.30-2.62 (m, 1H), 1.84-1.95 (m, 2H), 1.50-1.60 (m, 1H), 1.40-1.48 (m, 1H), 1.20 (d, J=3.91 Hz, 3H), 1.14-1.18 (m, 3H).

Intermediate R1-9

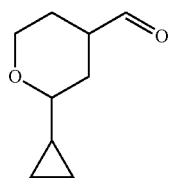

(S) and (R)-2-cyclopropyltetrahydro-2H-pyran-4-carbaldehyde

Step 1: 2-cyclopropyl-2H-pyran-4(3H)-one

To a solution of cyclopropanecarbaldehyde (24 g, 342 mmol) and (E)-((4-methoxybuta-1,3-dien-2-yl)oxy)trimethylsilane (29.5 g, 171 mmol) in Et$_2$O (300 mL) at −78° C. under N$_2$ was added BF$_3$.Et$_2$O (22.13 mL, 175 mmol). The mixture was stirred for 2.5 h, saturated aqueous NaHCO$_3$ solution (300 mL) was added, and the mixture was allowed to warm to 17° C. The mixture was then stirred for 14 h. The mixture was extracted with Et$_2$O (150 mL×3). The combined organic extracts were dried over Na$_2$SO$_4$. Filtered and the filtrate was concentrated in vacuo. The residue was purified via column chromatography (petroleum ether/EtOAc=4/1, v/v) to give the product as an oil. $^1$H NMR (400 MHz, CHLOROFORM-d) δ 7.09 (d, J=5.87 Hz, 1H), 5.12 (d, J=5.48 Hz, 1H), 3.42 (ddd, J=3.52, 8.90, 13.01 Hz, 1H), 2.35-2.45 (m, 1H), 2.23-2.32 (m, 1H), 0.86-0.95 (m, 1H), 0.32-0.46 (m, 2H), 0.16-0.26 (m, 1H), −0.01-0.08 (m, 1H).

Step 2: 2-cyclopropyldihydro-2H-pyran-4(3H)-one and 2-cyclopropyltetrahydro-2H-pyran-4-ol A mixture of 2-cyclopropyl-2H-pyran-4(3H)-one (16.5 g, 96 mmol) and Pd/C (2 g, 1.88 mmol) in THF (200 mL) was stirred at 20° C. under 20 psi H$_2$ for 2 h. The reaction mixture was filtered and the filtrate was concentrated in vacuo to give crude products as an oil which was used without further purification.

Step 3: 2-cyclopropyldihydro-2H-pyran-4(3H)-one

To a solution of 2-cyclopropyltetrahydro-2H-pyran-4-ol (16 g, 11.59 mmol), containing 2-cyclopropyldihydro-2H-pyran-4(3H)-one in DCM (200 mL) at 0° C. was added DMP (17.90 g, 42.2 mmol). Then the mixture was stirred at 17° C. for 2 h. The reaction was filtered and the filtrate was washed with saturated aqueous NaHCO$_3$ (70 mL×2) and brine (100 mL×2), dried over Na$_2$SO$_4$, filtered and the filtrate was concentrated in vacuo. The residue was purified via column chromatography (petroleum ether/EtOAc=5/1, v/v) to give the product as an oil. $^1$H NMR (400 MHz, CHLOROFORM-d) δ 4.09 (dd, J=7.43, 10.56 Hz, 1H), 3.40 (dt, J=2.74, 11.74 Hz, 1H), 2.67-2.76 (m, 1H), 2.20-2.45 (m, 3H), 2.10 (d, J=14.48 Hz, 1H), 0.76-0.86 (m, 1H), 0.37 (dqd, J=5.48, 8.77, 17.90 Hz, 2H), 0.21 (qd, J=4.70, 9.39 Hz, 1H), 0.03 (qd, J=4.70, 9.39 Hz, 1H).

Step 4: (Z)-2-cyclopropyl-4-(methoxymethylene)tetrahydro-2H-pyran

To a suspension of (methoxymethyl)triphenylphosphonium chloride (36.7 g, 107 mmol) in THF (130 mL) at −40° C. was added NaHMDS (107 mL, 107 mmol) and the reaction was stirred at −40° C. for 30 min. 2-cyclopropyldihydro-2H-pyran-4(3H)-one (12.5 g, 71.3 mmol) in THF (20 mL) was added to the mixture at −40° C. Then, the mixture was allowed to warm up to 18° C. and stirred for 2 h. The mixture was quenched with a saturated aqueous NH$_4$Cl (150 mL) and extracted with DCM (60 mL×3). The organic layers were washed with brine (60 mL), dried over Na$_2$SO$_4$, filtered and concentrated in vacuo to give the crude compound. Silica gel column chromatography eluting with petroleum ether/EtOAc=30/1 (v/v) furnished the product as an oil. $^1$H NMR (400 MHz, CHLOROFORM-d) δ 5.80 (s, 1H), 3.96-4.04 (m, 1H), 3.52 (d, J=1.51 Hz, 3H), 3.21-3.30 (m, 1H), 2.43-2.54 (m, 1H), 1.89-2.11 (m, 2H), 1.75-1.86 (m, 1H), 0.80-0.93 (m, 2H), 0.41-0.55 (m, 2H), 0.31 (qd, J=4.58, 8.85 Hz, 1H).

Step 5: (S) and (R)-2-cyclopropyltetrahydro-2H-pyran-4-carbaldehyde

To a solution of (Z)-2-cyclopropyl-4-(methoxymethylene)tetrahydro-2H-pyran (5 g, 23.78 mmol) in acetonitrile (20 mL) at 20° C. was added hydrogen chloride (20 mL, 40.0 mmol) and the mixture was stirred for 4 h. Solvent was removed under reduced pressure and the residue was dissolved in DCM (50 mL). The solution was washed with saturated aqueous NaHCO$_3$ (20 mL×3), dried over Na$_2$SO$_4$ and evaporated under reduced pressure to furnish the product as an oil. $^1$H NMR (400 MHz, chloroform-d) δ 9.59-9.77 (m, 1H), 3.33-3.48 (m, 1H), 2.40-2.71 (m, 2H), 1.64-1.85 (m, 3H), 1.34-1.47 (m, 1H), 0.82-0.97 (m, 1H), 0.45-0.60 (m, 2H), 0.35 (tt, J=5.09, 9.59 Hz, 1H), 0.16-0.24 (m, 1H).

Intermediate R1-10

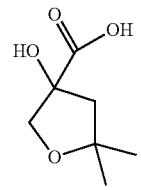

3-hydroxy-5,5-dimethyltetrahydrofuran-3-carboxylic Acid

Step 1: 2-methyl-5-((tetrahydro-2H-pyran-2-yl)oxy)pent-3-yn-2-ol

To a solution of 2-(prop-2-yn-1-yloxy)tetrahydro-2H-pyran (80 g, 571 mmol) in THF (1 L) at −78° C. under an inert atmosphere was added dropwise a solution of n-butyllithium (0.274 L, 685 mmol) over 30 min. The reaction mixture was stirred at −78° C. for 30 min. Acetone (0.063 L, 856 mmol) was added and stirring continued for 1 h. The reaction was quenched by the addition of a solution of saturated aqueous NH$_4$Cl (500 mL) while being vigorously stirred, and the temperature was allowed to warm to ambient temperature slowly. The resulting solution was extracted with EtOAC (3×1.5 L) and the combined organic extracts were dried over anhydrous Na$_2$SO$_4$ and concentrated to give 2-methyl-5-((tetrahydro-2H-pyran-2-yl)oxy)pent-3-yn-2-ol as a yellow oil.

Step 2: 4-methylpent-2-yne-1,4-diol

A solution of p-toluenesulfonic acid (4.78 g, 27.7 mmol) and 2-methyl-5-((tetrahydro-2H-pyran-2-yl)oxy)pent-3-yn-2-ol (110 g, 555 mmol) in MeOH (500 mL) was stirred for 4 h at 20° C. NaHCO$_3$ (20 g) was added. The mixture was filtered and concentrated to give an oil, which was purified by column chromatography on silica gel (petroleum ether: ethyl acetate=5:1 to 3:1) to afford 4-methylpent-2-yne-1,4-diol as a colorless oil.

Step 3: 5,5-dimethyldihydrofuran-3(2H)-one

To a solution of mercury (II) sulfate (7.80 g, 26.3 mmol) in water (100 mL) was added 4-methylpent-2-yne-1,4-diol (60 g, 526 mmol). The reaction was steam distilled until no further organic material appeared in the distillate. The organic layer was removed and saturated aqueous NaCl (200 mL) was added to the aqueous layer and extracted with EtOAc (3×200 mL). The combined organic layers were concentrated to afford 5,5-dimethyldihydrofuran-3(2H)-one as a colorless oil.

Step 4: 5,5-dimethyl-3-((trimethylsilyl)oxy)tetrahydrofuran-3-carbonitrile

A mixture of 5,5-dimethyldihydrofuran-3(2H)-one (8 g, 70.1 mmol), trimethylsilyl cyanide (10.43 g, 105 mmol), and zinc iodide (3.36 g, 10.51 mmol) in DCM (80 mL) was stirred for 6 h at 25° C. The mixture was diluted with water (100 mL) and extracted with DCM (2×200 mL). The combined organic layers were washed with saturated aqueous NaCl (100 mL), dried over anhydrous sodium sulfate and concentrated under reduced pressure to give 5,5-dimethyl-3-((trimethylsilyl)oxy)tetrahydrofuran-3-carbonitrile as a brown oil, which was used without further purification.

Step 5: 3-hydroxy-5,5-dimethyltetrahydrofuran-3-carboxylic Acid 5,5-dimethyl-3-((trimethylsilyl)oxy)tetrahydrofuran-3-carbonitrile (10 g, 46.9 mmol) in water (25 mL) and aqueous hydrochloric acid (12 M) (50 mL) was stirred for 24 h at 80° C. The mixture was concentrated under reduced pressure and filtered to furnish the title compound as a black oil, which was used without further purification.

Intermediate R1-11

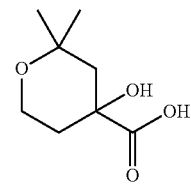

4-hydroxy-2,2-dimethyltetrahydro-2H-pyran-4-carboxylic Acid

Step 1: 2,2-dimethyl-4-((trimethylsilyl)oxy)tetrahydro-2H-pyran-4-carbonitrile

A mixture of 2,2-dimethyldihydro-2H-pyran-4(3H)-one (8.5 g, 66.3 mmol), trimethylsilyl cyanide (9.87 g, 99 mmol), and zinc iodide (3.18 g, 9.95 mmol) in DCM (200 mL) was stirred for 16 h at 26° C. The mixture was concentrated under reduced pressure, diluted with water (200 mL) and extracted with DCM (2×250 mL). The combined organic layers were washed with saturated aqueous NaCl (400 mL), dried over anhydrous sodium sulfate, filtered and concentrated under reduced pressure to give 2,2-dimethyl-4-((trimethylsilyl)oxy)tetrahydro-2H-pyran-4-carbonitrile as a brown oil, which was used without further purification.

Step 2: 4-hydroxy-2,2-dimethyltetrahydro-2H-pyran-4-carboxylic Acid 2,2-dimethyl-4-((trimethylsilyl)oxy)tetrahydro-2H-pyran-4-carbonitrile (5 g, 21.99 mmol) in acetic acid (6 mL) and aqueous hydrochloric acid (12 M) (6 mL) was stirred for 4 h at 80° C. The mixture was concentrated under reduced pressure and lyophilized to furnish the title compound as a brown solid, which was used without further purification.

Intermediate CR1-1

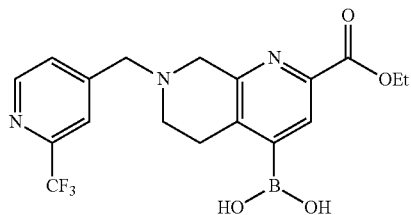 [SMILES: CCOC(=O)c1cc(B(O)O)c2c(n1)CN(Cc1ccnc(C(F)(F)F)c1)CC2]

2-(ethoxycarbonyl)-7-((2-(trifluoromethyl)pyridin-4-yl)methyl)-5,6,7,8-tetrahydro-1,7-naphthyridin-4-ylboronic Acid Step 1: (2-(trifluoromethyl)pyridin-4-yl)methanol A mixture of 2-(trifluoromethyl)isonicotinic acid (600 mg, 3 mmol), BH$_3$.SMe$_2$ (700 mg, 9 mmol) in THF (10 mL)

was stirred at 50° C. overnight. The reaction was quenched with 1 mL saturated aqueous NH₄Cl solution and extracted with ethyl acetate (5 mL×3). The combined extracts were concentrated in vacuo, and the residue was purified on silica gel (EtOAc\petroleum ether=1:2) to give the product as a solid. MS (ESI) calc'd for ($C_7H_6F_3NO$) [M+H]⁺: 178.0; found: 178.

Step 2: 4-(chloromethyl)-2-(trifluoromethyl)pyridine

To a mixture of (2-(trifluoromethyl)pyridin-4-yl)methanol A-2 (400 mg, 2 mmol) in dichloromethane (5 mL) was added SOCl₂(2 mL) slowly at 0° C. The reaction mixture was stirred at 60° C. for 1 h. The reaction mixture was then quenched with 1 mL saturated aqueous NH₄Cl and extracted with ethyl acetate (5 mL×3). The combined organic extracts were concentrated in vacuo, the residue was purified on silica gel (EtOAc:petroleum ether=1:5) to give the product as a solid (300 mg, 60%); MS (ESI) calc'd for ($C_7H_5ClF_3N$) [M+H]⁺: 195.0; found: 195.

Step 3: Ethyl-4-chloro-7-((2-(trifluoromethyl)pyridin-4-yl)methyl)-5,6,7,8-tetrahydro-1,7-naphthyridine-2-carboxylate To a solution of 4-(chloromethyl)-2-(trifluoromethyl)pyridine (300 mg, 1.5 mmol) and ethyl 4-chloro-5,6,7,8-tetrahydro-1,7-naphthyridine-2-carboxylate (450 mg, 1.5 mmol) in acetonitrile (2 ml) was added K₂CO₃ (52 mg, 0.4 mmol), The reaction mixture was stirred at 70° C. for 16 h, cooled and concentrated in vacuo. The residue was purified by reverse phase preparative HPLC (30%-to 95%, MeCN/H₂O containing 0.01% NH₄HCO₃) to afford the product as an oil. MS (ESI) calc'd for ($C_{18}H_{17}ClF_3N_3O_2$) [M+H]⁺: 400.1; found: 400.1.

Step 4: 2-(ethoxycarbonyl)-7-((2-(trifluoromethyl)pyridin-4-yl)methyl)-5,6,7,8-tetrahydro-1,7-naphthyridin-4-ylboronic Acid A mixture of ethyl 4-chloro-7-((2-(trifluoromethyl)pyridin-4-yl)methyl)-5,6,7,8-tetrahydro-1,7-naphthyridine-2-carboxamide (250 mg, 0.6 mmol), 2-(ethoxycarbonyl)-7-((2-(trifluoromethyl)pyridin-4-yl)methyl)-5,6,7,8-tetrahydro-1,7-naphthyridin-4-ylboronic acid (250 mg, 1 mmol), KOAc (200 mg, 2 mmol), Pd(dppf)Cl₂ (30 mg, 0.05 mmol) in 1,4-dioxane was stirred at 100° C. under N₂ overnight. The reaction mixture was filtered and concentrated in vacuo, the residue was purified by silica gel chromatography (eluting with EtOAc\petroleum ether=1:2) to give the title compound as a solid. MS (ESI) calc'd for ($C_HH_{19}BF_3N_3O_4$) [M+H]⁺: 410.1; found: 410.1.

Intermediate CR1-2

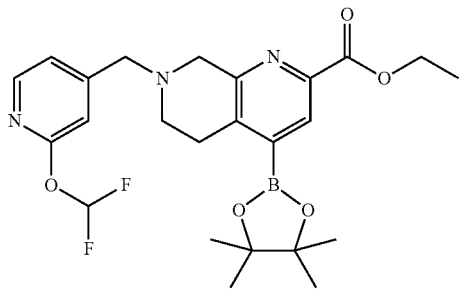 [SMILES: CCOC(=O)c1cc(B2OC(C)(C)C(C)(C)O2)c2c(n1)CN(Cc1ccnc(OC(F)F)c1)CC2]

Ethyl 7-((2-(difluoromethoxy)pyridin-4-yl)methyl)-4-(4,4,5,5-tetramethyl-1,3,2-dioxaborolan-2-yl)-5,6,7,8-tetrahydro-1,7-naphthyridine-2-carboxylate Step 1: Methyl 2-hydroxyisonicotinate 2-Hydroxyisonicotinic acid (4.2 g, 30.2 mmol) was dissolved in MeOH (200 ml), then H₂SO₄ (0.2 mL, 3.75 mmol) was added to the solution and the resulting solution was stirred at 100° C. for 48 h. Then the solution was concentrated under reduced pressure, and the crude product was used without future purification. MS (ESI) Calc'd for ($C_7H_7NO_3$) [M+H]⁺, 154.1; found 154.1.

Step 2: Methyl 2-(difluoromethoxy)isonicotinate

Methyl 2-hydroxyisonicotinate (4.5 g, 29.4 mmol) was dissolved in acetonitrile (200 ml), then sodium 2-chloro-2,2-difluoroacetate (8.96 g, 58.8 mmol) was added to the solution and the resulting solution was stirred at 90° C. overnight. Then the solution was evaporated under reduced pressure. The crude product was purified by silica gel column chromatograph eluting with ethyl acetate/petroleum ether=1:10 to obtain the product as an oil. MS (ESI) Calc'd for ($C_8H_7F_2NO_3$) [M+H]⁺, 204.0; found 204.0.

Step 3: 2-(difluoromethoxy)pyridin-4-yl)methanol

Methyl 2-(difluoromethoxy)isonicotinate (3.1 g, 15.26 mmol) was dissolved in THF (20 mL), then LiBH₄ (11.45 mL, 22.89 mmol) was added to the solution at 0° C. and the resulting solution was stirred at room temperature for 2 h. Then the solution was quenched with 1N HCl solution and then adjusted to pH ~9-10 with 1N aqueous NaOH solution and extracted with ethyl acetate (3*10 mL). The combined organic layers were washed with water, dried with anhydrous Na₂SO₄, filtered, concentrated. The crude product was used in the next step without further purification. MS (ESI) Calc'd for ($C_7H_7F_2NO_2$) [M+H]⁺, 176.1; found 176.1.

Step 4: 4-(chloromethyl)-2-(difluoromethoxy)pyridine 2-(difluoromethoxy)pyridin-4-yl)methanol (2.5 g, 14 mmol) was dissolved in DCM (10 mL), then sulfurous dichloride (20 mL, 275 mmol) was added to the solution at 0° C. and the resulting solution was stirred at room temperature overnight. Then the solution was concentrated under reduced pressure to afford the product which was used in the next step without further purification. MS (ESI) Calc'd for ($C_7H_6ClF_2NO$) [M+H]⁺, 194.0; found 194.0.

Step 5: Ethyl-4-chloro-7-((2-(difluoromethoxy)pyridin-4-yl)methyl)-5,6,7,8-tetrahydro-1,7-naphthyridine-2-carboxylate 4-(chloromethyl)-2-(difluoromethoxy)pyridine (2.7 g, 13.95 mmol), ethyl 4-chloro-5,6,7,8-tetrahydro-1,7-naphthyridine-2-carboxylate (1.8 g, 7.48 mmol) were dissolved in CH₃CN (50 ml) and the resulting solution was stirred at 80° C. for 5 h. Then the solution was filtered and the filtrate was evaporated under reduced pressure. The residue was purified by silica gel column chromatography (eluting with ethyl acetate/petroleum ether=1:1) to obtain the product as an oil. MS (ESI) Calc'd for ($C_{18}H_{18}ClF_2N_3O_3$) [M+H]⁺, 398.0; found 398.0.

Step 6: 7-((2-(difluoromethoxy)pyridin-4-yl)methyl)-4-(4,4,5,5-tetramethyl-1,3,2-dioxaborolan-2-yl)-5,6,7,8-tetrahydro-1,7-naphthyridine-2-carboxylate Ethyl-4-chloro-7-((2-(difluoromethoxy)pyridin-4-yl)methyl)-5,6,7,8-tetrahydro-1,7-naphthyridine-2-carboxylate (200 mg, 0.503 mmol), 4,4,4',4',5,5,5',5'-octamethyl-2,2'-bi(1,3,2-dioxaborolane) (319 mg, 1.257 mmol), potassium acetate (123 mg, 1.257 mmol), PdCl$_2$(dppf) (36.8 mg, 0.050 mmol) were mixed in dioxane (6 mL), the resulting solution was stirred at 110° C. overnight. The reaction was diluted with water (5 mL) and extracted with ethyl acetate (3*20 mL). The combined organic fractions were washed with water (10 mL), dried with anhydrous Na$_2$SO$_4$, filtered and concentrated in vacuo. The residue was purified by silica gel column chromatography (eluting with ethyl acetate/petroleum ether=5:1) to obtain the title compound as an oil. MS (ESI) Calc'd for (C$_{24}$H$_{30}$BF$_2$N$_3$O$_5$) [M+H]$^+$, 490.4; found 490.4.

Intermediate CR1-3A and CR1-3B

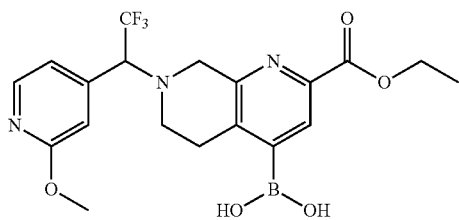 [SMILES: CCOC(=O)c1cc(B(O)O)c2c(n1)CN(C(c1ccnc(OC)c1)C(F)(F)F)CC2]

(S) and (R)-2-(ethoxycarbonyl)-7-(2,2,2-trifluoro-1-(2-methoxypyridin-4-yl)ethyl)-5,6,7,8-tetrahydro-1,7-naphthyridin-4-ylboronic Acid

Step 1: Ethyl 4-chloro-7-(2,2,2-trifluoro-1-(2-methoxypyridin-4-yl)ethyl)-5,6,7,8-tetrahydro-1,7-naphthyridine-2-carboxylate To a solution of 2,2,2-trifluoro-1-(2-methoxypyridin-4-yl) ethyl trifluoromethanesulfonate (4.2 g, 12.5 mmol) in THF (18 ml) was added DIPEA (2.4 g) and ethyl 4-chloro-5,6,7,8-tetrahydro-1,7-naphthyridine-2-carboxylate (3 g, 12.5 mmol, dissolved in 5 mL of THF). The reaction mixture was heated to 70° C. and stirred overnight. The reaction was allowed to cool to room temperature. Solvent was evaporated and the crude residue was extracted with ethyl acetate (50 mL×3). The combined organic layers were washed with brine (20 mL*2), dried over MgSO$_4$, filtered and evaporated. The residue was purified by silica gel chromatography (petroleum ether:EtOAc=6:1) to afford the product as an oil. MS (ESI) calc'd for (C$_{19}$H$_{19}$ClF$_3$N$_3$O$_3$) [M+H]$^+$, 430.1; found, 430.0.

Step 2: (S) and (R)-2-(ethoxycarbonyl)-7-(2,2,2-trifluoro-1-(2-methoxypyridin-4-yl)ethyl)-5,6,7,8-tetrahydro-1,7-naphthyridin-4-ylboronic Acid To a solution of ethyl 4-chloro-7-(2,2,2-trifluoro-1-(2-methoxypyridin-4-yl)ethyl)-5,6,7,8-tetrahydro-1,7-naphthyridine-2-carboxylate (850 mg, 2 mmol) in 1,4-dioxane (8 ml) was added 4,4,4',4',5,5,5',5'-octamethyl-2,2'-bi(1,3,2-dioxaborolane) (1 g, 4 mmol), KOAc (392 mg, 4 mmol) and Pd(dppf)Cl$_2$ (146 mg, 0.2 mmol). The reaction was warmed to 100° C. under N$_2$ and stirred overnight. The reaction mixture was cooled to room temperature, the solution was filtered through silica gel and the filtrate was purified by reverse phase preparative HPLC to afford the title compound which was used without further purification. MS (ESI) calc'd for (C$_{19}$H$_{21}$BF$_3$N$_3$O$_5$) [M+H]$^+$, 440.1; found, 439.9.

Intermediate CR1-4

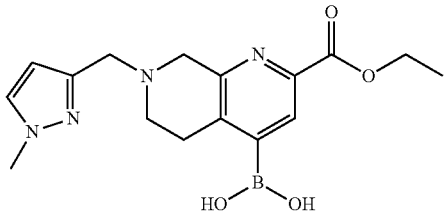 [SMILES: CCOC(=O)c1cc(B(O)O)c2c(n1)CN(Cc1ccn(C)n1)CC2]

2-(ethoxycarbonyl)-7-((1-methyl-1H-pyrazol-3-yl)methyl)-5,6,7,8-tetrahydro-1,7-naphthyridin-4-ylboronic Acid

Step 1: 5-(chloromethyl)-1-methyl-1H-pyrazole

A mixture of 1-methyl-1H-pyrazole-5-carboxylic acid (1.0 g, 7.93 mmol), BH$_3$.DMS (39.6 mL, 79 mmol) in THF (40 mL) was stirred at reflux overnight. The mixture was diluted with MeOH (30 mL) and stirred for 30 min, and the mixture was concentrated in vacuo. The residue was purified by silica gel column chromatography, eluting with CH$_2$Cl$_2$/MeOH. The residue was dissolved in DCM (20 mL) and to the solution was added SOCl$_2$ (5 mL, 68.5 mmol) at room temperature. The mixture was stirred for 3 h then concentrated to afford the product as an oil which was used in the next step without further purification. MS (ESI) calc'd for (C$_5$H$_7$ClN$_2$) [M+H]$^+$, 131.0, found, 131.0;

Step 2: Ethyl 4-chloro-7-((1-methyl-1H-pyrazol-3-yl)methyl)-5,6,7,8-tetrahydro-1,7-naphthyridine-2-carboxylate A mixture of 5-(chloromethyl)-1-methyl-1H-pyrazole (466 mg, 3.57 mmol), ethyl 4-chloro-5,6,7,8-tetrahydro-1,7-naphthyridine-2-carboxylate (500 mg, 2.077 mmol), K$_2$CO$_3$ (861 mg, 6.23 mmol) and acetonitrile (20 mL) was stirred at 80° C. overnight, The mixture was cooled, diluted with ethyl acetate (60 mL), washed with brine (saturated, 3×20 mL), dried (Na$_2$SO$_4$), filtered and the solvent was evaporated under reduced pressure. The residue was purified by silica gel column chromatography, eluting with CH$_2$Cl$_2$/MeOH to give the product as a solid. MS (ESI) calc'd for (C$_{16}$H$_{19}$ClN$_4$O$_2$) [M+H]$^+$, 335.1, found, 335.1;

Step 3: 2-(ethoxycarbonyl)-7-((1-methyl-1H-pyrazol-3-yl)methyl)-5,6,7,8-tetrahydro-1,7-naphthyridin-4-ylboronic Acid A mixture of ethyl 4-chloro-7-((1-methyl-1H-pyrazol-3-yl)methyl)-5,6,7,8-tetrahydro-1,7-naphthyridine-2-carboxylate (400 mg, 1.195 mmol),4,4,4',4',5,5,5',5'-octamethyl-2,2'-bi(1,3,2-dioxaborolane) (607 mg, 2.389 mmol), PdCl$_2$(dppf) (87 mg, 0.119 mmol), KOAc (352 mg, 3.58 mmol)

and 1,4-dioxane (15 mL) was stirred at 100° C. under N₂ overnight. The mixture was concentrated in vacuo. The residue was purified by silica gel column chromatography, eluting with EtOAc/MeOH to give the title compound as a solid. MS (ESI) calc'd for (C₁₆H₂₁BN₄O₄) [M+H]⁺, 345.2, found, 345.2.

Intermediate CR1-5

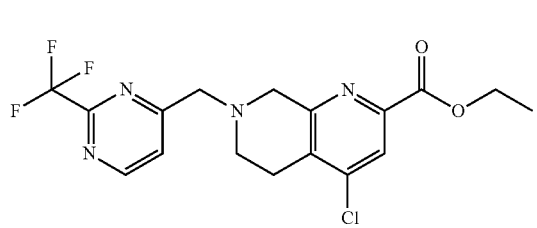 [SMILES: CCOC(=O)c1cc(Cl)c2c(n1)CN(Cc1ccnc(C(F)(F)F)n1)CC2]

Ethyl 4-chloro-7-((2-(trifluoromethyl)pyrimidin-4-yl)methyl)-5,6,7,8-tetrahydro-1,7-naphthyridine-2-carboxylate (2-(Trifluoromethyl)pyrimidin-4-yl)methanol (340 mg, 1.911 mmol) was placed under nitrogen in anhydrous DCM (8.0 ml). The reaction mixture was cooled to 0° C., and Dess-Martin Periodinane (1054 mg, 2.485 mmol) was added in one portion. The ice bath was removed and the reaction was allowed to stir at room temperature. After 30 min, the mixture was cooled to 0° C. To the reaction mixture was added ethyl 4-chloro-5,6,7,8-tetrahydro-1,7-naphthyridine-2-carboxylate (460 mg, 1.911 mmol) and sodium triacetoxyhydroborate (1013 mg, 4.78 mmol). The ice bath was removed and the mixture was allowed to stir at room temperature. After 1 hour, the mixture was quenched with a 1:1 mixture of 10% aqueous Na2S2O3 and saturated aqueous sodium bicarbonate (60 ml). The mixture was extracted with ethyl acetate (2×80 ml). The combined organic layers were washed with saturated aqueous sodium bicarbonate (50 ml), then dried over sodium sulfate and concentrated under reduced pressure. The resultant oil was chromatographed using a 40 g silica gel cartridge eluted with 0-100% ethyl acetate in hexanes over 25 column volumes. The product fractions were combined, concentrated under reduced pressure, and dried under high vacuum to provide the title compound as an oily film. LC-MS: calculated for C17H16ClF3N4O2 400.09, observed m/e: 401.32 (M+H)+.

Intermediate CR1-6

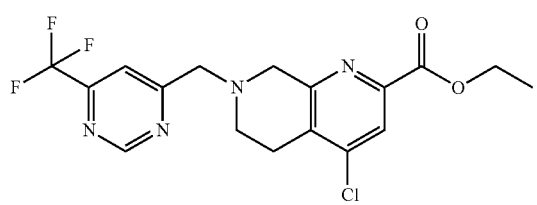 [SMILES: CCOC(=O)c1cc(Cl)c2c(n1)CN(Cc1cc(C(F)(F)F)ncn1)CC2]

Ethyl 4-chloro-7-((6-(trifluoromethyl)pyrimidin-4-yl)methyl)-5,6,7,8-tetrahydro-1,7-naphthyridine-2-carboxylate The title compound was prepared from (6-(trifluoromethyl)pyrimidin-4-yl)methanol according to the protocol outlined for Intermediate CR1-5. LC-MS: calculated for C₁₇H₁₆ClF₃N₄O₂ 400.09, observed m/e: 401.33 (M+H)+.

Intermediate CR2-1

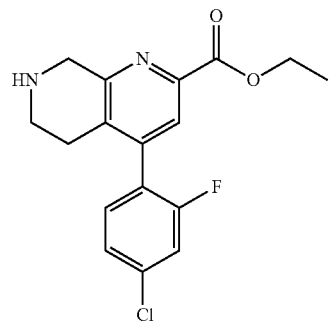 [SMILES: CCOC(=O)c1cc(-c2ccc(Cl)cc2F)c2c(n1)CNCC2]

Ethyl 4-(4-chloro-2-fluorophenyl)-5,6,7,8-tetrahydro-1,7-naphthyridine-2-carboxylate Ethyl 4-chloro-5,6,7,8-tetrahydro-1,7-naphthyridine-2-carboxylate (2000 mg, 8.31 mmol), (4-chloro-2-fluorophenyl)boronic acid (1811 mg, 10.39 mmol), and potassium fluoride (1448 mg, 24.93 mmol) were placed under nitrogen in 2-methyl THF (25.0 ml) and water (2.5 ml). The reaction mixture was degassed with vacuum while cooling in a dry-ice/acetone bath, then nitrogen was introduced (3×). Chloro[(tri-tert-butylphosphine)-2-(2-aminobiphenyl)]palladium (II) (213 mg, 0.415 mmol) was added to the mixture. The reaction was degassed again with vacuum while cooling in a dry-ice/acetone bath, then nitrogen was introduced (2×). The ice-bath was removed and mixture was heated to 60° C. After 16 h, the mixture was allowed to cool to room temperature, poured into saturated aqueous sodium bicarbonate (40 ml) and extracted with ethyl acetate (2×75 ml). The combined organic layers were washed with brine (50 ml), dried over sodium sulfate, and concentrated under reduced pressure. The resultant oil was chromatographed using a Waters Sunfire C18 column (30×150 mm) eluted with 10-90% MeCN in water (both with 0.05% TFA) over 12 min at 30 ml/min. The product fractions were converted to the free-base by stirring with saturated aqueous sodium bicarbonate and extracting with ethyl acetate. The organic layer was concentrated under reduced pressure, then dried under high vacuum to provide the title compound as an oily solid. LC-MS: calculated for C₁₇H₁₆ClFN₂O₂ 334.09, observed m/e: 335.27 (M+H)+.

The following examples in Table CR2-1 were prepared in an analogous manner to that described for intermediate CR2-1 using the coupling conditions noted and using commercial aryl boronates or amines; or aryl boronates or amines described in the intermediates section.

TABLE 6-1

| Intermediate Number | Structure | Conditions | IUPAC Name |
|---|---|---|---|
| CR2-2 | 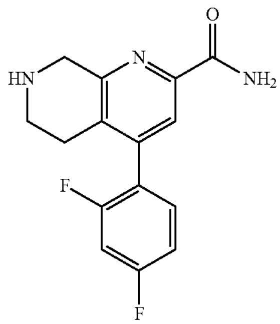 [SMILES: NC(=O)c1cc(-c2ccc(F)cc2F)c2c(n1)CNCC2] | Pd(dppf)Cl₂/K₂CO3/ Dioxane/H₂O | 4-(2,4-difluorophenyl)-5,6,7,8-tetrahydro-1,7-naphthyridine-2-carboxamide |
| CR2-3 | 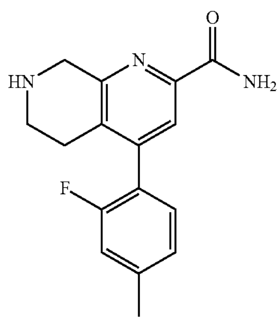 [SMILES: Cc1ccc(-c2cc(C(N)=O)nc3c2CCNC3)c(F)c1] | Pd(dppf)Cl₂/K₂CO₃/ Dioxane/H₂O | 4-(2-fluoro-4-methylphenyl)-5,6,7,8-tetrahydro-1,7-naphthyridine-2-carboxamide |
| CR2-4 | 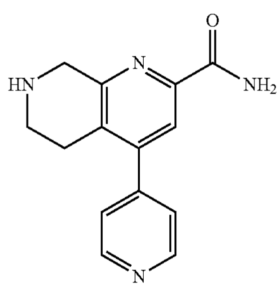 [SMILES: NC(=O)c1cc(-c2ccncc2)c2c(n1)CNCC2] | Pd(dppf)Cl₂/K₃PO₄/ THF/H₂O | Pd2(dba)3/PCy3/K3PO4/THF/H2O |
| CR2-5 | 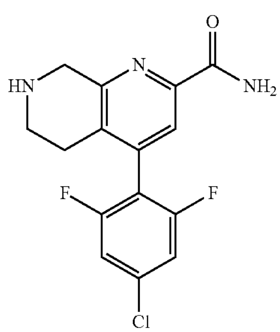 [SMILES: NC(=O)c1cc(-c2c(F)cc(Cl)cc2F)c2c(n1)CNCC2] | 2nd-xphos-precatalyst/ K₂CO₃/THF/H₂O | 4-(4-chloro-2,6-difluorophenyl)-5,6,7,8-tetrahydro-1,7-naphthyridine-2-carboxamide |
| CR2-6 | 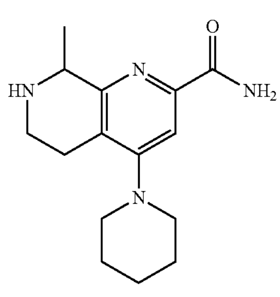 [SMILES: CC1NCCc2c(N3CCCCC3)cc(C(N)=O)nc21] | (RUPHOS) Pd (II) Phenethylamine/Cs₂CO₃/dioxane | (S) and (R)-8-methyl-4-(piperidin-1-yl)-5,6,7,8-tetrahydro-1,7-naphthyridine-2-carboxamide |

TABLE 6-1-continued

| Intermediate Number | Structure | Conditions | IUPAC Name |
|---|---|---|---|
| CR2-7 | 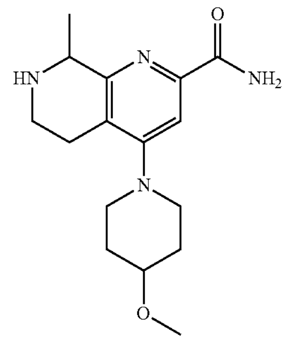 [SMILES: COC1CCN(c2cc(C(N)=O)nc3c2CCNC3C)CC1] | RUPHOS) Pd (II) Phenethylamine/Cs$_2$CO$_3$/dioxane | (S) and (R)-4-(4-methoxypiperidin-1-yl)-8-methyl-5,6,7,8-tetrahydro-1,7-naphthyridine-2-carboxamide |
| CR2-8 | 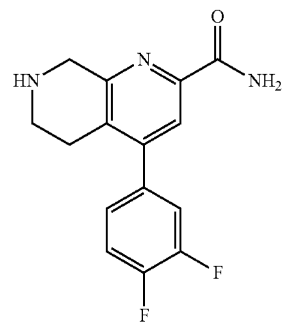 [SMILES: NC(=O)c1cc(-c2ccc(F)c(F)c2)c2c(n1)CNCC2] | Pd(dppf)Cl$_2$/K$_2$CO$_3$/Dioxane/H$_2$O | 4-(3,4-difluorophenyl)-5,6,7,8-tetrahydro-1,7-naphthyridine-2-carboxamide |
| CR2-9 | 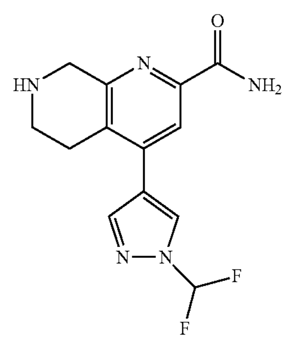 [SMILES: NC(=O)c1cc(-c2cnn(C(F)F)c2)c2c(n1)CNCC2] | Pd(dppf)Cl$_2$/K$_2$CO$_3$/dioxane/H$_2$O | 4-(1-(difluoromethyl)-1H-pyrazol-4-yl)-5,6,7,8-tetrahydro-1,7-naphthyridine-2-carboxamide |
| CR2-10 | 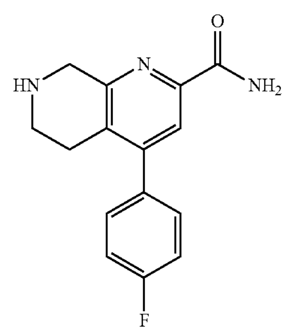 [SMILES: NC(=O)c1cc(-c2ccc(F)cc2)c2c(n1)CNCC2] | Pd(dppf)Cl$_2$/K$_2$CO$_3$/Dioxane/H$_2$O | 4-(4-fluorophenyl)-5,6,7,8-tetrahydro-1,7-naphthyridine-2-carboxamide |

TABLE 6-1-continued

| Intermediate Number | Structure | Conditions | IUPAC Name |
| --- | --- | --- | --- |
| CR2-11 | 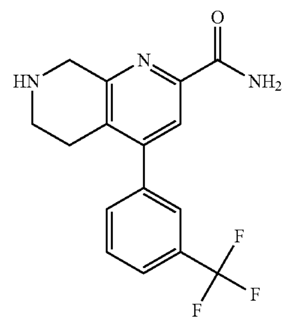 [SMILES: NC(=O)c1cc(-c2cccc(C(F)(F)F)c2)c2c(n1)CNCC2] | Pd(dppf)Cl$_2$/K$_2$CO$_3$/ Dioxane/H$_2$O | 4-(3-(trifluoromethyl)phenyl)-5,6,7,8-tetrahydro-1,7-naphthyridine-2-carboxamide |
| CR2-12 | 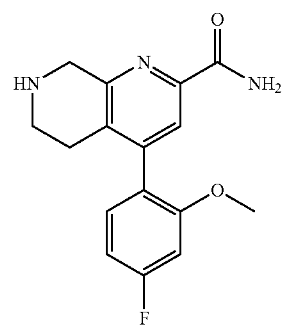 [SMILES: COc1cc(F)ccc1-c1cc(C(N)=O)nc2c1CCNC2] | Pd(dppf)Cl$_2$/K$_2$CO$_3$/ Dioxane/H$_2$O | 4-(4-fluoro-2-methoxyphenyl)-5,6,7,8-tetrahydro-1,7-naphthyridine-2-carboxamide |
| CR2-13 | 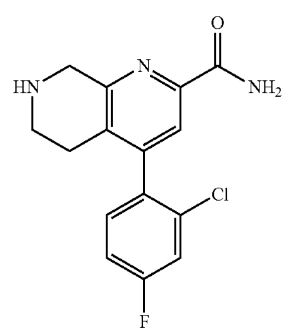 [SMILES: NC(=O)c1cc(-c2ccc(F)cc2Cl)c2c(n1)CNCC2] | Pd(dppf)Cl$_2$/K$_3$PO$_4$/ THF/H$_2$O | 4-(2-chloro-4-fluorophenyl)-5,6,7,8-tetrahydro-1,7-naphthyridine-2-carboxamide |
| CR2-14 | 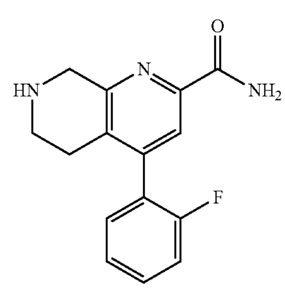 [SMILES: NC(=O)c1cc(-c2ccccc2F)c2c(n1)CNCC2] | Pd(dppf)Cl$_2$/K$_2$CO$_3$/ Dioxane/H$_2$O | 4-(2-fluorophenyl)-5,6,7,8-tetrahydro-1,7-naphthyridine-2-carboxamide |
| CR2-15 | 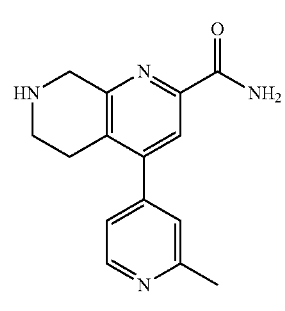 [SMILES: Cc1cc(-c2cc(C(N)=O)nc3c2CCNC3)ccn1] | Pd(dppf)Cl$_2$/K$_2$CO$_3$/ Toluene/H$_2$O | 4-(2-methylpyridin-4-yl)-5,6,7,8-tetrahydro-1,7-naphthyridine-2-carboxamide |

TABLE 6-1-continued

| Intermediate Number | Structure | Conditions | IUPAC Name |
| --- | --- | --- | --- |
| CR2-16 | 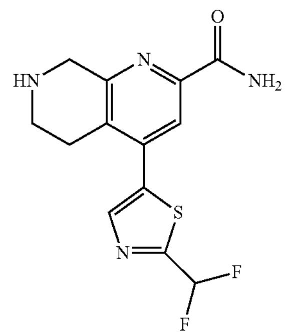 [SMILES: NC(=O)c1cc(-c2cnc(C(F)F)s2)c2c(n1)CNCC2] | Pd(Pt-Bu₃)₂/KF/dioxane | 4-(2-(difluoromethyl)thiazol-5-yl)-5,6,7,8-tetrahydro-1,7-naphthyridine-2-carboxamide |
| CR2-17 | 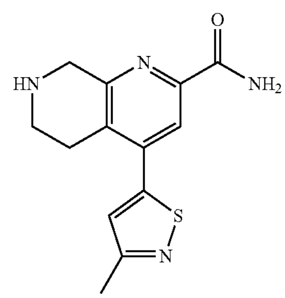 [SMILES: Cc1cc(-c2cc(C(N)=O)nc3c2CCNC3)sn1] | Pd(Pt-Bu₃)₂/KF/dioxane | 4-(3-methylisothiazol-5-yl)-5,6,7,8-tetrahydro-1,7-naphthyridine-2-carboxamide |
| CR2-18 | 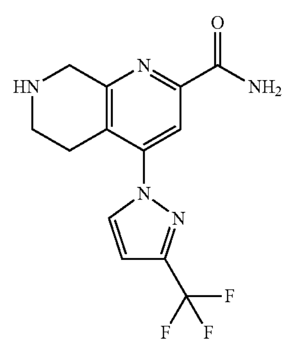 [SMILES: NC(=O)c1cc(-n2ccc(C(F)(F)F)n2)c2c(n1)CNCC2] | Pd(Pt-Bu₃)₂/K₃PO₄/DM | 4-(3-(trifluoromethyl)-1H-pyrazol-1-yl)-5,6,7,8-tetrahydro-1,7-naphthyridine-2-carboxamide |
| CR2-19 | 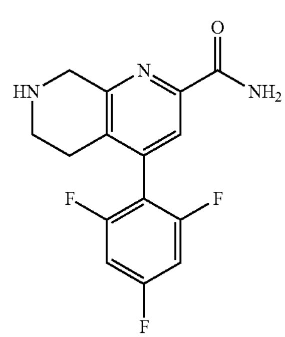 [SMILES: NC(=O)c1cc(-c2c(F)cc(F)cc2F)c2c(n1)CNCC2] | 2nd-xphos-precatalyst/ K₂CO₃/THF/H₂O | 4-(2,4,6-trifluorophenyl)-5,6,7,8-tetrahydro-1,7-naphthyridine-2-carboxamide |

TABLE 6-1-continued

| Intermediate Number | Structure | Conditions | IUPAC Name |
|---|---|---|---|
| CR2-20 | 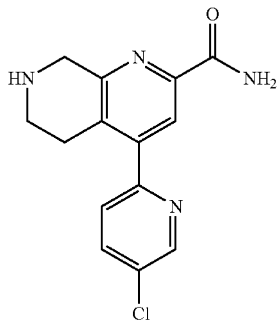 [SMILES: NC(=O)c1cc(-c2ccc(Cl)cn2)c2c(n1)CNCC2] | Pd(dppf)Cl$_2$/K2CO$_3$/ Toluene/H$_2$O | 4-(5-chloropyridin-2-yl)-5,6,7,8-tetrahydro-1,7-naphthyridine-2-carboxamide |
| CR2-21 | 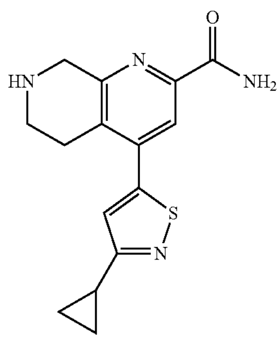 [SMILES: NC(=O)c1cc(-c2cc(C3CC3)ns2)c2c(n1)CNCC2] | Pd(Pt-Bu$_3$)$_2$/KF/dioxane | 4-(3-cyclopropylisothiazol-5-yl)-5,6,7,8-tetrahydro-1,7-naphthyridine-2-carboxamide |
| CR2-22 | 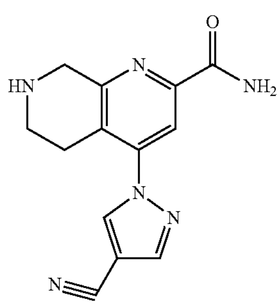 [SMILES: N#Cc1cnn(-c2cc(C(N)=O)nc3c2CCNC3)c1] | Pd(Pt-Bu$_3$)$_2$/K$_3$PO$_4$/DMF | 4-(4-cyano-1H-pyrazol-1-yl)-5,6,7,8-tetrahydro-1,7-naphthyridine-2-carboxamide |
| CR2-23 | 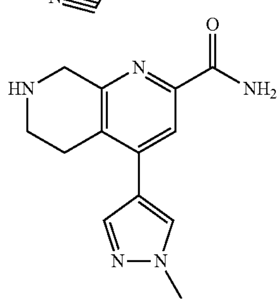 | Pd(dppf)Cl$_2$/K$_2$CO$_3$/ Toluene/H$_2$O | 4-(1-methyl-1H-pyrazol-4-yl)-5,6,7,8-tetrahydro-1,7-naphthyridine-2-carboxamide |
| CR2-24 | 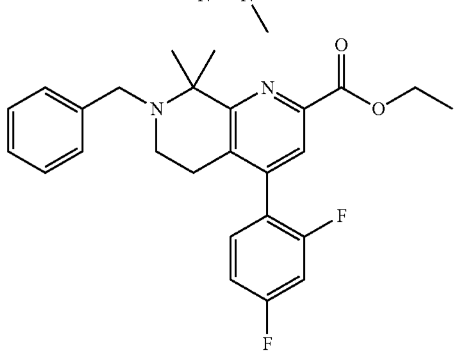 | Pd(dppf)Cl$_2$/K$_2$CO$_3$/ Dioxane/H$_2$O | 7-benzyl-4-(2,4-difluorophenyl)-8,8-dimethyl-5,6,7,8-tetrahydro-1,7-naphthyridine-2-carboxylate |

Intermediate CR2-25

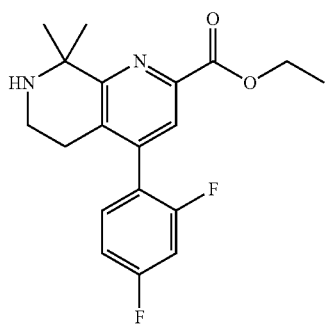 [SMILES: CCOC(=O)c1cc(-c2ccc(F)cc2F)c2c(n1)C(C)(C)NCC2]

Step 1: 7-benzyl-4-(2,4-difluorophenyl)-8,8-dimethyl-5,6,7,8-tetrahydro-1,7-naphthyridine-2-carboxylate A mixture of ethyl 7-benzyl-4-chloro-8,8-dimethyl-5,6,7,8-tetrahydro-1,7-naphthyridine-2-carboxylate (380 mg, 1.059 mmol), (2,4-difluorophenyl)boronic acid (217 mg, 1.377 mmol) and $K_2CO_3$ (439 mg, 3.18 mmol) in 1,4-dioxane (5 mL) and water (1 mL) was degassed and backfilled with $N_2$ (three times), then $PdCl_2(dppf)$ (77 mg, 0.106 mmol) was added. The mixture was degassed and backfilled with $N_2$ (three times) and heated to 100° C. for 2 h. Saturated aqueous NaCl (20 mL) was added, and the mixture was extracted with EtOAc (3×20 mL). The organic layers were washed with saturated aqueous NaCl (20 mL), dried over sodium sulfate, filtered and concentrated in vacuo. The crude product was purified by column chromatography on silica gel eluting with (petroleum ether:ethyl acetate=10:1) to give ethyl 7-benzyl-4-(2,4-difluorophenyl)-8,8-dimethyl-5,6,7,8-tetrahydro-1,7-naphthyridine-2-carboxylate as an orange solid. MS (ESI) calcd. for ($C_{26}H_{27}F_2N_2O_2$) [M+H]+, 437.2, found, 437.2.

Step 2: ethyl 4-(2,4-difluorophenyl)-8,8-dimethyl-5,6,7,8-tetrahydro-1,7-naphthyridine-2-carboxylate To a solution of ethyl 7-benzyl-4-(2,4-difluorophenyl)-8,8-dimethyl-5,6,7,8-tetrahydro-1,7-naphthyridine-2-carboxylate (300 mg, 0.687 mmol) in MeOH (15 mL) was added Pd—C (73.1 mg, 0.069 mmol, 10%). The mixture was stirred under $H_2$ atmosphere (50 psi) at 50° C. for 2 h. The reaction mixture was filtered and concentrated in vacuo to furnish the title compound as a yellow oil which was used without further purification. MS (ESI) calcd. for ($C_{19}H_{21}F_2N_2O_2$) [M+H]$^+$, 347.1, found, 347.2.

Scheme 1

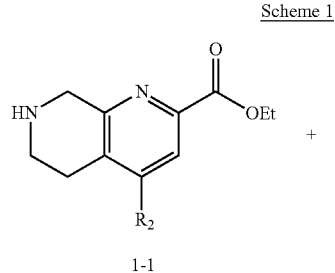

1-1

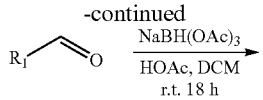

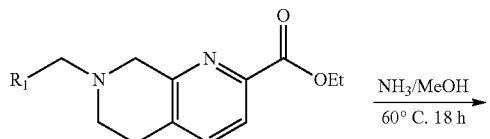

1-2

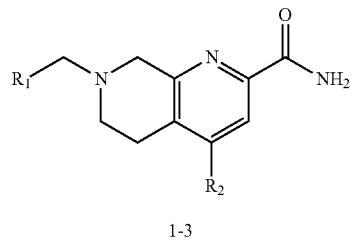

1-3

Compounds of formula 1 are prepared by the reductive amination of an aldehyde and amines 1-1 followed by treatment with ammonia

Example 1-1A and 1-1B

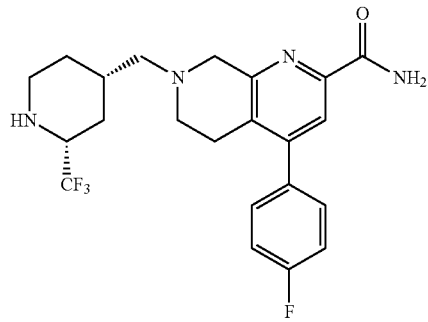

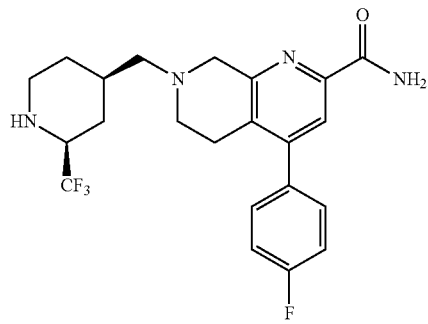

4-(4-fluorophenyl)-7-(((2R,4S)-2-(trifluoromethyl) piperidin-4-yl)methyl)-5,6,7,8-tetrahydro-1,7-naphthyridine-2-carboxamide and 4-(4-fluorophenyl)-7-(((2S,4R)-2-(trifluoromethyl)piperidin-4-yl)methyl)-5,6,7,8-tetrahydro-1,7-naphthyridine-2-carboxamide Step 1: Ethyl 4-(4-fluorophenyl)-7-((2-(trifluoromethyl)piperidin-4-yl)methyl)-5,6,7,8-tetrahydro-1,7-naphthyridine-2-carboxylate 2-(trifluoromethyl)piperidine-4-carbaldehyde (70 mg, 0.386 mmol) and AcOH (0.07 mL, 1.199 mmol) were added to a stirred, cooled 0° C. mixture of ethyl 4-(4-fluorophenyl)-5,6,7,8-tetrahydro-1,7-naphthyridine-2-carboxylate (100 mg, 0.333 mmol) in DCM (1.6 mL) and the mixture was stirred at 0° C. for 1 h. NaBH(OAc)$_3$ (141 mg, 0.666 mmol) was added to the reaction mixture and stirred at room temperature for 18 h. Saturated aqueous sodium hydrogen carbonate (10 mL) was added dropwise. The mixture was extracted with ethyl acetate (3×30 mL). The combined organic fractions were washed with brine (20 mL), dried (Na$_2$SO$_4$), filtered and the solvent was evaporated under reduced pressure to obtain the desired compound ethyl4-(4-fluorophenyl)-7-((2-(trifluoromethyl)piperidin-4-yl)methyl)-5,6,7,8-tetrahydro-1,7-naphthyridine-2-carboxylate as an oil which was used in the next step without further purification. MS (ESI) calc'd for (C$_{24}$H$_{27}$F$_4$N$_3$O$_2$) [M+H]$^+$, 466.2; found, 466.2.

Step 2: 4-(4-fluorophenyl)-7-(((2R,4S)-2-(trifluoromethyl)piperidin-4-yl)methyl)-5,6,7,8-tetrahydro-1,7-naphthyridine-2-carboxamide and 4-(4-fluorophenyl)-7-(((2S,4R)-2-(trifluoromethyl)piperidin-4-yl)methyl)-5,6,7,8-tetrahydro-1,7-naphthyridine-2-carboxamide Ethyl 4-(4-fluorophenyl)-7-((2-(trifluoromethyl)piperidin-4-yl)methyl)-5,6,7,8-tetrahydro-1,7-naphthyridine-2-carboxylate (80 mg, 0.172 mmol) and ammonia (2 ml, 7M in MeOH) were combined in a sealed tube at 0° C. The resulting mixture was stirred at 60° C. for 18 h. the solvent was removed in vacuo, The residue was purified by reverse phase preparative HPLC eluting with acetonitrile/water+ 0.05% NH$_3$, to give the title compounds as a solid, MS (ESI) calc'd for (C$_{22}$H$_{24}$F$_4$N$_4$O) [M+H]$^+$, 437.2; found, 437.2. $^1$H NMR (400 MHz, CDCl3) ä 7.93 (s, 1H), 7.84 (s, 1H), 7.32 (dd, J=7.8, 5.6 Hz, 2H), 7.14 (t, J=8.4 Hz, 2H), 5.93 (s, 1H), 3.84-3.71 (m, 2H), 3.24 (d, J=11.5 Hz, 1H), 3.20-3.10 (m, 1H), 2.83 (t, J=5.3 Hz, 2H), 2.75-2.61 (m, 3H), 2.51-2.40 (m, 2H), 2.07 (d, J=13.2 Hz, 1H), 1.82 (d, J=12.7 Hz, 2H), 1.27-1.06 (m, 2H).

Example 1-2A and 1-2B

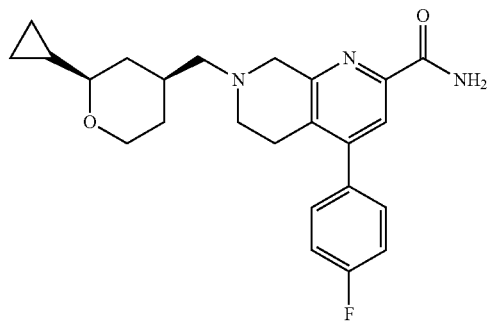

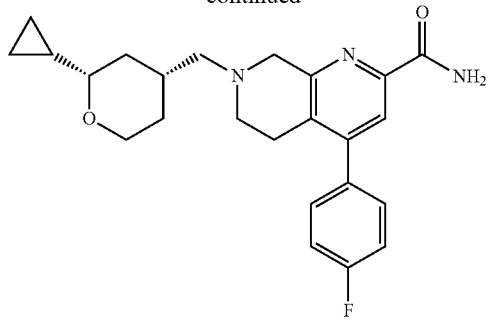

7-(((2S,4R)-2-cyclopropyltetrahydro-2H-pyran-4-yl) methyl)-4-(4-fluorophenyl)-5,6,7,8-tetrahydro-1,7-naphthyridine-2-carboxamide and 7-(((2R,4S)-2-cyclopropyltetrahydro-2H-pyran-4-yl)methyl)-4-(4-fluorophenyl)-5,6,7,8-tetrahydro-1,7-naphthyridine-2-carboxamide The title compounds were prepared from 2-cyclopropyltetrahydro-2H-pyran-4-carbaldehyde according to the protocol outlined for Example 1-1. MS (ESI) calc'd for (C$_{24}$H$_{28}$FN$_3$O$_2$) [M+H]$^+$, 410.2; found, 410.2. $^1$H NMR (400 MHz, CDCl3) δ 7.92 (s, 1H), 7.82 (d, J=3.4 Hz, 1H), 7.32 (dd, J=8.5, 5.4 Hz, 2H), 7.14 (t, J=8.6 Hz, 2H), 5.65 (brs, 1H), 4.06 (dd, J=11.3, 4.1 Hz, 1H), 3.77 (s, 2H), 3.40 (t, J=11.1 Hz, 1H), 2.83 (t, J=5.5 Hz, 2H), 2.67 (t, J=5.6 Hz, 2H), 2.60 (t, J=9.4 Hz, 1H), 2.42 (d, J=7.0 Hz, 2H), 1.96-1.81 (m, 2H), 1.69 (d, J=13.0 Hz, 1H), 1.28 (qd, J=12.5, 4.6 Hz, 1H), 1.12 (q, J=11.7 Hz, 1H), 0.96-0.84 (m, 1H), 0.59-0.43 (m, 2H), 0.36 (td, J=9.4, 4.8 Hz, 1H), 0.19 (td, J=9.4, 4.8 Hz, 1H).

Example 1-3A and 1-3B

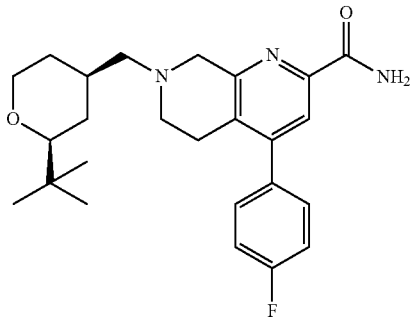

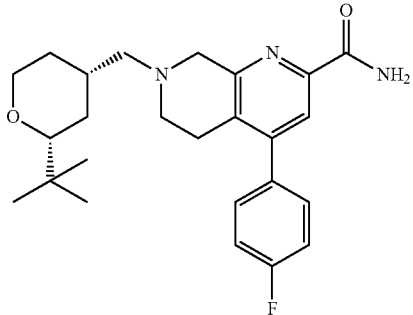

7-(((2S,4R)-2-(tert-butyl)tetrahydro-2H-pyran-4-yl) methyl)-4-(4-fluorophenyl)-5,6,7,8-tetrahydro-1,7-naphthyridine-2-carboxamide and 7-(((2R,4S)-2-(tert-butyl)tetrahydro-2H-pyran-4-yl)methyl)-4-(4-fluorophenyl)-5,6,7,8-tetrahydro-1,7-naphthyridine-2-carboxamide The title compounds were prepared from 2-tert-butyltetrahydro-2H-pyran-4-carbaldehyde according to the protocol outlined for Example 1-1. MS (ESI) calc'd for (C$_{25}$H$_{32}$FN$_3$O$_2$) [M+H]$^+$, 426.2; found, 426.2. $^1$H NMR (400 MHz, DMSO) δ 7.96 (s, 1H), 7.69 (s, 1H), 7.64 (s, 1H), 7.55-7.48 (m, 2H), 7.32 (m, 2H), 3.95 (dd, J=11.1, 4.0 Hz, 1H), 3.71 (s, 2H), 3.39-3.29 (m, 2H), 2.89 (d, J=11.0 Hz, 1H), 2.73 (m, 2H), 2.69-2.54 (m, 2H), 2.36 (d, J=6.9 Hz, 2H), 1.86 (s, 1H), 1.67 (m, 2H), 1.14-0.98 (m, 1H), 0.85 (s, 9H).

Example 1-4

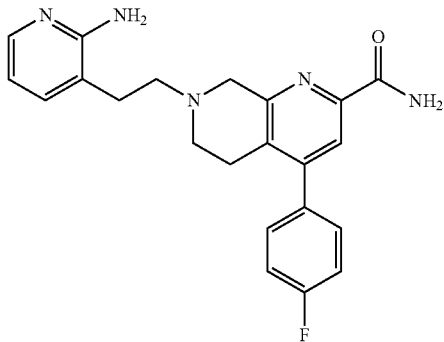 [SMILES: NC(=O)c1cc(-c2ccc(F)cc2)c2c(n1)CN(CCc1cccnc1N)CC2]

7-(2-(2-aminopyridin-3-yl)ethyl)-4-(4-fluorophenyl)-5,6,7,8-tetrahydro-1,7-naphthyridine-2-carboxamide The title compound was prepared from 2-(2-bromopyridin-3-yl)acetaldehyde according to the protocol outlined outlined for Example 1-1. MS (ESI) calc'd for (C$_{22}$H$_{22}$FN$_5$O) [M+H]$^+$, 392.2, found, 392.2; $^1$H NMR (400 MHz, CDCl$_3$) δ 7.95 (s, 2H), 7.81 (s, 1H), 7.39-7.28 (m, 3H), 7.16 (t, J=8.6 Hz, 2H), 6.70-6.54 (m, 1H), 5.63 (s, 1H), 5.21 (s, 2H), 3.90 (s, 2H), 2.93-2.68 (m, 8H).

Example 1-5A and 1-5B

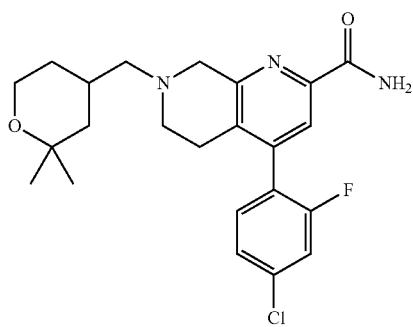

(R) and (S)-4-(4-chloro-2-fluorophenyl)-7-((2,2-dimethyltetrahydro-2H-pyran-4-yl)methyl)-5,6,7,8-tetrahydro-1,7-naphthyridine-2-carboxamide and (S)-4-(4-chloro-2-fluorophenyl)-7-((2,2-dimethyltetrahydro-2H-pyran-4-yl)methyl)-5,6,7,8-tetrahydro-1,7-naphthyridine-2-carboxamide Step 1: Ethyl 4-(4-chloro-2-fluorophenyl)-7-((2,2-dimethyltetrahydro-2H-pyran-4-yl) methyl)-5,6,7,8-tetrahydro-1,7-naphthyridine-2-carboxylate A mixture of ethyl 4-(4-chloro-2-fluorophenyl)-5,6,7,8-tetrahydro-1,7-naphthyridine-2-carboxylate hydrochloride (420 mg, 1.255 mmol), 2,2-dimethyltetrahydro-2H-pyran-4-carbaldehyde (214 mg, 1.505 mmol), NaHB(OAc)$_3$ (798 mg, 3.76 mmol) and dichloroethane (10 mL) was stirred at 15° C. for 4 h. The reaction was quenched with water (10 mL) and extracted with DCM (20 mL*2). The combined organics were washed with brine (30 mL), dried over anhydrous Na$_2$SO$_4$, filtered and concentrated. The residue was purified by silica gel column chromatography eluting with 50-60% EtOAc/petroleum ether to give the product as a solid. MS (ESI) calcd. for (C$_{25}$H$_{31}$ClFN$_2$O$_3$) [M+H]$^+$, 461.2, found, 461.2. $^1$H NMR (400 MHz, CDCl$_3$) δ 7.81 (s, 1H), 7.06-7.31 (m, 3H), 4.46 (q, J=6.78 Hz, 2H), 3.57-3.97 (m, 4H), 2.68 (d, J=14.48 Hz, 4H), 2.35 (t, J=7.43 Hz, 2H), 1.98-2.10 (m, 1H), 1.65 (t, J=16.04 Hz, 2H), 1.40 (t, J=7.04 Hz, 3H), 0.93-1.28 (m, 8H).

The racemic ethyl 4-(4-chloro-2-fluorophenyl)-7-((2,2-dimethyltetrahydro-2H-pyran-4-yl)methyl)-5,6,7,8-tetrahydro-1,7-naphthyridine-2-carboxylate (0.33 g, 0.68 mmol) was resolved by Chiral SFC (Column: IC 250×4.6 mm I.D., 5 um; Mobile phase: IPA (0.05% DEA) in CO$_2$ from 5% to 40%; Flow rate: 2.5 mL/min) to give a faster eluting enantiomer (RT=4.09 min) and a slower moving enantiomer (RT=4.52 min).

Step 2A: (R) or (S)-4-(4-chloro-2-fluorophenyl)-7-((2,2-dimethyltetrahydro-2H-pyran-4-yl)methyl)-5,6,7,8-tetrahydro-1,7-naphthyridine-2-carboxamide A mixture of ethyl 4-(4-chloro-2-fluorophenyl)-7-((2,2-dimethyltetrahydro-2H-pyran-4-yl)methyl)-5,6,7,8-tetrahydro-1,7-naphthyridine-2-carboxylate (faster moving enantiomer) (130 mg, 0.28 mmol) and NH$_3$/MeOH (10 mL, 10 M) was stirred at 15° C. for 18 h. The mixture was concentrated under reduced pressure to give the crude product which was recrystalized with CH$_3$CN (2 mL) to afford the title compound as a solid. MS (ESI) calcd. for (C$_{23}$H$_{28}$ClFN$_3$O$_2$) [M+H]$^+$, 432.2, found, 432.2. $^1$H NMR (400 MHz, CDCl$_3$) δ 7.90 (s, 1H), 7.81 (br. s., 1H), 7.12-7.29 (m, 3H), 5.75 (br. s., 1H), 3.61-3.81 (m, 4H), 2.69 (d, J=7.43 Hz, 4H), 2.30-2.43 (m, 2H), 2.01-2.13 (m, 1H), 1.67 (t, J=11.54 Hz, 2H), 1.04-1.30 (m, 8H).

Step 2B: (S) or (R)-4-(4-chloro-2-fluorophenyl)-7-((2,2-dimethyltetrahydro-2H-pyran-4-yl)methyl)-5,6,7,8-tetrahydro-1,7-naphthyridine-2-carboxamide A mixture of ethyl 4-(4-chloro-2-fluorophenyl)-7-((2,2-dimethyltetrahydro-2H-pyran-4-yl)methyl)-5,6,7,8-tetrahydro-1,7-naphthyridine-2-carboxylate (slower moving enantiomer) (130 mg, 0.28 mmol) and NH$_3$/MeOH (10 mL, 10 M) was stirred at 15° C. for 18 h. The mixture was concentrated under reduced pressure to give crude product which was recrystallized with CH$_3$CN (2 mL) to afford the title compound as a solid. MS (ESI) calcd. for ($C_{23}H_{28}ClFN_3O_2$) [M+H]$^+$, 432.2, found, 432.2. $^1$H NMR (400 MHz, CDCl$_3$) δ 7.91 (s, 1H), 7.81 (br. s., 1H), 7.11-7.29 (m, 3H), 5.68 (br. s., 1H), 3.58-3.88 (m, 4H), 2.69 (d, J=7.43 Hz, 4H), 2.31-2.43 (m, 2H), 2.05 (br. s., 1H), 1.65-1.73 (m, 2H), 1.03-1.31 (m, 8H).

The following examples in Table 1-1 were prepared in an analogous manner to that described in general scheme 1 using intermediate 1-1 and commercial aldehydes or ketones or aldehydes or ketones described in the intermediates section. Compounds that were resolved into individual enantiomers were separated after step 1 or step 2 using the supercritical fluid chromatography (SFC) conditions noted (column size: 250 mm×30 mm; I.D. 5 μm). Examples of the Compounds of the Invention in the tables below where SFC Conditions are indicated with an asterisk ("*") either do not contain chiral centers or chiral reagents were employed to synthesize the single shown enantiomer or individual enantiomers were not separated.

TABLE 1-1

| Example | Structure | IUPAC Name | SFC Conditions | Exact Mass [M + H]+ |
|---|---|---|---|---|
| 1-6 | 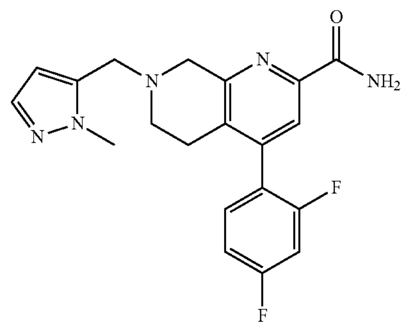 [SMILES: Cn1nccc1CN1CCc2c(-c3ccc(F)cc3F)cc(C(N)=O)nc2C1] | 4-(2,4-difluorophenyl)-7-[(1-methyl-1H-pyrazol-5-yl)methyl]-5,6,7,8-tetrahydro-1,7-naphthyridine-2-carboxamide | * | Calc'd 384.2, found 384.2 |
| 1-7 | 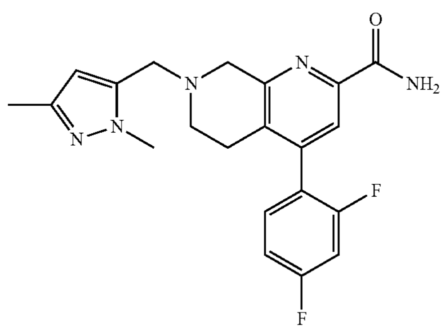 [SMILES: Cc1cc(CN2CCc3c(-c4ccc(F)cc4F)cc(C(N)=O)nc3C2)n(C)n1] | 4-(2,4-difluorophenyl)-7-[(1,3-dimethyl-1H-pyrazol-5-yl)methyl]-5,6,7,8-tetrahydro-1,7-naphthyridine-2-carboxamide | * | Calc'd 398.2, found 398.2 |
| 1-8 | 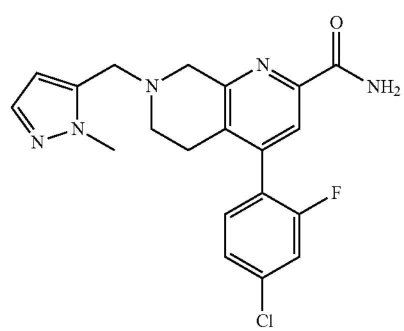 [SMILES: Cn1nccc1CN1CCc2c(-c3ccc(Cl)cc3F)cc(C(N)=O)nc2C1] | 4-(4-chloro-2-fluorophenyl)-7-[(1-methyl-1H-pyrazol-5-yl)methyl]-5,6,7,8-tetrahydro-1,7-naphthyridine-2-carboxamide | * | Calc'd 400.1, found 400.1 |
| 1-9 | 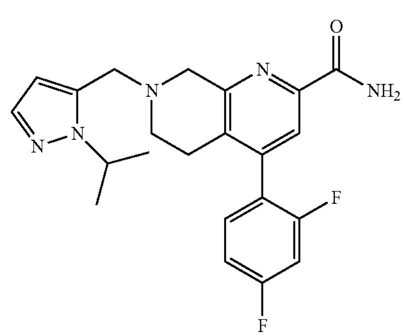 [SMILES: CC(C)n1nccc1CN1CCc2c(-c3ccc(F)cc3F)cc(C(N)=O)nc2C1] | 4-(2,4-difluorophenyl)-7-{[1-(1-methylethyl)-1H-pyrazol-5-yl]methyl}-5,6,7,8-tetrahydro-1,7-naphthyridine-2-carboxamide | * | Calc'd 412.2, found 412.2 |

TABLE 1-1-continued

| Example | Structure | IUPAC Name | SFC Conditions | Exact Mass [M + H]+ |
|---|---|---|---|---|
| 1-10 | 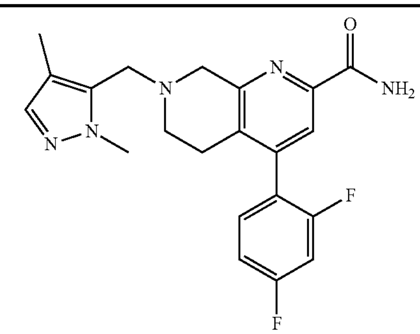 | 4-(2,4-difluorophenyl)-7-[(1,4-dimethyl-1H-pyrazol-5-yl)methyl]-5,6,7,8-tetrahydro-1,7-naphthyridine-2-carboxamide | * | Calc'd 398.2, found 398.1 |
| 1-11A | 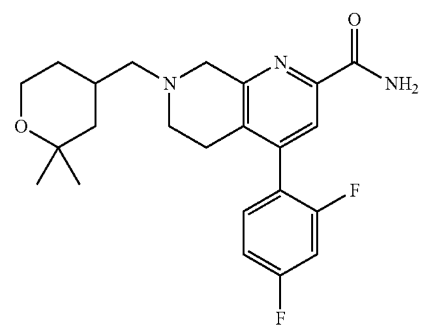 [SMILES: CC1(C)CC(CN2CCc3c(-c4ccc(F)cc4F)cc(C(N)=O)nc3C2)CCO1] | (R) or (S)-4-(2,4-difluorophenyl)-7-[(2,2-dimethyltetrahydro-2H-pyran-4-yl)methyl]-5,6,7,8-tetrahydro-1,7-naphthyridine-2-carboxamide | Step 2; Column: Chiralcel OJ; Mobile phase: 50 mL/min 85:15 supercritical $CO_2$/IPA (0.1%): $NH_3 \cdot H_2O$; faster eluting enantiomer | Calc'd 416.2, found 416.1 |
| 1-11B | 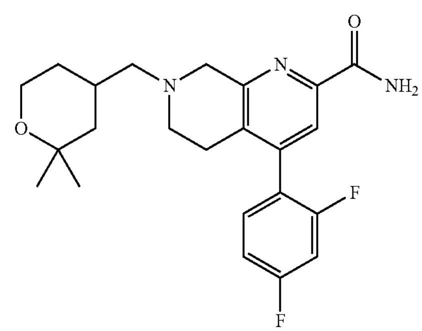 [SMILES: CC1(C)CC(CN2CCc3c(-c4ccc(F)cc4F)cc(C(N)=O)nc3C2)CCO1] | (S) or (R)-4-(2,4-difluorophenyl)-7-[(2,2-dimethyltetrahydro-2H-pyran-4-yl)methyl]-5,6,7,8-tetrahydro-1,7-naphthyridine-2-carboxamide | Step 2; Column: Chiralcel OJ; Mobile phase: 50 mL/min 85:15 supercritical $CO_2$/IPA (0.1%): $NH_3 \cdot H_2O$; slower eluting enantiomer | Calc'd 416.2, found 416.2 |
| 1-12 | 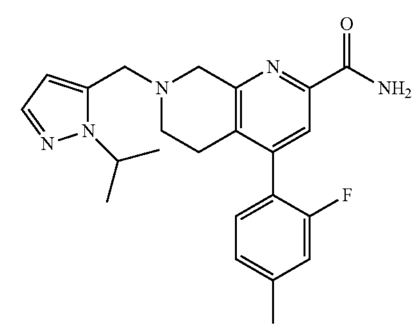 [SMILES: Cc1ccc(-c2cc(C(N)=O)nc3c2CCN(Cc2ccnn2C(C)C)C3)c(F)c1] | 4-(2-fluoro-4-methylphenyl)-7-{[1-(1-methylethyl)-1H-pyrazol-5-yl]methyl}-5,6,7,8-tetrahydro-1,7-naphthyridine-2-carboxamide | * | Calc'd 408.2, found 408.2 |
| 1-13 | 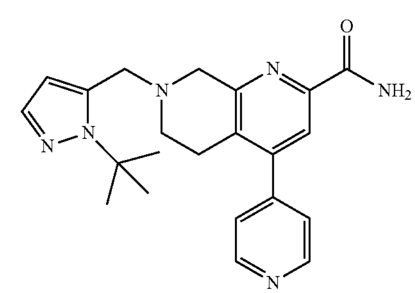 [SMILES: CC(C)(C)n1nccc1CN1CCc2c(-c3ccncc3)cc(C(N)=O)nc2C1] | 7-[(1-tert-butyl-1H-pyrazol-5-yl)methyl]-4-pyridin-4-yl-5,6,7,8-tetrahydro-1,7-naphthyridine-2-carboxamide | * | Calc'd 391.2, found 391.3 |

TABLE 1-1-continued

| Example | Structure | IUPAC Name | SFC Conditions | Exact Mass [M + H]+ |
|---|---|---|---|---|
| 1-14 | 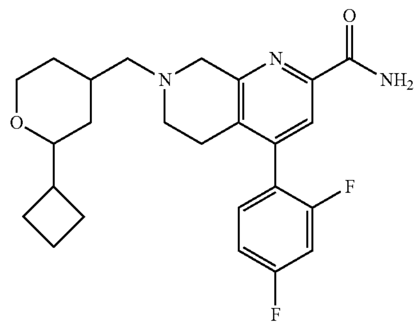 [SMILES: NC(=O)c1cc(-c2ccc(F)cc2F)c2c(n1)CN(CC1CCOC(C3CCC3)C1)CC2] | 7-(((2S,4R) or (2R,4S)-2-cyclobutyltetrahydro-2H-pyran-4-yl)methyl)-4-(2,4-difluorophenyl)-5,6,7,8-tetrahydro-1,7-naphthyridine-2-carboxamide | Step 2: Column: Chiralpak AD; Mobile phase: 60 mL/min 75:25 supercritical $CO_2$: IPA (0.05% $NH_3 \cdot H_2O$); slower eluting enantiomer | Calc'd 442.2, found 442.1 |
| 1-15A | 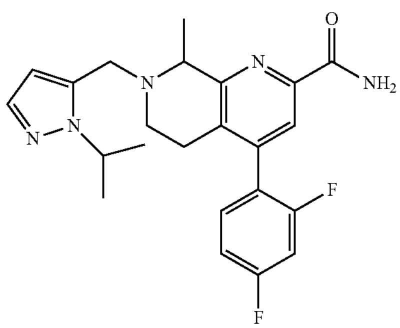 [SMILES: CC1c2nc(C(N)=O)cc(-c3ccc(F)cc3F)c2CCN1Cc1ccnn1C(C)C] | (S) or (R)-4-(2,4-difluorophenyl)-8-methyl-7-{[1-(1-methylethyl)-1H-pyrazol-5-yl]methyl}-5,6,7,8-tetrahydro-1,7-naphthyridine-2-carboxamide | Step 2: Column: Chiralpak OD; Mobile phase: 60 mL/min 80:20 supercritical $CO_2$: EtOH (0.05% $NH_3 \cdot H_2O$); faster eluting enantiomer | Calc'd 426.2, found 426.2 |
| 1-15B | 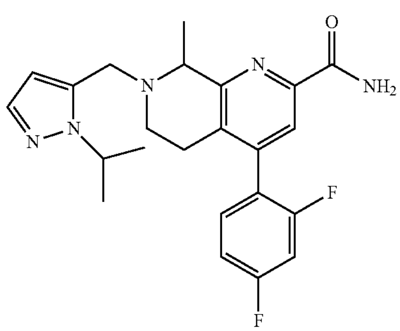 [SMILES: CC1c2nc(C(N)=O)cc(-c3ccc(F)cc3F)c2CCN1Cc1ccnn1C(C)C] | (R) or (S)-4-(2,4-difluorophenyl)-8-methyl-7-{[1-(1-methylethyl)-1H-pyrazol-5-yl]methyl}-5,6,7,8-tetrahydro-1,7-naphthyridine-2-carboxamide | Step 2: Column: Chiralpak OD; Mobile phase: 60 mL/min 80:20 supercritical $CO_2$: EtOH (0.05% $NH_3 \cdot H_2O$); slower eluting enantiomer | Calc'd 426.2, found 426.2 |
| 1-16 | 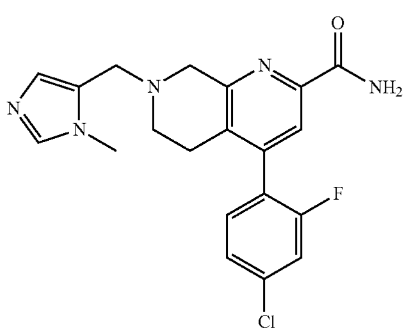 [SMILES: Cn1cncc1CN1CCc2c(-c3ccc(Cl)cc3F)cc(C(N)=O)nc2C1] | 4-(4-chloro-2-fluorophenyl)-7-[(1-methyl-1H-imidazol-5-yl)methyl]-5,6,7,8-tetrahydro-1,7-naphthyridine-2-carboxamide | * | Calc'd 400.1, found 400.1 |

TABLE 1-1-continued

| Example | Structure | IUPAC Name | SFC Conditions | Exact Mass [M + H]+ |
|---|---|---|---|---|
| 1-17 | 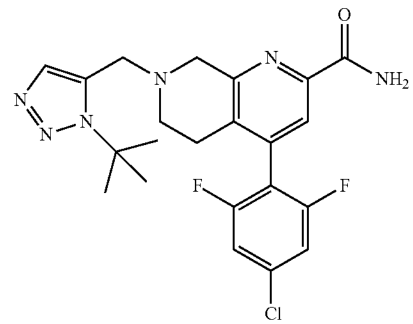 [SMILES: CC(C)(C)n1nncc1CN1CCc2c(-c3c(F)cc(Cl)cc3F)cc(C(N)=O)nc2C1] | 7-[(1-tert-butyl-1H-1,2,3-triazol-5-yl)methyl]-4-(4-chloro-2,6-difluorophenyl)-5,6,7,8-tetrahydro-1,7-naphthyridine-2-carboxamide | * | Calc'd 461.2, found 461.2 |
| 1-18 | 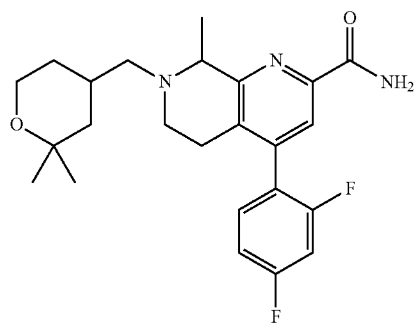 [SMILES: CC1c2nc(C(N)=O)cc(-c3ccc(F)cc3F)c2CCN1CC1CCOC(C)(C)C1] | (S) or (R)-4-(4-chloro-2-fluorophenyl)-7-(((S) or (R)-2,2-dimethyltetrahydro-2H-pyran-4-yl)methyl)-8-methyl-5,6,7,8-tetrahydro-1,7-naphthyridine-2-carboxamide | Step 1: Column: Chiralpak IC; Mobile phase: 60 mL/min 75:25 supercritical CO₂: IPA (0.1% NH₃•H₂O); fourth eluting enantiomer | Calc'd 430.2, found 430.3 |
| 1-19 | 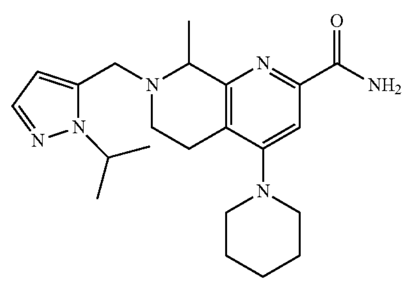 [SMILES: CC1c2nc(C(N)=O)cc(N3CCCCC3)c2CCN1Cc1ccnn1C(C)C] | (S) or (R)-8-methyl-7-{[1-(1-methylethyl)-1H-pyrazol-5-yl]methyl}-4-piperidin-1-yl-5,6,7,8-tetrahydro-1,7-naphthyridine-2-carboxamide | Step 1: Column: Chiralpak AD; Mobile phase: 2.5 mL/min 65:35 supercritical CO₂: IPA (0.05% NH₃•H₂O); second eluting enantiomer | Calc'd 397.3, found 397.3 |
| 1-20 | 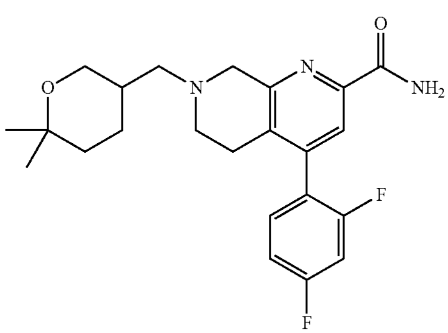 [SMILES: CC1(C)CCC(CN2CCc3c(-c4ccc(F)cc4F)cc(C(N)=O)nc3C2)CO1] | (S) or (R)-4-(2,4-difluorophenyl)-7-[(6,6-dimethyltetrahydro-2H-pyran-3-yl)methyl]-5,6,7,8-tetrahydro-1,7-naphthyridine-2-carboxamide | Step 1: Column: Chiralpak AD; Mobile phase: 60 mL/min 80:20 supercritical CO₂: EtOH (0.1% NH₃•H₂O); slower eluting enantiomer | Calc'd 416.2, found 416.2 |
| 1-21 | 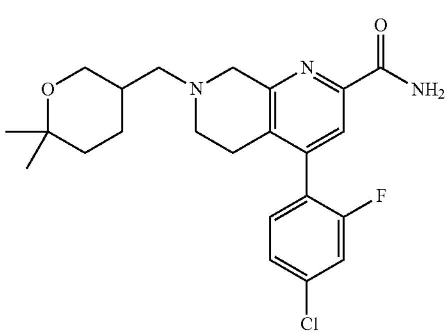 [SMILES: CC1(C)CCC(CN2CCc3c(-c4ccc(Cl)cc4F)cc(C(N)=O)nc3C2)CO1] | (S) or (R)-4-(4-chloro-2-fluorophenyl)-7-[(6,6-dimethyltetrahydro-2H-pyran-3-yl)methyl]-5,6,7,8-tetrahydro-1,7-naphthyridine-2-carboxamide | Step 1: Column: Chiralpak AD; Mobile phase: 60 mL/min 73:27 supercritical CO₂: EtOH (0.1% NH₃•H₂O); slower eluting enantiomer | Calc'd 432.2, found 432.4 |

TABLE 1-1-continued

| Example | Structure | IUPAC Name | SFC Conditions | Exact Mass [M + H]+ |
|---|---|---|---|---|
| 1-22 | 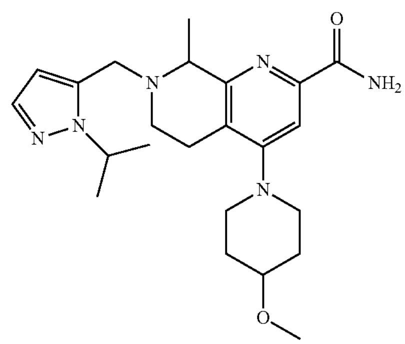 [SMILES: COC1CCN(c2cc(C(N)=O)nc3c2CCN(Cc2ccnn2C(C)C)C3C)CC1] | (S) or (R)-4-(4-methoxypiperidin-1-yl)-8-methyl-7-{[1-(1-methylethyl)-1H-pyrazol-5-yl]methyl}-5,6,7,8-tetrahydro-1,7-naphthyridine-2-carboxamide | Step 1: Column: Chiralpak AD; Mobile phase: 60 mL/min 75:25 supercritical $CO_2$: IPA (0.1% $NH_3 \cdot H_2O$); slower eluting enantiomer | Calc'd 427.3, found 427.3 |

Example 1-23A and 1-23B

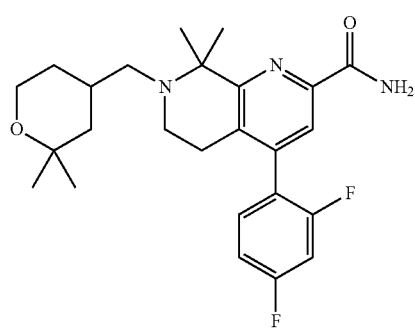 [SMILES: CC1(C)CC(CN2CCc3c(-c4ccc(F)cc4F)cc(C(N)=O)nc3C2(C)C)CCO1]

(R) and (S)-4-(2,4-difluorophenyl)-7-((2,2-dimethyl-tetrahydro-2H-pyran-4-yl)methyl)-8,8-dimethyl-5,6,7,8-tetrahydro-1,7-naphthyridine-2-carboxamide Step 1: ethyl 4-(2,4-difluorophenyl)-7-((2,2-dimethyltetrahydro-2H-pyran-4-yl)methyl)-8,8-dimethyl-5,6,7,8-tetrahydro-1,7-naphthyridine-2-carboxylate To a solution of ethyl 4-(2,4-difluorophenyl)-8,8-dimethyl-5,6,7,8-tetrahydro-1,7-naphthyridine-2-carboxylate (8.75 g, 25.3 mmol) in DCE (100 mL) was added 2,2-dimethyltetrahydro-2H-pyran-4-carbaldehyde (5.39 g, 37.9 mmol) and AcOH (0.145 ml, 2.53 mmol) at 20° C. The reaction mixture was stirred at 20° C. for 1 h. Sodium triacetoxyhydroborate (8.03 g, 37.9 mmol) was added. The reaction mixture was stirred at 20° C. for 10 h. Water (50 mL) was added and the mixture was extracted with DCM (3×50 mL). The combined organic layers were dried over anhydrous $Na_2SO_4$, filtered and the filtrate was evaporated in vacuo to give the crude product which was purified by flash silica gel chromatography (ISCO®; 120 g SepaFlash® Silica Flash Column, Eluent of 0-50% ethyl acetate/petroleum ether gradient @ 30 mL/min) to give ethyl 4-(2,4-difluorophenyl)-7-((2,2-dimethyltetrahydro-2H-pyran-4-yl) methyl)-8,8-dimethyl-5,6,7,8-tetrahydro-1,7-naphthyridine-2-carboxylate as a yellow solid. MS (ESI) calcd. for ($C_{27}H_{35}F_2N_2O_3$) [M+H]+, 473.2, found, 473.2.

The racemic mixture was resolved by chiral SFC (Column IC (250 mm×50 mm I.D.,10 um), Mobile phase: 35% EtOH in CO2; FlowRate 200 ml/min) to give two enantiomers as yellow solids.

Step 2: (R) and (S)-4-(2,4-difluorophenyl)-7-((2,2-dimethyltetrahydro-2H-pyran-4-yl)methyl)-8,8-dimethyl-5,6,7,8-tetrahydro-1,7-naphthyridine-2-carboxamide A solution of the first eluting enantiomer of ethyl 4-(2,4-difluorophenyl)-7-((2,2-dimethyltetrahydro-2H-pyran-4-yl) methyl)-8,8-dimethyl-5,6,7,8-tetrahydro-1,7-naphthyridine-2-carboxylate (9.3 g, 19.68 mmol) in 10M $NH_3$/MeOH (1000 mL) was stirred at 20° C. for 16 h. The mixture was evaporated in vacuo. EtOAc (20 mL) and petroleum ether (60 mL) were added and the resulting mixture was stirred for 0.5 h and filtered. The residue was dissolved in MeOH (50 mL) and HCl (4 M in MeOH) (8 mL) was added, and the resulting mixture was stirred at 20° C. for 0.5 h. The mixture was evaporated in vacuo to give one enantiomer of the title compound which was lyophilized as a white solid (HCl salt). 1-23A MS (ESI) Calcd. for ($C_{25}H_{32}F_2N_3O_2$) [M+H]+, 444.2, found, 444.2. $^1$H NMR (400 MHz, METHANOL-$d_4$) δ 7.94 (s, 1H), 7.38-7.50 (m, 1H), 7.11-7.27 (m, 2H), 3.71-3.92 (m, 3H), 3.36-3.68 (m, 3H), 2.98 (dd, J=6.84, 11.03 Hz, 1H), 2.75-2.88 (m, 1H), 2.28-2.47 (m, 1H), 1.96-2.14 (m, 4H), 1.61-1.87 (m, 4H), 1.15-1.49 (m, 8H).

Similar treatment of the second eluting enantiomer of ethyl 4-(2,4-difluorophenyl)-7-((2,2-dimethyltetrahydro-2H-pyran-4-yl)methyl)-8,8-dimethyl-5,6,7,8-tetrahydro-1,7-naphthyridine-2-carboxylate afforded the other enantiomer of the title compound. 1-23B MS (ESI) Calcd. for ($C_{25}H_{32}F_2N_3O_2$) [M+H]+, 444.2, found, 444.2. $^1$H NMR (400 MHz, METHANOL-d4) δ 7.78-7.68 (m, 1H), 7.34 (d, J=6.8 Hz, 1H), 7.16-7.04 (m, 2H), 3.69 (d, J=8.2 Hz, 2H), 2.77 (br. s., 2H), 2.61 (br. s., 2H), 2.39 (br. s., 2H), 1.91 (br. s., 1H), 1.73 (t, J=13.6 Hz, 2H), 1.48 (br. s., 6H), 1.20 (d, J=11.7 Hz, 6H), 1.14-0.91 (m, 2H).

Scheme 2

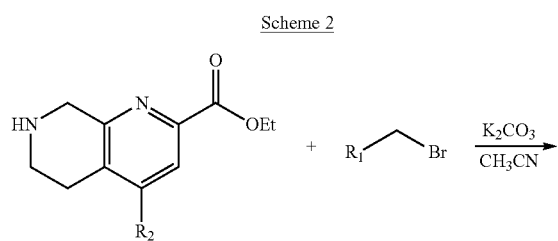

2-1

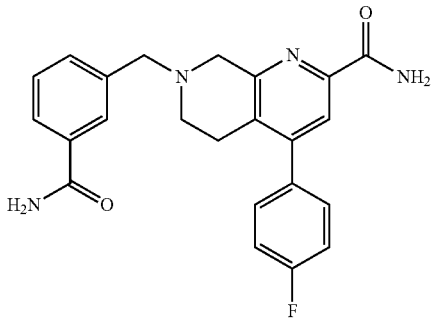

Compounds of formula 1 are prepared by the alkylation of ethyl 4-(4-fluorophenyl)-5,6,7,8-tetrahydro-1,7-naphthyridine-2-carboxylate (2-1) followed by treatment with ammonia. If R1 contains an ester, the compounds may require further, sequential treatment with sodium hydroxide and ammonia.

Example 2-1

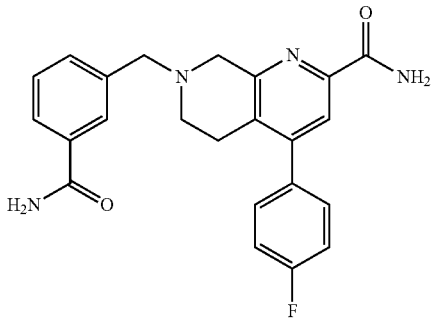

7-(3-carbamoylbenzyl)-4-(4-fluorophenyl)-5,6,7,8-tetrahydro-1,7-naphthyridine-2-carboxamide Step 1: Ethyl 4-(4-fluorophenyl)-7-(3-(methoxycarbonyl)benzyl)-5,6,7,8-tetrahydro-1,7-naphthyridine-2-carboxylate $K_2CO_3$ (28 mg, 0.203 mmol) was added to a stirred mixture of ethyl 4-(4-fluorophenyl)-5,6,7,8-tetrahydro-1,7-naphthyridine-2-carboxylate (30 mg, 0.100 mmol) and methyl 3-(bromomethyl)benzoate (23 mg, 0.100 mmol) in MeCN (1 mL) and the mixture was stirred at 80° C. for 4 h. The mixture was filtered and the filtrate was concentrated to give the crude product as an oil, which was used in the next step without further purification. MS (ESI) calc'd for ($C_{26}H_{25}FN_2O_4$) [M+H]$^+$: 449.48; found: 449.0.

Step 2: Methyl 3-((2-carbamoyl-4-(4-fluorophenyl)-5,6-dihydro-1,7-naphthyridin-7(8H)-yl)methyl)benzoate A mixture of ethyl 4-(4-fluorophenyl)-7-(3-(methoxycarbonyl)benzyl)-5,6,7,8-tetrahydro-1,7-naphthyridine-2-carboxylate (45 mg, 0.100 mmol) in ammonia in MeOH (2 mL, 14.00 mmol) was stirred at room temperature overnight. The mixture was concentrated to give the crude product as a solid, which was used directly in the next step. MS (ESI) calc'd for ($C_{24}H_{22}FN_3O_3$) [M+H]$^+$: 420.1; found: 420.0.

Step 3: 7-(3-carboxybenzyl)-4-(4-fluorophenyl)-5,6,7,8-tetrahydro-1,7-naphthyridine-2-carboxylic Acid NaOH (12 mg, 0.300 mmol) was added to a stirred mixture of methyl 3-((2-carbamoyl-4-(4-fluorophenyl)-5,6-dihydro-1,7-naphthyridin-7(8H)-yl)methyl)benzoate (40 mg, 0.095 mmol) in EtOH (0.5 mL) and water (0.5 mL) and the mixture was stirred at reflux for 6 h. The mixture was concentrated to give the crude product as a slurry which was used in the next step without further purification. MS (ESI) calc'd for ($C_{23}H_{19}FN_2O_4$) [M+H]$^+$: 407.1; found: 407.0.

Step 4: 7-(3-carbamoylbenzyl)-4-(4-fluorophenyl)-5,6,7,8-tetrahydro-1,7-naphthyridine-2-carboxamide HATU (56 mg, 0.147 mmol) and DIPEA (0.034 mL, 0.193 mmol) were added to a stirred mixture of 7-(3- carboxybenzyl)-4-(4-fluorophenyl)-5,6,7,8-tetrahydro-1,7-naphthyridine-2-carboxylic acid (40 mg, 0.098 mmol) and NH₄Cl (10 mg, 0.187 mmol) in DMF (1 mL) and the mixture was stirred at room temperature for 3 days. Water (20 mL) was added and the mixture was extracted with ethyl acetate (3×50 mL). The combined organic fractions were washed with brine (50 mL), dried (Na₂SO₄), filtered and the solvent was evaporated under reduced pressure. The residue was purified by reverse phase preparative HPLC (eluting with MeCN/H₂O containing NH₄HCO₃) to give the title compound as a solid. MS (ESI) calc'd for (C₂₃H₂₁FN₄O₂) [M+H]⁺: 405.1; Found: 405.1. ¹H NMR δ (400 MHz, CDCl₃): 7.93 (s, 2H), 7.72 (s, 2H), 7.59 (s, 1H), 7.46 (m, 1H), 7.30 (m, 3H), 7.26 (m, 2H), 5.49 (s, 1H), 3.79 (m, 4H), 2.84 (s, 2H), 2.74 (s, 2H).

Example 2-2

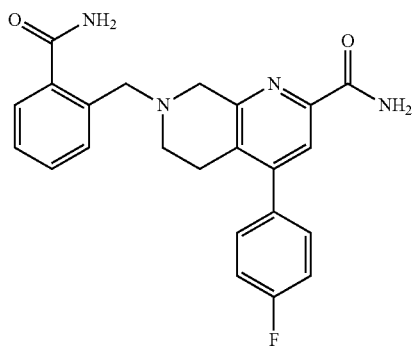 [SMILES: NC(=O)c1cc(-c2ccc(F)cc2)c2c(n1)CN(Cc1ccccc1C(N)=O)CC2]

7-(2-carbamoylbenzyl)-4-(4-fluorophenyl)-5,6,7,8-tetrahydro-1,7-naphthyridine-2-carboxamide The title compound was prepared from methyl 2-(bromomethyl)benzoate according to the protocol outlined for Example 2-1. MS (ESI) calc'd for (C23H21FN4O2) [M+H]+: 405.1; Found: 405.1. ¹H NMR δ (400 MHz, CDCl3): 9.73 (s, 1H), 7.99 (s, 2H), 7.76 (s, 1H), 7.47 (s, 2H), 7.31 (m, 3H), 7.15 (m, 2H), 5.91 (m, 1H), 5.67 (s, 1H), 3.86 (m, 4H), 2.80 (s, 4H).

Example 2-3

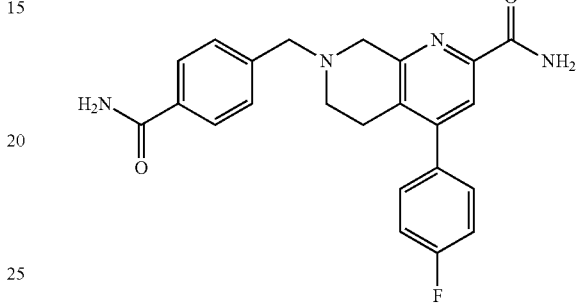

7-(4-carbamoylbenzyl)-4-(4-fluorophenyl)-5,6,7,8-tetrahydro-1,7-naphthyridine-2-carboxamide The title compound was prepared from methyl 4-(bromomethyl)benzoate according to the protocol outlined for Example 2-1. MS (ESI) calc'd for (C₂₃H₂₁FN₄O₂) [M+H]⁺: 405.1; found: 405.1. ¹H NMR δ (400 MHz, CDCl₃): 7.90 (s, 2H), 7.81 (s, 1H), 7.56 (s, 2H), 7.43 (m, 2H), 7.26 (m, 2H), 3.85 (m, 4H), 3.36 (s, 4H), 2.87 (s, 4H).

The following examples in Table 2-1 were prepared in an analogous manner to that described in general scheme 2 using intermediate 2-1 or analogous intermediates and commercial bromides or bromides described in the intermediates section. Compounds that do not contain an ester in the starting alkyl halide do not require steps 3 and 4.

TABLE 2-1

| EXAMPLE | Structure | IUPAC Name | Exact Mass [M + H]+ |
|---|---|---|---|
| 2-4 | 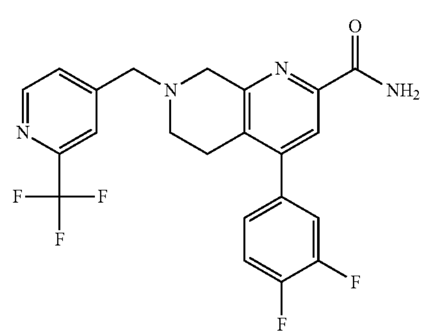 [SMILES: NC(=O)c1cc(-c2ccc(F)c(F)c2)c2c(n1)CN(Cc1ccnc(C(F)(F)F)c1)CC2] | 4-(3,4-difluorophenyl)-7-{[2-(trifluoromethyl)pyridin-4-yl]methyl}-5,6,7,8-tetrahydro-1,7-naphthyridine-2-carboxamide | Calc'd 449.1, found 449.2 |

TABLE 2-1-continued

| EXAMPLE | Structure | IUPAC Name | Exact Mass [M + H]+ |
|---|---|---|---|
| 2-5 | 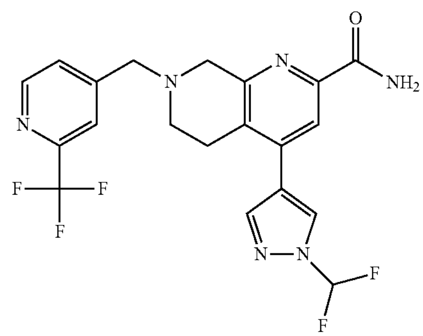 [SMILES: NC(=O)c1cc(-c2cnn(C(F)F)c2)c2c(n1)CN(Cc1ccnc(C(F)(F)F)c1)CC2] | 4-[1-(difluoromethyl)-1H-pyrazol-4-yl]-7-{[2-(trifluoromethyl)pyridin-4-yl]methyl}-5,6,7,8-tetrahydro-1,7-naphthyridine-2-carboxamide | Calc'd 453.1, found 453.1 |
| 2-6 | 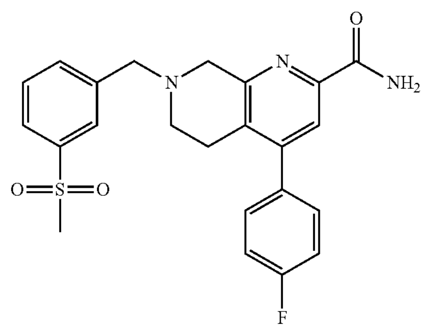 [SMILES: CS(=O)(=O)c1cccc(CN2CCc3c(-c4ccc(F)cc4)cc(C(N)=O)nc3C2)c1] | 4-(4-fluorophenyl)-7-[3-(methylsulfonyl)benzyl]-5,6,7,8-tetrahydro-1,7-naphthyridine-2-carboxamide | Calc'd 440.1, found 440.1 |
| 2-7 | 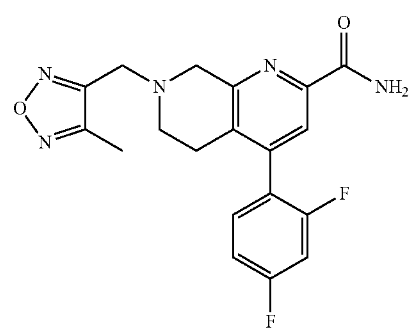 | 4-(2,4-difluorophenyl)-7-[(4-methyl-1,2,5-oxadiazol-3-yl)methyl]-5,6,7,8-tetrahydro-1,7-naphthyridine-2-carboxamide | Calc'd 386.1, found 386.2 |
| 2-8 | 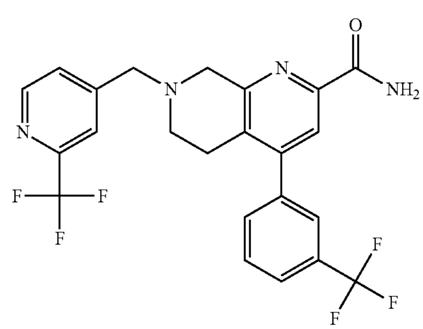 [SMILES: NC(=O)c1cc(-c2cccc(C(F)(F)F)c2)c2c(n1)CN(Cc1ccnc(C(F)(F)F)c1)CC2] | 4-[3-(trifluoromethyl)phenyl]-7-{[2-(trifluoromethyl)pyridin-4-yl]methyl}-5,6,7,8-tetrahydro-1,7-naphthyridine-2-carboxamide | Calc'd 481.1, found 481.2 |

TABLE 2-1-continued

| EXAMPLE | Structure | IUPAC Name | Exact Mass [M + H]+ |
|---|---|---|---|
| 2-9 | 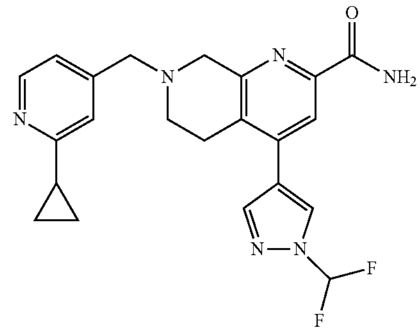 [SMILES: NC(=O)c1cc(-c2cnn(C(F)F)c2)c2c(n1)CN(Cc1ccnc(C3CC3)c1)CC2] | 7-[(2-cyclopropylpyridin-4-yl)methyl]-4-[1-(difluoromethyl)-1H-pyrazol-4-yl]-5,6,7,8-tetrahydro-1,7-naphthyridine-2-carboxamide | Calc'd 425.2, found 425.2 |
| 2-10 | 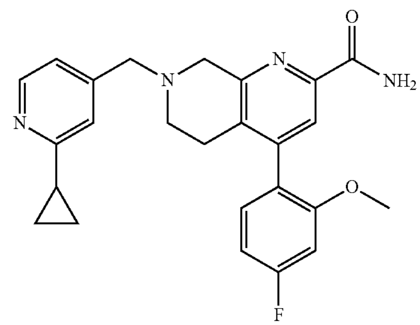 [SMILES: COc1cc(F)ccc1-c1cc(C(N)=O)nc2c1CCN(Cc1ccnc(C3CC3)c1)C2] | 7-[(2-cyclopropylpyridin-4-yl)methyl]-4-(4-fluoro-2-methoxyphenyl)-5,6,7,8-tetrahydro-1,7-naphthyridine-2-carboxamide | Calc'd 433.2, found 433.2 |
| 2-11 | 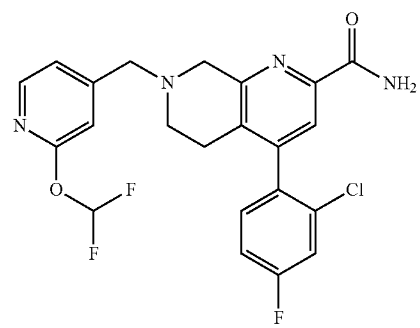 [SMILES: NC(=O)c1cc(-c2ccc(F)cc2Cl)c2c(n1)CN(Cc1ccnc(OC(F)F)c1)CC2] | 4-(2-chloro-4-fluorophenyl)-7-{[2-(difluoromethoxy)pyridin-4-yl]methyl}-5,6,7,8-tetrahydro-1,7-naphthyridine-2-carboxamide | Calc'd 463.1, found 463.3 |
| 2-12 | 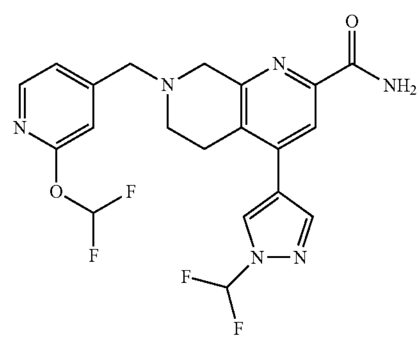 [SMILES: NC(=O)c1cc(-c2cnn(C(F)F)c2)c2c(n1)CN(Cc1ccnc(OC(F)F)c1)CC2] | 7-{[2-(difluoromethoxy)pyridin-4-yl]methyl}-4-[1-(difluoromethyl)-1H-pyrazol-4-yl]-5,6,7,8-tetrahydro-1,7-naphthyridine-2-carboxamide | Calc'd 451.2, found 451.1 |
| 2-13 | 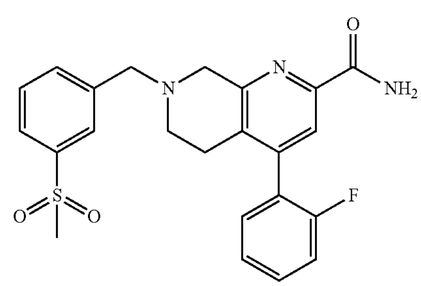 [SMILES: CS(=O)(=O)c1cccc(CN2CCc3c(-c4ccccc4F)cc(C(N)=O)nc3C2)c1] | 4-(2-fluorophenyl)-7-[3-(methylsulfonyl)benzyl]-5,6,7,8-tetrahydro-1,7-naphthyridine-2-carboxamide | Calc'd 440.1, found 440.2 |

TABLE 2-1-continued

| EXAMPLE | Structure | IUPAC Name | Exact Mass [M + H]+ |
|---|---|---|---|
| 2-14 | 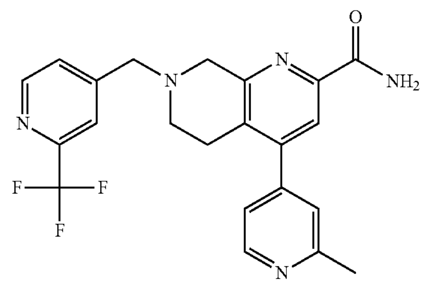 [SMILES: Cc1cc(-c2cc(C(N)=O)nc3c2CCN(Cc2ccnc(C(F)(F)F)c2)C3)ccn1] | 4-(2-methylpyridin-4-yl)-7-{[2-(trifluoromethyl)pyridin-4-yl]methyl}-5,6,7,8-tetrahydro-1,7-naphthyridine-2-carboxamide | Calc'd 428.2, found 428.2 |
| 2-15 | 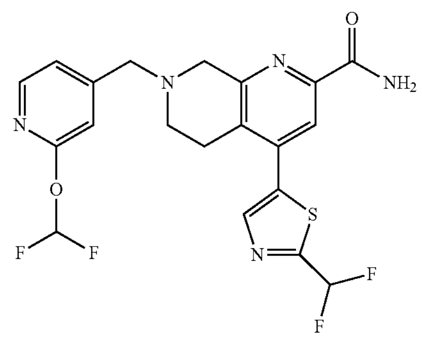 [SMILES: NC(=O)c1cc(-c2cnc(C(F)F)s2)c2c(n1)CN(Cc1ccnc(OC(F)F)c1)CC2] | 7-{[2-(difluoromethoxy)pyridin-4-yl]methyl}-4-[2-(difluoromethyl)-1,3-thiazol-5-yl]-5,6,7,8-tetrahydro-1,7-naphthyridine-2-carboxamide | Calc'd 468.1, found 468.2 |
| 2-16 | 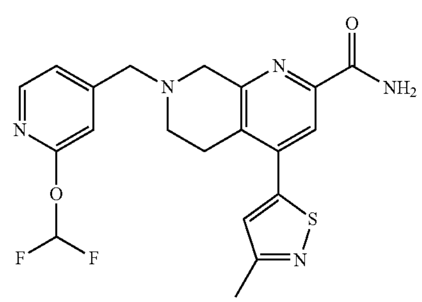 [SMILES: Cc1cc(-c2cc(C(N)=O)nc3c2CCN(Cc2ccnc(OC(F)F)c2)C3)sn1] | 7-{[2-(difluoromethoxy)pyridin-4-yl]methyl}-4-(3-methylisothiazol-5-yl)-5,6,7,8-tetrahydro-1,7-naphthyridine-2-carboxamide | Calc'd 432.1, found 432.2 |
| 2-17 | 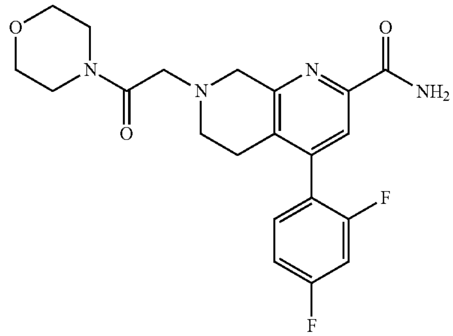 [SMILES: NC(=O)c1cc(-c2ccc(F)cc2F)c2c(n1)CN(CC(=O)N1CCOCC1)CC2] | 4-(2,4-difluorophenyl)-7-(2-morpholin-4-yl-2-oxoethyl)-5,6,7,8-tetrahydro-1,7-naphthyridine-2-carboxamide | Calc'd 417.2, found 417.2 |

TABLE 2-1-continued

| EXAMPLE | Structure | IUPAC Name | Exact Mass [M + H]+ |
|---|---|---|---|
| 2-18 | 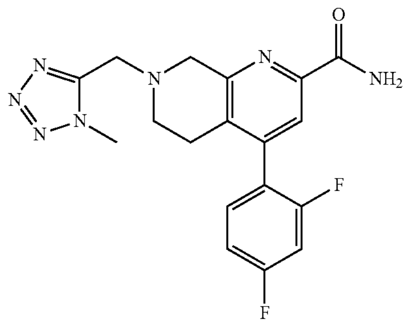 [SMILES: Cn1nnnc1CN1CCc2c(-c3ccc(F)cc3F)cc(C(N)=O)nc2C1] | 4-(2,4-difluorophenyl)-7-[(1-methyl-1H-tetrazol-5-yl)methyl]-5,6,7,8-tetrahydro-1,7-naphthyridine-2-carboxamide | Calc'd 386.2, found 386.2 |
| 2-19 | 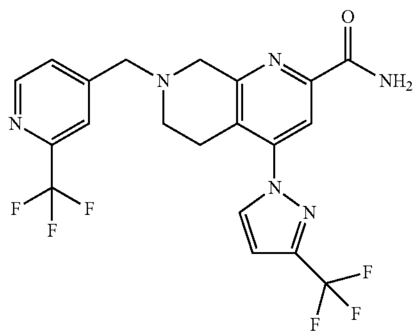 [SMILES: NC(=O)c1cc(-n2ccc(C(F)(F)F)n2)c2c(n1)CN(Cc1ccnc(C(F)(F)F)c1)CC2] | 4-[3-(trifluoromethyl)-1H-pyrazol-1-yl]-7-{[2-(trifluoromethyl)pyridin-4-yl]methyl}-5,6,7,8-tetrahydro-1,7-naphthyridine-2-carboxamide | Calc'd 471.1, found 471.3 |
| 2-20 | 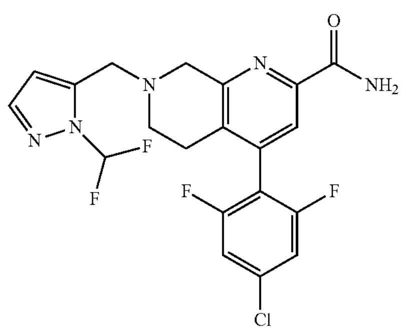 [SMILES: NC(=O)c1cc(-c2c(F)cc(Cl)cc2F)c2c(n1)CN(Cc1ccnn1C(F)F)CC2] | 4-(4-chloro-2,6-difluorophenyl)-7-{[1-(difluoromethyl)-1H-pyrazol-5-yl]methyl}-5,6,7,8-tetrahydro-1,7-naphthyridine-2-carboxamide | Calc'd 454.1, found 454.4 |
| 2-21 | 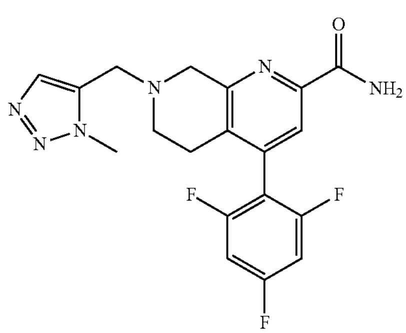 [SMILES: Cn1nncc1CN1CCc2c(-c3c(F)cc(F)cc3F)cc(C(N)=O)nc2C1] | 7-[(1-methyl-1H-1,2,3-triazol-5-yl)methyl]-4-(2,4,6-trifluorophenyl)-5,6,7,8-tetrahydro-1,7-naphthyridine-2-carboxamide | Calc'd 403.1, found 403.2 |

TABLE 2-1-continued

| EXAMPLE | Structure | IUPAC Name | Exact Mass [M + H]+ |
|---|---|---|---|
| 2-22 | 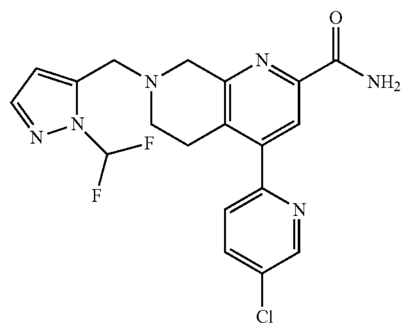 [SMILES: NC(=O)c1cc(-c2ccc(Cl)cn2)c2c(n1)CN(Cc1ccnn1C(F)F)CC2] | 4-(5-chloropyridin-2-yl)-7-{[1-(difluoromethyl)-1H-pyrazol-5-yl]methyl}-5,6,7,8-tetrahydro-1,7-naphthyridine-2-carboxamide | Calc'd 419.1, found 419.3 |
| 2-23 | 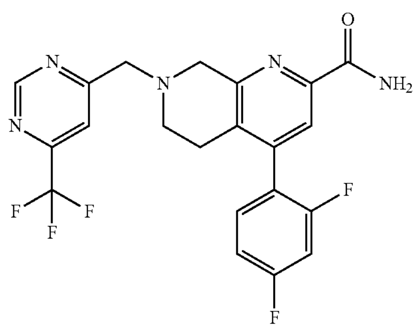 [SMILES: NC(=O)c1cc(-c2ccc(F)cc2F)c2c(n1)CN(Cc1cc(C(F)(F)F)ncn1)CC2] | 4-(2,4-difluorophenyl)-7-{[6-(trifluoromethyl)pyrimidin-4-yl]methyl}-5,6,7,8-tetrahydro-1,7-naphthyridine-2-carboxamide | Calc'd 450.1, found 450.1 |
| 2-24 | 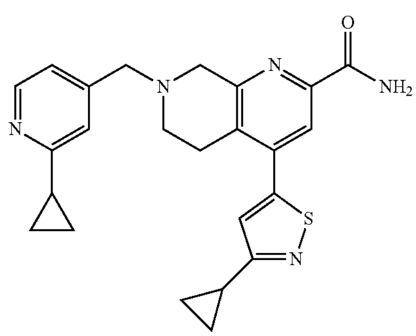 [SMILES: NC(=O)c1cc(-c2cc(C3CC3)ns2)c2c(n1)CN(Cc1ccnc(C3CC3)c1)CC2] | 4-(3-cyclopropylisothiazol-5-yl)-7-[(2-cyclopropylpyridin-4-yl)methyl]-5,6,7,8-tetrahydro-1,7-naphthyridine-2-carboxamide | Calc'd 432.2, found 432.1 |
| 2-25 | 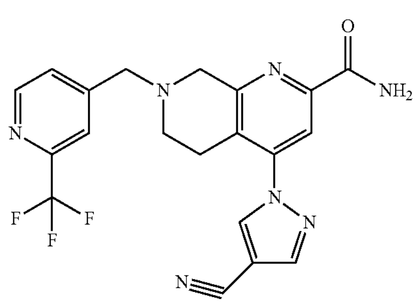 [SMILES: N#Cc1cnn(-c2cc(C(N)=O)nc3c2CCN(Cc2ccnc(C(F)(F)F)c2)C3)c1] | 4-(4-cyano-1H-pyrazol-1-yl)-7-{[2-(trifluoromethyl)pyridin-4-yl]methyl}-5,6,7,8-tetrahydro-1,7-naphthyridine-2-carboxamide | Calc'd 428.1, found 428.2 |

TABLE 2-1-continued

| EXAMPLE | Structure | IUPAC Name | Exact Mass [M + H]+ |
|---|---|---|---|
| 2-26 | 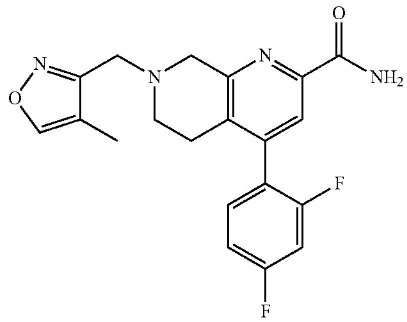 [SMILES: Cc1conc1CN1CCc2c(-c3ccc(F)cc3F)cc(C(N)=O)nc2C1] | 4-(2,4-difluorophenyl)-7-[(4-methylisoxazol-3-yl)methyl]-5,6,7,8-tetrahydro-1,7-naphthyridine-2-carboxamide | Calc'd 385.1, found 385.1 |
| 2-27 | 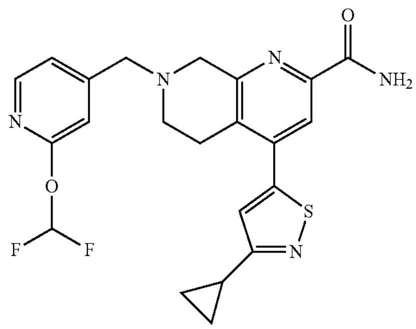 [SMILES: NC(=O)c1cc(-c2cc(C3CC3)ns2)c2c(n1)CN(Cc1ccnc(OC(F)F)c1)CC2] | 4-(3-cyclopropylisothiazol-5-yl)-7-{[2-(difluoromethoxy)pyridin-4-yl]methyl}-5,6,7,8-tetrahydro-1,7-naphthyridine-2-carboxamide | Calc'd 458.1, found 458.1 |

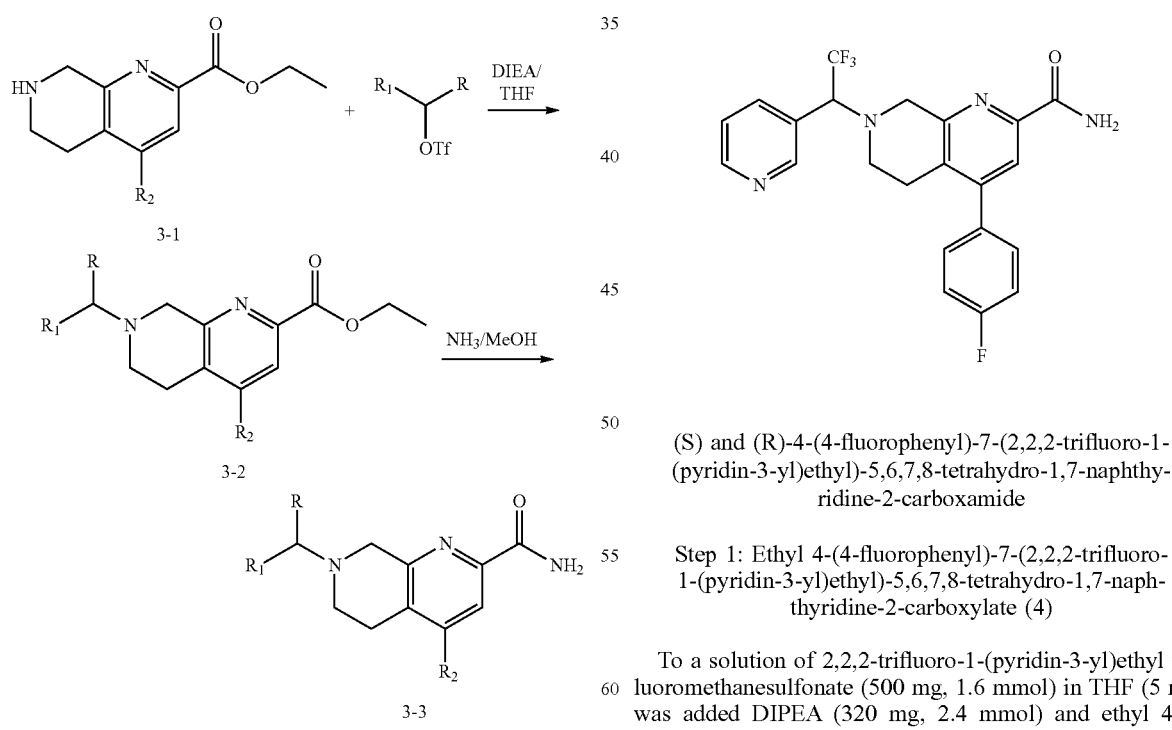

Example 3-1A and 3-1B (S) and (R)-4-(4-fluorophenyl)-7-(2,2,2-trifluoro-1-(pyridin-3-yl)ethyl)-5,6,7,8-tetrahydro-1,7-naphthyridine-2-carboxamide Step 1: Ethyl 4-(4-fluorophenyl)-7-(2,2,2-trifluoro-1-(pyridin-3-yl)ethyl)-5,6,7,8-tetrahydro-1,7-naphthyridine-2-carboxylate (4)

To a solution of 2,2,2-trifluoro-1-(pyridin-3-yl)ethyl trifluoromethanesulfonate (500 mg, 1.6 mmol) in THF (5 mL) was added DIPEA (320 mg, 2.4 mmol) and ethyl 4-(4-fluorophenyl)-5,6,7,8-tetrahydro-1,7-naphthyridine-2-carboxylate (100 mg, 0.33 mmol). The reaction mixture was heated to 70° C. overnight. The reaction was allowed to cool to room temperature. Solvent was evaporated and the crude residue was extracted with EtOAc (50 mL*3). The organic layer was washed with brine (20 mL*2), dried over $MgSO_4$, Compounds of formula 1 are prepared by the alkylation of amines 3-1 with commercial triflates or triflates described in the intermediates section followed by treatment with ammonia.

filtered and evaporated. The residue was purified by silica gel (petroleum ether:EtOAc=6:1) to afford the title compound as an oil. MS (ESI): calc'd for ($C_{24}H_{21}F_4N_3O_2$) [M+H]+: 460; found: 460.0.

Step 2: (S) and (R)-4-(4-fluorophenyl)-7-(2,2,2-trifluoro-1-(pyridin-3-yl)ethyl)-5,6,7,8-tetrahydro-1,7-naphthyridine-2-carboxamide A solution of Ethyl 4-(4-fluorophenyl)-7-(2,2,2-trifluoro-1-(pyridin-3-yl)ethyl)-5,6,7,8-tetrahydro-1,7-naphthyridine-2-carboxylate (50 mg, 0.11 mmol) in $NH_3$/MeOH (7 M, 3 ml) was warmed to 45° C. and stirred overnight. The reaction mixture was cooled, evaporated and the residue was purified by preparative chiral HPLC (Column: AS-H (4.6 mm*250 mm, 5 μM), mobile phase: $CO_2$/MEOH/DEA=65/35/0.1, column temperature: 40.1, $CO_2$ flow rate: 2.25, co-solvent flow rate: 0.75, back pressure: 152 BAR, instrument: SFC80) to afford the title compound as two enantiomers.

Faster moving enantiomer (RT=4.1 min), MS (ESI): calc'd for ($C_{22}H_{18}F_4N_4O$) [M+H]+: 431; found: 431.2. $^1$H NMR (400 MHz, $CDCl_3$) δ 8.81-8.57 (m, 2H), 7.98-7.65 (m, 3H), 7.38 (dd, J=7.9, 4.8 Hz, 1H), 7.33-7.28 (m, 2H), 7.14 (t, J=8.6 Hz, 2H), 5.57 (s, 1H), 4.38 (q, J=8.3 Hz, 1H), 4.04 (s, 2H), 3.07-2.93 (m, 1H), 2.92-2.66 (m, 3H).

Slower moving enantiomer (RT=5.19 min), MS (ESI): calc'd for ($C_{22}H_{18}F_4N_4O$) [M+H]+: 431; found: 431.2. $^1$H NMR (400 MHz, $CDCl_3$) δ 8.81-8.59 (m, 2H), 7.98-7.70 (m, 3H), 7.39 (dd, J=7.9, 4.8 Hz, 1H), 7.35-7.27 (m, 2H), 7.14 (t, J=8.6 Hz, 2H), 5.58 (s, 1H), 4.38 (q, J=8.3 Hz, 1H), 4.04 (s, 2H), 3.04-2.93 (m, 1H), 2.91-2.70 (m, 3H).

Example 3-2A and 3-2B

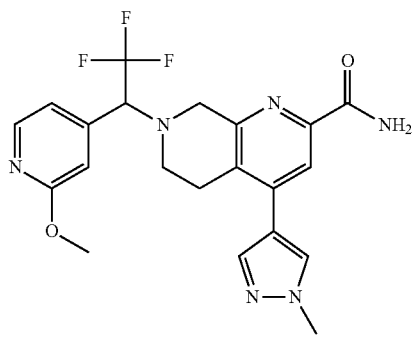 [SMILES: COc1cc(C(N2CCc3c(-c4cnn(C)c4)cc(C(N)=O)nc3C2)C(F)(F)F)ccn1]

(S) and (R)-4-(1-methyl-1H-pyrazol-4-yl)-7-(2,2,2-trifluoro-1-(2-methoxypyridin-4-yl)ethyl)-5,6,7,8-tetrahydro-1,7-naphthyridine-2-carboxamide and (S)-4-(1-methyl-1H-pyrazol-4-yl)-7-(2,2,2-trifluoro-1-(2-methoxypyridin-4-yl)ethyl)-5,6,7,8-tetrahydro-1,7-naphthyridine-2-carboxamide The title compounds were prepared from ethyl 4-(1-methyl-1H-pyrazol-4-yl)-5,6,7,8-tetrahydro-1,7-naphthyridine-2-carboxylate according to the protocol outlined outlined for Example 3-1. Enantiomers were separated after step 1. Separation conditions: Column: OJ (250 mm*30 mm, 5 μM); Mobile phase: 30% EtOH $NH_3H_2O$ 60 mL/min; MS (ESI) calc'd for ($C_{21}H_{21}F_3N_6O_2$) [M+H]+: 447.2; found: 447.1

Scheme 4

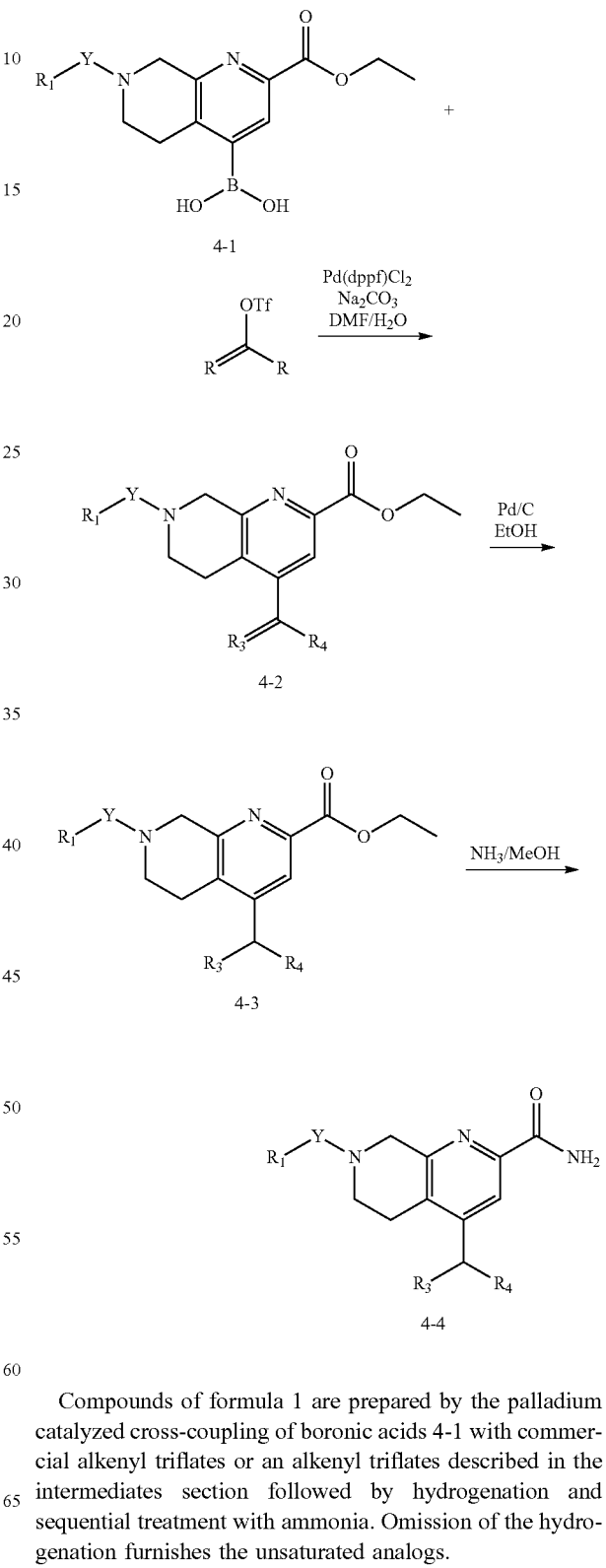

Compounds of formula 1 are prepared by the palladium catalyzed cross-coupling of boronic acids 4-1 with commercial alkenyl triflates or an alkenyl triflates described in the intermediates section followed by hydrogenation and sequential treatment with ammonia. Omission of the hydrogenation furnishes the unsaturated analogs.

Example 4-1

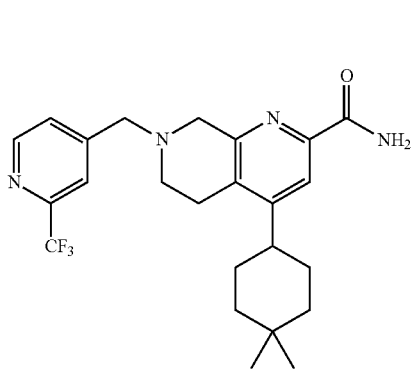 [SMILES: CC1(C)CCC(c2cc(C(N)=O)nc3c2CCN(Cc2ccnc(C(F)(F)F)c2)C3)CC1]

4-(4,4-dimethylcyclohexyl)-7-((2-(trifluoromethyl)
pyridin-4-yl)methyl)-5,6,7,8-tetrahydro-1,7-naphthy-
ridine-2-carboxamide Step 1: Ethyl 4-(4,4-dimethylcyclohex-1-enyl)-7-
((2-(trifluoromethyl)pyridin-4-yl)methyl)-5,6,7,8-
tetrahydro-1,7-naphthyridine-2-carboxylate A mixture of 2-(ethoxycarbonyl)-7-((2-(trifluoromethyl) pyridin-4-yl)methyl)-5,6,7,8-tetrahydro-1,7-naphthyridin-4-ylboronic acid (60 mg, 0.1467 mmol), 4,4-dimethylcyclohex-1-enyl trifluoromethanesulfonate (56 mg, 0.22 mmol), Pd(dppf)Cl$_2$ (11 mg, 0.01 mmol), Na$_2$CO$_3$ (31 mg, 0.2934 mmol), DMF/H$_2$O (10/1, 3 mL) was stirred at 80° C. under N$_2$ overnight, the mixture was diluted with EtOAc (30 mL), washed with brine (20 mL*3) and dried over Na$_2$SO$_4$. The organic layer was concentrated in vacuo and the residue was purified by reverse phase preparative HPLC to give the title compound as a solid.

Step 2: 4-(4,4-dimethylcyclohexyl)-7-((2-(trifluo-
romethyl)pyridin-4-yl)methyl)-5,6,7,8-tetrahydro-1,
7-naphthyridine-2-carboxamide A mixture of the ethyl 4-(4,4-dimethylcyclohex-1-enyl)-7-((2-(trifluoromethyl)pyridin-4-yl)methyl)-5,6,7,8-tetrahydro-1,7-naphthyridine-2-carboxylate (40 mg, 0.08 mmol), Pd/C (10%, 10 mg), EtOH (10 mL) was stirred at room temperature under H$_2$ overnight. The mixture was filtered to remove the catalyst. The filtrate was concentrated in vacuo. The residue was diluted with NH$_3$ in MeOH (7 N, 10 mL, 70 mmol) and the mixture was stirred at room temperature overnight. The mixture was concentrated and the residue was purified by reverse phase preparative HPLC to give the desired product as a solid. MS (ESI) calc'd [M+H]$^+$, 447.2, found, 447.2; $^1$H NMR (400 MHz, CDCl$_3$) δ 8.70 (d, J=4.4 Hz, 1H), 7.99 (s, 1H), 7.76 (s, 2H), 7.56 (s, 1H), 5.46 (s, 1H), 3.78 (d, J=30.9 Hz, 4H), 2.88 (d, J=46.1 Hz, 4H), 2.59 (t, J=11.9 Hz, 1H), 1.71 (dd, J=23.8, 11.5 Hz, 2H), 1.56 (s, 4H), 1.33 (t, J=11.7 Hz, 2H), 0.99 (d, J=16.0 Hz, 6H).

Example 4-2

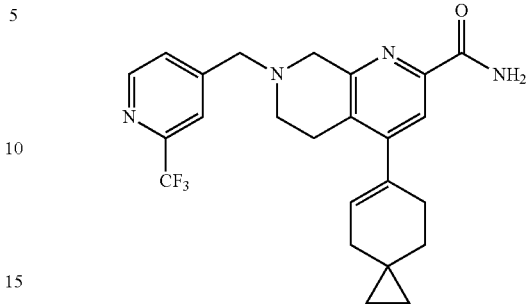

4-spiro[2.5]oct-5-en-6-yl-7-{[2-(trifluoromethyl)
pyridin-4-yl]methyl}-5,6,7,8-tetrahydro-1,7-naph-
thyridine-2-carboxamide A mixture of 2-(ethoxycarbonyl)-7-((2-(trifluoromethyl) pyridin-4-yl)methyl)-5,6,7,8-tetrahydro-1,7-naphthyridin-4-ylboronic acid (60 mg, 0.1467 mmol), spiro[2.5]oct-5-en-6-yl trifluoromethanesulfonate (56 mg, 0.22 mmol), Pd(dppf)Cl$_2$ (11 mg, 0.01467 mmol), Na$_2$CO$_3$ (31 mg, 0.2934 mmol) in DMF/H$_2$O (10/1, 3 mL) was stirred at 80° C. under N$_2$ overnight. The mixture was diluted with EtOAc (30 ml), washed with brine (20 ml*3), dried over Na$_2$SO$_4$ and concentrated in vacuo, The residue was diluted with NH$_3$ in MeOH (7 N, 10 mL, 70 mmol) and the mixture was stirred at room temperature overnight. The mixture was concentrated in vacuo and the residue was purified by reverse phase preparative HPLC to give the desired product as a solid. (20 mg, 31%). MS (ESI) calc'd for (C$_{24}$H$_{25}$F$_3$N$_4$O) [M+H]$^+$, 443.2, found, 443.2; $^1$H NMR (400 MHz, CDCl$_3$) δ 8.71 (d, J=4.7 Hz, 1H), 7.85 (s, 1H), 7.76 (d, J=8.1 Hz, 2H), 7.56 (s, 1H), 5.70 (s, 1H), 5.46 (s, 1H), 3.77-3.81 (m, 4H), 2.94 (s, 2H), 2.77 (s, 2H), 2.30 (s, 2H), 1.52 (t, J=6.0 Hz, 2H), 0.37 (s, 4H).

Example 4-3A and 4-3B

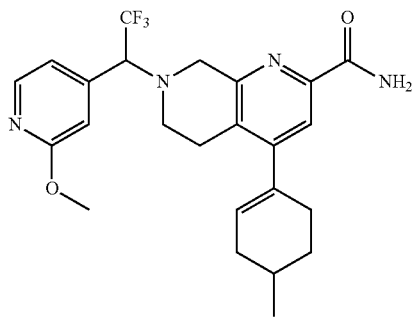 [SMILES: COc1cc(C(N2CCc3c(C4=CCC(C)CC4)cc(C(N)=O)nc3C2)C(F)(F)F)ccn1]

4-((S) and (R)-4-methylcyclohex-1-en-1-yl)-7-((S) and (R)-2,2,2-trifluoro-1-(2-methoxypyridin-4-yl)ethyl)-5,6,7,8-tetrahydro-1,7-naphthyridine-2-carboxamide

Step 1: Ethyl 4-(4-methylcyclohex-1-enyl)-7-(2,2,2-trifluoro-1-(2-methoxypyridin-4-yl)ethyl)-5,6,7,8-tetrahydro-1,7-naphthyridine-2-carboxylate To a solution of 2-(ethoxycarbonyl)-7-(2,2,2-trifluoro-1-(2-methoxypyridin-4-yl)ethyl)-5,6,7,8-tetrahydro-1,7-naphthyridin-4-ylboronic acid (280 mg, 0.64 mmol) in toluene (5 mL) was added 4-methylcyclohex-1-enyl trifluoromethanesulfonate (235 mg, 0.96 mmol), Pd(dppf)Cl$_2$ (47 mg, 0.064 mmol) and K$_2$CO$_3$ (221 mg, 1.6 mmol, dissolved in 0.5 mL of H$_2$O). The reaction was warmed to 80° C. under N$_2$ and stirred overnight. The reaction was cooled to room temperature and concentrated in vacuo. The residue was extracted with EtOAc (20 mL*3), washed with brine (10 mL*2), dried over Na$_2$SO$_4$, filtered, evaporated to afford the title compound as a solid. MS (ESI) calc'd for (C$_{26}$H$_{30}$F$_3$N$_3$O$_3$) [M+H]$^+$, 490.2; found, 490.2.

Step 2: 4-((S) and (R)-4-methylcyclohex-1-en-1-yl)-7-((S) and (R)-2,2,2-trifluoro-1-(2-methoxypyridin-4-yl)ethyl)-5,6,7,8-tetrahydro-1,7-naphthyridine-2-carboxamide A solution of ethyl 4-(4-methylcyclohex-1-enyl)-7-(2,2,2-trifluoro-1-(2-methoxypyridin-4-yl)ethyl)-5,6,7,8-tetrahydro-1,7-naphthyridine-2-carboxylate (250 mg, 0.5 mmol) in NH$_3$/MeOH (7M, 5 mL) was warmed to 45° C. and stirred overnight. The reaction mixture was cooled, evaporated and the residue was purified by reverse phase preparative HPLC. MS (ESI) calc'd for (C$_{24}$H$_{27}$F$_3$N$_4$O$_2$) [M+H]$^+$, 461.2; found, 461.1. The mixture of enantiomers was separated by chiral HPLC to furnish the title compounds as solids. The conditions of chiral HPLC: Column: OZ—H (4.6*250 mm, 5 um), Mobile Phase: MeOH, Column Temperature: 39.9, CO$_2$ Flow Rate: 2.25, Co-Solvent Flow Rate: 0.75, Co-Solvent %: 25; Back Pressure: 119 Bar, Instrument: SFC80. 4-3A: RT=4.67 min; MS (ESI) calc'd for (C$_{24}$H$_{27}$F$_3$N$_4$O$_2$) [M+H]$^+$, 461.2; found, 461.2; $^1$H NMR (400 MHz, CDCl$_3$) δ 8.23 (d, 1H), 7.91 (s, 1H), 7.77 (s, 1H), 7.00 (d, 1H), 6.87 (s, 1H), 6.47 (s, 1H), 5.63 (s, 1H), 4.30-4.23 (m, 1H), 3.97 (s, 5H), 3.01 (dd, 1H), 2.94-2.78 (m, 3H), 2.36-2.09 (m, 3H), 1.78 (d, 3H), 1.36 (s, 1H), 1.02 (d, 3H).
4-3B: RT=5.97 min; MS (ESI) calc'd for (C$_{24}$H$_{27}$F$_3$N$_4$O$_2$) [M+H]$^+$, 461.2; found, 461.2; $^1$H NMR (400 MHz, CDCl$_3$) δ 8.23 (d, 1H), 7.90 (s, 1H), 7.77 (s, 1H), 7.00 (d, 1H), 6.87 (s, 1H), 6.42 (s, 1H), 5.63 (s, 1H), 4.27 (dd, 1H), 3.97 (s, 5H), 3.01 (dd, 1H), 2.95-2.75 (m, 3H), 2.35-2.09 (m, 3H), 1.78 (d, 3H), 1.36 (s, 1H), 1.02 (d, 3H).

Scheme 5

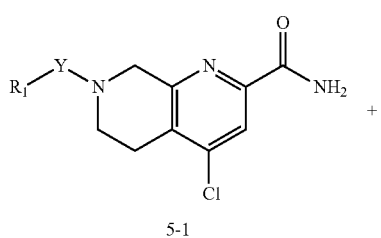

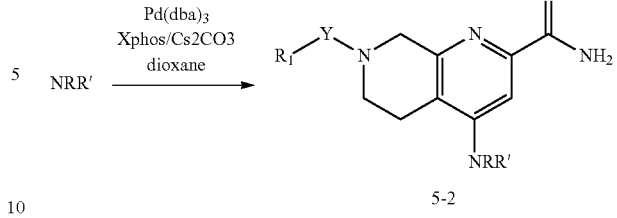

Compounds of formula 1 are prepared by the palladium catalyzed cross-coupling of carboxamide 5-1 with suitable commercial nitrogen containing compounds or suitable nitrogen containing compounds described in the intermediates section.

Example 5-1

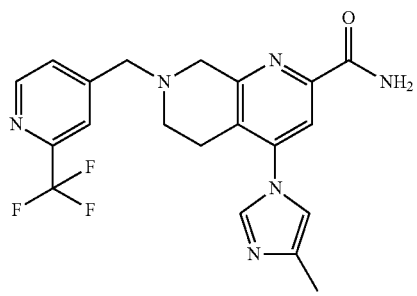 [SMILES: Cc1cn(-c2cc(C(N)=O)nc3c2CCN(Cc2ccnc(C(F)(F)F)c2)C3)cn1]

4-(4-methyl-1H-imidazol-1-yl)-7-((2-(trifluoromethyl)pyridin-4-yl)methyl)-5,6,7,8-tetrahydro-1,7-naphthyridine-2-carboxamide A mixture of ethyl 4-chloro-7-((2-(trifluoromethyl)pyridin-4-yl)methyl)-5,6,7,8-tetrahydro-1,7-naphthyridine-2-carboxamide (60 mg, 0.2 mmol), 4-methyl-1H-imidazole (32 mg, 0.4 mmol), Cs$_2$CO$_3$ (52 mg, 0.4 mmol), X-Phos (10 mg, 0.02 mmol), Pd$_2$(dba)$_3$(10 mg, 0.01 mmol) in anhydrous 1,4-dioxane (2 mL) was stirred at 100° C. under N$_2$ overnight. The reaction was cooled, filtered and the filtrate was concentrated in vacuo. The residue was purified by preparative TLC (EtOAc\petroleum ether=1:1) to give the title compound as a solid. MS (ESI): calc'd for (C$_{20}$H$_{19}$F$_3$N$_6$O) [M+H]$^+$: 416.2; found: 416.2. $^1$H NMR (400 MHz, CDCl$_3$) δ 8.73 (d, J=5.0 Hz, 1H), 7.95 (d, J=6.7 Hz, 1H), 7.81-7.53 (m, 4H), 6.91 (s, 1H), 5.58 (s, 1H), 3.84 (d, J=9.9 Hz, 4H), 2.83-2.89 (m, 4H), 2.31 (s, 3H).

The following examples in Table 5-1 were prepared in an analogous manner to that described in general scheme 5 using intermediate 5-1 and commercial amines or amines described in the intermediates section. Compounds that were resolved into individual enantiomers were separated after step 1 or step 2 using the SFC conditions noted (column size: 250 mm×30 mm; I.D. 5 μm).

TABLE 5-1

| Example | Structure | IUPAC Name | SFC Conditions | Exact Mass [M + H]+ |
| --- | --- | --- | --- | --- |
| 5-2 | 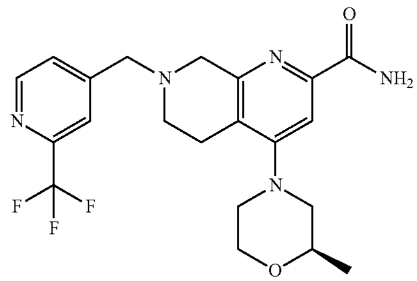 [SMILES: C[C@@H]1CN(c2cc(C(N)=O)nc3c2CCN(Cc2ccnc(C(F)(F)F)c2)C3)CCO1] | (R)-4-(2-methylmorpholino)-7-((2-(trifluoromethyl)pyridin-4-yl)methyl)-5,6,7,8-tetrahydro-1,7-naphthyridine-2-carboxamide | * | Calc'd 436.2, found 436.1 |
| 5-3 | 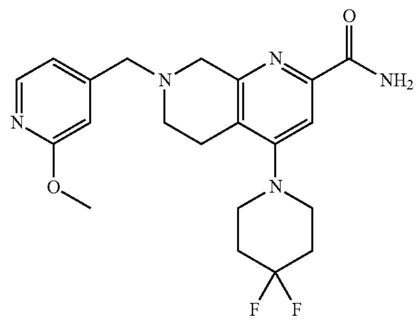 [SMILES: COc1cc(CN2CCc3c(N4CCC(F)(F)CC4)cc(C(N)=O)nc3C2)ccn1] | 4-(4,4-difluoropiperidin-1-yl)-7-[(2-methoxypyridin-4-yl)methyl]-5,6,7,8-tetrahydro-1,7-naphthyridine-2-carboxamide | * | Calc'd 418.2, found 418.3 |
| 5-4 | 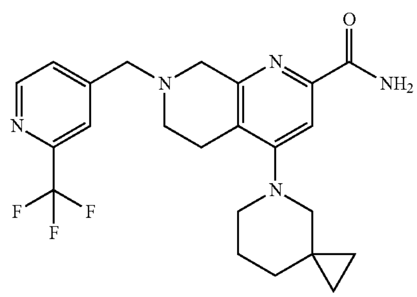 [SMILES: NC(=O)c1cc(N2CCCC3(CC3)C2)c2c(n1)CN(Cc1ccnc(C(F)(F)F)c1)CC2] | 4-(5-azaspiro[2.5]oct-5-yl)-7-{[2-(trifluoromethyl)pyridin-4-yl]methyl}-5,6,7,8-tetrahydro-1,7-naphthyridine-2-carboxamide | * | Calc'd 446.2, found 446.3 |
| 5-5A | 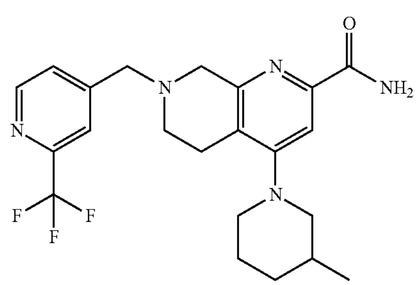 [SMILES: CC1CCCN(c2cc(C(N)=O)nc3c2CCN(Cc2ccnc(C(F)(F)F)c2)C3)C1] | (S) or (R)-4-(3-methylpiperidin-1-yl)-7-((2-(trifluoromethyl)pyridin-4-yl)methyl)-5,6,7,8-tetrahydro-1,7-naphthyridine-2-carboxamide | Step 2: Column: Chiralpak AD; Mobile phase: 60 mL/min 65:35 supercritical CO$_2$: MeOH (0.05% NH$_3$•H$_2$O); faster eluting enantiomer | Calc'd 434.2, found 434.1 |
| 5-5B | 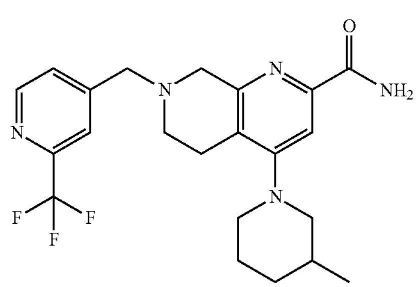 [SMILES: CC1CCCN(c2cc(C(N)=O)nc3c2CCN(Cc2ccnc(C(F)(F)F)c2)C3)C1] | (R) or (S)-4-(3-methylpiperidin-1-yl)-7-((2-(trifluoromethyl)pyridin-4-yl)methyl)-5,6,7,8-tetrahydro-1,7-naphthyridine-2-carboxamide | Step 2: Column: Chiralpak AD; Mobile phase: 60 mL/min 65:35 supercritical CO$_2$: MeOH (0.05% NH$_3$•H$_2$O); slower eluting enantiomer | Calc'd 434.2, found 434.1 |

TABLE 5-1-continued

| Example | Structure | IUPAC Name | SFC Conditions | Exact Mass [M + H]+ |
|---|---|---|---|---|
| 5-6A | 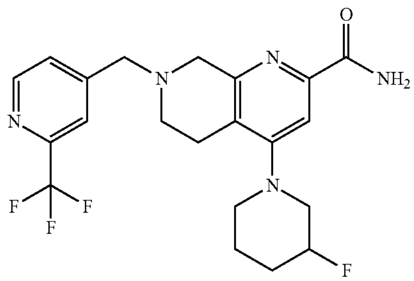 [SMILES: NC(=O)c1cc(N2CCCC(F)C2)c2c(n1)CN(Cc1ccnc(C(F)(F)F)c1)CC2] | (S) or (R)-4-(3-fluoropiperidin-1-yl)-7-((2-(trifluoromethyl)pyridin-4-yl)methyl)-5,6,7,8-tetrahydro-1,7-naphthyridine-2-carboxamide | Step 2: Column: Chiralpak ID; Mobile phase: 60 mL/min 75:25 supercritical $CO_2$: MeOH (0.1% $NH_3 \cdot H_2O$); faster eluting enantiomer | Calc'd 438.2, found 438.3 |
| 5-6B | 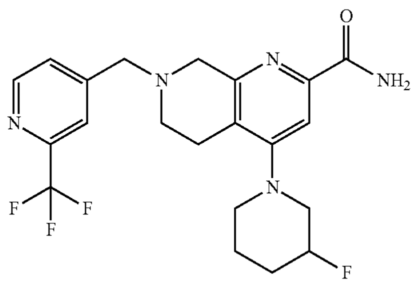 [SMILES: NC(=O)c1cc(N2CCCC(F)C2)c2c(n1)CN(Cc1ccnc(C(F)(F)F)c1)CC2] | (R) or (S)-4-(3-fluoropiperidin-1-yl)-7-((2-(trifluoromethyl)pyridin-4-yl)methyl)-5,6,7,8-tetrahydro-1,7-naphthyridine-2-carboxamide | Step 2: Column: Chiralpak ID; Mobile phase: 60 mL/min 75:25 supercritical $CO_2$: MeOH (0.1% $NH_3 \cdot H_2O$); slower eluting enantiomer | Calc'd 438.2, found 438.3 |
| 5-7 | 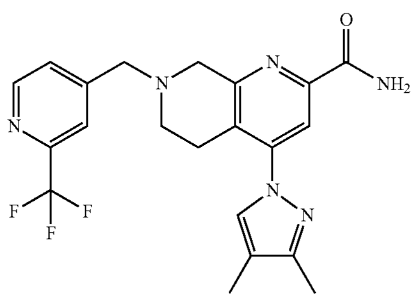 [SMILES: Cc1cn(-c2cc(C(N)=O)nc3c2CCN(Cc2ccnc(C(F)(F)F)c2)C3)nc1C] | 4-(3,4-dimethyl-1H-pyrazol-1-yl)-7-{[2-(trifluoromethyl)pyridin-4-yl]methyl}-5,6,7,8-tetrahydro-1,7-naphthyridine-2-carboxamide | * | Calc'd 431.2, found 431.1 |
| 5-8 | 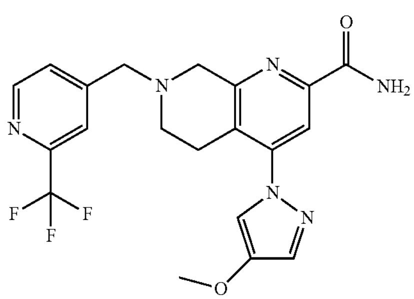 [SMILES: COc1cnn(-c2cc(C(N)=O)nc3c2CCN(Cc2ccnc(C(F)(F)F)c2)C3)c1] | 4-(4-methoxy-1H-pyrazol-1-yl)-7-{[2-(trifluoromethyl)pyridin-4-yl]methyl}-5,6,7,8-tetrahydro-1,7-naphthyridine-2-carboxamide | * | Calc'd 433.2, found 433.3 |
| 5-9 | 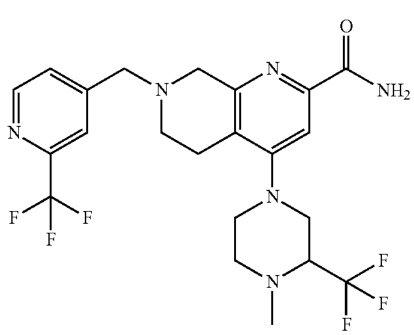 [SMILES: CN1CCN(c2cc(C(N)=O)nc3c2CCN(Cc2ccnc(C(F)(F)F)c2)C3)CC1C(F)(F)F] | (S) or (R)-4-(4-methyl-3-(trifluoromethyl)piperazin-1-yl)-7-((2-(trifluoromethyl)pyridin-4-yl)methyl)-5,6,7,8-tetrahydro-1,7-naphthyridine-2-carboxamide | Step 2: Column: Chiralpak AD; Mobile phase: 60 mL/min 70:30 supercritical $CO_2$: MeOH (0.1% $NH_3 \cdot H_2O$); faster eluting enantiomer | Calc'd 503.2, found 503.2 |

TABLE 5-1-continued

| Example | Structure | IUPAC Name | SFC Conditions | Exact Mass [M + H]+ |
|---|---|---|---|---|
| 5-10 | 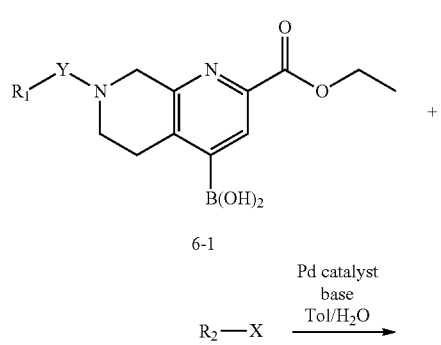 | 4-[4-(trifluoromethyl)-1H-pyrazol-1-yl]-7-{[2-(trifluoromethyl)pyridin-4-yl]methyl}-5,6,7,8-tetrahydro-1,7-naphthyridine-2-carboxamide | * | Calc'd 471.1, found 471.1 |

Scheme 6

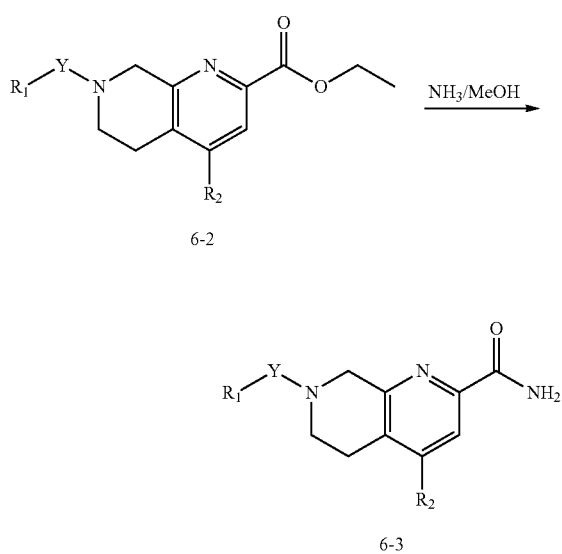

Compounds of formula 1 are prepared by the palladium catalyzed cross-coupling of boronates 6-1 with a suitable commercial coupling partner or a coupling partner described in the intermediates section [using one of the following conditions: Pd(dppf)Cl$_2$/K$_2$CO$_3$/Toluene/H$_2$O, Pd$_2$(dba)$_3$/P(Cy)$_3$/Na$_2$CO$_3$, 2nd-xphos-precatalyst/K$_2$CO$_3$/THF/H$_2$O], followed by treatment with ammonia.

Example 6-1

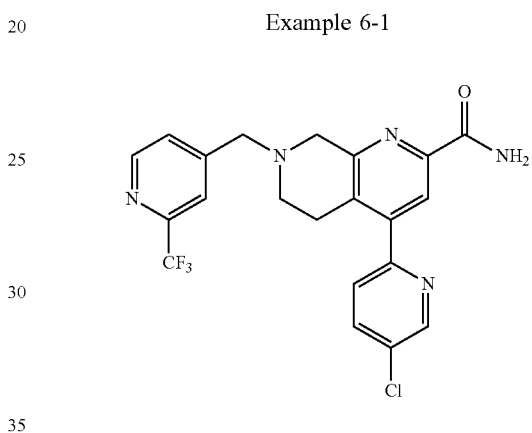

4-(5-chloropyridin-2-yl)-7-((2-(trifluoromethyl)pyridin-4-yl)methyl)-5,6,7,8-tetrahydro-1,7-naphthyridine-2-carboxamide Step 1: Ethyl 4-(5-chloropyridin-2-yl)-7-((2-(trifluoromethyl)pyridin-4-yl)methyl)-5,6,7,8-tetrahydro-1,7-naphthyridine-2-carboxylate A mixture of 2-(ethoxycarbonyl)-7-((2-(trifluoromethyl)pyridin-4-yl)methyl)-5,6,7,8-tetrahydro-1,7-naphthyridin-4-ylboronic acid (40 mg, 0.1 mmol), 2-bromo-5-chloropyridine, (25 mg, 0.15 mmol), K$_2$CO$_3$ (30 mg, 0.2 mmol), Pd(dppf)Cl$_2$ (4 mg, 0.005 mmol) in H$_2$O (0.1 mL) and toluene (1 mL) was stirred at 100° C. under N$_2$ overnight. The reaction mixture was filtered and concentrated in vacuo, the residue was purified on silica gel (EtOAc) to give the title compound as a solid.

Step 2: 4-(5-chloropyridin-2-yl)-7-((2-(trifluoromethyl)pyridin-4-yl)methyl)-5,6,7,8-tetrahydro-1,7-naphthyridine-2-carboxamide A solution of ethyl 4-(5-chloropyridin-2-yl)-7-((2-(trifluoromethyl)pyridin-4-yl)methyl)-5,6,7,8-tetrahydro-1,7-naphthyridine-2-carboxylate (20 mg, 0.6 mmol) in a solution of ammonia methanol solution (2 M, 5 ml) was stirred at room temperature overnight, then concentrated in vacuo. The residue was purified by preparative TLC (EtOAc/petroleum ether=6:1) to afford the target compound as a solid. MS (ESI) calc'd for (C$_{21}$H$_{17}$ClF$_3$N$_5$O) [M+H]$^+$: 448.1; found: 448.1 $^1$H NMR (400 MHz, CDCl$_3$) δ 8.62 (dd, J=10.8, 3.5 Hz, 2H), 8.03 (s, 1H), 7.89-7.63 (m, 3H), 7.46 (dd, J=32.6, 6.5 Hz, 2H), 5.46 (s, 1H), 3.76 (s, 4H), 3.02 (t, J=5.6 Hz, 2H), 2.70 (t, J=5.8 Hz, 2H).

The following examples in Table 6-1 were prepared in an analogous manner to that described in general scheme 6 using intermediate 6-1 and commercial aryl halides or aryl halides described in the intermediates section.

TABLE 6-1

| Example | Structure | Conditions | IUPAC Name | Exact Mass [M + H]+ |
|---|---|---|---|---|
| 6-2 | 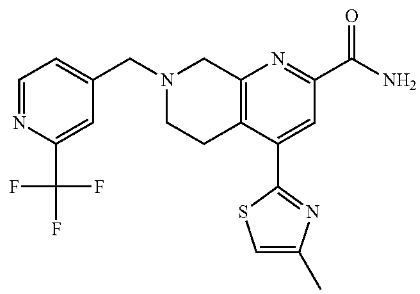 [SMILES: Cc1csc(-c2cc(C(N)=O)nc3c2CCN(Cc2ccnc(C(F)(F)F)c2)C3)n1] | Pd(dppf)Cl₂/ K₂CO₃/Toluene/ H₂O | 4-(4-methyl-1,3-thiazol-2-yl)-7-{[2-(trifluoromethyl)pyridin-4-yl]methyl}-5,6,7,8-tetrahydro-1,7-naphthyridine-2-carboxamide | Calc'd 434.1, found 434.1 |
| 6-3 | 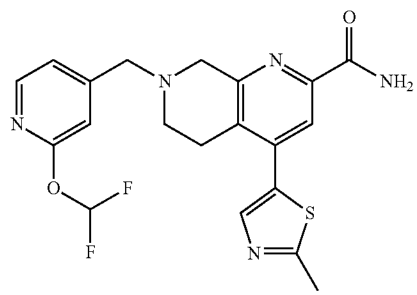 [SMILES: Cc1ncc(-c2cc(C(N)=O)nc3c2CCN(Cc2ccnc(OC(F)F)c2)C3)s1] | Pd(dppf)Cl₂/ K₂CO₃/Toluene/ H₂O | 7-{[2-(difluoromethoxy)pyridin-4-yl]methyl}-4-(2-methyl-1,3-thiazol-5-yl)-5,6,7,8-tetrahydro-1,7-naphthyridine-2-carboxamide | Calc'd 432.1, found 432.2 |
| 6-4 | 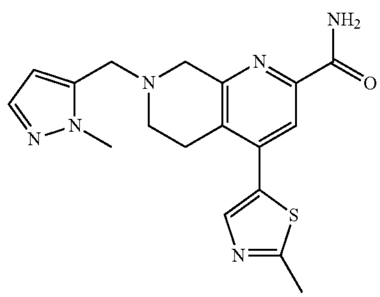 [SMILES: Cc1ncc(-c2cc(C(N)=O)nc3c2CCN(Cc2ccnn2C)C3)s1] | 2nd-xphos-precatalyst/ K₂CO₃/THF/ H₂O | 7-[(1-methyl-1H-pyrazol-5-yl)methyl]-4-(2-methyl-1,3-thiazol-5-yl)-5,6,7,8-tetrahydro-1,7-naphthyridine-2-carboxamide | Calc'd 469.1, found 469.2 |

Scheme 7

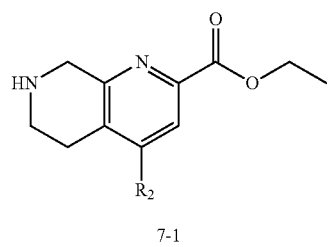

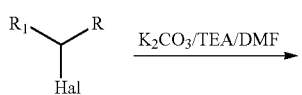

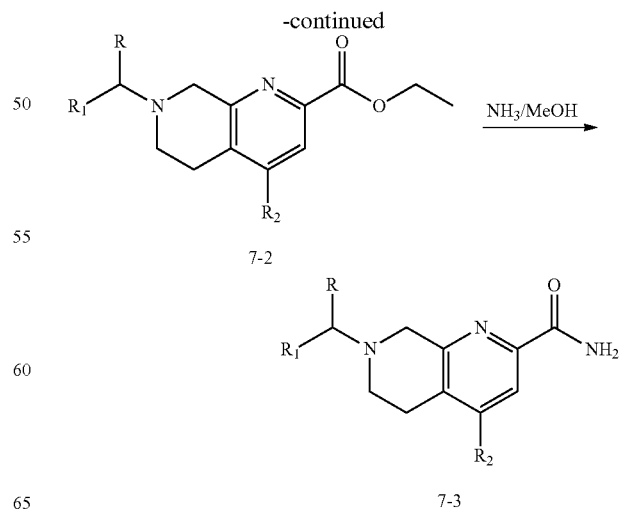

Compounds of formula 1 are prepared by the alkylation of amines 7-1 with commercial halides or halides described in the intermediates section followed by treatment with ammonia.

Example 7-1

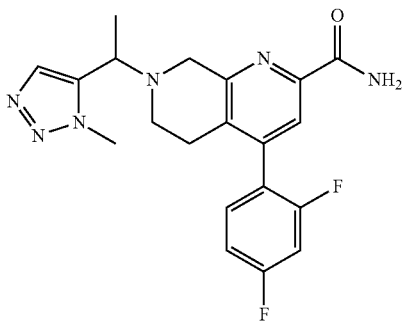 [SMILES: CC(c1cnnn1C)N1CCc2c(-c3ccc(F)cc3F)cc(C(N)=O)nc2C1]

(S) or (R)-4-(2,4-difluorophenyl)-7-(1-(1-methyl-1H-1,2,3-triazol-5-yl)ethyl)-5,6,7,8-tetrahydro-1,7-naphthyridine-2-carboxamide Step 1: Ethyl 4-(2,4-difluorophenyl)-7-(1-(1-methyl-1H-1,2,3-triazol-5-yl)ethyl)-5,6,7,8-tetrahydro-1,7-naphthyridine-2-carboxylate To the solution of 5-(1-bromoethyl)-1-methyl-1H-1,2,3-triazole (90 mg, 0.474 mmol) in the anhydrous DMF (8 mL) was added TEA (0.095 mL, 0.684 mmol), followed by K$_2$CO$_3$ (142 mg, 1.027 mmol) and ethyl 4-(2,4-difluorophenyl)-5,6,7,8-tetrahydro-1,7-naphthyridine-2-carboxylate (109 mg, 0.342 mmol), the resulting mixture was stirred at 60° C. under nitrogen for 3 h. The reaction was cooled to room temperature and diluted with water. The aqueous layer was extracted with EtOAc (15 mL×3). The combined extracts were washed with water and brine, dried over Na$_2$SO$_4$, filtered and concentrated in vacuo. The crude residue was purified by preparative TLC (petroleum ether: EtOAc=2:1) to afford ethyl 4-(2,4-difluorophenyl)-7-(1-(1-methyl-1H-1,2,3-triazol-5-yl)ethyl)-5,6,7,8-tetrahydro-1,7-naphthyridine-2-carboxylate as a solid. MS (ESI) calcd. for (C$_{22}$H$_{24}$F$_2$N$_5$O$_2$) [M+H]+, 428.2, found, 428.2 $^1$H-NMR: (Methanol-d$_4$ 400 MHz) δ 7.83 (s, 1H), 7.73 (s, 1H), 7.33-7.46 (m, 1H), 7.07-7.22 (m, 2H), 4.42 (q, J=6.91 Hz, 2H), 4.28-4.38 (m, 1H), 4.11 (s, 3H), 3.91 (br. s., 2H), 2.62-2.82 (m, 4H), 1.54 (d, J=6.65 Hz, 3H), 1.40 (t, J=7.04 Hz, 3H).

Step 2: 4-(2,4-difluorophenyl)-7-(1-(1-methyl-1H-1,2,3-triazol-5-yl)ethyl)-5,6,7,8-tetrahydro-1,7-naphthyridine-2-carboxamide Ethyl 4-(2,4-difluorophenyl)-7-(1-(1-methyl-1H-1,2,3-triazol-5-yl)ethyl)-5,6,7,8-tetrahydro-1,7-naphthyridine-2-carboxylate (330 mg, 0.772 mmol) in NH$_3$/MeOH (50 mL, 10 M) was stirred at 16° C. for 14 h. LCMS showed starting material was consumed up. The mixture was concentrated to give a yellow solid. The crude solid was purified by reverse phase preparative HPLC eluting with 17-37% MeCN in water (both with 0.1% TFA) to afford the product as a white solid. MS (ESI) calcd. for (C$_{20}$H$_{21}$F$_2$N$_6$O) [M+H]+, 399.2, found, 399.2 $^1$H-NMR: (Methanol-d$_4$ 400 MHz) δ 7.97 (s, 1H), 7.89 (s, 1H), 7.34-7.45 (m, 1H), 7.09-7.23 (m, 2H), 4.82 (d, J=6.26 Hz, 1H), 4.31 (br. s., 2H), 4.19 (s, 3H), 3.24 (d, J=5.09 Hz, 2H), 2.80-2.98 (m, 2H), 1.74 (d, J=7.04 Hz, 3H)

Step 3: (S) or (R)-4-(2,4-difluorophenyl)-7-(1-(1-methyl-1H-1,2,3-triazol-5-yl)ethyl)-5,6,7,8-tetrahydro-1,7-naphthyridine-2-carboxamide 4-(2,4-difluorophenyl)-7-(1-(1-methyl-1H-1,2,3-triazol-5-yl)ethyl)-5,6,7,8-tetrahydro-1,7-naphthyridine-2-carboxamide (240 mg) was separated by SFC to give two enantiomers. The slower moving enantiomer was crystalized from MeCN to give the title compound as a solid. SFC condition: Column: Chiral Pak AD, 5 μm, Daicel Chemical Industries, Ltd. 250×30 mmI.D. Mobile phase: A: Supercritical CO$_2$, B: MeOH (contained 0.1% NH$_3$H$_2$O), A:B=70:30 at 60 mL/min. Column Temp: 38° C. Wavelength: 220 nm. Nozzle Pressure: 100 Bar. Nozzle Temp: 60° C. Evaporator Temp: 20° C. Trimmer Temp: 25° C. MS (ESI) calcd. for (C$_{20}$H$_{21}$F$_2$N$_6$O) [M+H]$^+$, 399.2, found, 399.2 $^1$H NMR (400 MHz, Methanol-d4) ppm 7.74-7.81 (m, 1H), 7.71 (s, 1H), 7.30-7.39 (m, 1H), 7.06-7.16 (m, 2H), 4.24-4.40 (m, 1H), 4.10 (s, 3H), 3.81-3.95 (m, 2H), 2.52-2.84 (m, 4H), 1.52 (d, J=6.65 Hz, 3H).

The following examples in Table 7-1 were prepared in an analogous manner to that described in general scheme 7 using intermediate 7-1 and commercial halides or halides described in the intermediates section. Compounds that were resolved into individual enantiomers were separated after step 1 or step 2 using the SFC conditions noted (column size: 250 mm×30 mm; I.D. 5 μm).

TABLE 7-1

| Example | Structure | IUPAC Name | SFC Conditions | Exact Mass [M + H]+ |
|---|---|---|---|---|
| 7-2 | 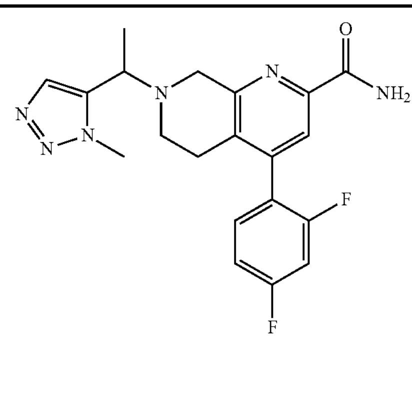 | (R) or (S)-4-(2,4-difluorophenyl)-7-[(1R)-1-(1-methyl-1H-1,2,3-triazol-5-yl)ethyl]-5,6,7,8-tetrahydro-1,7-naphthyridine-2-carboxamide | Step 2: Column: Chiralpak AD; Mobile phase: 60 mL/min 70:30 supercritical CO$_2$: MeOH (0.1% NH$_3$•H$_2$O); faster eluting enantiomer | Calc'd 399.2, found 399.2 |

TABLE 7-1-continued

| Example | Structure | IUPAC Name | SFC Conditions | Exact Mass [M + H]+ |
|---|---|---|---|---|
| 7-3A | 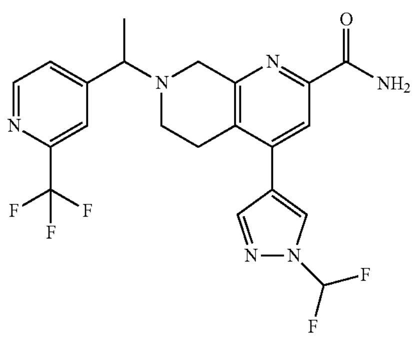 [SMILES: CC(c1ccnc(C(F)(F)F)c1)N1CCc2c(-c3cnn(C(F)F)c3)cc(C(N)=O)nc2C1] | (S) or (R)-4-[1-(difluoromethyl)-1H-pyrazol-4-yl]-7-{(1R)-1-[2-(trifluoromethyl)pyridin-4-yl]ethyl}-5,6,7,8-tetrahydro-1,7-naphthyridine-2-carboxamide | Step 2: Column: Chiralpak AD; Mobile phase: 60 mL/min 75:25 supercritical $CO_2$: MeOH (0.1% $NH_3 \cdot H_2O$); faster eluting enantiomer | Calc'd 476.2, found 476.1 |
| 7-3B | 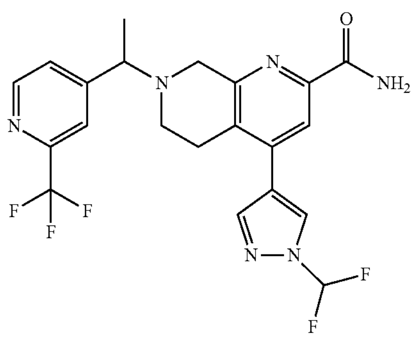 [SMILES: CC(c1ccnc(C(F)(F)F)c1)N1CCc2c(-c3cnn(C(F)F)c3)cc(C(N)=O)nc2C1] | (R) or (S)-4-[1-(difluoromethyl)-1H-pyrazol-4-yl]-7-{(1S)-1-[2-(trifluoromethyl)pyridin-4-yl]ethyl}-5,6,7,8-tetrahydro-1,7-naphthyridine-2-carboxamide | Step 2: Column: Chiralpak AD; Mobile phase: 60 mL/min 75:25 supercritical $CO_2$: MeOH (0.1% $NH_3 \cdot H_2O$); slower eluting enantiomer | Calc'd 476.2, found 476.1 |
| 7-4 | 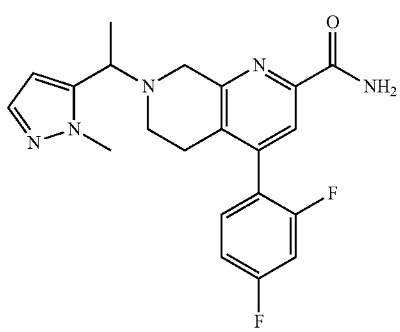 [SMILES: CC(c1ccnn1C)N1CCc2c(-c3ccc(F)cc3F)cc(C(N)=O)nc2C1] | (S) or (R)-4-(2,4-difluorophenyl)-7-[(1S)-1-(1-methyl-1H-pyrazol-5-yl)ethyl]-5,6,7,8-tetrahydro-1,7-naphthyridine-2-carboxamide | Step 2: Column: Chiralpak AD-H; Mobile phase: 60 mL/min 60:40 supercritical $CO_2$: EtOH (0.05% $NH_3 \cdot H_2O$); slower eluting enantiomer | Calc'd 398.2, found 398.2 |

Scheme 8

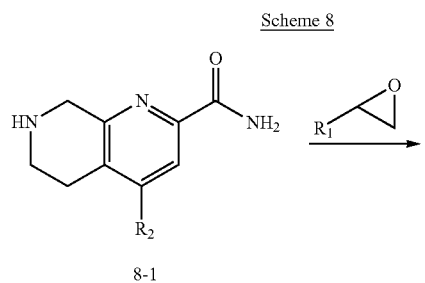

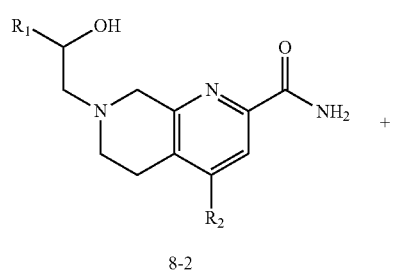

8-1

8-2

+

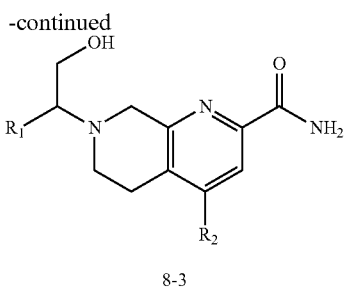

Compounds of formula 1 are prepared by the alkylation of esters 8-1 with commercial epoxides or epoxides described in the intermediates section.

Example 8-1A and 8-1B

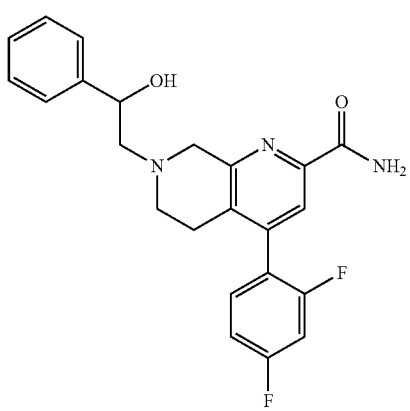 [SMILES: NC(=O)c1cc(-c2ccc(F)cc2F)c2c(n1)CN(CC(O)c1ccccc1)CC2]

(S) and (R)-4-(2,4-difluorophenyl)-7-(2-hydroxy-2-phenylethyl)-5,6,7,8-tetrahydro-1,7-naphthyridine-2-carboxamide To a solution of 4-(2,4-difluorophenyl)-5,6,7,8-tetrahydro-1,7-naphthyridine-2-carboxamide (100 mg, 0.34 mmol) and 2-phenyloxirane (49 mg, 0.4 mmol) in EtOH (10 mL) was added TEA (1.5 mL), the solution was stirred at 80° C. for 2 h. The reaction mixture was concentrated to remove the solvent, and the residue was partitioned between water (50 mL) and EtOAc (50 mL). The organic layer was dried over $Na_2SO_4$ and concentrated under reduced pressure. The residue was purified by preparative TLC to afford a mixture of the products as solids.

The racemic mixture of 4-(2,4-difluorophenyl)-7-(2-hydroxy-2-phenylethyl)-5,6,7,8-tetrahydro-1,7-naphthyridine-2-carboxamide was separated by chiral SFC (Column: Chiralpak AD-H 250×4.6 mm I.D., 5 um Mobile phase: 40% methanol (0.05% DEA) in $CO_2$ Flow rate: 2.35 mL/min Wavelength: 220 nm) to afford the title two enantiomers as solids.

8-2A $^1$H NMR (400 MHz, Methanol-$d_4$) δ 7.71 (s, 1H), 7.36-7.22 (m, 5H), 7.20-7.14 (m, 1H), 7.09-6.98 (m, 2H), 4.89 (dd, J=3.1, 9.0 Hz, 1H), 4.02-3.87 (m, 2H), 2.92-2.76 (m, 3H), 2.69 (br s, 3H). MS ESI calcd. for $C_{23}H_{21}F_2N_3O_2$ [M+H]$^+$ 410.2 found 410.3

8-2B $^1$H NMR (400 MHz, Methanol-$d_4$) δ 7.81 (s, 1H), 7.44-7.33 (m, 4H), 7.31-7.23 (m, 1H), 7.18-7.09 (m, 2H), 4.98 (dd, J=2.7, 9.0 Hz, 1H), 4.08-3.93 (m, 2H), 2.98-2.82 (m, 3H), 2.81-2.69 (m, 3H). MS ESI calcd. For $C_{23}H_{21}F_2N_3O_2$ [M+H]$^+$ 410 found 410.

Example 8-2A and 8-2B

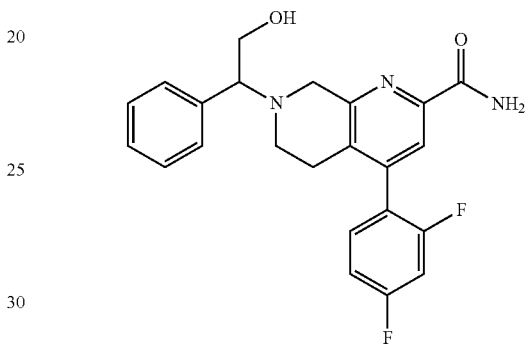

(S) and (R)-4-(2,4-difluorophenyl)-7-(2-hydroxy-1-phenylethyl)-5,6,7,8-tetrahydro-1,7-naphthyridine-2-carboxamide The same reaction used to synthesize Example 8-1 was used to furnish a mixture of Example 8-2A and 8-2B. The racemic mixture of 4-(2,4-difluorophenyl)-7-(2-hydroxy-1-phenylethyl)-5,6,7,8-tetrahydro-1,7-naphthyridine-2-carboxamide was separated by chiral SFC (Column: Chiralpak AD-H 250×4.6 mm I.D., 5 um Mobile phase: 40% methanol (0.05% DEA) in $CO_2$ Flow rate: 2.35 mL/min Wavelength: 220 nm) to afford two enantiomers as solids.

8-2A $^1$H NMR (400 MHz, Methanol-$d_4$) δ 7.78 (s, 1H), 7.44-7.28 (m, 6H), 7.18-7.09 (m, 2H), 4.10 (dd, J=6.7, 11.3 Hz, 1H), 4.03-3.82 (m, 3H), 3.72 (t, J=5.9 Hz, 1H), 2.83 (d, J=6.7 Hz, 1H), 2.77-2.66 (m, 2H). MS ESI calcd. For $C_{23}H_{21}F_2N_3O_2$ [M+H]$^+$ 410.2 found 410.3.

8-2B $^1$H NMR (400 MHz, Methanol-$d_4$) δ 7.78 (s, 1H), 7.44-7.27 (m, 6H), 7.18-7.07 (m, 2H), 4.14-3.67 (m, 6H), 2.90-2.62 (m, 5H). MS ESI calcd. For $C_{23}H_{21}F_2N_3O_2$[M+H]$^+$ 410.2 found 410.3.

The following examples in Table 8-1 were prepared in an analogous manner to that described in general scheme 8 using intermediate 8-1 and commercial epoxides or epoxides described in the intermediates section. Compounds that were resolved into individual enantiomers were separated after step 1 or step 2 using the SFC conditions noted (column size: 250 mm×30 mm; I.D. 5 μm).

TABLE 8-1

| Example | Structure | IUPAC Name | | Exact Mass [M + H]+ |
|---|---|---|---|---|
| 8-3A | 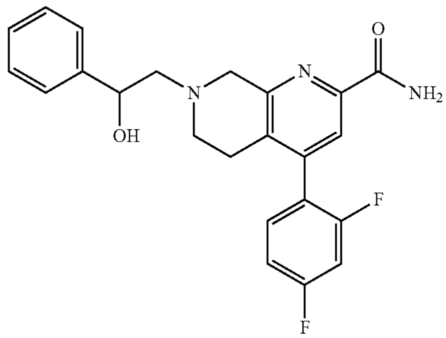 | (S) or (R)-4-(2,4-difluorophenyl)-7-[(2S or 2R)-2-hydroxy-2-phenylethyl]-5,6,7,8-tetrahydro-1,7-naphthyridine-2-carboxamide | Step 2: Column: Chiralpak AD-H; Mobile phase: 60 mL/min 60:40 supercritical CO$_2$: MeOH (0.05% DEA); faster eluting enantiomer | Calc'd 410.2, found 410.3 |
| 8-3B | 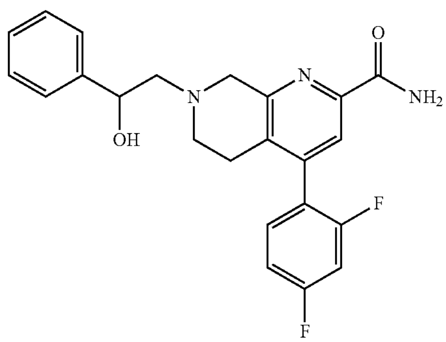 | (R) or (S)-4-(2,4-difluorophenyl)-7-[(2R or 2S)-2-hydroxy-2-phenylethyl]-5,6,7,8-tetrahydro-1,7-naphthyridine-2-carboxamide | Step 2: Column: Chiralpak AD-H; Mobile phase: 60 mL/min 60:40 supercritical CO$_2$: MeOH (0.05% DEA); slower eluting enantiomer | Calc'd 410.2, found 410.3 |

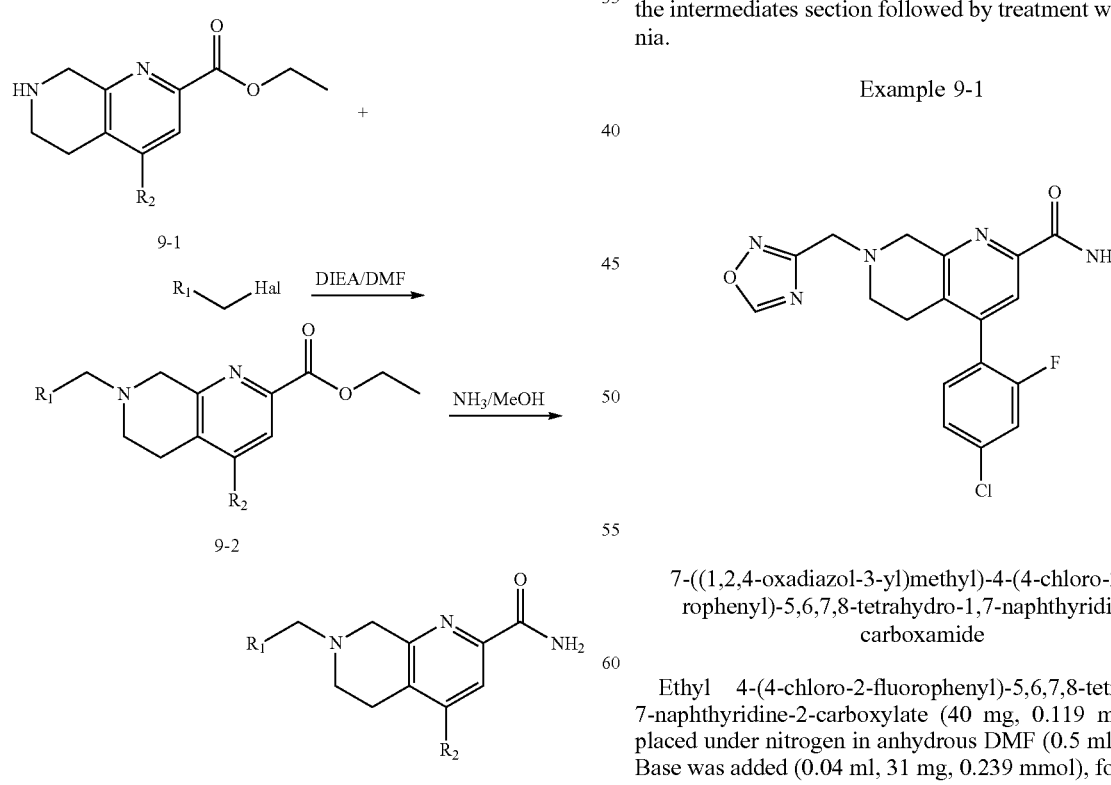

Compounds of formula 1 are prepared by the alkylation of amines 9-1 with commercial halides or halides described in the intermediates section followed by treatment with ammonia.

Example 9-1

7-((1,2,4-oxadiazol-3-yl)methyl)-4-(4-chloro-2-fluorophenyl)-5,6,7,8-tetrahydro-1,7-naphthyridine-2-carboxamide Ethyl 4-(4-chloro-2-fluorophenyl)-5,6,7,8-tetrahydro-1,7-naphthyridine-2-carboxylate (40 mg, 0.119 mmol) was placed under nitrogen in anhydrous DMF (0.5 ml). Hunig's Base was added (0.04 ml, 31 mg, 0.239 mmol), followed by 3-(chloromethyl)-1,2,4-oxadiazole (18 mg, 0.149 mmol) in anhydrous DMF (0.5 ml). The reaction mixture was allowed to stir at room temperature. After 18 h the mixture was concentrated under reduced pressure. The resultant residue was dissolved in 7 N NH$_3$ in methanol (2.0 ml). The mixture was stirred 17 h at room temperature, then for 1 hour at 50° C. The mixture was allowed to cool, then concentrated under reduced pressure. The resultant residue was dissolved in DMSO (1.5 ml) and purified by reverse phase preparative HPLC eluting with 8 to 40% MeCN in water (both with 0.1% TFA) over 10 min at 25 ml/min to provide the title compound. LC-MS: calculated for C$_{18}$H$_{15}$ClFN$_5$O$_2$ 387.09 observed m/e: 388.09 (M+H)$^+$.

The following examples in Table 9-1 were prepared in an analogous manner to that described in general scheme 9 using intermediate 9-1 and commercial chlorides or chlorides described in the intermediates section.

TABLE 9-1

| Example | Structure | IUPAC Name | Exact Mass [M + H]+ |
|---|---|---|---|
| 9-2 | 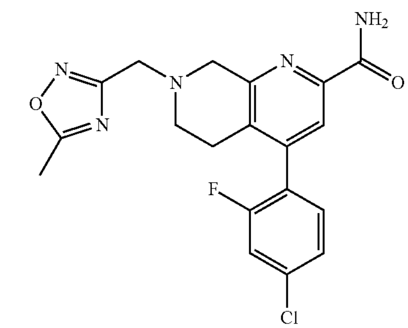 [SMILES: Cc1nc(CN2CCc3c(-c4ccc(Cl)cc4F)cc(C(N)=O)nc3C2)no1] | 4-(4-chloro-2-fluorophenyl)-7-[(5-methyl-1,2,4-oxadiazol-3-yl)methyl]-5,6,7,8-tetrahydro-1,7-naphthyridine-2-carboxamide | Calc'd 402.11, found 402.11 |
| 9-3 | 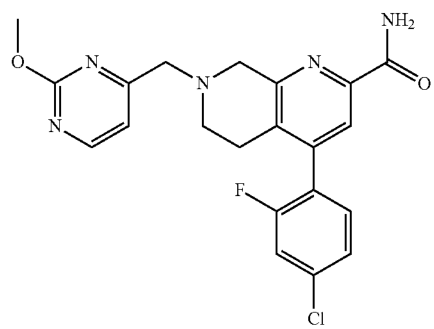 [SMILES: COc1nccc(CN2CCc3c(-c4ccc(Cl)cc4F)cc(C(N)=O)nc3C2)n1] | 4-(4-chloro-2-fluorophenyl)-7-[(2-methoxypyrimidin-4-yl)methyl]-5,6,7,8-tetrahydro-1,7-naphthyridine-2-carboxamide | Calc'd 428.13, found 428.12 |
| 9-4 | 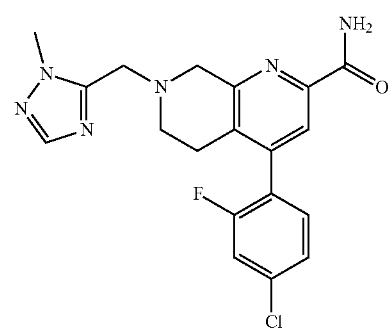 [SMILES: Cn1ncnc1CN1CCc2c(-c3ccc(Cl)cc3F)cc(C(N)=O)nc2C1] | 4-(4-chloro-2-fluorophenyl)-7-[(1-methyl-1H-1,2,4-triazol-5-yl)methyl]-5,6,7,8-tetrahydro-1,7-naphthyridine-2-carboxamide | Calc'd 401.13, found 401.12 |
| 9-5 | 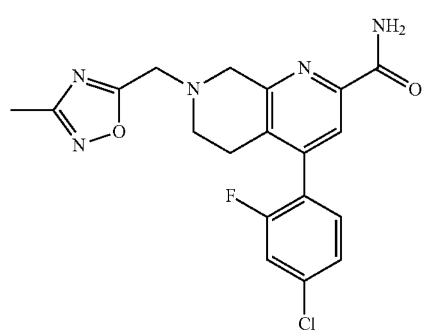 [SMILES: Cc1noc(CN2CCc3c(-c4ccc(Cl)cc4F)cc(C(N)=O)nc3C2)n1] | 4-(4-chloro-2-fluorophenyl)-7-[(3-methyl-1,2,4-oxadiazol-5-yl)methyl]-5,6,7,8-tetrahydro-1,7-naphthyridine-2-carboxamide | Calc'd 402.11, found 402.11 |

TABLE 9-1-continued

| Example | Structure | IUPAC Name | Exact Mass [M + H]+ |
|---|---|---|---|
| 9-6 | 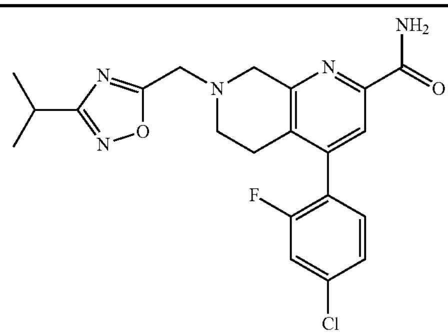 | 4-(4-chloro-2-fluorophenyl)-7-{[3-(1-methylethyl)-1,2,4-oxadiazol-5-yl]methyl}-5,6,7,8-tetrahydro-1,7-naphthyridine-2-carboxamide | Calc'd 430.14, found 430.14 |
| 9-7 | 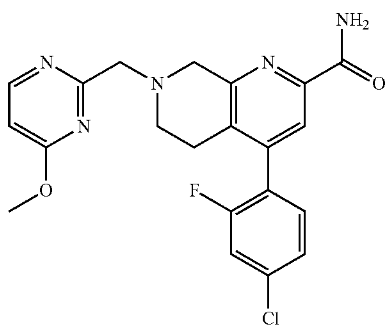 [SMILES: COc1ccnc(CN2CCc3c(-c4ccc(Cl)cc4F)cc(C(N)=O)nc3C2)n1] | 4-(4-chloro-2-fluorophenyl)-7-[(4-methoxypyrimidin-2-yl)methyl]-5,6,7,8-tetrahydro-1,7-naphthyridine-2-carboxamide | Calc'd 428.13, found 428.12 |

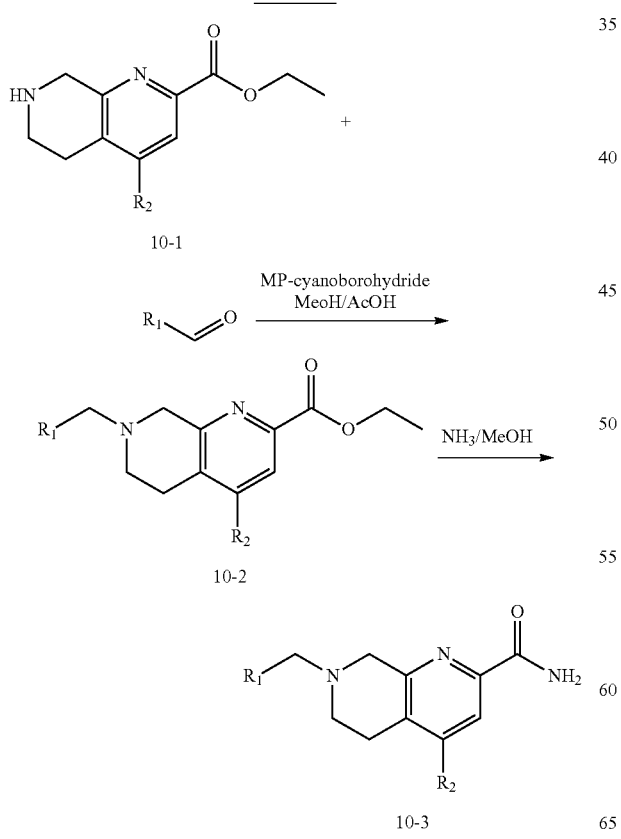

Compounds of formula 1 are prepared by the reduction amination of amines 10-1 with a commercial aldehyde or an aldehyde described in the intermediates section followed by treatment with ammonia.

Example 10-1

4-(4-chloro-2-fluorophenyl)-7-((3-methyloxetan-3-yl)methyl)-5,6,7,8-tetrahydro-1,7-naphthyridine-2-carboxamide Ethyl 4-(4-chloro-2-fluorophenyl)-5,6,7,8-tetrahydro-1,7-naphthyridine-2-carboxylate (40 mg, 0.119 mmol) and 3-methyloxetane-3-carbaldehyde (30 mg, 0.300 mmol) were placed under nitrogen in anhydrous MeOH (1.0 ml) and acetic acid (0.1 ml). MP-cyanoborohydride (2.49 mmol/g, 100 mg, 0.249 mmol) was added. The reaction mixture was stirred at room temperature for 21 h, then diluted with MeOH and filtered. The filtrate was concentrated under reduced pressure. The resultant residue was dissolved in 7 N NH₃ in MeOH (2.0 ml). The mixture was stirred 72 h at room temperature, then concentrated under reduced pressure. The resultant residue was dissolved in DMSO (1.5 ml) and purified by reverse phase preparative HPLC eluting with 20 to 55% MeCN in water (both with 0.1% NH₃) to provide the title compound. LC-MS: calculated for $C_{20}H_{21}ClFN_3O_2$ 389.13 observed m/e: 390.13 (M+H)⁺.

The following examples in Table 10-1 were prepared in an analogous manner to that described in general scheme 10 using intermediate 10-1 and commercial aldehydes or aldehydes described in the intermediates section.

TABLE 10-1

| Example | Structure | IUPAC Name | Exact Mass [M + H]+ |
|---------|-----------|------------|---------------------|
| 10-2 | 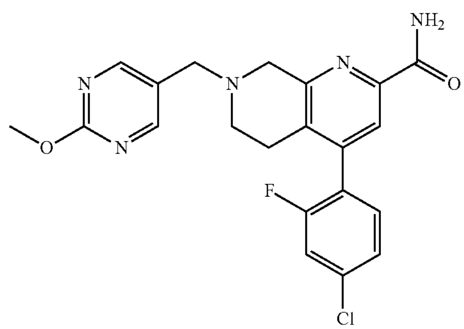 [SMILES: COc1ncc(CN2CCc3c(-c4ccc(Cl)cc4F)cc(C(N)=O)nc3C2)cn1] | 4-(4-chloro-2-fluorophenyl)-7-[(2-methoxypyrimidin-5-yl)methyl]-5,6,7,8-tetrahydro-1,7-naphthyridine-2-carboxamide | Calc'd 428.13, found 428.12 |
| 10-3 | 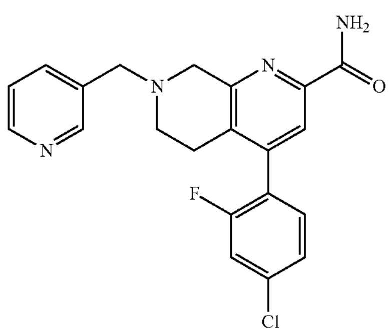 [SMILES: NC(=O)c1cc(-c2ccc(Cl)cc2F)c2c(n1)CN(Cc1cccnc1)CC2] | 4-(4-chloro-2-fluorophenyl)-7-(pyridin-3-ylmethyl)-5,6,7,8-tetrahydro-1,7-naphthyridine-2-carboxamide | Calc'd 397.12, found 397.11 |
| 10-4 | 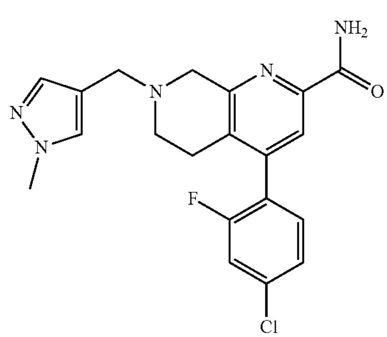 [SMILES: Cn1cc(CN2CCc3c(-c4ccc(Cl)cc4F)cc(C(N)=O)nc3C2)cn1] | 4-(4-chloro-2-fluorophenyl)-7-[(1-methyl-1H-pyrazol-4-yl)methyl]-5,6,7,8-tetrahydro-1,7-naphthyridine-2-carboxamide | Calc'd 400.13, found 400.13 |

Scheme 11

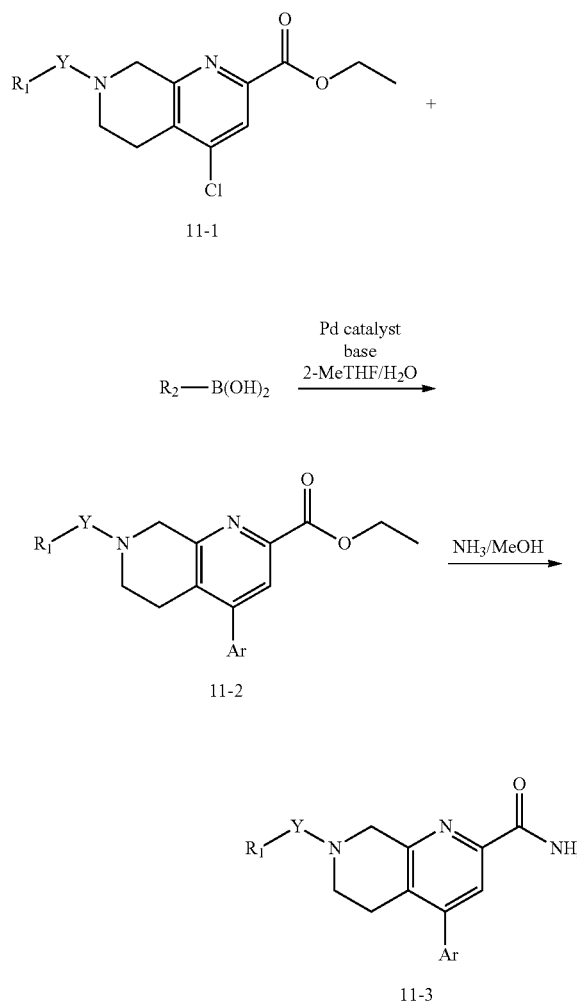

Compounds of formula 1 are prepared by the palladium catalyzed cross-coupling of aryl chlorides 11-1 with a suitable, commercial boronate or a suitable boronate described in the intermediates section followed by treatment with ammonia.

Example 11-1

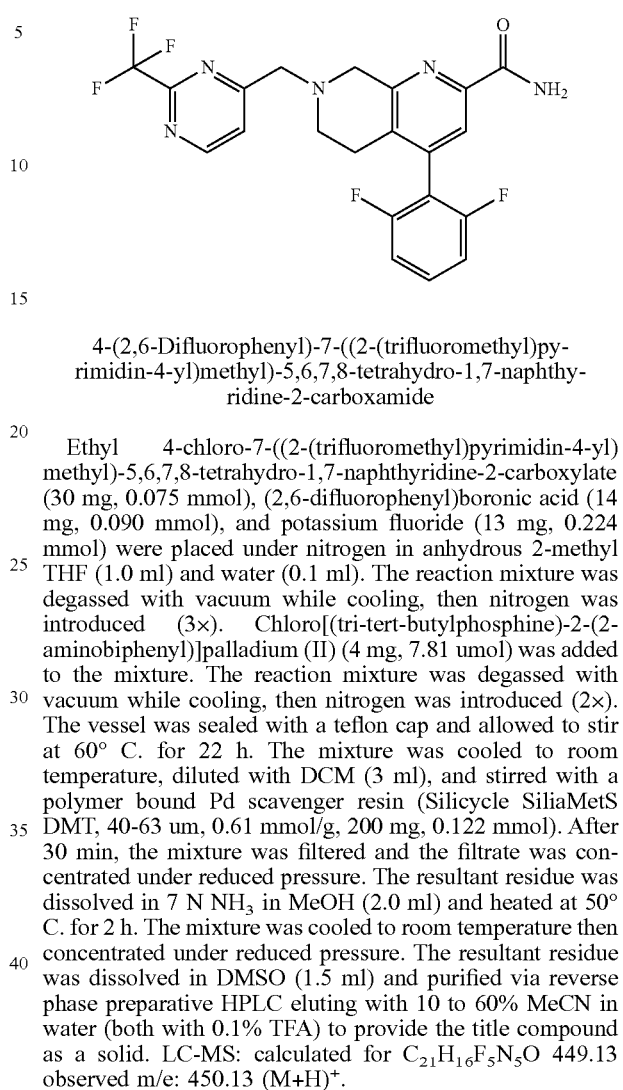

4-(2,6-Difluorophenyl)-7-((2-(trifluoromethyl)pyrimidin-4-yl)methyl)-5,6,7,8-tetrahydro-1,7-naphthyridine-2-carboxamide Ethyl 4-chloro-7-((2-(trifluoromethyl)pyrimidin-4-yl)methyl)-5,6,7,8-tetrahydro-1,7-naphthyridine-2-carboxylate (30 mg, 0.075 mmol), (2,6-difluorophenyl)boronic acid (14 mg, 0.090 mmol), and potassium fluoride (13 mg, 0.224 mmol) were placed under nitrogen in anhydrous 2-methyl THF (1.0 ml) and water (0.1 ml). The reaction mixture was degassed with vacuum while cooling, then nitrogen was introduced (3×). Chloro[(tri-tert-butylphosphine)-2-(2-aminobiphenyl)]palladium (II) (4 mg, 7.81 umol) was added to the mixture. The reaction mixture was degassed with vacuum while cooling, then nitrogen was introduced (2×). The vessel was sealed with a teflon cap and allowed to stir at 60° C. for 22 h. The mixture was cooled to room temperature, diluted with DCM (3 ml), and stirred with a polymer bound Pd scavenger resin (Silicycle SiliaMetS DMT, 40-63 um, 0.61 mmol/g, 200 mg, 0.122 mmol). After 30 min, the mixture was filtered and the filtrate was concentrated under reduced pressure. The resultant residue was dissolved in 7 N $NH_3$ in MeOH (2.0 ml) and heated at 50° C. for 2 h. The mixture was cooled to room temperature then concentrated under reduced pressure. The resultant residue was dissolved in DMSO (1.5 ml) and purified via reverse phase preparative HPLC eluting with 10 to 60% MeCN in water (both with 0.1% TFA) to provide the title compound as a solid. LC-MS: calculated for $C_{21}H_{16}F_5N_5O$ 449.13 observed m/e: 450.13 (M+H)$^+$.

The following examples in Table 11-1 were prepared in an analogous manner to that described in general scheme 11 using intermediate 11-1 and commercial aryl boronates or aryl boronates described in the intermediates section.

TABLE 11-1

| Example | Structure | IUPAC Name | Exact Mass [M + H]+ |
|---|---|---|---|
| 11-2 | (structure) | 4-(2,5-difluorophenyl)-7-{[2-(trifluoromethyl)pyrimidin-4-yl]methyl}-5,6,7,8-tetrahydro-1,7-naphthyridine-2-carboxamide | Calc'd 450.14, found 450.13 |

TABLE 11-1-continued

| Example | Structure | IUPAC Name | Exact Mass [M + H]+ |
|---|---|---|---|
| 11-3 | 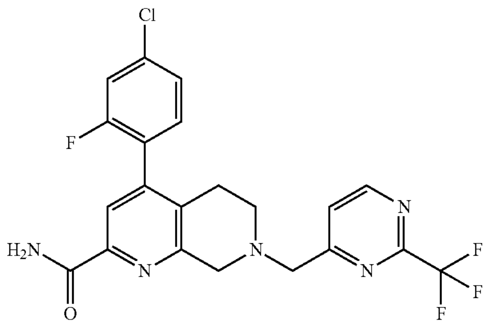 [SMILES: NC(=O)c1cc(-c2ccc(Cl)cc2F)c2c(n1)CN(Cc1ccnc(C(F)(F)F)n1)CC2] | 4-(4-chloro-2-fluorophenyl)-7-{[2-(trifluoromethyl)pyrimidin-4-yl]methyl}-5,6,7,8-tetrahydro-1,7-naphthyridine-2-carboxamide | Calc'd 466.11, found 466.11 |
| 11-4 | 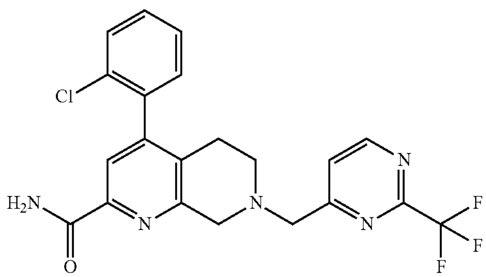 [SMILES: NC(=O)c1cc(-c2ccccc2Cl)c2c(n1)CN(Cc1ccnc(C(F)(F)F)n1)CC2] | 4-(2-chlorophenyl)-7-{[2-(trifluoromethyl)pyrimidin-4-yl]methyl}-5,6,7,8-tetrahydro-1,7-naphthyridine-2-carboxamide | Calc'd 448.12, found 448.11 |
| 11-5 | 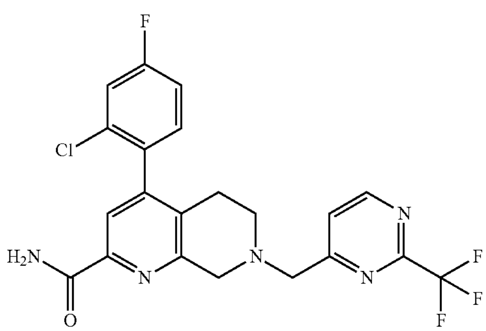 [SMILES: NC(=O)c1cc(-c2ccc(F)cc2Cl)c2c(n1)CN(Cc1ccnc(C(F)(F)F)n1)CC2] | 4-(2-chloro-4-fluorophenyl)-7-{[2-(trifluoromethyl)pyrimidin-4-yl]methyl}-5,6,7,8-tetrahydro-1,7-naphthyridine-2-carboxamide | Calc'd 466.11, found 466.10 |
| 11-6 | 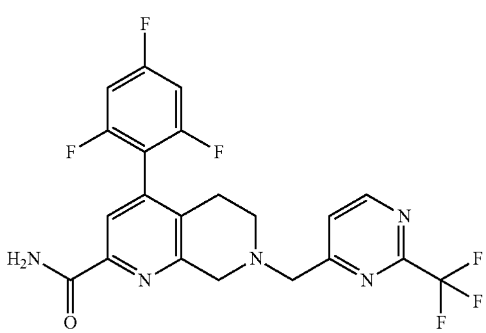 [SMILES: NC(=O)c1cc(-c2c(F)cc(F)cc2F)c2c(n1)CN(Cc1ccnc(C(F)(F)F)n1)CC2] | 7-{[2-(trifluoromethyl)pyrimidin-4-yl]methyl}-4-(2,4,6-trifluorophenyl)-5,6,7,8-tetrahydro-1,7-naphthyridine-2-carboxamide | Calc'd 468.13, found 468.12 |
| 11-7 | 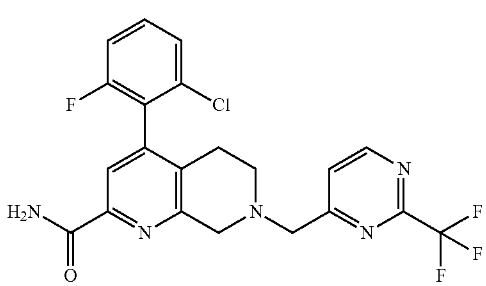 [SMILES: NC(=O)c1cc(-c2c(F)cccc2Cl)c2c(n1)CN(Cc1ccnc(C(F)(F)F)n1)CC2] | 4-(2-chloro-6-fluorophenyl)-7-{[2-(trifluoromethyl)pyrimidin-4-yl]methyl}-5,6,7,8-tetrahydro-1,7-naphthyridine-2-carboxamide | Calc'd 466.11, found 466.10 |

TABLE 11-1-continued

| Example | Structure | IUPAC Name | Exact Mass [M + H]+ |
|---|---|---|---|
| 11-8 | 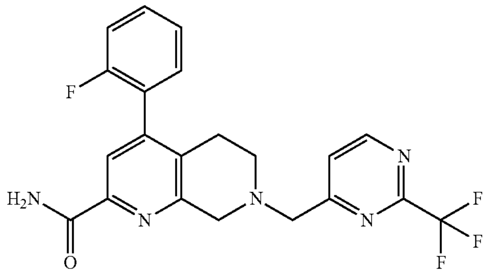 [SMILES: NC(=O)c1cc(-c2ccccc2F)c2c(n1)CN(Cc1ccnc(C(F)(F)F)n1)CC2] | 4-(2-fluorophenyl)-7-{[2-(trifluoromethyl)pyrimidin-4-yl]methyl}-5,6,7,8-tetrahydro-1,7-naphthyridine-2-carboxamide | Calc'd 432.14, found 432.14 |
| 11-9 | 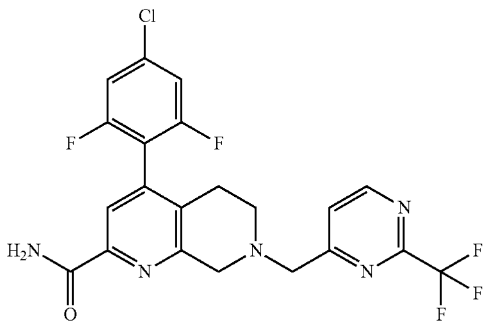 | 4-(4-chloro-2,6-difluorophenyl)-7-{[2-(trifluoromethyl)pyrimidin-4-yl]methyl}-5,6,7,8-tetrahydro-1,7-naphthyridine-2-carboxamide | Calc'd 484.1, found 484.09 |
| 11-10 | 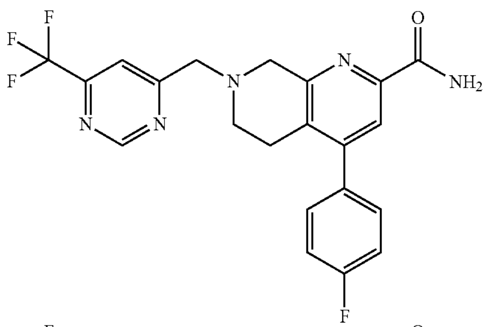 | 4-(4-fluorophenyl)-7-{[6-(trifluoromethyl)pyrimidin-4-yl]methyl}-5,6,7,8-tetrahydro-1,7-naphthyridine-2-carboxamide | Calc'd 432.14, found 432.14 |
| 11-11 | 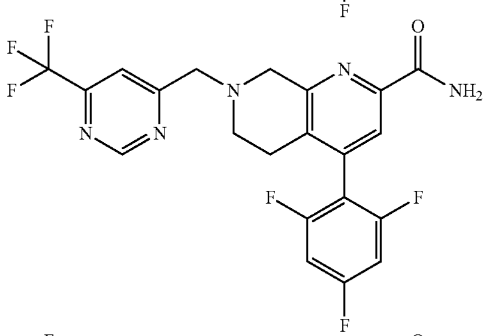 | 7-{[6-(trifluoromethyl)pyrimidin-4-yl]methyl}-4-(2,4,6-trifluorophenyl)-5,6,7,8-tetrahydro-1,7-naphthyridine-2-carboxamide | Calc'd 468.13, found 468.12 |
| 11-12 | 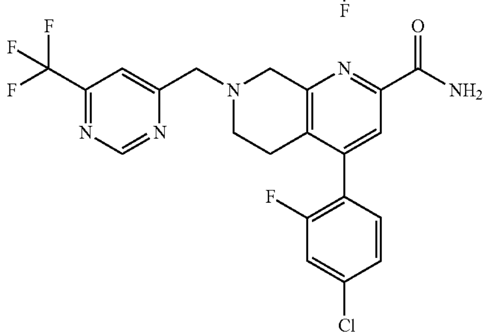 | 4-(4-chloro-2-fluorophenyl)-7-{[6-(trifluoromethyl)pyrimidin-4-yl]methyl}-5,6,7,8-tetrahydro-1,7-naphthyridine-2-carboxamide | Calc'd 466.11, found 466.10 |

Scheme 12

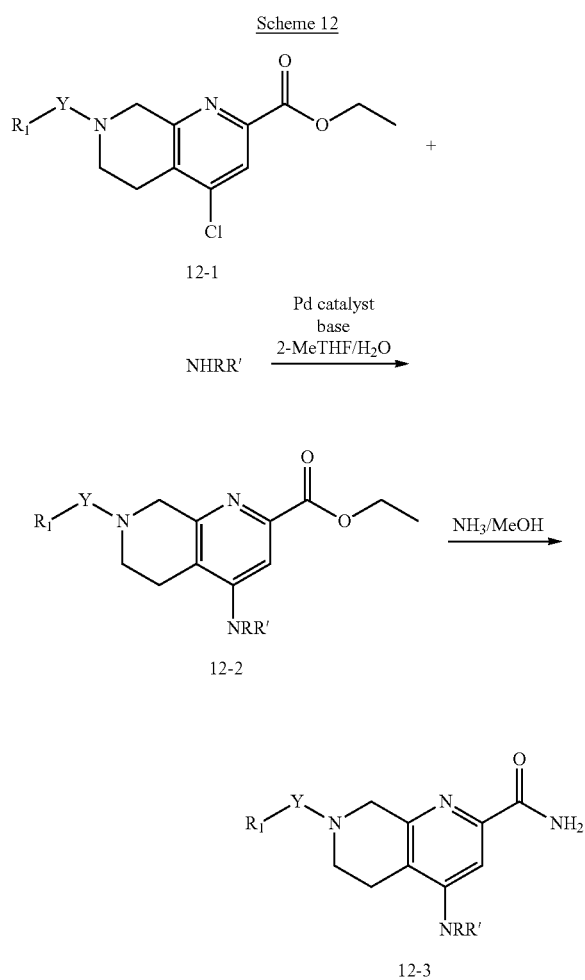

Compounds of formula 1 are prepared by the palladium catalyzed cross-coupling of aryl chlorides 12-1 with a suitable, commercial nitrogen containing compound or a suitable nitrogen containing compound described in the intermediates section followed by treatment with ammonia.

Example 12-1

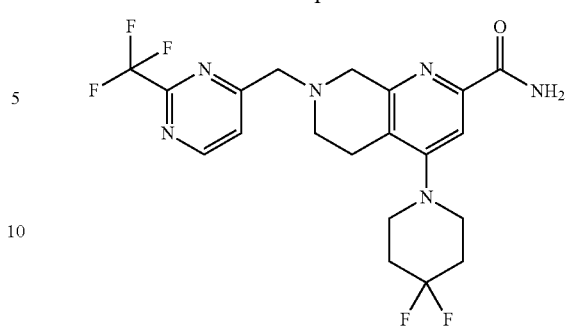

4-(4,4-difluoropiperidin-1-yl)-7-((2-(trifluoromethyl)pyrimidin-4-yl)methyl)-5,6,7,8-tetrahydro-1,7-naphthyridine-2-carboxamide Ethyl 4-chloro-7-((2-(trifluoromethyl)pyrimidin-4-yl)methyl)-5,6,7,8-tetrahydro-1,7-naphthyridine-2-carboxylate (30 mg, 0.075 mmol), 4,4-difluoropiperidine hydrochloride (14 mg, 0.090 mmol), and cesium carbonate (73 mg, 0.225 mmol) were placed under nitrogen in anhydrous 1,4-dioxane (1.0 ml). The reaction mixture was degassed with vacuum while cooling, then nitrogen was introduced (3×). 2nd generation RuPhos Pre-catalyst (6 mg, 7.72 umol) was added to the reaction mixture. The reaction mixture was degassed with vacuum while cooling, then nitrogen was introduced (2×). The vessel was sealed with a teflon cap and allowed to stir at 95° C. for 18 h. The mixture was cooled to room temperature, diluted with DCM (3 ml), and stirred with a polymer bound Pd scavenger resin (Silicycle SiliaMetS DMT, 40-63 um, 0.61 mmol/g, 200 mg, 0.122 mmol). After 30 min, the mixture was filtered and the filtrate was concentrated under reduced pressure. The resultant residue was dissolved in 7 N $NH_3$ in MeOH (2.0 ml) and stirred at room temperature for 22 h. The mixture was concentrated under reduced pressure. The resultant residue was dissolved in DMSO (1.5 ml) and purified via reverse phase preparative HPLC eluting with 10 to 40% MeCN in water (both with 0.1% TFA) to provide the title compound as a solid. LC-MS: calculated for $C_{20}H_{21}F_5N_6O$ 456.17 observed m/e: 457.17 $(M+H)^+$.

The following examples in Table 12-1 were prepared in an analogous manner to that described in general scheme 12 using intermediate 12-1 and commercial nitrogen containing heterocycles or nitrogen containing heterocycles described in the intermediates section.

TABLE 12-1

| Example | Structure | IUPAC Name | Exact Mass [M + H]+ |
|---|---|---|---|
| 12-2 | 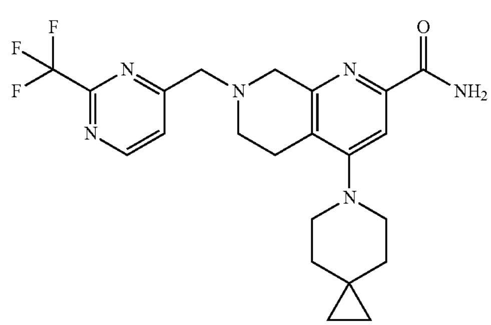 [SMILES: NC(=O)c1cc(N2CCC3(CC2)CC3)c2c(n1)CN(Cc1ccnc(C(F)(F)F)n1)CC2] | 4-(6-azaspiro[2.5]oct-6-yl)-7-{[2-(trifluoromethyl)pyrimidin-4-yl]methyl}-5,6,7,8-tetrahydro-1,7-naphthyridine-2-carboxamide | Calc'd 447.21, found 447.20 |

TABLE 12-1-continued

| Example | Structure | IUPAC Name | Exact Mass [M + H]+ |
|---|---|---|---|
| 12-3 | 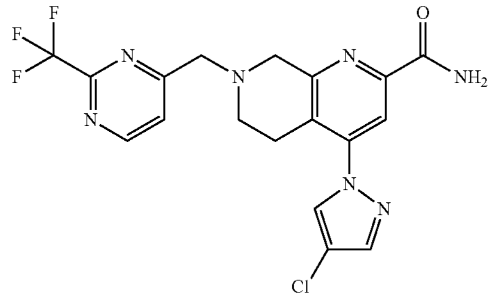 [SMILES: NC(=O)c1cc(-n2cc(Cl)cn2)c2c(n1)CN(Cc1ccnc(C(F)(F)F)n1)CC2] | 4-(4-chloro-1H-pyrazol-1-yl)-7-{[2-(trifluoromethyl)pyrimidin-4-yl]methyl}-5,6,7,8-tetrahydro-1,7-naphthyridine-2-carboxamide | Calc'd 438.11, found 438.10 |
| 12-4 | 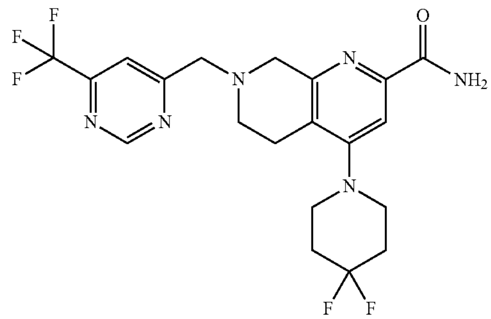 [SMILES: NC(=O)c1cc(N2CCC(F)(F)CC2)c2c(n1)CN(Cc1cc(C(F)(F)F)ncn1)CC2] | 4-(4,4-difluoropiperidin-1-yl)-7-{[6-(trifluoromethyl)pyrimidin-4-yl]methyl}-5,6,7,8-tetrahydro-1,7-naphthyridine-2-carboxamide | Calc'd 457.18, found 457.17 |
| 12-5 | 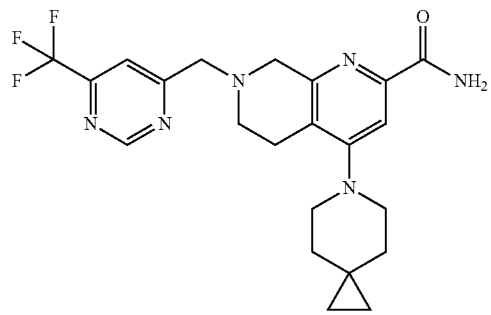 [SMILES: NC(=O)c1cc(N2CCC3(CC2)CC3)c2c(n1)CN(Cc1cc(C(F)(F)F)ncn1)CC2] | 4-(6-azaspiro[2.5]oct-6-yl)-7-{[6-(trifluoromethyl)pyrimidin-4-yl]methyl}-5,6,7,8-tetrahydro-1,7-naphthyridine-2-carboxamide | Calc'd 447.21, found 447.20 |

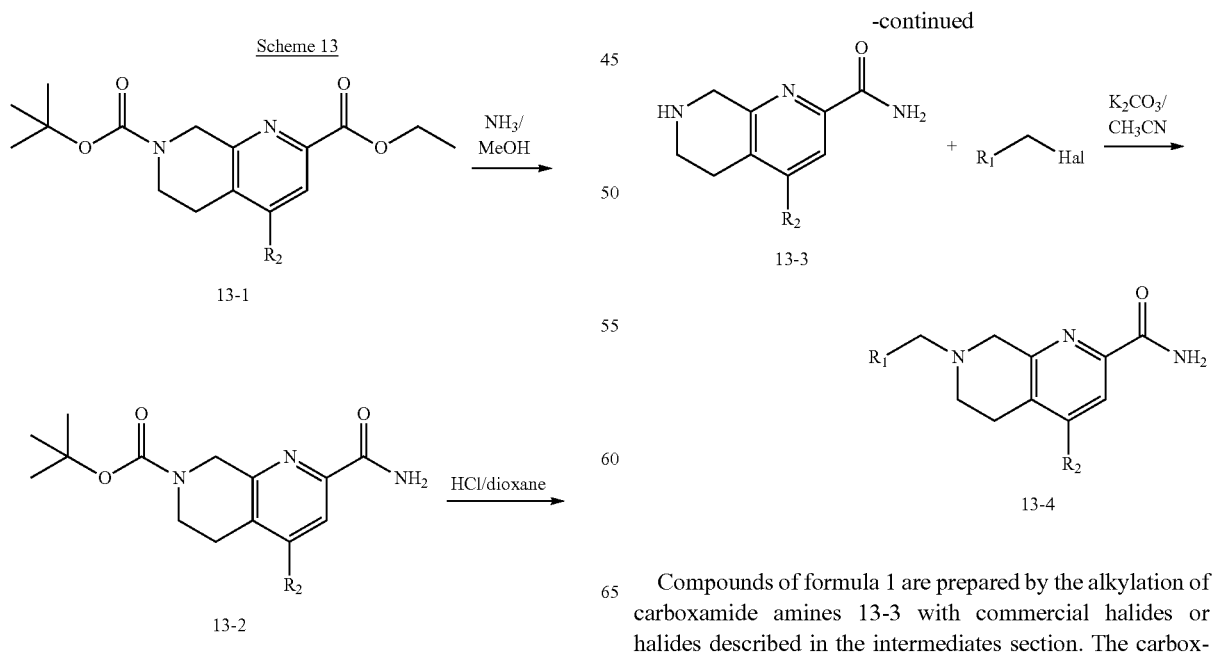

Compounds of formula 1 are prepared by the alkylation of carboxamide amines 13-3 with commercial halides or halides described in the intermediates section. The carboxamide amindes are derived from the BOC protected amine esters 13-1 via sequential treatment with ammonia and HCl.

Example 13-1

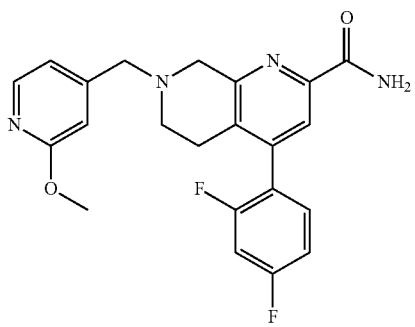 [SMILES: COc1cc(CN2CCc3c(-c4ccc(F)cc4F)cc(C(N)=O)nc3C2)ccn1]

4-(2,4-difluorophenyl)-7-((2-methoxypyridin-4-yl)methyl)-5,6,7,8-tetrahydro-1,7-naphthyridine-2-carboxamide Step 1: 4-(2,4-Difluorophenyl)-5,6,7,8-tetrahydro-1,7-naphthyridine-2-carboxamide Step 1: Tert-butyl-2-carbamoyl-4-(2,4-difluorophenyl)-5,6-dihydro-1,7-naphthyridine-7(8H)-carboxylate To a mixture of 7-tert-butyl 2-ethyl 4-(2,4-difluorophenyl)-5,6-dihydro-1,7-naphthyridine-2,7(8H)-dicarboxylate (800 mg, 2 mmol) in MeOH (5 mL) was added $NH_3$ in MeOH (8 M, 20 mL) at room temperature, and the resulting mixture was stirred at room temperature for 12 h. The reaction was concentrated in vacuo to afford the crude product as a solid that was used without further purification. MS ESI calcd. For $C_{20}H_{21}F_2N_3O_3$ $[M+H]^+$ 390, found 390. $^1$H NMR (400 MHz, DMSO-$d_6$) d 8.09 (br s, 1H), 7.72 (s, 1H), 7.66 (br s, 1H), 7.47-7.56 (m, 1H), 7.39-7.47 (m, 1H), 7.18-7.29 (m, 1H), 4.66 (br s, 2H), 3.54 (br s, 2H), 2.56-2.65 (m, 2H), 1.42 (br s, 9H).

Step 2: 4-(2,4-difluorophenyl)-5,6,7,8-tetrahydro-1,7-naphthyridine-2-carboxamide To a mixture of tert-butyl 2-carbamoyl-4-(2,4-difluorophenyl)-5,6-dihydro-1,7-naphthyridine-7(8H)-carboxylate (700 mg, 1.8 mmol) in DCM (5 mL) was added 4M HCl in dioxane (15 mL) dropwise at room temperature, and the resulting mixture was stirred at room temperature for 3 h. The mixture was concentrated in vacuo to give the product as a solid that was used without further purification. MS ESI calcd. For $C_{15}H_{13}F_2N_3O$ $[M+H]^+$ 290, found 290. 1H NMR (400 MHz, DMSO-$d_6$) d 9.87 (br s, 2H), 8.10 (br s., 1H), 7.70-7.83 (m, 2H), 7.38-7.52 (m, 2H), 7.27 (t, J=7.6 Hz, 1H), 4.38 (br s, 2H), 3.35 (br s, 2H), 2.83 (br s, 2H)

Step 3: 4-(2,4-difluorophenyl)-7-((2-methoxypyridin-4-yl)methyl)-5,6,7,8-tetrahydro-1,7-naphthyridine-2-carboxamide To a solution of 4-(2,4-difluorophenyl)-5,6,7,8-tetrahydro-1,7-naphthyridine-2-carboxamide (200 mg, 0.691 mmol) and 4-(chloromethyl)-2-methoxypyridine (131 mg, 0.830 mmol) in acetonitrile (10 ml) was added $K_2CO_3$ (287 mg, 2.074 mmol). The mixture was heated to 90° C. and stirred for 16 h. The solution was poured into water (10 mL) and extracted with EtOAc (3×20 mL), dried over $Na_2SO_4$, filtered and concentrated under reduced pressure. The residue was purified by reverse phase preparative HPLC eluting with 5-35% acetonitrile/water (containing 0.1% TFA) followed by recrystallization from $CH_3CN$ (2 ml) to give the title compound as a white solid. MS (ESI) calcd. for $(C_{22}H_{20}F_2N_4O_2)$ $[M+H]^+$, 411.2, found, 411.2. $^1$H NMR (400 MHz, METHANOL-$d_4$) δ 8.08 (d, J=5.1 Hz, 1H), 7.80 (s, 1H), 7.43-7.32 (m, 1H), 7.18-7.08 (m, 2H), 7.04 (d, J=5.1 Hz, 1H), 6.87 (s, 1H), 3.90 (s, 3H), 3.82 (s, 2H), 3.75 (s, 2H), 2.76 (br s, 4H).

The following examples in Table 13-1 were prepared in an analogous manner to that described in general scheme 13 using intermediate 13-1 and commercial aryl halides or aryl halides described in the intermediates section.

TABLE 13-1

| Example | Structure | Conditions | IUPAC Name | Exact Mass [M + H]+ |
|---------|-----------|------------|------------|---------------------|
| 13-2 | 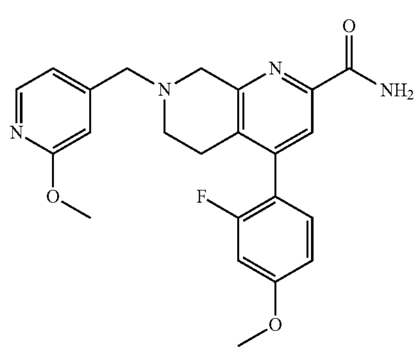 [SMILES: COc1ccc(-c2cc(C(N)=O)nc3c2CCN(Cc2ccnc(OC)c2)C3)c(F)c1] | Pd(dppf)Cl2/ K2CO3/Toluene/ H2O | 4-(2-fluoro-4-methoxyphenyl)-7-[(2-methoxypyridin-4-yl)methyl]-5,6,7,8-tetrahydro-1,7-naphthyridine-2-carboxamide | Calc'd 423.2, found 423.1 |

TABLE 13-1-continued

| Example | Structure | Conditions | IUPAC Name | Exact Mass [M + H]+ |
|---|---|---|---|---|
| 13-3 | 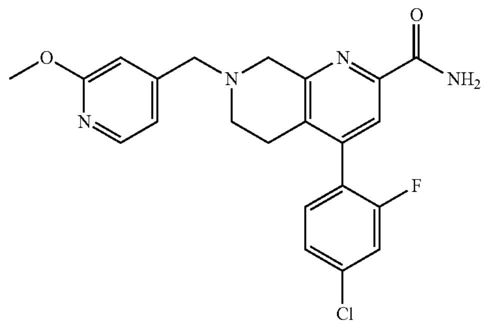 [SMILES: COc1cc(CN2CCc3c(-c4ccc(Cl)cc4F)cc(C(N)=O)nc3C2)ccn1] | Pd(dppf)Cl2/ K2CO3/Toluene/ H2O | 4-(4-chloro-2-fluorophenyl)-7-[(2-methoxypyridin-4-yl)methyl]-5,6,7,8-tetrahydro-1,7-naphthyridine-2-carboxamide | Calc'd 427.1, found 427.1 |
| 13-4 | 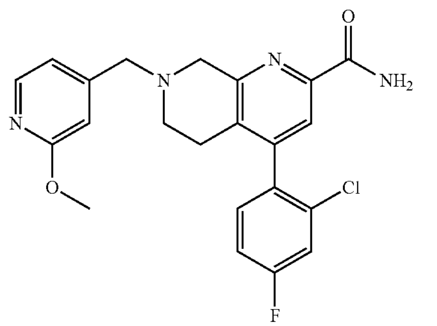 [SMILES: COc1cc(CN2CCc3c(-c4ccc(F)cc4Cl)cc(C(N)=O)nc3C2)ccn1] | Pd(dppf)Cl2/ K2CO3/Toluene/ H2O | 4-(2-chloro-4-fluorophenyl)-7-[(2-methoxypyridin-4-yl)methyl]-5,6,7,8-tetrahydro-1,7-naphthyridine-2-carboxamide | Calc'd 427.1, found 427.1 |

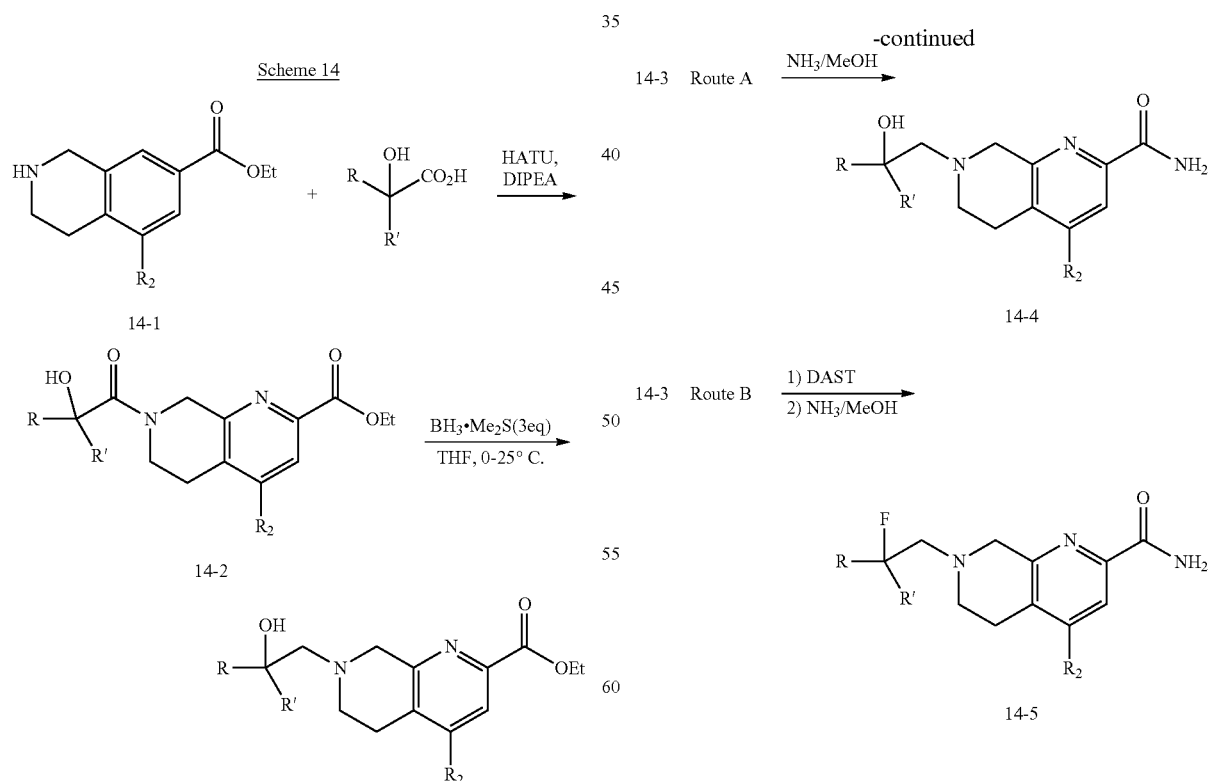

Scheme 14

Compounds of formula 14 are prepared by coupling of amines 14-1 to a carboxylic acid with subsequent reduction. Intermediates are then either treated with ammonia or treated with DAST followed by ammonia.

Example 14-1A and 14-1B

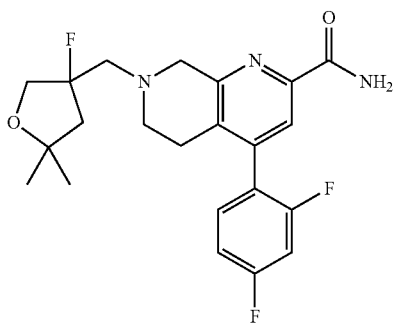

(R)- and (S)-4-(2,4-difluorophenyl)-7-((3-fluoro-5,5-dimethyltetrahydrofuran-3-yl)methyl)-5,6,7,8-tetrahydro-1,7-naphthyridine-2-carboxamide A mixture of 3-hydroxy-5,5-dimethyltetrahydrofuran-3-carboxylic acid (0.8 g, 4.99 mmol), ethyl4-(2,4-difluorophenyl)-5,6,7,8-tetrahydro-1,7-naphthyridine-2-carboxylate (1.590 g, 4.99 mmol), HATU (2.279 g, 5.99 mmol) and DIPEA (2.62 ml, 14.98 mmol) in DCM (20 mL) was stirred at 20° C. for 1 h. The mixture was concentrated and the crude product was purified by flash silica gel chromatography (ISCO®; 24 g SepaFlash® Silica Flash Column, Eluent of 25~50% ethyl acetate/petroleum ether gradient @ 35 mL/min) to give ethyl 4-(2,4-difluorophenyl)-7-(3-hydroxy-5,5-dimethyltetrahydrofuran-3-carbonyl)-5,6,7,8-tetrahydro-1,7-naphthyridine-2-carboxylate as a yellow oil.

Step 2: Ethyl 4-(2,4-difluorophenyl)-7-((3-hydroxy-5,5-dimethyltetrahydrofuran-3-yl)methyl)-5,6,7,8-tetrahydro-1,7-naphthyridine-2-carboxylate BH$_3$.DMS (1.368 mL, 13.68 mmol) was added to ethyl 4-(2,4-difluorophenyl)-7-(3-hydroxy-5,5-dimethyltetrahydrofuran-3-carbonyl)-5,6,7,8-tetrahydro-1,7-naphthyridine-2-carboxylate (2.1 g, 4.56 mmol) in THF (10 mL) dropwise at 0° C. The mixture was heated to 20° C. for 1 h. MeOH (8 mL) was added and the mixture was concentrated in vacuo. The crude product was purified by flash silica gel chromatography (ISCO®; 25 g SepaFlash® Silica Flash Column, Eluent of 0~50% ethyl acetate/petroleum ether gradient @ 35 mL/min) to give ethyl 4-(2,4-difluorophenyl)-7-((3-hydroxy-5,5-dimethyltetrahydrofuran-3-yl)methyl)-5,6,7,8-tetrahydro-1,7-naphthyridine-2-carboxylate as a yellow oil. MS (ESI) calcd. for (C$_{24}$H$_{28}$F$_2$N$_2$O$_4$) [M+H]$^+$, 447.2, found, 447.2.

Step 3: Ethyl 4-(2,4-difluorophenyl)-7-((3-fluoro-5,5-dimethyltetrahydrofuran-3-yl)methyl)-5,6,7,8-tetrahydro-1,7-naphthyridine-2-carboxylate DAST (0.621 ml, 4.70 mmol) was added to a mixture of ethyl 4-(2,4-difluorophenyl-7-((3-hydroxy-5,5-dimethyltetrahydrofuran-3-yl)methyl)-5,6,7,8-tetrahydro-1,7-naphthyridine-2-carboxylate (700 mg, 1.568 mmol) in DCM (10 mL) at −40° C. The mixture was stirred at 25° C. for 1 h. H$_2$O (15 mL) was added and the mixture was extracted with DCM (3×30 mL). The combined organic layers were washed with saturated aqueous sodium chloride (30 mL), dried (Na$_2$SO$_4$), filtered and concentrated under reduced pressure. The crude product was purified by flash silica gel chromatography (ISCO®; 25 g SepaFlash® Silica Flash Column, eluting with 0-50% ethyl acetate/petroleum ether gradient @ 35 mL/min) to give ethyl 4-(2,4-difluorophenyl)-7-((3-fluoro-5,5-dimethyltetrahydrofuran-3-yl)methyl)-5,6,7,8-tetrahydro-1,7-naphthyridine-2-carboxylate as a yellow oil. MS (ESI) calcd. for (C$_{24}$H$_{27}$F$_3$N$_2$O$_3$) [M+H]$^+$, 449.2, found, 449.3.

Step 4: (R)- and (S)-4-(2,4-difluorophenyl)-7-((3-fluoro-5,5-dimethyltetrahydrofuran-3-yl)methyl)-5,6,7,8-tetrahydro-1,7-naphthyridine-2-carboxamide Ethyl 4-(2,4-difluorophenyl)-7-((3-fluoro-5,5-dimethyltetrahydrofuran-3-yl)methyl)-5,6,7,8-tetrahydro-1,7-naphthyridine-2-carboxylate (300 mg, 0.669 mmol) in NH$_3$ in MeOH (7 M) (3345 µL, 33.4 mmol) was stirred at 20° C. for 14 h. The mixture was concentrated and purified by preparative-TLC (SiO2, petroleum ether:ethyl acetate=1:1) to give 4-(2,4-difluorophenyl)-7-((3-fluoro-5,5-dimethyltetrahydrofuran-3-yl)methyl)-5,6,7,8-tetrahydro-1,7-naphthyridine-2-carboxamide as a white solid. MS (ESI) calcd. for (C$_{22}$H$_{24}$F$_3$N$_3$O$_2$) [M+H]$^+$, 420.2, found, 420.1.

The racemic mixture of 4-(2,4-difluorophenyl)-7-((3-fluoro-5,5-dimethyltetrahydrofuran-3-yl)methyl)-5,6,7,8-tetrahydro-1,7-naphthyridine-2-carboxamide was separated by chiral SFC (Column: Chiralcel OJ-H 250×4.6 mm I.D., Sum Mobile phase: 5-40% methanol (containing 0.05% DEA) in CO$_2$ Flow rate: 2.5 mL/min) to afford the title two enantiomers as yellow solids.

Faster eluting enantiomer 14-1A $^1$H NMR (400 MHz, METHANOL-d$_4$) δ 7.94 (s, 1H), 7.50-7.35 (m, 1H), 7.24-7.08 (m, 2H), 4.61 (br. s., 2H), 4.28-4.12 (m, 1H), 4.05 (d, J=11.0 Hz, 1H), 3.98 (d, J=11.0 Hz, 1H), 3.75 (d, J=19.6 Hz, 2H), 3.58 (br. s., 2H), 3.03 (br. s., 2H), 2.47-2.31 (m, 1H), 2.26-2.09 (m, 1H), 1.38 (s, 3H), 1.32 (s, 3H).

Slower eluting enantiomer 14-1B $^1$H NMR (400 MHz, METHANOL-d$_4$) δ7.96 (s, 1H), 7.48-7.35 (m, 1H), 7.26-7.11 (m, 2H), 4.69 (s, 2H), 4.29-4.14 (m, 1H), 4.09-3.95 (m, 1H), 3.89-3.78 (m, 2H), 3.67 (br. s., 2H), 3.07 (br. s., 2H), 2.51-2.34 (m, 1H), 2.29-2.10 (m, 1H), 1.38 (s, 3H), 1.33 (s, 3H).

Example 14-2A and 14-2B

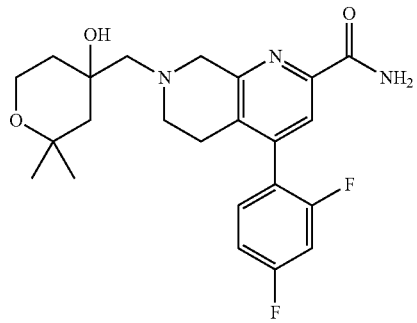

(R)- and (S)-4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxamide Step 1: Ethyl 4-(2,4-difluorophenyl)-7-(4-hydroxy-2,2-dimethyltetrahydro-2H-pyran-4-carbonyl)-5,6,7,8-tetrahydro-1,7-naphthyridine-2-carboxylate A mixture of 4-hydroxy-2,2-dimethyltetrahydro-2H-pyran-4-carboxylic acid (164 mg, 0.942 mmol), ethyl 4-(2,4-difluorophenyl)-5,6,7,8-tetrahydro-1,7-naphthyridine-2-carboxylate (200 mg, 0.628 mmol), HATU (311 mg, 0.817 mmol) and DIPEA (0.549 mL, 3.14 mmol) in DMF (10 mL) was stirred at 23° C. for 14 h. The mixture was poured into water (50 mL) and extracted with EtOAc (3×50 mL). The combined organic layers were washed with saturated aqueous sodium chloride (30 mL), dried over sodium sulfate, filtered and concentrated in vacuo to give the crude product, which was purified by column chromatography (silica gel: 100-200 mesh, petroleum ether:ethyl acetate=5:1 to 1:1, v/v) to give the ethyl 4-(2,4-difluorophenyl)-7-(4-hydroxy-2,2-dimethyltetrahydro-2H-pyran-4-carbonyl)-5,6,7,8-tetrahydro-1,7-naphthyridine-2-carboxylate as a pale-yellow solid. MS (ESI) calcd for $(C_{25}H_{28}F_2N_2O_5)$ $[M+H]^+$, 475.2, found, 475.2.

Step 2: Ethyl (R)- and (S)-4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxylate and Ethyl (S)-4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxylate To a solution of ethyl 4-(2,4-difluorophenyl)-7-(4-hydroxy-2,2-dimethyltetrahydro-2H-pyran-4-carbonyl)-5,6,7,8-tetrahydro-1,7-naphthyridine-2-carboxylate (160 mg, 0.337 mmol) in THF (10 mL) was dropwise added borane in THF (1.0 M) (1.349 mL, 1.349 mmol) under $N_2$ at 0° C. The reaction was stirred at ambient temperature (23° C.) for 2 h. The reaction was quenched with MeOH (20 mL) and the solvent was removed under reduced pressure to give the crude product as a yellow solid, which was purified by preparative-TLC ($SiO_2$, petroleum ether:ethyl acetate=1:2) to give ethyl 4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxylate as a yellow solid. MS (ESI) calcd for $(C_{25}H_{31}F_2N_2O_4)$ $[M+H]^+$, 461.2, found, 461.2.
The racemic mixture of ethyl 4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxylate was separated by chiral SFC (Column: Chiralcel AD 250×30 mm I.D., 5 um; Mobile phase: Base-IPA; FlowRate (mL/min): 60 mL/min Flow rate: 2.5 mL/min) to afford two enantiomers as yellow solids.

Step 3: (R)- and (S)-4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxamide The faster eluting enantiomer of ethyl 4-(2,4-difluorophenyl)-7-((4-hydroxy-2,2-dimethyltetrahydro-2H-pyran-4-yl)methyl)-5,6,7,8-tetrahydro-1,7-naphthyridine-2-carboxylate (7-2, 40 mg, 0.087 mmol) was taken up in $NH_3$ in MeOH (10 M) (10 mL) and stirred at 17° C. for 14 h. The mixture was concentrated in vacuo. The residue was purified by preparative HPLC (TFA, YMC-Actus Triart C18 150*30 mm*5 um) to give one enantiomer of the title compounds as a white solid. 14-2A MS (ESI) calcd for $(C_{23}H_{27}F_2N_3O_3)$ $[M+H]^+$, 432.2, found, 432.2. $^1$H NMR (400 MHz, methanol-d$_4$) 7.96 (s, 1H), 7.35-7.46 (m, 1H), 7.09-7.26 (m, 2H), 4.71 (br. s., 2H), 3.93-4.10 (m, 1H), 3.66 (d, J=11.74 Hz, 2H), 3.29 (br. s., 3H), 2.94-3.17 (m, 2H), 1.63-1.83 (m, 3H), 1.47-1.58 (m, 1H), 1.42 (s, 3H), 1.19 (s, 3H).

Similar treatment of the slower eluting enantiomer of ethyl 4-(2,4-difluorophenyl)-7-((4-hydroxy-2,2-dimethyltetrahydro-2H-pyran-4-yl)-methyl)-5,6,7,8-tetrahydro-1,7-naphthyridine-2-carboxylate furnished the other enantiomer of the title compounds. 14-2B MS (ESI) calcd for (C23H27F2N3O3)[M+H]+, 432.2, found, 432.2. 1H NMR (400 MHz, methanol-d4) 7.95 (s, 1H), 7.35-7.47 (m, 1H), 7.09-7.23 (m, 2H), 4.59-4.79 (m, 2H), 3.94-4.09 (m, 1H), 3.66 (d, J=11.35 Hz, 2H), 3.29 (br. s., 3H), 2.93-3.16 (m, 2H), 1.63-1.85 (m, 3H), 1.48-1.59 (m, 1H), 1.42 (s, 3H), 1.19 (s, 3H)

Scheme 15

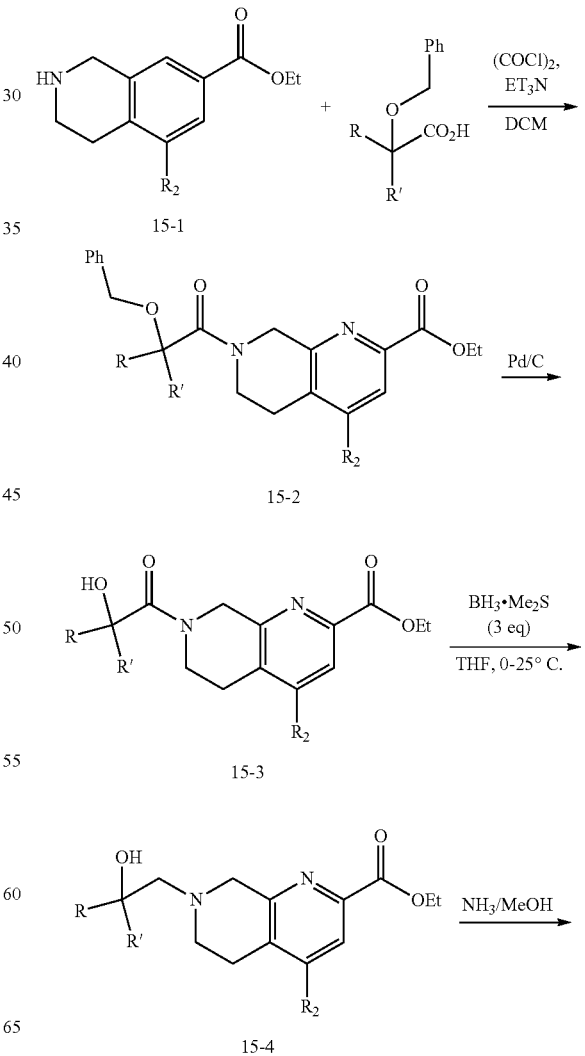

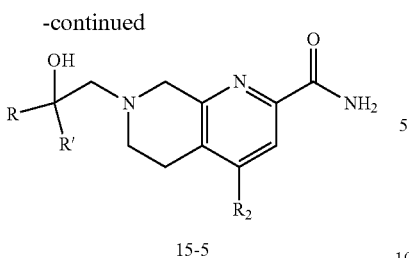

15-5

Compounds of formula 15 are prepared by coupling of amines 15-1 to a carboxylic acid with subsequent debenzylation followed by reduction. Intermediates are then treated with ammonia.

Example 15-1A and 15-1B

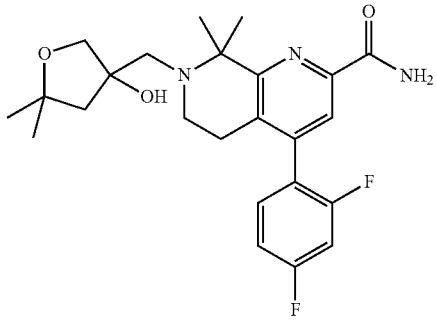 [SMILES: CC1(C)CC(O)(CN2CCc3c(-c4ccc(F)cc4F)cc(C(N)=O)nc3C2(C)C)CO1]

(R)- and (S)-4-(2,4-difluorophenyl)-7-((3-hydroxy-5,5-dimethyltetrahydrofuran-3-yl)methyl)-8,8-dimethyl-5,6,7,8-tetrahydro-1,7-naphthyridine-2-carboxamide Step 1: ethyl 7-(3-(benzyloxy)-5,5-dimethyltetrahydrofuran-3-carbonyl)-4-(2,4-difluorophenyl)-8,8-dimethyl-5,6,7,8-tetrahydro-1,7-naphthyridine-2-carboxylate To a mixture of 3-(benzyloxy)-5,5-dimethyltetrahydrofuran-3-carboxylic acid (0.18 g, 0.72 mmol) in DCM (5 mL) was added DMF (0.026 mL) and oxalyl dichloride (0.08 mL, 0.88 mmol) at 0° C. under $N_2$ atmosphere. The mixture was stirred at 15° C. for 1 h. The reaction mixture was concentrated under reduced pressure. To a solution of the residue in DCM (5 mL) was added $Et_3N$ (0.02 ml, 1.56 mmol) followed by 3-(benzyloxy)-5,5-dimethyltetrahydrofuran-3-carbonyl chloride (0.18 g, 0.68 mmol) in DCM (3 mL) dropwise under $N_2$ atmosphere. The mixture was stirred at 15° C. for 2 h. The mixture was diluted with $H_2O$ (3 mL) and extracted with DCM (3×4 mL). The organic layers were dried ($Na_2SO_4$), filtered and the solvent was concentrated in vacuo. The residue was purified by column chromatography on silica gel, eluting with petroleum ether:ethyl acetate=10:1 to give ethyl 7-(3-(benzyloxy)-5,5-dimethyltetrahydrofuran-3-carbonyl)-4-(2,4-difluorophenyl)-8,8-dimethyl-5,6,7,8-tetrahydro-1,7-naphthyridine-2-carboxylate as a yellow oil. MS (ESI) calcd. for ($C_{33}H_{36}F_2N_2O_5$) [M+H]$^+$, 579.3, found, 579.7.

Step 2: ethyl 4-(2,4-difluorophenyl)-7-(3-hydroxy-5,5-dimethyltetrahydrofuran-3-carbonyl)-8,8-dimethyl-5,6,7,8-tetrahydro-1,7-naphthyridine-2-carboxylate A mixture of ethyl 7-(3-(benzyloxy)-5,5-dimethyltetrahydrofuran-3-carbonyl)-4-(2,4-difluorophenyl)-8,8-dimethyl-5,6,7,8-tetrahydro-1,7-naphthyridine-2-carboxylate (180 mg, 0.31 mmol), aqueous HCl (12M) (0.09 ml, 1.04 mmol) and Pd—C (33 mg, 0.03 mmol) in EtOH (10 mL) was stirred at 15° C. under an atmosphere of $H_2$ (25 psi) for 1 h. The mixture was filtered and the filtrate was concentrated in vacuo to give ethyl 4-(2,4-difluorophenyl)-7-(3-hydroxy-5,5-dimethyltetrahydrofuran-3-carbonyl)-8,8-dimethyl-5,6,7,8-tetrahydro-1,7-naphthyridine-2-carboxylate as a white solid, which was used directly in next step without further purification. MS (ESI) calcd. for ($C_{26}H_{31}F_2N_2O_5$) [M+H]$^+$, 489.2, found, 489.4.

Step 3: ethyl 4-(2,4-difluorophenyl)-7-((3-hydroxy-5,5-dimethyltetrahydrofuran-3-yl)-methyl)-8,8-dimethyl-5,6,7,8-tetrahydro-1,7-naphthyridine-2-carboxylate $BH_3$.DMS (0.15 mL, 1.5 mmol) was added to a solution of ethyl 4-(2,4-difluorophenyl)-7-(3-hydroxy-5,5-dimethyltetrahydrofuran-3-carbonyl)-8,8-dimethyl-5,6,7,8-tetrahydro-1,7-naphthyridine-2-carboxylate (150 mg, 0.31 mmol) in THF (5 mL) dropwise at 0° C. The mixture was stirred at 20° C. for 1 h. EtOH (2 mL) was added and the mixture was concentrated in vacuo to give the crude product ethyl 4-(2,4-difluorophenyl)-7-((3-hydroxy-5,5-dimethyltetrahydrofuran-3-yl)methyl)-8,8-dimethyl-5,6,7,8-tetrahydro-1,7-naphthyridine-2-carboxylate as yellow oil, which was used in the next step without further purification. MS (ESI) calcd. for ($C_{26}H_{33}F_2N_2O_4$) [M+H]$^+$, 475.2, found, 475.2.

Step 4: 4-(2,4-difluorophenyl)-7-((3-hydroxy-5,5-dimethyltetrahydrofuran-3-yl)methyl)-8,8-dimethyl-5,6,7,8-tetrahydro-1,7-naphthyridine-2-carboxamide Ethyl 4-(2,4-difluorophenyl)-7-((3-hydroxy-5,5-dimethyltetrahydrofuran-3-yl)methyl)-8,8-dimethyl-5,6,7,8-tetrahydro-1,7-naphthyridine-2-carboxylate (160 mg, 0.34 mmol) in $NH_3$ in MeOH (10M) (10 mL) was stirred at 20° C. for 16 h. The mixture was concentrated to give 4-(2,4-difluorophenyl)-7-((3-hydroxy-5,5-dimethyltetrahydrofuran-3-yl)methyl)-8,8-dimethyl-5,6,7,8-tetrahydro-1,7-naphthyridine-2-carboxamide as a yellow solid. MS (ESI) calcd. for ($C_{24}H_{30}F_2N_3O_3$) [M+H]$^+$, 446.5, found, 446.5.

The racemic mixture of 4-(2,4-difluorophenyl)-7-((3-hydroxy-5,5-dimethyltetrahydrofuran-3-yl)methyl)-8,8-dimethyl-5,6,7,8-tetrahydro-1,7-naphthyridine-2-carboxamide was separated by chiral SFC (Column: Chiralpak AD-3 100×4.6 mm I.D., 3 um Mobile phase: 5-40% isopropanol (containing 0.05% DEA) in $CO_2$ Flow rate: 2.8 mL/min) to afford the two title enantiomers as yellow solids.

Faster eluting enantiomer 15-1A $^1$H NMR (400 MHz, METHANOL-d4)=7.93 (s, 1H), 7.47-7.34 (m, 1H), 7.25-7.10 (m, 2H), 4.07 (dd, J=5.4, 12.7 Hz, 1H), 3.98-3.78 (m, 4H), 3.68 (d, J=11.7 Hz, 1H), 3.45-3.34 (m, 1H), 2.77 (d, J=18.1 Hz, 1H), 2.24-2.00 (m, 5H), 1.81 (s, 3H), 1.41 (br. s., 3H), 1.31 (s, 3H).

Slower eluting enantiomer 15-1B MS (ESI) calcd. for (C24H30F2N3O3) [M+H]+, 446.5, found, 446.5. $^1$H NMR (400 MHz, METHANOL-d4)=7.93 (s, 1H), 7.42-7.36 (m, 1H), 7.21-7.15 (m, 2H), 3.95-3.76 (m, 6H), 2.80 (m, 2H), 2.16-1.95 (m, 10H), 1.41 (s, 3H), 1.31 (s, 3H).

Biological Assays

The utility of the compounds of the invention as antagonists of metabotropic glutamate receptor activity, in particular mGluR2 activity, may be demonstrated by methodology known in the art. Antagonist constants are determined as follows. The compounds of the invention were tested in a fluorescence laser imaging plate reader based assay. This assay is a common functional assay to monitor Ca2+ mobilization in whole cells expressing recombinant receptor coupled with a promiscuous G-protein. CHO dhfr-cells stably expressing recombinant human mGluR2 and Gα16 loaded with Fluo-4 AM (Invitrogen, Carlsbad Calif.) were treated with various concentrations of antagonists of compounds and the Ca2+ response was monitored on a FLIPR384 (Molecular Devices, Sunnydale Calif.) for agonist activity. Then 2,500 nM glutamate was added and the antagonist response was monitored. The maximum calcium response at each concentration of compound for agonist or antagonist were plotted as dose responses and the curves were fitted with a four parameter logistic equation giving $IC_{50}$ and Hill coefficient using the iterative non linear curve fitting software ADA (Merck & Co). Data in the following table represent activities in the antagonist assay.

| Example Number | $IC_{50}$ value |
|---|---|
| 1-1A | 98.2 |
| 1-1B | 98.2 |
| 1-2A | 128.7 |
| 1-2B | 128.7 |
| 1-3A | 131.8 |
| 1-3B | 178.6 |
| 1-4 | 83.5 |
| 1-5A | 5.6 |
| 1-5B | 7.5 |
| 1-6 | 14.5 |
| 1-7 | 13.8 |
| 1-8 | 8.7 |
| 1-9 | 8.2 |
| 1-10 | 21.8 |
| 1-11A | 30.1 |
| 1-11B | 45.2 |
| 1-12 | 9.9 |
| 1-13 | 84.1 |
| 1-14 | 40.3 |
| 1-15A | 5.8 |
| 1-15B | 5.3 |
| 1-16 | 14.1 |
| 1-17 | 7.4 |
| 1-18 | 12.3 |
| 1-19 | 13.2 |
| 1-20 | 24.4 |
| 1-21 | 9.3 |
| 1-22 | 50.6 |
| 1-23A | 14.7 |
| 1-23B | 28.5 |
| 2-1 | 52.7 |
| 2-2 | 28.2 |
| 2-3 | 117.0 |
| 2-4 | 20.4 |
| 2-5 | 30.3 |
| 2-6 | 23.0 |
| 2-7 | 7.6 |
| 2-8 | 188.2 |
| 2-9 | 10.8 |
| 2-10 | 40.9 |
| 2-11 | 10.4 |
| 2-12 | 8.5 |
| 2-13 | 47.8 |
| 2-14 | 153.3 |
| 2-15 | 45.2 |
| 2-16 | 26.7 |

-continued

| Example Number | $IC_{50}$ value |
|---|---|
| 2-17 | 100.5 |
| 2-18 | 49.5 |
| 2-19 | 61.6 |
| 2-20 | 11.0 |
| 2-21 | 33.7 |
| 2-22 | 19.4 |
| 2-23 | 5.7 |
| 2-24 | 18.2 |
| 2-25 | 40.9 |
| 2-26 | 13.1 |
| 2-27 | 23.0 |
| 3-1A | 21.2 |
| 3-1B | 22.3 |
| 3-2A | 9.6 |
| 3-2B | 11.4 |
| 4-1 | 117.4 |
| 4-2 | 49.7 |
| 4-3A | 51.2 |
| 4-3B | 86.6 |
| 5-1 | 115.4 |
| 5-2 | 79.1 |
| 5-3 | 41.0 |
| 5-4 | 29.0 |
| 5-5A | 18.4 |
| 5-5B | 12.9 |
| 5-6A | 21.4 |
| 5-6B | 17.3 |
| 5-7 | 42.7 |
| 5-8 | 88.7 |
| 5-9 | 92.7 |
| 5-10 | 32.0 |
| 6-1 | 11.7 |
| 6-2 | 1151.0 |
| 6-3 | 18.6 |
| 6-4 | 119.0 |
| 7-1 | 37.4 |
| 7-2 | 45.9 |
| 7-3A | 29.3 |
| 7-3B | 21.2 |
| 7-4 | 20.1 |
| 8-1A | 18.5 |
| 8-1B | 12.7 |
| 8-2A | 9.9 |
| 8-2B | 11.5 |
| 8-3A | 18.5 |
| 8-3B | 12.7 |
| 9-1 | 27.7 |
| 9-2 | 9.7 |
| 9-3 | 14.2 |
| 9-4 | 23.9 |
| 9-5 | 12.7 |
| 9-6 | 8.0 |
| 9-7 | 11.7 |
| 10-1 | 31.0 |
| 10-2 | 7.4 |
| 10-3 | 12.0 |
| 10-4 | 14.6 |
| 11-1 | 25.8 |
| 11-2 | 52.1 |
| 11-3 | 7.2 |
| 11-4 | 19.7 |
| 11-5 | 17.6 |
| 11-6 | 13.2 |
| 11-7 | 45.2 |
| 11-8 | 11.8 |
| 11-9 | 6.5 |
| 11-10 | 7.6 |
| 11-11 | 26.1 |
| 11-12 | 10.0 |
| 12-1 | 40.9 |
| 12-2 | 13.1 |
| 12-3 | 93.2 |
| 12-4 | 35.9 |
| 12-5 | 20.4 |
| 13-1 | 7.8 |
| 13-2 | 6.6 |
| 13-3 | 16.0 |

-continued

| Example Number | IC$_{50}$ value |
|---|---|
| 13-4 | 5.7 |
| 14-1A | 17.4 |
| 14-1B | 17.8 |
| 14-2A | 31.7 |
| 14-2B | 27.1 |
| 15-1A | 24.9 |
| 15-1B | 23.6 |

The following abbreviations may be used throughout the text:

Me=methyl; Et=ethy; t-Bu:=tert-butyl; Ar:=aryl; Ph=phenyl; Bn=benzyl; EtOAC=ethyl acetate; DCE=dichloroethylene; HMDS=hexamethyldisilazane; DMF:=dimethylformamide; DMFDMA=N,N-dimethylformamide dimethylacetal; THF=tetrahydrofuran; BOP:=benzotriazolyloxytris (dimethylamino) phosphonium hexafluorophosphate; Boc=tert-butyloxycarbonyl; TEA=triethylamine; DIPEA=di-iso-propylethylamine; TPAP=tetra-n-propyl ammonium perruthenate; NMO=N-methyl morpholine N-oxide; dppf=diphenylphosphorousferrocenyl; PMB=p-methoxybenzyl; Ms=mesyl; Ac=acetyl; DMSO=dimethylsulfoxide; DCM=dichloromethane; m-CPBA=meta-chloroperoxybenzoic acid; DMEM=Dulbecco's Modified Eagle Medium (High Glucose); FBS=fetal bovine serum; rt=room temperature; RT=retention time; aq=aqueous; HPLC=high performance liquid chromatography; MS=mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of Formula (I):

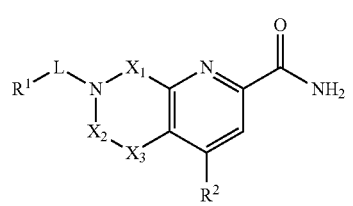

(I)

or a stereoisomer thereof, or a pharmaceutically acceptable salt of said compound or said stereoisomer, wherein:

$X_1$ is selected from the group consisting of —C(R$^{X1}$)$_2$—,

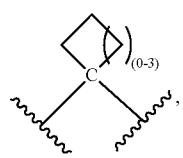

—CHcyclopropyl-, and —CHcyclobutyl-;

wherein each R$^{X1}$ is independently selected from the group consisting of H, —(C$_{1-4}$)alkyl, —(C$_{2-4}$)alkenyl, and —(C$_{2-4}$)alkynyl;

$X_2$ is selected from the group consisting of, —C(R$^{X2}$)$_2$—,

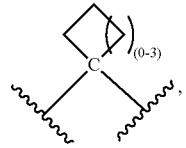

—CHcyclopropyl-, —CHcyclobutyl-;

wherein each R$^{X2}$ is independently selected from the group consisting of H, —(C$_{1-4}$)alkyl, —(C$_{2-4}$)alkenyl, and —(C$_{2-4}$)alkynyl;

$X_3$ is selected from the group consisting of —C(R$^{X3}$)$_2$—;

wherein each R$^{X3}$ is independently selected from the group consisting of H, —(C$_{1-4}$)alkyl, and fluoro;

R$^1$ is selected from the group consisting of phenyl, heteroaryl, cycloalkyl, and heterocycloalkyl, wherein each of said phenyl, heteroaryl, cycloalkyl, and heterocycloalkyl of R$^1$ is unsubstituted or substituted with from 1 to 3 R$^{1A}$ groups;

each R$^{1A}$ (when present) is independently selected from the group consisting of halo, OH, CN, —(C$_{1-4}$)alkyl, —(C$_{1-4}$)haloalkyl, —(C$_{1-4}$)alkoxy, —(C$_{1-4}$)haloalkoxy, cyclopropyl, cyclobutyl, —NH$_2$, —C(O)NH$_2$, —C(O)N(CH$_3$)$_2$, —S(O)$_2$(C$_{1-4}$)alkyl, CH$_2$OH, CH$_2$CH$_2$OH, NH(CO)CH$_3$, oxadiazole, triazole, and pyrazole;

or, alternatively, two R$^{1A}$ groups on the same or adjacent atoms are taken together with the ring atom of R$^1$ to which they are attached to form a a cyclopropyl, cyclobutyl, spirocyclopropyl, or spirocyclobutyl group;

-L- is a divalent moiety selected from the group consisting of —(C(R$^{L1}$)$_2$)$_p$—, —C(O)—, —C(O)CH$_2$—, and —CH$_2$C(O)—, wherein p is 1 to 3, and each R$^{L1}$ is independently selected from the group consisting of H, OH, —CH$_3$, —CH$_2$CH$_3$, —CH$_2$CF$_3$, —CHF$_2$, —CF$_3$, and —CH$_2$OH; and R$^2$ is selected from the group consisting of phenyl, heteroaryl, cycloalkyl, and heterocycloalkyl, wherein each of said phenyl, heteroaryl, cycloalkyl, and heterocycloalkyl of R$^2$ is unsubstituted or substituted with from 1 to 3 R$^{2A}$ groups;

each R$^{2A}$ (when present) is independently selected from the group consisting of halo, OH, CN, —(C$_{1-4}$)alkyl, —(C$_{1-4}$)haloalkyl, —(C$_{1-4}$)alkoxy, —(C$_{1-4}$)haloalkoxy, cyclopropyl, cyclobutyl, —NH$_2$, —C(O)NH$_2$, —C(O)N(CH$_3$)$_2$, —S(O)$_2$(C$_{1-4}$)alkyl, CH$_2$OH, CH$_2$CH$_2$OH, NH(CO)CH$_3$, oxadiazole, triazole, and pyrazole;

or, alternatively, two R$^{2A}$ groups on the same or adjacent atoms are taken together with the ring atom of R$^2$ to which they are attached to form a cyclopropyl, cyclobutyl, spirocyclopropyl, or spirocyclobutyl group.

2. A compound of claim 1, or a pharmaceutically acceptable salt thereof, of Formula (II):

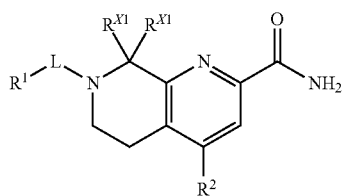

(II)

wherein each $R^{X1}$ is independently selected from the group consisting of H, —$(C_{1-4})$alkyl, —$(C_{2-4})$alkenyl, and —$(C_{2-4})$alkynyl.

3. A compound of claim 2, or a pharmaceutically acceptable salt thereof, wherein $R^1$ is selected from the group consisting of phenyl, cyclobutyl, cyclohexyl, cyclopentyl, benzimidazolyl, imidazolyl, imidazopyridinyl, imidazopyridinyl, imidazopyrimidinyl, isoxazolyl, oxadiazolyl, oxadiazolyl, oxazolyl, oxetanyl, piperidinyl, pyrazolyl, pyridinyl, pyrimidinyl, tetrahydrofuranyl, tetrahydropyranyl, tetrazolyl, thiadiazolyl, thiazolyl, and triazolyl; and $R^{1A}$ is 1, 2, or 3 groups independently selected from the group consisting of F, OH, —$(C_{1-4})$alkyl, —$(C_{1-4})$haloalkyl, —$(C_{1-4})$alkoxy, —$(C_{1-4})$haloalkoxy, cyclopropyl, cyclobutyl, —$NH_2$, —$C(O)NH_2$, and —$S(O)_2$—$(C_{1-4})$alkyl.

4. A compound of claim 3, or a pharmaceutically acceptable salt thereof, wherein $R^2$ is selected from the group consisting of phenyl, azetidinyl, cyclopropyl, cyclobutyl, cyclopentyl, cyclohexyl, imidazolyl, isothiazolyl, morpholinyl, oxazolyl, piperazinyl, piperidinyl, pyrazolyl, pyridazinyl, pyridinyl, pyrimidinyl, pyrrolidinyl, and thiazolyl; and $R^{2A}$ is 1, 2, or 3 groups independently selected from the group consisting of H, halo, CN, —$(C_{1-4})$alkyl, —$(C_{1-4})$haloalkyl, —$(C_{1-4})$alkoxy, cyclopropyl, and spirocyclopropyl.

5. A compound of claim 4, wherein -L- is —$(C(R^{L1})_2)_p$—, wherein p is 1 to 3, and each $R^{L1}$ is independently selected from the group consisting of H, OH, —$CH_3$, —$CH_2CH_3$, —$CH_2CF_3$, —$CHF_2$, —$CF_3$, and —$CH_2OH$.

6. A compound of claim 5, wherein -L- is —$CH_2$—.

7. A compound of claim 1, or a pharmaceutically acceptable salt thereof, wherein said compound is selected from the group consisting of:

| Structure |
|---|
| 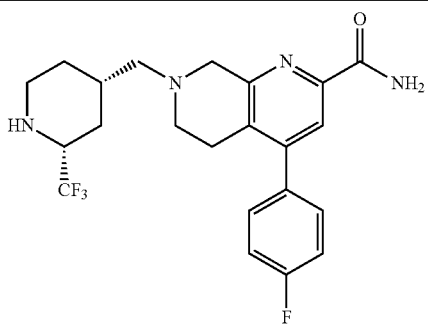 |

| Structure |
|---|
| 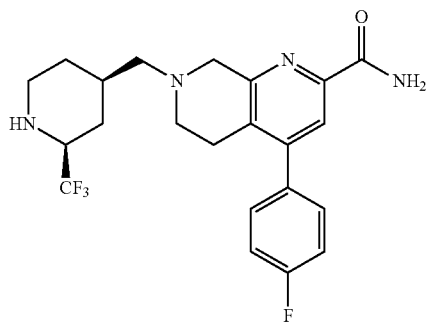 [SMILES: NC(=O)c1cc(-c2ccc(F)cc2)c2c(n1)CN(C[C@@H]1CCN[C@H](C(F)(F)F)C1)CC2] |
| 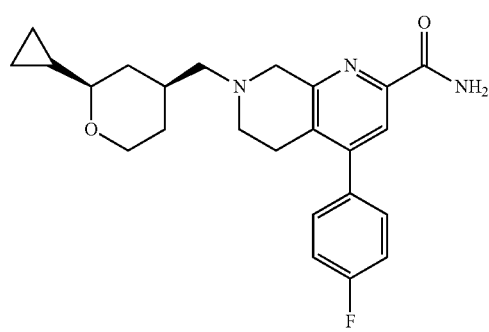 [SMILES: NC(=O)c1cc(-c2ccc(F)cc2)c2c(n1)CN(C[C@H]1CCO[C@@H](C3CC3)C1)CC2] |
| 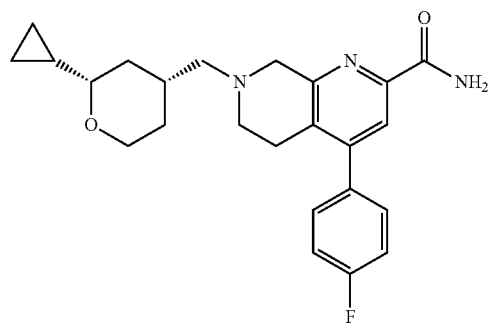 [SMILES: NC(=O)c1cc(-c2ccc(F)cc2)c2c(n1)CN(C[C@@H]1CCO[C@H](C3CC3)C1)CC2] |
| 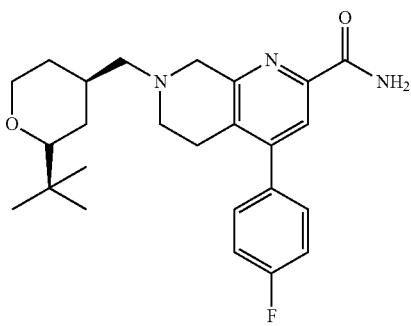 |

| 165 -continued | | 166 -continued | |
|---|---|---|---|
| Structure | | Structure | |
| 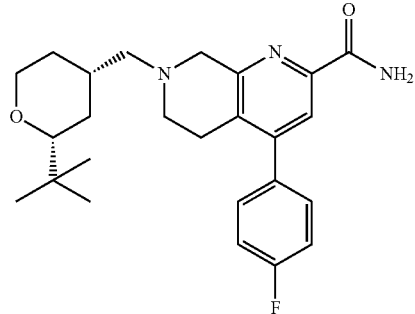 [SMILES: CC(C)(C)[C@H]1C[C@@H](CN2CCc3c(-c4ccc(F)cc4)cc(C(N)=O)nc3C2)CCO1] | | 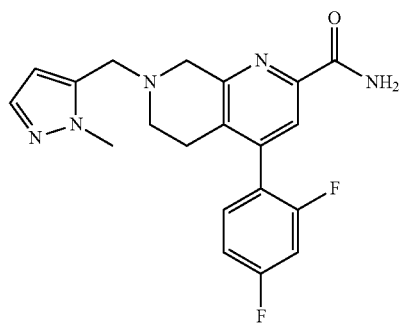 | |
| 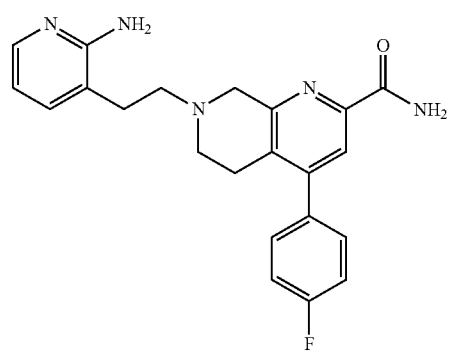 [SMILES: NC(=O)c1cc(-c2ccc(F)cc2)c2c(n1)CN(CCc1cccnc1N)CC2] | | 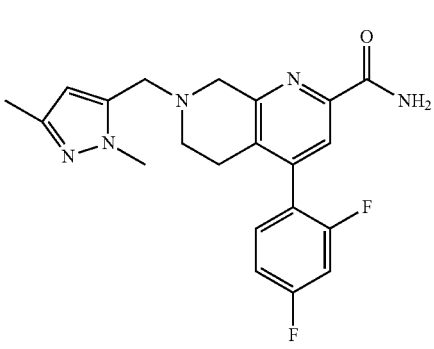 | |
| 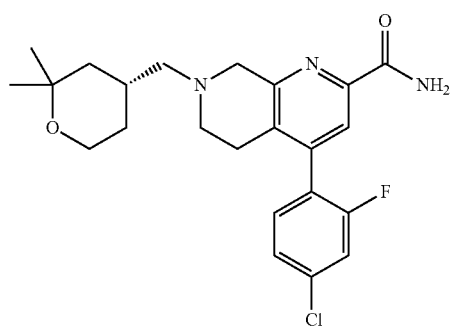 [SMILES: CC1(C)C[C@H](CN2CCc3c(-c4ccc(Cl)cc4F)cc(C(N)=O)nc3C2)CCO1] | | 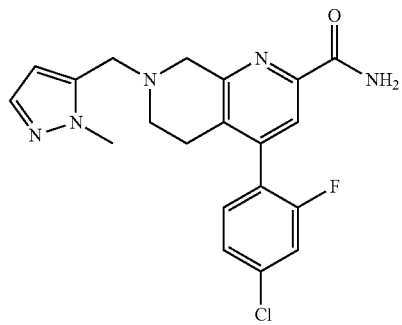 | |
| 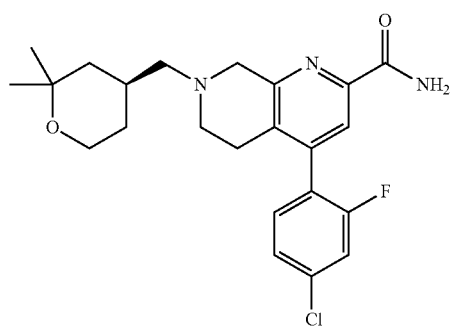 [SMILES: CC1(C)C[C@@H](CN2CCc3c(-c4ccc(Cl)cc4F)cc(C(N)=O)nc3C2)CCO1] | | 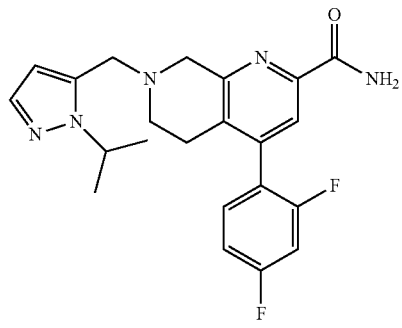 | |

| 167 -continued | | 168 -continued | |
|---|---|---|---|
| Structure | | Structure | |
| 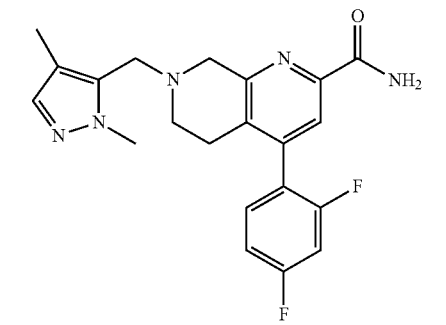 [SMILES: Cc1cnn(C)c1CN1CCc2c(-c3ccc(F)cc3F)cc(C(N)=O)nc2C1] | | 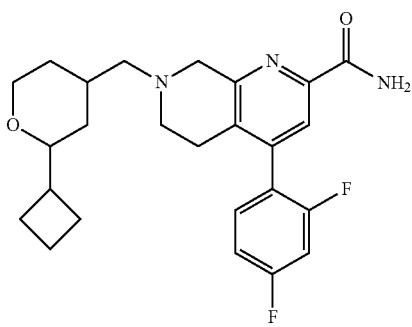 | |
| 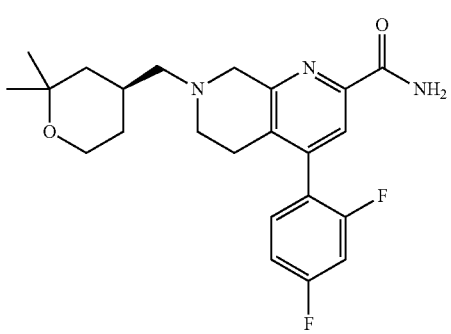 [SMILES: CC1(C)C[C@@H](CN2CCc3c(-c4ccc(F)cc4F)cc(C(N)=O)nc3C2)CCO1] | | 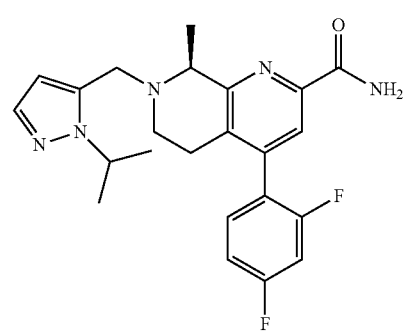 | |
| 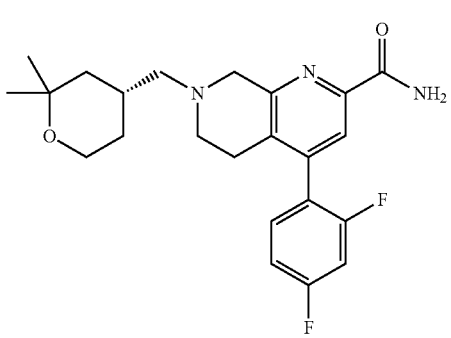 [SMILES: CC1(C)C[C@H](CN2CCc3c(-c4ccc(F)cc4F)cc(C(N)=O)nc3C2)CCO1] | | | |
| 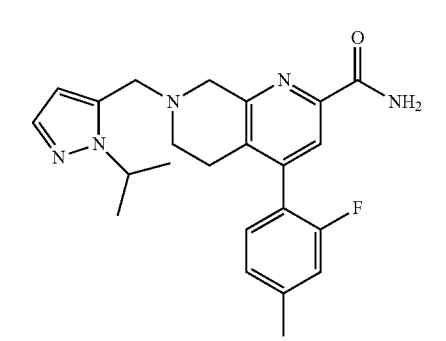 [SMILES: Cc1ccc(-c2cc(C(N)=O)nc3c2CCN(Cc2ccnn2C(C)C)C3)c(F)c1] | | 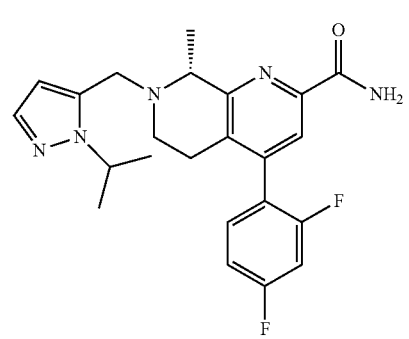 | |
| 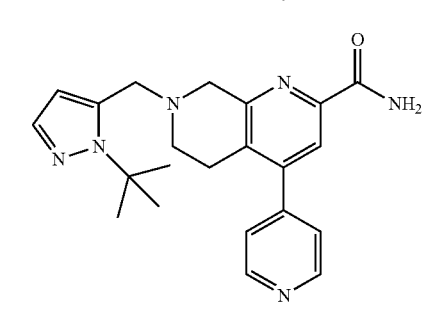 [SMILES: CC(C)(C)n1nccc1CN1CCc2c(-c3ccncc3)cc(C(N)=O)nc2C1] | | 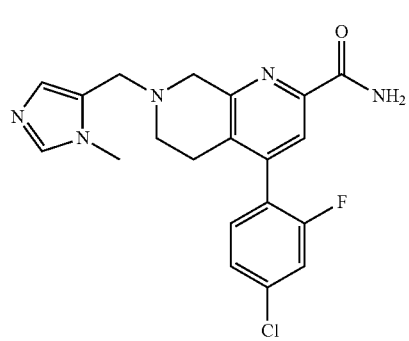 [SMILES: Cn1cncc1CN1CCc2c(-c3ccc(Cl)cc3F)cc(C(N)=O)nc2C1] | |

| Structure | | Structure |
|---|---|---|
| 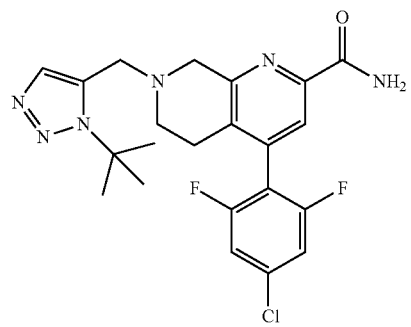 [SMILES: CC(C)(C)n1nncc1CN1CCc2c(-c3c(F)cc(Cl)cc3F)cc(C(N)=O)nc2C1] | | 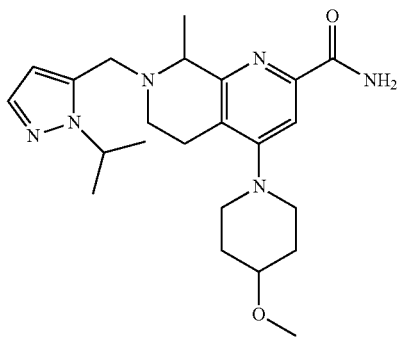 |
| 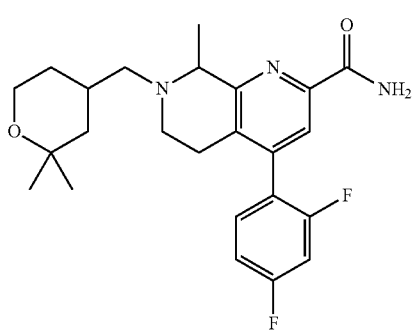 [SMILES: CC1c2nc(C(N)=O)cc(-c3ccc(F)cc3F)c2CCN1CC1CCOC(C)(C)C1] | | 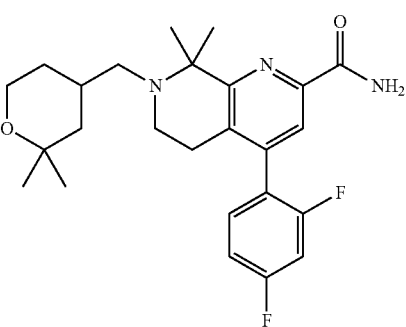 |
| 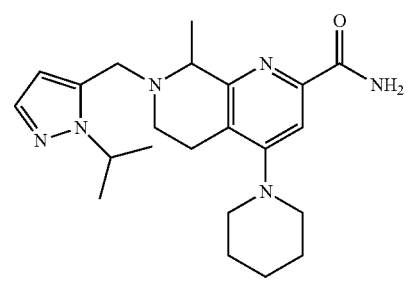 [SMILES: CC1c2nc(C(N)=O)cc(N3CCCCC3)c2CCN1Cc1ccnn1C(C)C] | | 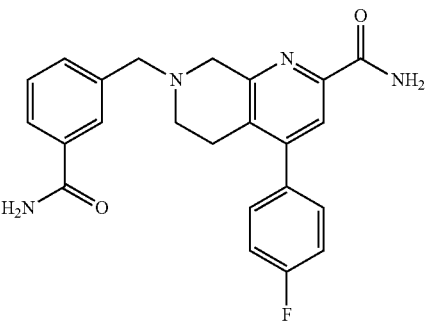 |
| 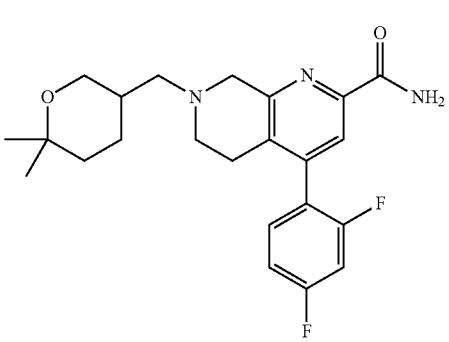 [SMILES: CC1(C)CCC(CN2CCc3c(-c4ccc(F)cc4F)cc(C(N)=O)nc3C2)CO1] | | 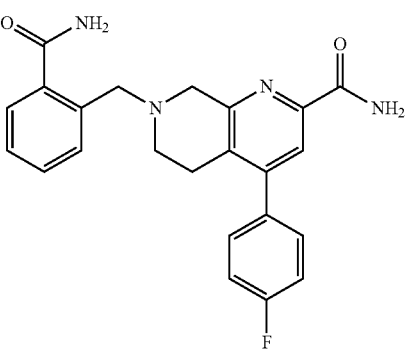 |
| 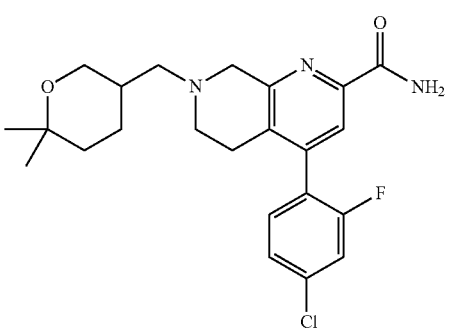 [SMILES: CC1(C)CCC(CN2CCc3c(-c4ccc(Cl)cc4F)cc(C(N)=O)nc3C2)CO1] | | |

| 171 -continued | 172 -continued |
|---|---|
| Structure | Structure |
| 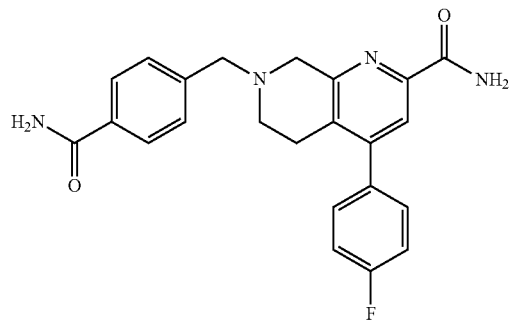 [SMILES: NC(=O)c1ccc(CN2CCc3c(-c4ccc(F)cc4)cc(C(N)=O)nc3C2)cc1] | 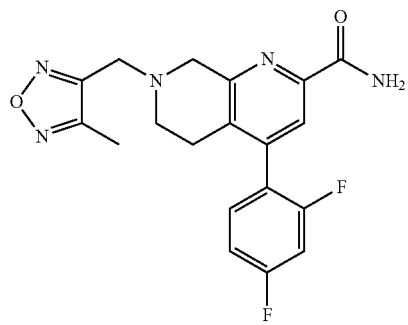 [SMILES: Cc1nonc1CN1CCc2c(-c3ccc(F)cc3F)cc(C(N)=O)nc2C1] |
| 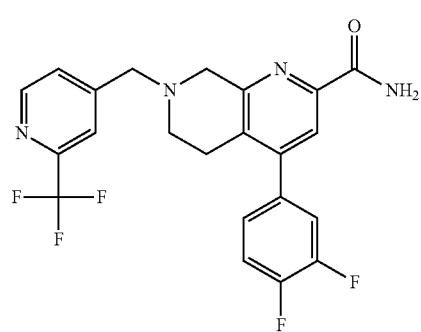 | 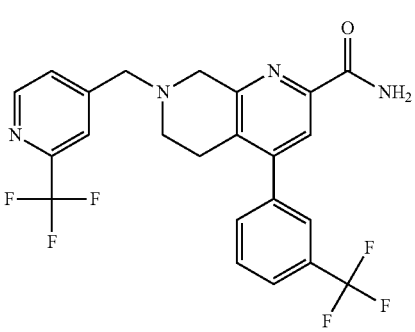 [SMILES: NC(=O)c1cc(-c2cccc(C(F)(F)F)c2)c2c(n1)CN(Cc1ccnc(C(F)(F)F)c1)CC2] |
| 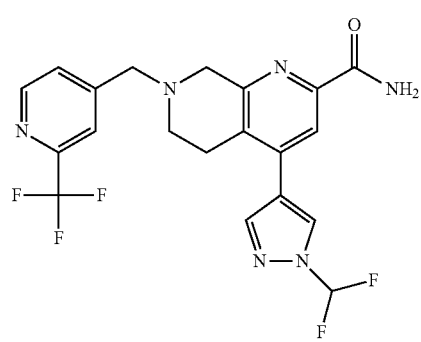 | 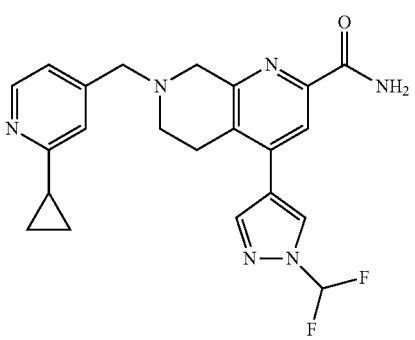 [SMILES: NC(=O)c1cc(-c2cnn(C(F)F)c2)c2c(n1)CN(Cc1ccnc(C3CC3)c1)CC2] |
| 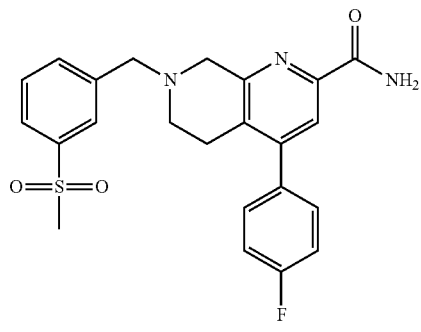 | 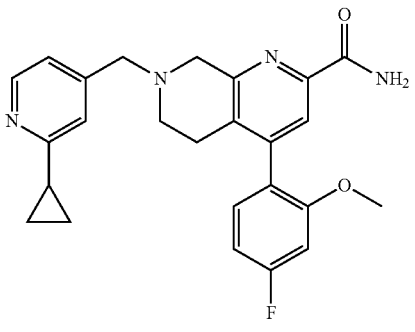 [SMILES: COc1cc(F)ccc1-c1cc(C(N)=O)nc2c1CCN(Cc1ccnc(C3CC3)c1)C2] |

| 173 -continued | 174 -continued |
|---|---|
| Structure | Structure |
| 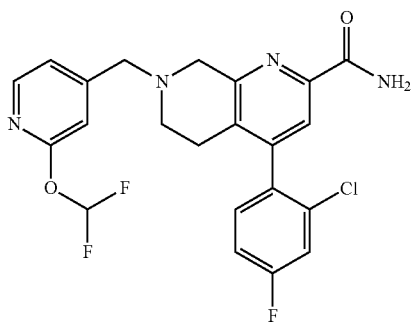 [SMILES: NC(=O)c1cc(-c2ccc(F)cc2Cl)c2c(n1)CN(Cc1ccnc(OC(F)F)c1)CC2] | 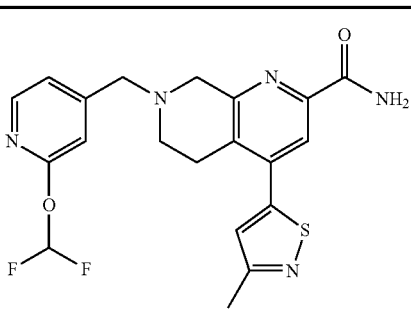 |
| 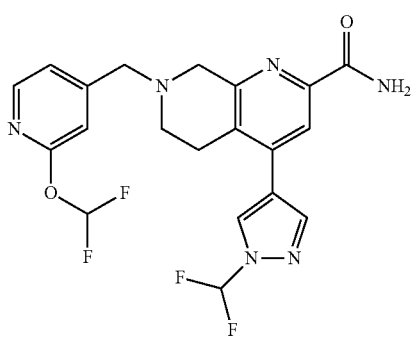 [SMILES: NC(=O)c1cc(-c2cnn(C(F)F)c2)c2c(n1)CN(Cc1ccnc(OC(F)F)c1)CC2] | 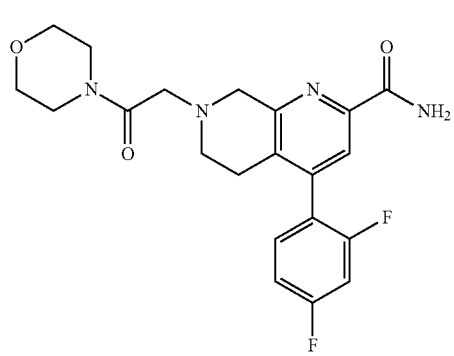 |
| 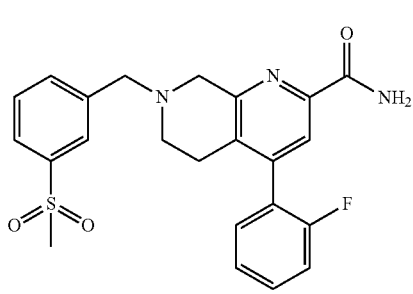 [SMILES: CS(=O)(=O)c1cccc(CN2CCc3c(-c4ccccc4F)cc(C(N)=O)nc3C2)c1] | 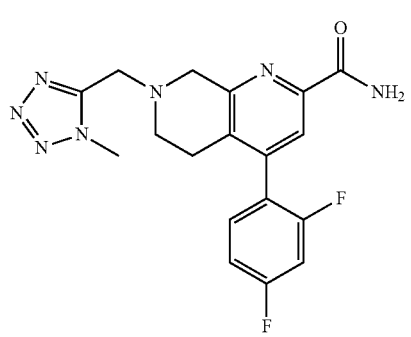 |
| 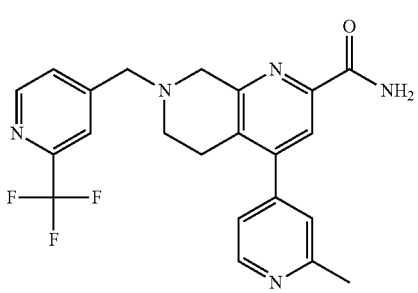 | |
| 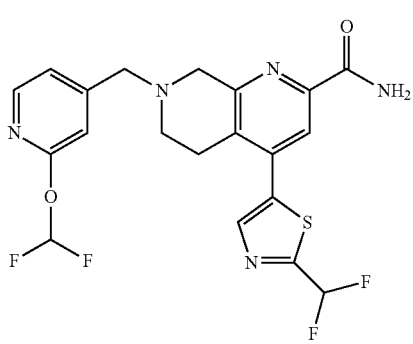 [SMILES: NC(=O)c1cc(-c2cnc(C(F)F)s2)c2c(n1)CN(Cc1ccnc(OC(F)F)c1)CC2] | 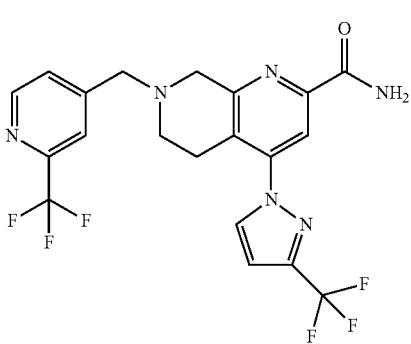 [SMILES: NC(=O)c1cc(-n2ccc(C(F)(F)F)n2)c2c(n1)CN(Cc1ccnc(C(F)(F)F)c1)CC2] |

Structure
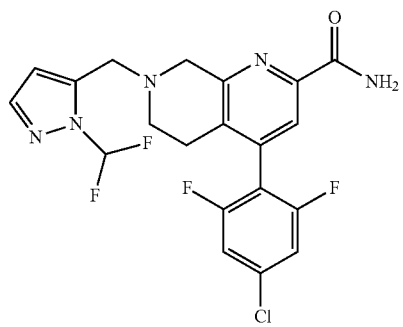 [SMILES: NC(=O)c1cc(-c2c(F)cc(Cl)cc2F)c2c(n1)CN(Cc1ccnn1C(F)F)CC2]
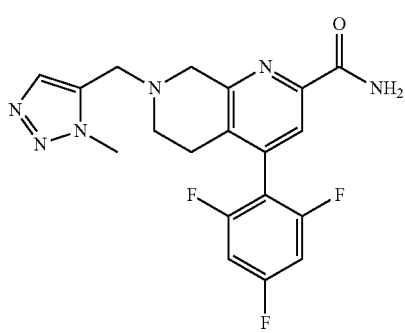 [SMILES: Cn1nncc1CN1CCc2c(-c3c(F)cc(F)cc3F)cc(C(N)=O)nc2C1]
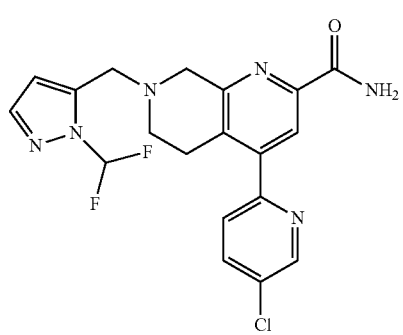 [SMILES: NC(=O)c1cc(-c2ccc(Cl)cn2)c2c(n1)CN(Cc1ccnn1C(F)F)CC2]
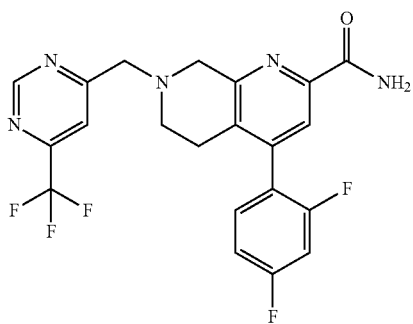 [SMILES: NC(=O)c1cc(-c2ccc(F)cc2F)c2c(n1)CN(Cc1cc(C(F)(F)F)ncn1)CC2]
Structure
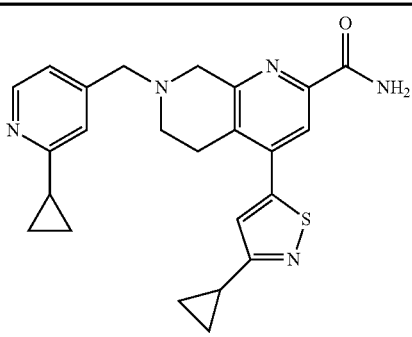
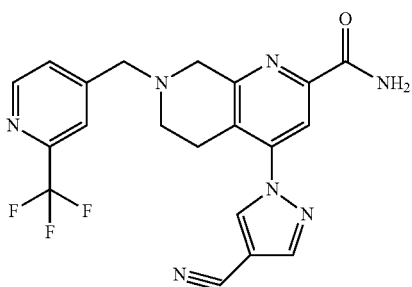
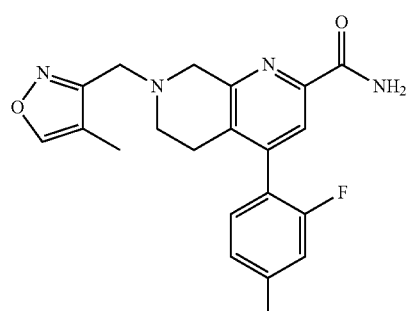
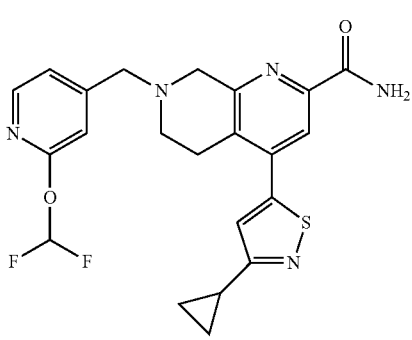 [SMILES: NC(=O)c1cc(-c2cc(C3CC3)ns2)c2c(n1)CN(Cc1ccnc(OC(F)F)c1)CC2]
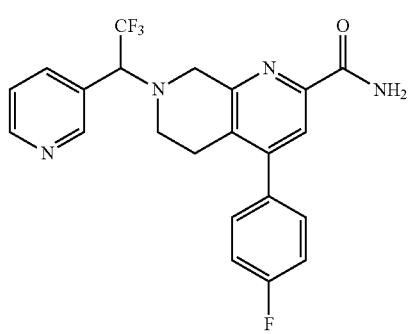 [SMILES: NC(=O)c1cc(-c2ccc(F)cc2)c2c(n1)CN(C(c1cccnc1)C(F)(F)F)CC2]

US 10,072,003 B2
| 177 -continued | 178 -continued |
|---|---|
| Structure | Structure |
| 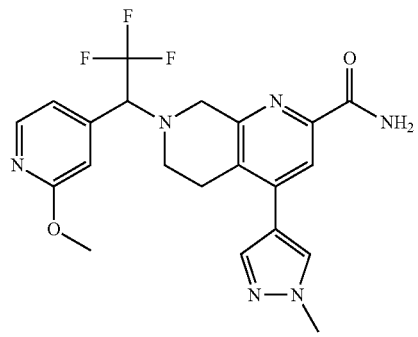 [SMILES: COc1cc(C(N2CCc3c(-c4cnn(C)c4)cc(C(N)=O)nc3C2)C(F)(F)F)ccn1] | 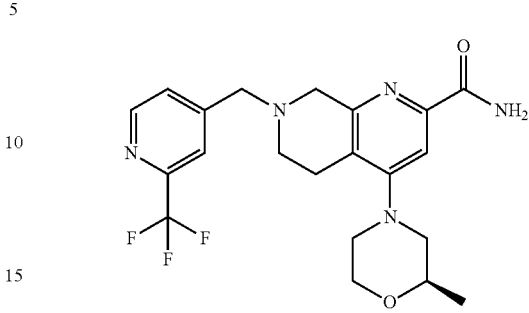 |
| 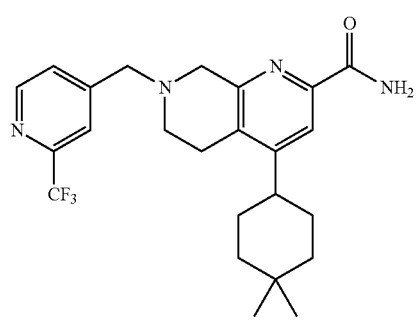 | 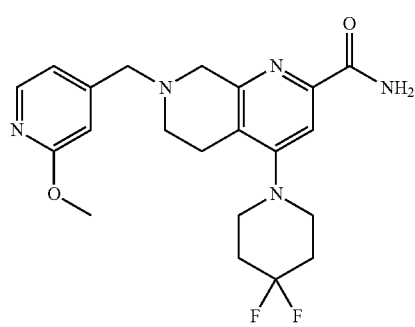 |
| 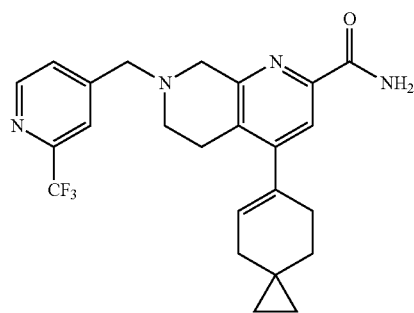 [SMILES: NC(=O)c1cc(C2=CCC3(CC2)CC3)c2c(n1)CN(Cc1ccnc(C(F)(F)F)c1)CC2] | 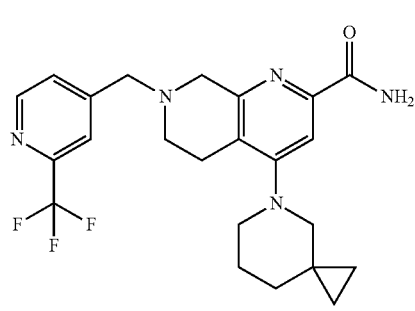 |
| 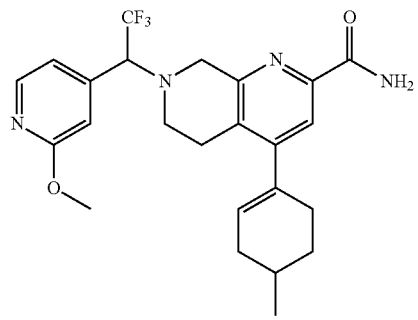 [SMILES: COc1cc(C(N2CCc3c(C4=CCC(C)CC4)cc(C(N)=O)nc3C2)C(F)(F)F)ccn1] | 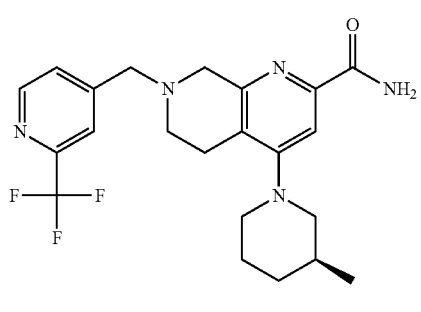 |
| 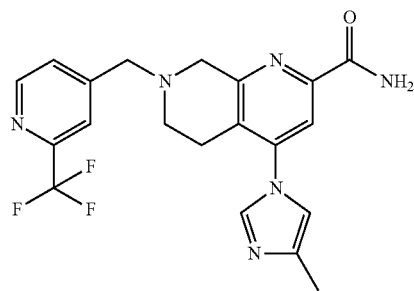 [SMILES: Cc1cn(-c2cc(C(N)=O)nc3c2CCN(Cc2ccnc(C(F)(F)F)c2)C3)cn1] | 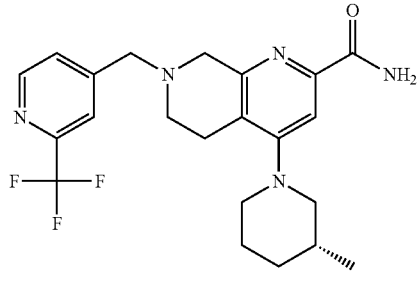 [SMILES: C[C@@H]1CCCN(c2cc(C(N)=O)nc3c2CCN(Cc2ccnc(C(F)(F)F)c2)C3)C1] |

| 179 -continued | | 180 -continued |
|---|---|---|
| Structure | | Structure |
| 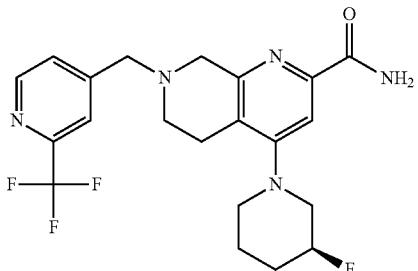 | | 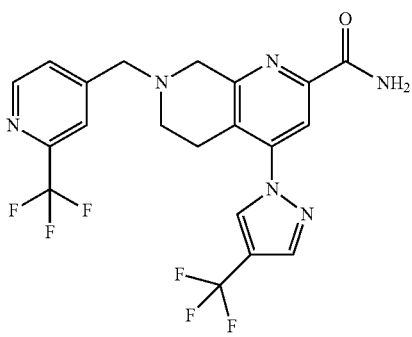 |
| 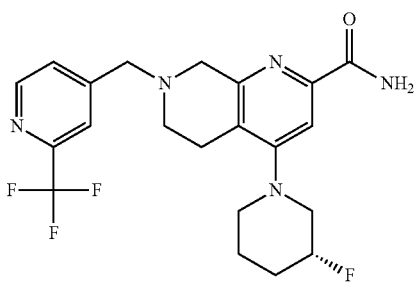 [SMILES: NC(=O)c1cc(N2CCC[C@@H](F)C2)c2c(n1)CN(Cc1ccnc(C(F)(F)F)c1)CC2] | | 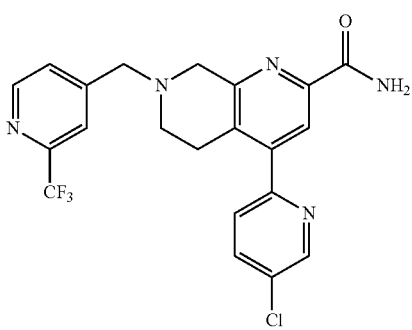 |
| 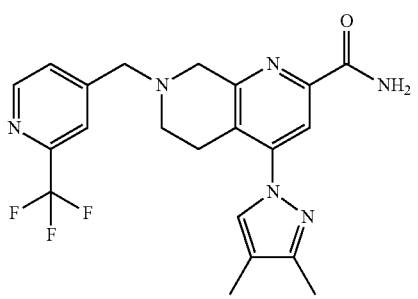 [SMILES: Cc1cn(-c2cc(C(N)=O)nc3c2CCN(Cc2ccnc(C(F)(F)F)c2)C3)nc1C] | | 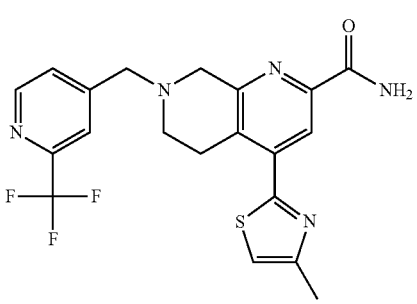 [SMILES: Cc1csc(-c2cc(C(N)=O)nc3c2CCN(Cc2ccnc(C(F)(F)F)c2)C3)n1] |
| 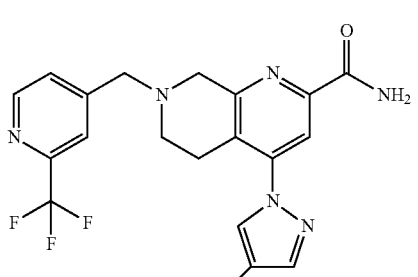 | | 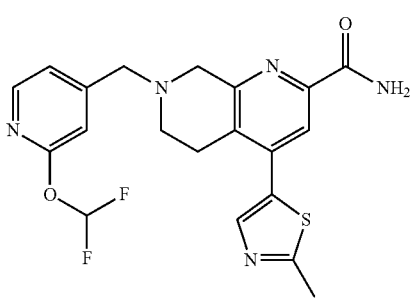 [SMILES: Cc1ncc(-c2cc(C(N)=O)nc3c2CCN(Cc2ccnc(OC(F)F)c2)C3)s1] |
| 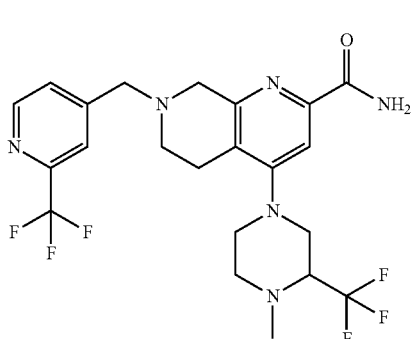 | | 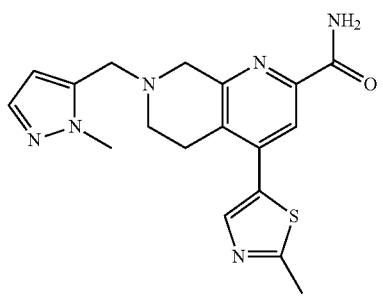 [SMILES: Cc1ncc(-c2cc(C(N)=O)nc3c2CCN(Cc2ccnn2C)C3)s1] |

| 181 -continued | 182 -continued |
|---|---|
| Structure | Structure |
| 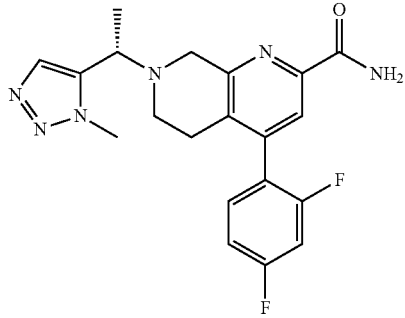 [SMILES: C[C@@H](c1cnnn1C)N1CCc2c(-c3ccc(F)cc3F)cc(C(N)=O)nc2C1] | 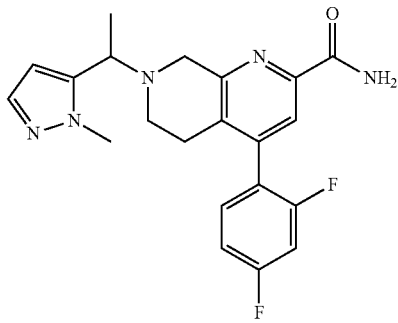 |
| 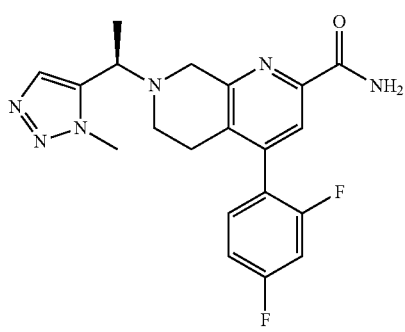 [SMILES: C[C@H](c1cnnn1C)N1CCc2c(-c3ccc(F)cc3F)cc(C(N)=O)nc2C1] | 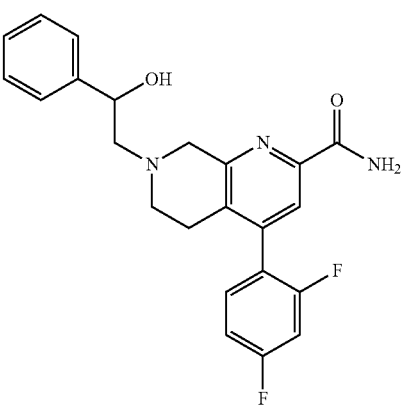 |
| 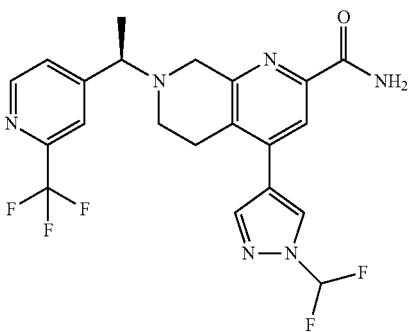 [SMILES: C[C@H](c1ccnc(C(F)(F)F)c1)N1CCc2c(-c3cnn(C(F)F)c3)cc(C(N)=O)nc2C1] | 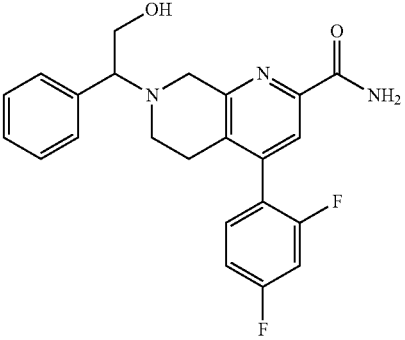 [SMILES: NC(=O)c1cc(-c2ccc(F)cc2F)c2c(n1)CN(C(CO)c1ccccc1)CC2] |
| 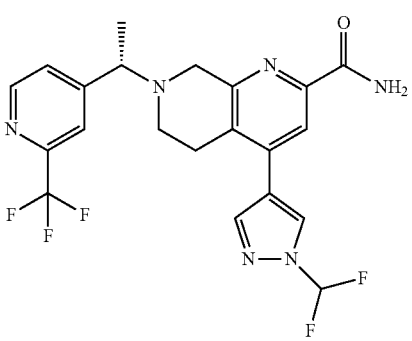 | 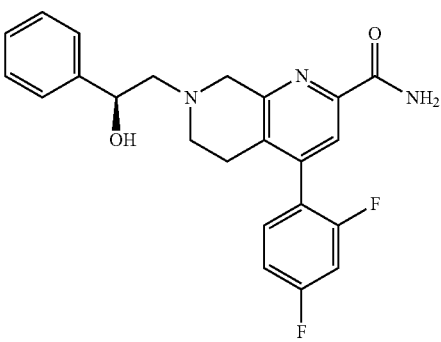 [SMILES: NC(=O)c1cc(-c2ccc(F)cc2F)c2c(n1)CN(C[C@@H](O)c1ccccc1)CC2] |

-continued
| Structure | Structure |
|---|---|
| 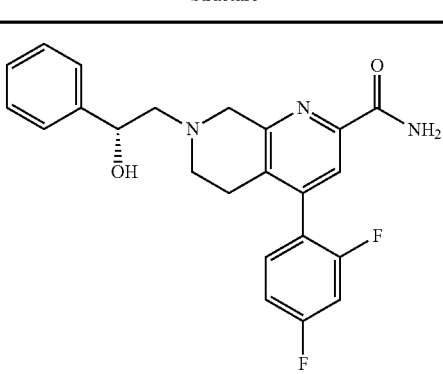 | 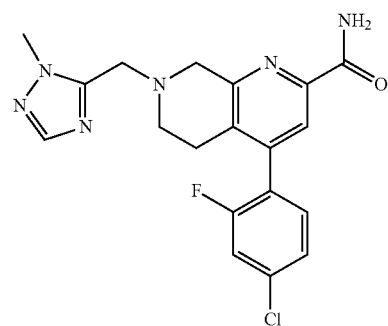 |
| 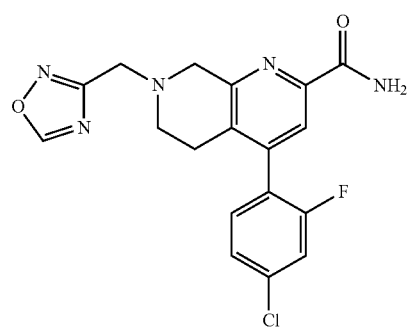 [SMILES: NC(=O)c1cc(-c2ccc(Cl)cc2F)c2c(n1)CN(Cc1ncon1)CC2] | 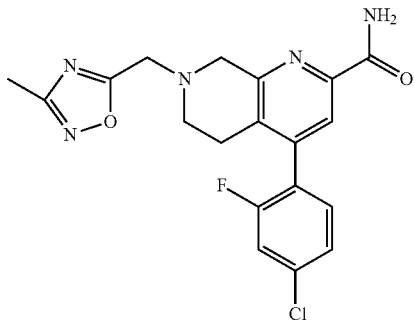 |
| 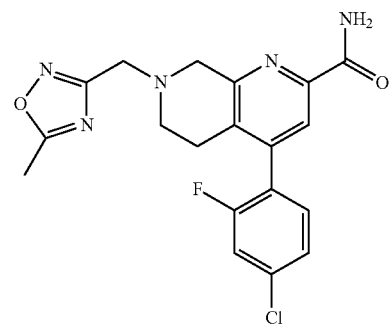 [SMILES: Cc1nc(CN2CCc3c(-c4ccc(Cl)cc4F)cc(C(N)=O)nc3C2)no1] | 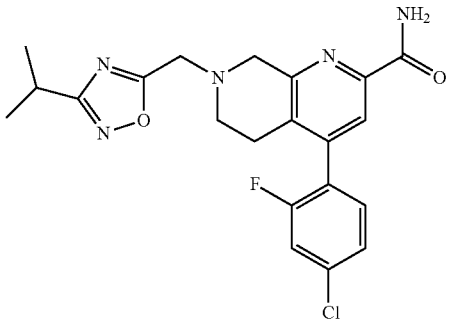 |
| 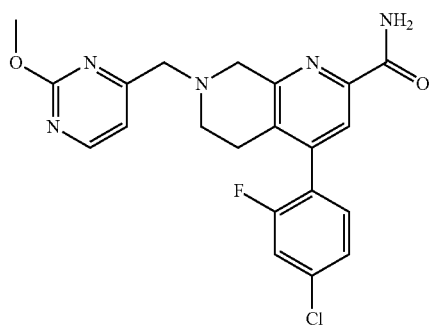 [SMILES: COc1nccc(CN2CCc3c(-c4ccc(Cl)cc4F)cc(C(N)=O)nc3C2)n1] | 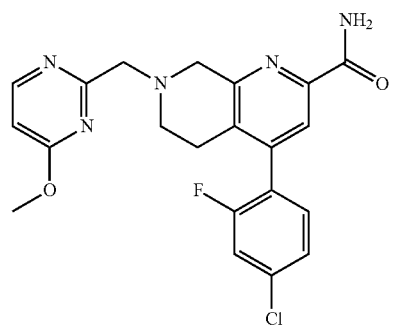 |

TABLE-continued
| Structure |
|---|
| 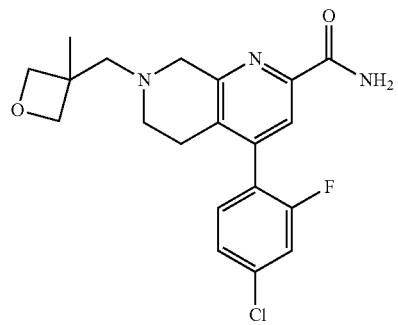 [SMILES: CC1(CN2CCc3c(-c4ccc(Cl)cc4F)cc(C(N)=O)nc3C2)COC1] |
| 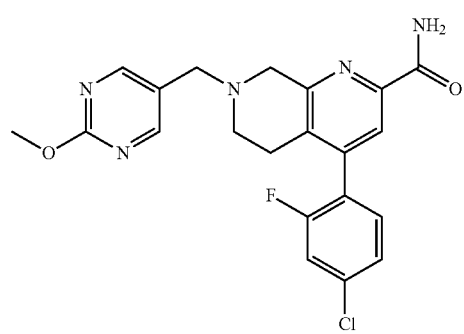 [SMILES: COc1ncc(CN2CCc3c(-c4ccc(Cl)cc4F)cc(C(N)=O)nc3C2)cn1] |
| 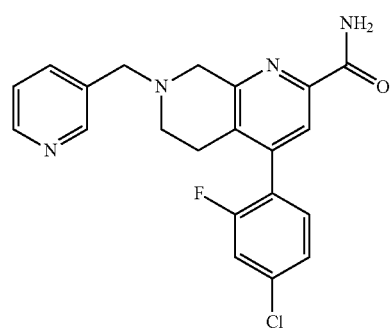 [SMILES: NC(=O)c1cc(-c2ccc(Cl)cc2F)c2c(n1)CN(Cc1cccnc1)CC2] |
| 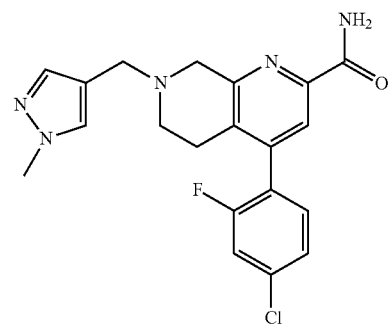 [SMILES: Cn1cc(CN2CCc3c(-c4ccc(Cl)cc4F)cc(C(N)=O)nc3C2)cn1] |
| 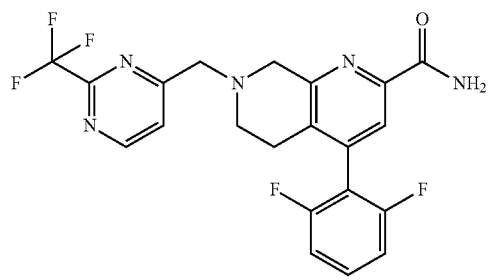 [SMILES: NC(=O)c1cc(-c2c(F)cccc2F)c2c(n1)CN(Cc1ccnc(C(F)(F)F)n1)CC2] |
| 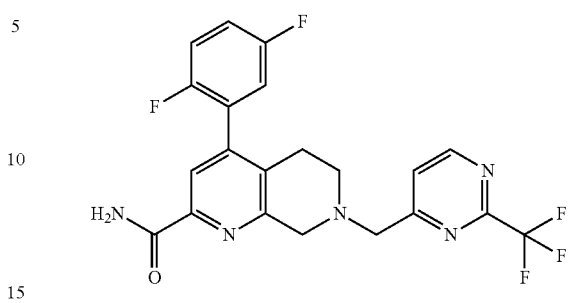 |
| 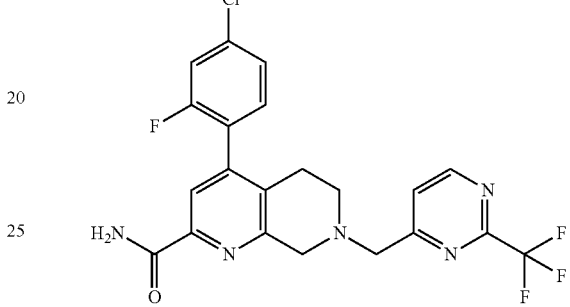 |
| 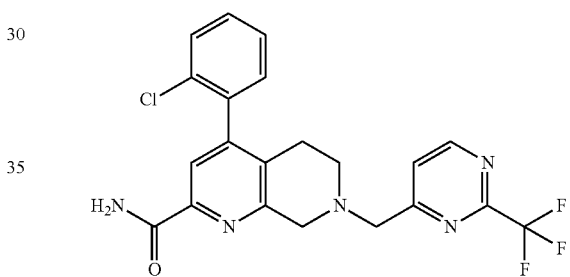 |
| 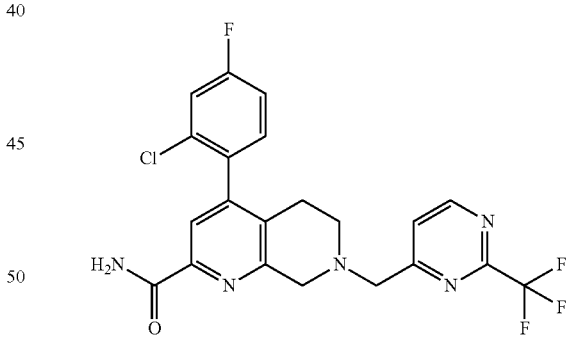 |
| 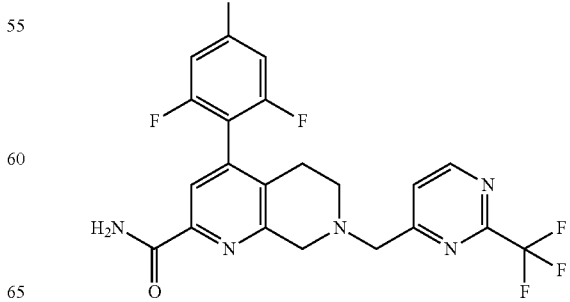 |

| 187 -continued | 188 -continued |
|---|---|
| Structure | Structure |
| 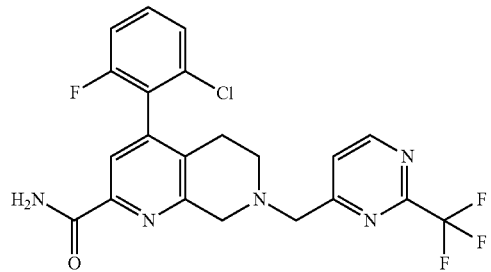 | 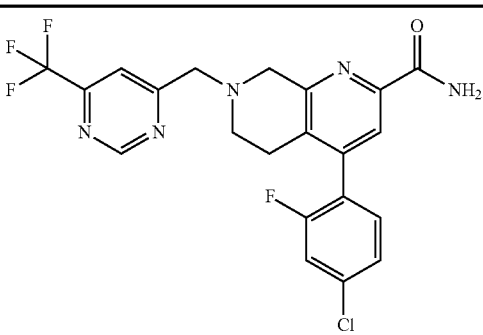 |
| 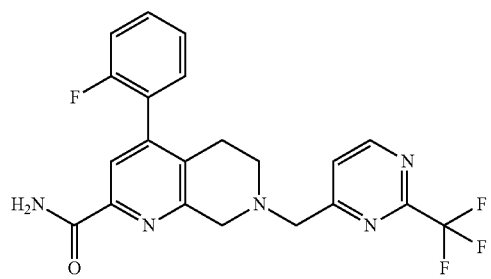 | 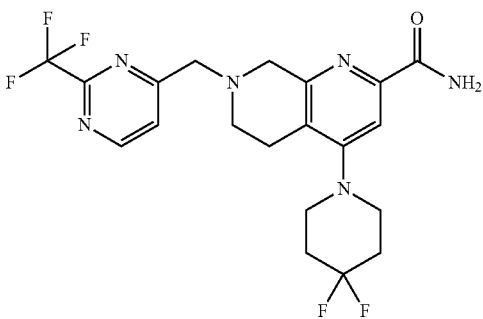 [SMILES: NC(=O)c1cc(N2CCC(F)(F)CC2)c2c(n1)CN(Cc1ccnc(C(F)(F)F)n1)CC2] |
| 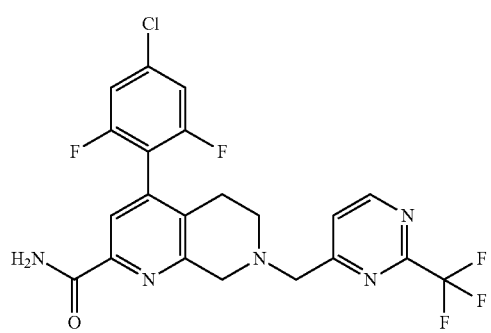 | 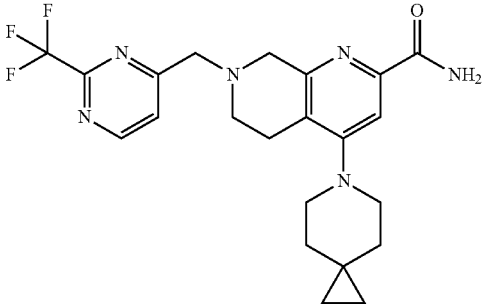 [SMILES: NC(=O)c1cc(N2CCC3(CC2)CC3)c2c(n1)CN(Cc1ccnc(C(F)(F)F)n1)CC2] |
| 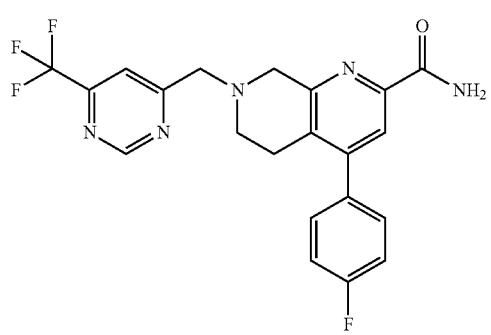 | 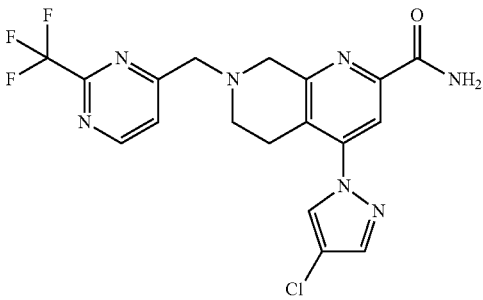 [SMILES: NC(=O)c1cc(-n2cc(Cl)cn2)c2c(n1)CN(Cc1ccnc(C(F)(F)F)n1)CC2] |
| 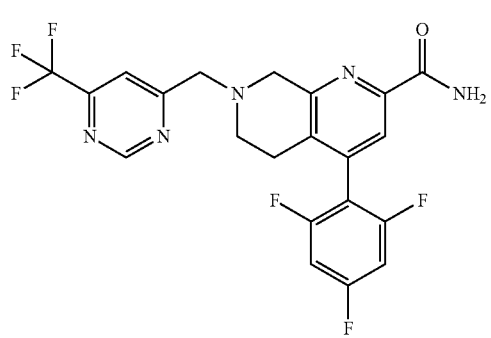 | 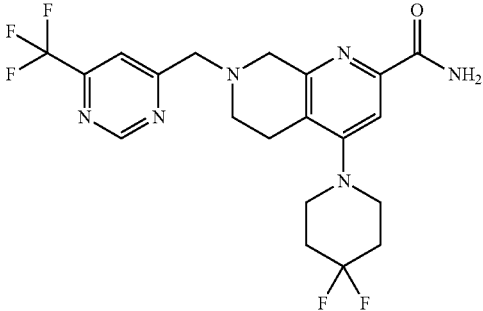 [SMILES: NC(=O)c1cc(N2CCC(F)(F)CC2)c2c(n1)CN(Cc1cc(C(F)(F)F)ncn1)CC2] |

| 189 -continued | 190 -continued |
|---|---|
| Structure | Structure |
| 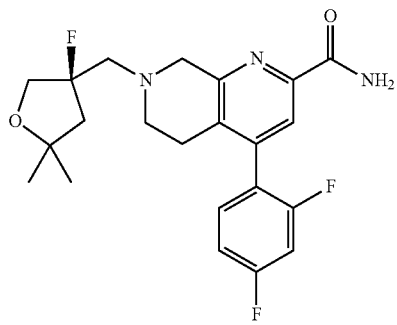 [SMILES: CC1(C)C[C@@](F)(CN2CCc3c(-c4ccc(F)cc4F)cc(C(N)=O)nc3C2)CO1] | 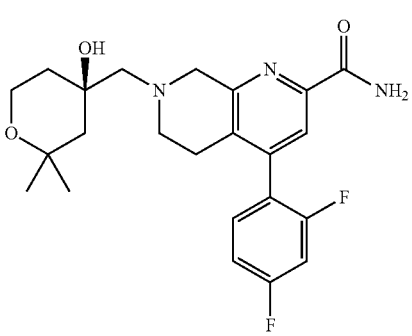 [SMILES: CC1(C)C[C@@](O)(CN2CCc3c(-c4ccc(F)cc4F)cc(C(N)=O)nc3C2)CCO1] |
| 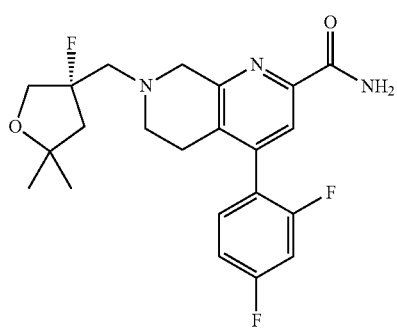 [SMILES: CC1(C)C[C@](F)(CN2CCc3c(-c4ccc(F)cc4F)cc(C(N)=O)nc3C2)CO1] | 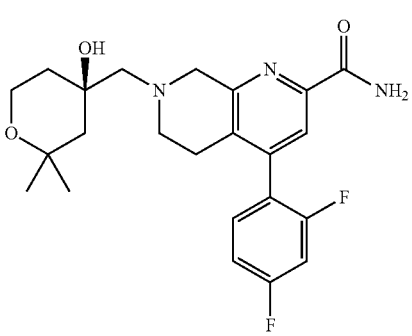 [SMILES: CC1(C)C[C@@](O)(CN2CCc3c(-c4ccc(F)cc4F)cc(C(N)=O)nc3C2)CCO1], and |
| 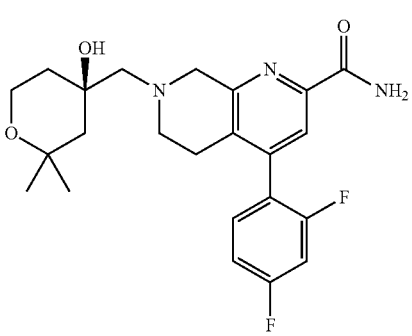 [SMILES: CC1(C)C[C@@](O)(CN2CCc3c(-c4ccc(F)cc4F)cc(C(N)=O)nc3C2)CCO1] | 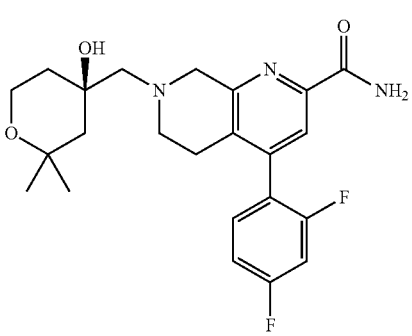 [SMILES: CC1(C)C[C@@](O)(CN2CCc3c(-c4ccc(F)cc4F)cc(C(N)=O)nc3C2)CCO1]. |
8. A pharmaceutical composition comprising a compound of claim 1, or a pharmaceutically acceptable salt thereof, and a pharmaceutically acceptable carrier.
* * * * *